United States Patent
Orimoto et al.

(10) Patent No.: US 11,001,567 B2
(45) Date of Patent: May 11, 2021

(54) PYRAZINE COMPOUND

(71) Applicant: Sumitomo Chemical Company, Limited, Tokyo (JP)

(72) Inventors: Kohei Orimoto, Takarazuka (JP); Yoshihiko Nokura, Takarazuka (JP); Yuji Nakajima, Takarazuka (JP); Takamasa Tanabe, Takarazuka (JP); Takahiro Kimura, Takarazuka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 16/710,035

(22) Filed: Dec. 11, 2019

(65) Prior Publication Data

US 2020/0109128 A1 Apr. 9, 2020

Related U.S. Application Data

(62) Division of application No. 15/766,034, filed as application No. PCT/JP2016/080410 on Oct. 13, 2016, now Pat. No. 10,577,343.

(30) Foreign Application Priority Data

Oct. 16, 2015 (JP) ............... JP2015-204376
Oct. 23, 2015 (JP) ............... JP2015-208639
Jul. 29, 2016 (JP) ............... JP2016-149448

(51) Int. Cl.
C07D 241/16 (2006.01)
C07D 401/04 (2006.01)
A01N 43/60 (2006.01)
C07D 241/18 (2006.01)

(52) U.S. Cl.
CPC ........... C07D 401/04 (2013.01); A01N 43/60 (2013.01); C07D 241/16 (2013.01); C07D 241/18 (2013.01)

(58) Field of Classification Search
CPC ................ C07D 241/16; C07D 401/04
See application file for complete search history.

(56) References Cited

U.S. PATENT DOCUMENTS

| | | | |
|---|---|---|---|
| 7,767,626 B2 | 8/2010 | Toriyabe et al. | |
| 2003/0069242 A1 | 4/2003 | Toriyabe et al. | |
| 2015/0191474 A1 | 7/2015 | Takahashi et al. | |
| 2017/0295787 A1 | 10/2017 | Tanabe et al. | |
| 2018/0009778 A1 | 1/2018 | Tanabe et al. | |
| 2019/0106411 A1* | 4/2019 | Orimoto | C07D 403/04 |

FOREIGN PATENT DOCUMENTS

| | | |
|---|---|---|
| CN | 104395298 A | 3/2015 |
| JP | 200026421 A | 1/2000 |
| JP | 2000198768 A | 7/2000 |
| JP | 2013-060420 A | 4/2013 |
| RU | 2473541 C9 | 5/2011 |
| WO | 9746530 A1 | 12/1997 |
| WO | 2008128711 A1 | 10/2008 |
| WO | 2013/027660 A1 | 2/2013 |
| WO | 2016/052455 A1 | 4/2016 |
| WO | 2016121969 A1 | 8/2016 |

OTHER PUBLICATIONS

STN International, Compound Name 1-(3,5-dimethoxy-2-pyrazinyl)-2-(methylsulfonyl)-ethanone, File Registry [online], Supplier: Aurora Fine Chemicals, 2015, Entered STN; May 22, 2015, CAS Registry No. 1710612-50-2.
STN International, Compound Name 1-(3,5-dimethoxy-2-pyrazinyl)-2-(methylthio)-ethanone, File Registry [online], Supplier: Ukrorgsyntez Ltd., 2014, Entered STN: Mar 11, 2014, CAS Registry No. 1566402-11-6.
STN International, Compound Name 1-(3,5-dimethoxy-2-pyrazinyl)-2-(ethylthio)-ethanone, File Registry [online], Supplier: Ukrorgsyntez Ltd., 2014, Entered STN: Mar. 10, 2014, CAS Registry No. 1565683-44-4.
STN International, Compound Name 3,5-dimethoxy-a-[(methylthio) methyl]-2-pyrazinemethanamine, File Registry [online], Supplier: Ukrorgsyntez Ltd., 2014, Entered STN: May 11, 2014, CAS Registry No. 1602052-18-5.
Marco, "Michael Reactions of b-Keto Sulfoxides and b-Keto Sulfones," Journal of Organic Chemistry, vol. 62, No. 19, pp. 6575-6581 (1997).
Xiong et al, "Synthesis and SAR of sulfoxide substituted carboxyquinolines as NK3 receptor antagonists," Bioorganic & Medicinal Chemistry Letters, vol. 21, pp. 1896-1899 (2011).
Int'l Search Report dated Dec. 20, 2016 in Int'l Application No. PCT/JP2016/080410.
Int'l Preliminary Report on Patentability dated Apr. 17, 2018 in Int'l Application No. PCT/JP2016/080410.

(Continued)

*Primary Examiner* — Brian E McDowell
(74) *Attorney, Agent, or Firm* — Panitch Schwarze Belisario & Nadel LLP

(57) ABSTRACT

Provided is a compound represented by formula (I):

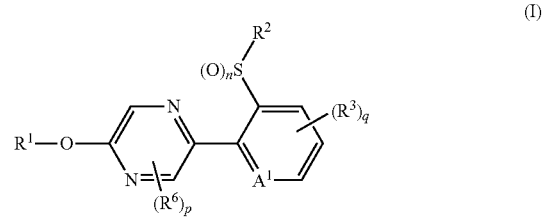

or an N-oxide compound thereof, wherein the variable groups are as defined in the specification. Also provided is an arthropod pest control agent containing a compound represented by formula (I) and an inert carrier. The compound represented by formula (I) and arthropod pest control agent exhibit an excellent controlling effect against arthropod pests.

1 Claim, No Drawings

(56) References Cited

OTHER PUBLICATIONS

Extended European Search Report dated Mar. 25, 2019 in European Application No. 16855481.4.
Office Action dated Jun. 11, 2019 in U.S. Appl. No. 15/766,034 by Orimoto.
Office Action dated Apr. 28, 2020 in RU Application No. 2018117696.
Office Action dated Dec. 6, 2019 in RU Application No. 2018117696.
Search Report dated Dec. 3, 2019 in RU Application No. 2018117696.
Office Action dated May 26, 2020 in JP Application No. 2017545466.
Office Action dated Apr. 9, 2020 in ID Application No. P00201803327 (Partial English Translation).
Office Action dated Jul. 11, 2020 in IN Application No. 201847013625.
Office Action dated Sep. 27, 2020 in CN Application No. 201680060229.1.
Office Action dated Aug. 5, 2020 in AR Application No. P20160103140.
Office Action dated Nov. 29, 2020 in EG Application No. 2018040618.

* cited by examiner

PYRAZINE COMPOUND

CROSS-REFERENCE TO RELATED APPLICATION

This application is a Division of U.S. patent application Ser. No. 15/766,034 filed Apr. 5, 2018, now allowed, which is a Section 371 of International Application No. PCT/JP2016/080410, filed Oct. 13, 2016, which was published in the Japanese language on Apr. 20, 2017, under International Publication No. WO 2017/065228 A1, which claims priority under 35 U.S.C. § 119(b) to Japanese Application No. 2015-204376, filed Oct. 16, 2015, Japanese Application No. 2015-208639, filed Oct. 23, 2015 and Japanese Application No. 2016-149448, filed Jul. 29, 2016, the disclosures of all of which are incorporated herein by reference in their entireties.

TECHNICAL FIELD

The present invention is related to a certain class of pyrazine compound and its use for controlling harmful arthropods.

BACKGROUND ART

To date, some compounds for controlling harmful arthropods have been developed and come into practical use. Also, a certain class of compounds has been known to be effective for controlling harmful organisms (see Patent Document 1).

CITATION LIST

Patent Document

Patent Document 1: JP2000-26421 A

SUMMARY OF THE INVENTION

Problems to be Solved by Invention

An object of the present invention is to provide a compound having an excellent efficacy for controlling harmful arthropods.

Means to Solve Problems

The present invention provides, for example, the following embodiments.

[1] A compound represented by formula (I) or its N oxide compound:

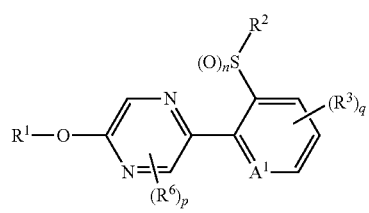

(I)

[wherein
$A^1$ represents a nitrogen atom or a $CR^4$;
$R^4$ represents a hydrogen atom, a $OR^{27}$, a $NR^{27}R^{28}$, a cyano group, a nitro group, or a halogen atom;

$R^1$ represents a C2-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;

$R^2$ represents a C1-C6 alkyl group optionally having one or more halogen atoms, a cyclopropylmethyl group, or a cyclopropyl group;

q represents 0, 1, 2, or 3;

$R^3$ represents independently of each other, a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $S(O)_yR^{15}$, a $C(O)OR^{17}$, a $C(O)NR^{11}R^{12}$, a cyano group, a nitro group, or a halogen atom, and when q is 2 or 3, a plurality of $R^3$ may be identical or different;

p represents 0, 1, or 2, $R^6$ represents independently of each other, a C1-C6 alkyl group optionally having one or more halogen atoms, a $OR^{18}$, a $NR^{18}R^{19}$, a cyano group, a nitro group, or a halogen atom, and when p is 2, a plurality of $R^6$ may be identical or different;

$R^{17}$, $R^{18}$, $R^{19}$, $R^{24}$ and $R^{29}$ represent independently of each other a hydrogen atom, or a C1-C6 chain hydrocarbon group optionally having one or more halogen atoms;

$R^{12}$ represents a hydrogen atom, a C1-C6 chain hydrocarbon group optionally having one or more halogen atoms, a C1-C6 alkyl group having one substituent selected from Group F, or a $S(O)_2R^{23}$;

$R^{23}$ represents a C1-C6 chain hydrocarbon group optionally having one or more halogen atoms, or a phenyl group optionally having one or more substituents selected from Group D;

$R^{11a}$ and $R^{12a}$ combine together with a nitrogen atom to which they are attached to form a 3 to 7 membered nonaromatic heterocyclic group optionally having one or more substituents selected from Group E {the 3 to 7 membered nonaromatic heterocyclic group represents aziridine, azetidine, pyrrolidine, imidazoline, imidazolidine, piperidine, tetrahydropyrimidine, hexahydropyrimidine, piperazine, azepane, oxazolidine, isooxazolidine, 1,3-oxazinane, morpholine, 1,4-oxazepane, thiazolidine, isothiazolidine, 1,3-thiazinane, thiomorpholine, or 1,4-thiazepane};

$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a 5 or 6 membered aromatic heterocyclic group optionally having one or more substituents selected from Group D;

$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl optionally having one or more halogen atoms, or a phenylC1-C3 alkyl group {the phenyl moiety in the phenylC1-C3 alkyl group may optionally have one or more substituents selected from Group D};

$R^{15}$ and $R^{16}$ represent independently of each other, a C1-C6 alkyl group optionally having one or more halogen atoms;

$R^{27}$ and $R^{28}$ represent independently of each other, a hydrogen atom, or a C1-C6 alkyl group optionally having one or more halogen atoms;

n and y represent independently of each other, 0, 1, or 2;

x represents 0 or 1;

Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom {$R^{21}$ and $R^{22}$ represent independently of each other a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, an amino group, a $NHR^{21}$, a $NR^{21}R^{22}$, a cyano group, a phenyl group optionally having one or more substituents selected from Group D, a 5 or 6 membered aromatic heterocyclic group optionally having one or more substituents selected from Group D, a C3-C7 cycloalkyl group optionally having one or more halogen atoms, and a 3 to 7 membered nonaromatic heterocyclic group optionally having one or more substituents selected from Group C;

Group G: a group consisting of a halogen atom, and a C1-C6 haloalkyl group].

[2] The compound described in [1] wherein $R^4$ represents a hydrogen atom or a halogen atom, and $R^3$ represents a C1-C6 chain hydrocarbon group optionally having one or more halogen atoms, a phenyl group optionally having one or more substituents selected from Group D, a 6 membered aromatic heterocyclic group containing one to two nitrogen atoms {the 6 membered aromatic heterocyclic group optionally has one or more substituents selected from Group D}, a 5 membered aromatic heterocyclic group containing one to four nitrogen atoms {the 5 membered aromatic heterocyclic group optionally has one or more substituents selected from Group D}, a $OR^{12}$, a $NR^{11}R^{12}$, or a halogen atom.

[3] The compound described in [1] wherein $R^3$ represents a C1-C6 alkyl group having one or more halogen atoms, a $OR^{12}$, a $NR^{11}R^{12}$, or a halogen atom, and $R^{11}$ and $R^{12}$ represent independently of each other a hydrogen atom or a C1-C3 alkyl group optionally having one or more halogen atoms.

[4] The compound described in [1] wherein q is 0.

[5] The compound described in any one of [1] to [4] wherein p is 0 or 1, and $R^6$ represents a C1-C6 alkyl group optionally having one or more halogen atoms, or a halogen atom.

[6] The compound described in any one of [1] to [4] wherein p is 0.

[7] The compound described in any one of [1] to [5] wherein $R^1$ represents a C2-C10 haloalkyl group.

[8] The compound described in any one of [1] to [6] wherein $R^1$ represents a C2-C10 fluoroalkyl group.

[9] The compound described in any one of [1] to [6] wherein $R^1$ represents a C2-C10 alkyl group having two or more fluorine atoms.

[10] The compound described in any one of [1] to [6] wherein $R^1$ represents a C3-C5 alkyl group having four or more fluorine atoms.

[11] The compound described in any one of [1] to [10] wherein $R^2$ represents a C1-C6 alkyl group optionally having one or more halogen atoms.

[12] The compound described in any one of [1] to [10] wherein $R^2$ represents an ethyl group.

[13] The compound described in [1] wherein
  $R^1$ represents a C2-C10 haloalkyl group;
  $R^2$ represents an ethyl group;
  q is 0 or 1, and $R^3$ represents a C1-C6 alkyl group optionally having one or more halogen atoms, or a halogen atom; and
  p is 0 or 1, and $R^6$ represents a C1-C6 alkyl group optionally having one or more halogen atoms, or a halogen atom.

[14] The compound described in [1] wherein
  $R^1$ represents a C3-C5 alkyl group having four or more fluorine atoms;
  $R^2$ represents an ethyl group;
  q is 0; and
  p is 0.

[15] A composition comprising the compound described in any one of [1] to [14], and one or more ingredients selected from the group consisting of Groups (a), (b), (c), and (d):
  Group (a): a group consisting of insecticidal ingredients, miticidal ingredients, and nematicidal ingredients;
  Group (b): fungicidal ingredients;
  Group (c): plant growth modulating ingredients; and
  Group (d): phytotoxicity-reducing ingredients.

[16] A method for controlling a harmful arthropod which comprises applying an effective amount of the compound described in any one of [1] to [14] or the composition described in [15] to a harmful arthropod or a habitat where a harmful arthropod lives.

[17] A method for controlling a harmful arthropod which comprises applying an effective amount of the compound described in any one of [1] to [14] or the composition described in [15] to a plant or soil for growing a plant.

[18] A method for controlling a harmful arthropod which comprises applying an effective amount of the compound described in [1] to [14] or the composition described in [15] to a seed or bulb.

[19] A seed or bulb carrying an effective amount of the compound described in any one of [1] to [14] or the composition described in [15].

[20] An agent for controlling a harmful arthropod comprising the compound described in any one of [1] to [14] or the composition described in [15], and an inert carrier.

[21] A compound represented by formula (M-3):

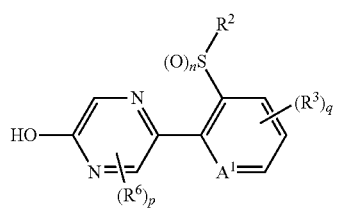

(M-3)

[wherein $A^1$ represents a nitrogen atom or a $CR^4$;

$R^4$ represents a hydrogen atom, a $OR^{27}$, a $NR^{27}R^{28}$, a cyano group, a nitro group, or a halogen atom;

$R^2$ represents a C1-C6 alkyl group optionally having one or more halogen atoms, a cyclopropylmethyl group, or a cyclopropyl group;

q represents 0, 1, 2, or 3;

$R^3$ represents independently of each other a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}c(0)$ a $NR^{11}C(O)OR^{14}$, a $NR^{29}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $S(O)_yR^{15}$, a $C(O)OR^{17}$, a $C(O)NR^{11}R^{12}$, a cyano group, a nitro group, or a halogen atom, and when q is 2 or 3, a plurality of $R^3$ may be identical or different;

p represents 0, 1, or 2; and $R^6$ represents independently of each other a C1-C6 alkyl group optionally having one or more halogen atoms, a $OR^{18}$, a $NR^{18}R^{19}$, a cyano group, a nitro group, or a halogen atom, and when p is 2, a plurality of $R^6$ may be identical or different].

[22] A compound represented by formula (M-4):

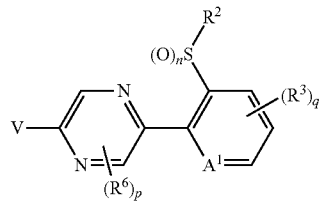

(M-4)

[wherein
V represents a halogen atom;
$A^1$ represents a nitrogen atom or a $CR^4$;

$R^4$ represents a hydrogen atom, a $OR^{27}$, a $NR^{27}R^{28}$, a cyano group, a nitro group, or a halogen atom;

$R^2$ represents a C1-C6 alkyl group optionally having one or more halogen atoms, a cyclopropylmethyl group, or a cyclopropyl group;

q represents 0, 1, 2, or 3;

$R^3$ represents independently of each other a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $S(O)_yR^{15}$, a $C(O)OR^{17}$, a $C(O)NR^{11}R^{12}$, a cyano group, a nitro group, or a halogen atom, and when q is 2 or 3, a plurality of $R^3$ may be identical or different;

p represents 0, 1, or 2; and $R^6$ represents independently of each other a C1-C6 alkyl group optionally having one or more halogen atoms, a $OR^{18}$, a $NR^{18}R^{19}$, a cyano group, a nitro group, or a halogen atom, and when p is 2, a plurality of $R^6$ may be identical or different].

[23] A compound represented by formula (M-30):

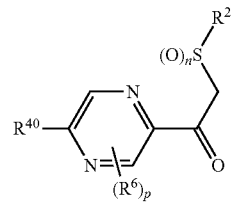

(M-30)

[wherein $R^{40}$ represents a halogen atom, a C1-C4 alkoxy group, or a $OR^1$;

$R^1$ represents a C2-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;

$R^2$ represents a C1-C6 alkyl group optionally having one or more halogen atoms, a cyclopropylmethyl group, or a cyclopropyl group;

p represents 0, 1, or 2; and $R^6$ represents independently of each other a C1-C6 alkyl group optionally having one or more halogen atoms, a $OR^{18}$, a $NR^{18}R^{19}$, a cyano group, a nitro group, or a halogen atom, and when p is 2, a plurality of $R^6$ may be identical or different].

[24] A compound represented by formula (M-31):

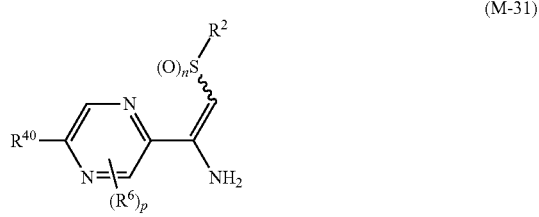

(M-31)

[wherein $R^{40}$ represents a halogen atom, a C1-C4 alkoxy group, or a $OR^1$;

$R^1$ represents a C2-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;

$R^2$ represents a C1-C6 alkyl group optionally having one or more halogen atoms, a cyclopropylmethyl group, or a cyclopropyl group;

p represents 0, 1, or 2; and $R^6$ represents independently of each other a C1-C6 alkyl group optionally having one or more halogen atoms, a $OR^{18}$, a $NR^{18}R^{19}$, a cyano group, a nitro group, or a halogen atom, and when p is 2, a plurality of $R^6$ may be identical or different].

Effect of Invention

The Present compound has an excellent control efficacy against harmful arthropods, and is thus useful as an active ingredient of an agent for controlling harmful arthropods. Also, a composition comprising the Present compound and one or more ingredients selected from the group consisting of Groups (a), (b), (c) and (d) (hereinafter, referred to as "Present composition") shows an excellent control effect against harmful arthropods.

MODE FOR CARRYING OUT THE INVENTION

The substituent(s) as described herein is/are explained.

The term of "optionally having one or more halogen atoms" represents that when two or more halogen atoms are present, these halogen atoms may be identical to or different from each other.

The expression of "CX-CY" as used herein represents that the number of carbon atom is from X to Y. For example, the expression of "C1-C6" represents that the number of carbon atom is from 1 to 6.

The term of "halogen atom" represents fluorine atom, chlorine atom, bromine atom, or iodine atom.

The term of "chain hydrocarbon group" represents an alkyl group, an alkenyl group, or an alkynyl group.

Examples of the term of "alkyl group" include methyl group, ethyl group, propyl group, isopropyl group, 1,1-dimethylpropyl group, 1,2-dimethylpropyl group, 1-ethyl-propyl group, butyl group, tert-butyl group, pentyl group, hexyl group, heptyl group, octyl group, nonyl group, and decyl group.

Examples of the term of "alkenyl group" include vinyl group, 1-propenyl group, 2-propenyl group, 1-methyl-1-propenyl group, 1-methyl-2-propenyl group, 1,2-dimethyl-1-propenyl group, 1,1-dimethyl-2-propenyl group, 1-ethyl-1-propenyl group, 1-ethyl-2-propenyl group, 3-butenyl group, 4-pentenyl group, 5-hexenyl group, heptenyl group, octenyl group, nonenyl group, and decenyl group.

Examples of the term of "alkynyl group" includes ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, 5-hexynyl group, heptynyl group, octinyl group, nonynyl group, and decynyl group.

The term of "C2-C10 chain hydrocarbon group having one or more halogens" represents a C2-C10 alkyl group, a C2-C10 alkenyl group, a C2-C10 alkynyl group, each having one or more halogens.

The term of "C2-C10 haloalkyl group" represents a group wherein one or more hydrogen atoms in the C2-C10 alkyl group is/are substituted by halogen atoms, and includes, for example, a C2-C10 fluoroalkyl group. Examples of the term of "C2-C10 haloalkyl group" include chloroethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, perfluorohexyl group, and perfluorodecyl group.

Examples of the term of "C2-C10 fluoroalkyl group" include 2,2,2-trifluoroethyl group, 2,2,3,3-tetrafluoropropyl group, 1-methyl-2,2,3,3-tetrafluoropropyl group, perfluorohexyl group, and perfluorodecyl group.

Examples of the term of "C2-C10 alkyl group having two or more fluoro atoms" include 2,2,2-trifluoroethyl group, 2,2,3,3-tetrafluoropropyl group, 1-methyl-2,2,3,3-tetrafluoropropyl group, perfluorohexyl group, and perfluorodecyl group.

Examples of the term of "C2-C10 alkyl group having four or more fluoro atoms" include 2,2,3,3-tetrafluoropropyl group, 1-methyl-2,2,3,3-tetrafluoropropyl group, perfluorohexyl group, and perfluorodecyl group.

The term of "C2-C10 haloalkenyl group" represents a group wherein one or more hydrogen atoms in the C2-C10 alkenyl group is/are substituted by halogen atoms, and includes, for example, a C2-C10 fluoroalkenyl group. Examples of the "C2-C10 fluoroalkenyl group" includes, for example, 4,4,4-trifluoro-2-butenyl group, and 2,4,4,4-tetrafluoro-2-butenyl group.

The term of "C2-C10 haloalkynyl group" represents a group wherein one or more hydrogen atoms in the C2-C10 alkynyl group is/are substituted by halogen atoms, and includes, for example, a C2-C10 fluoroalkynyl group. Examples of the "C2-C10 fluoroalkynyl group" includes, for example, 4,4,4-trifluoro-2-butynyl group.

Examples of the term of "C1-C6 alkyl group optionally having one or more halogen atoms" include 2,2,2-trifluoroethyl group, 2,2,3,3-tetrafluoropropyl group, and 2,2,3,4,4,4-hexafluoropropyl group.

The term of "C1-C6 chain hydrocarbon group having one or more halogen atoms" represents a C1-C6 alkyl group, a C1-C6 alkenyl group, or a C1-C6 alkynyl group, each having one or more halogen atoms. The term of "C1-C6 alkyl group having one or more halogen atoms" is encompassed into the above-mentioned terms of "C1-C6 alkyl group optionally having one or more halogen atoms" and the above-mentioned term of "C2-C10 chain hydrocarbon group having one or more halogen atoms". The term of "C1-C6 alkenyl group having one or more halogen atoms" and the term of "C1-C6 alkynyl group having one or more halogen atoms" are encompassed into the above-mentioned term of "C2-C10 chain hydrocarbon group having one or more halogen atoms".

Examples of the term of "cycloalkyl group" include cyclopropyl group, cyclobutyl group, cyclopentyl group, cyclohexyl group, and cycloheptyl group.

The term of "alkoxy group" represents a monovalent group wherein the above-mentioned "alkyl group" binds to an oxygen atom, and examples of a C1-C6 alkoxy group include methoxy, ethoxy, n-propoxy, i-propoxy, n-butoxy, t-butoxy, s-butoxy, and 3-methylbutoxy.

Examples of the term of "3 to 7 membered nonaromatic heterocyclic group" include aziridine, azetidine, pyrrolidine, imidazoline, imidazolidine, piperidine, tetrahydropyrimidine, hexahydropyrimidine, piperazine, azepane, oxazolidine, isooxazolidine, 1,3-oxazinane, morpholine, 1,4-oxazepane, thiazolidine, isothiazolidine, 1,3-thiazinane, thiomorpholine, and 1,4-thiazepane. Examples of the 3 to 7 membered nonaromatic heterocyclic group optionally having one or more substituents selected from Group E include the followings:

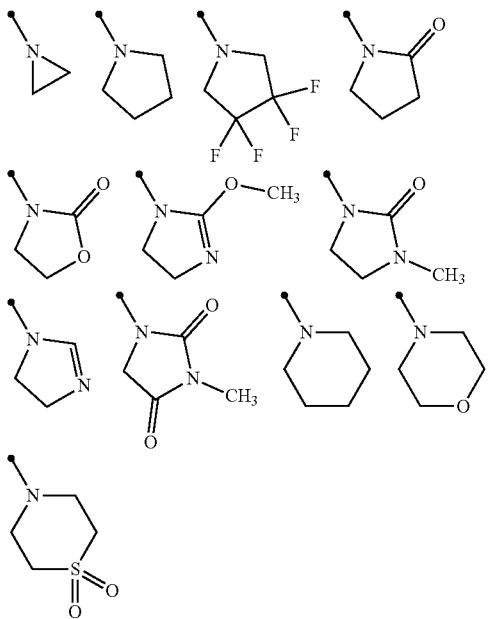

Examples of the term of "phenylC1-C3 alkyl group {the phenyl moiety in the phenylC1-C3 alkyl group may optionally have one or more substituents selected from Group D}" include benzyl group, 2-fluorobenzyl group, 4-chlorobenzyl group, 4-(trifluoromethyl)benzyl group, and 2-[4-(trifluoromethyl)phenyl]ethyl group.

The term of "(C1-C5 alkoxy)C2-C5 alkyl group having one or more halogen atoms" represents a group wherein the (C1-C5 alkoxy) and/or the (C2-C5 alkyl) have/has one or more halogen atoms, and includes, for example, 2-(trifluoromethoxy) ethyl group, 2,2-difluoro-3-methoxypropyl group, 2,2-difluoro-3-(2,2,2-trifluoroethoxy)propyl group, and 3-(2-chloroethoxy)propyl group.

The term of "(C1-C5 alkylsulfanyl)C2-C5 alkyl group having one or more halogen atoms" represents a group wherein the (C1-C5 alkylsulfanyl) and/or the (C2-C5 alkyl) have/has one or more halogen atoms, and includes, for example, 2,2-difluoro-2-(trifluoromethylthio))ethyl group.

The term of "(C1-C5 alkylsulfinyl)C2-C5 alkyl group having one or more halogen atoms" represents a group wherein the (C1-C5 alkylsulfinyl) and/or the (C2-C5 alkyl) have/has one or more halogen atoms, and includes, for example, 2,2-difluoro-2-(trifluoromethansulfinyl)ethyl group.

The term of "(C1-C5 alkylsulfonyl) C2-C5 alkyl group having one or more halogen atoms" represents a group wherein the (C1-C5 alkylsulfonyl) and/or the (C2-C5 alkyl) group have/has one or more halogen atoms, and includes, for example, 2,2-difluoro-2-(trifluoromethansulfonyl)ethyl group.

The term of "(C3-C6 cycloalkyl)C1-C3 alkyl group having one or more halogen atoms" represents a group wherein the (C3-C6 cycloalkyl) and/or the (C1-C3 alkyl) has/have one or more halogen atoms, and includes, for example, (2,2-difluorocyclopropyl)methyl group, 2-cyclopropyl-1,1,2,2-tetrafluoroethyl group, and 2-(2,2-difluorocyclopropyl)-1,1,2,2-tetrafluoroethyl group.

The term of "(C3-C7 cycloalkyl)C1-C3 alkyl group having one or more substituents selected from Group G" represents a group wherein the (C3-C7 cycloalkyl) and/or the (C1-C3 alkyl) has/have one or more substituents selected from Group G, and includes, for example, (2,2-difluorocyclopropyl)methyl group, [1-(trifluoromethyl)cyclopropyl] methyl group, [2-(trifluoromethyl)cyclopropyl]methyl group, 2-cyclopropyl-1,1,2,2-tetrafluoroethyl group, 2-cyclopropyl-3,3,3-trifluoropropyl group, and 1,1,2,2-tetrafluoro-2-[2-(trifluoromethyl)cyclopropyl]ethyl group.

The term of "C3-C7 cycloalkyl group having one or more substituents selected from Group G" includes, for example, 2,2-difluorocyclopropyl group, 1-(2,2,2-trifluoroethyl)cyclopropyl group, and 4-trifluoromethyl)cyclohexyl group, The term of "5 or 6 membered aromatic heterocyclic group" represents a 5 membered aromatic heterocyclic group or a 6 membered aromatic heterocyclic group. Examples of the 5 membered aromatic heterocyclic group include pyrrolyl group, furyl group, thienyl group, pyrazolyl group, imidazolyl group, triazolyl group, tetrazolyl group, oxazolyl group, isoxazolyl group, triazolyl group, oxadiazolyl group, and thiadiazolyl group. Examples of the membered aromatic heterocyclic group include pyridyl group, pyridazinyl group, pyrimidinyl group and pyrazinyl group.

The term of "6 membered aromatic heterocyclic group containing one to two nitrogen atoms" represents pyridyl group, pyridazinyl group, pyrimidinyl group and pyrazinyl group.

The term of "5 membered aromatic heterocyclic group containing one to four nitrogen atoms" represents pyrrolyl group, pyrazolyl group, imidazolyl group, 1,2,4-triazolyl group, 1,2,3-triazolyl group, and tetrazolyl group.

The terms of "alkylsulfanyl", "alkylsulfinyl", and "alkylsulfonyl" represent an alkyl group containing a S(O)z moiety, respectively.

For example, example of the "alkylsulfanyl" when z is includes methylsulfanyl group, ethylsulfanyl group, propylsulfanyl group, and isopropylsulfanyl group.

For example, example of the "alkylsulfinyl" when z is 1 includes methylsulfinyl group, ethylsulfinyl group, propylsulfinyl group, and isopropylsulfinyl group.

For example, example of the "alkylsulfonyl" when z is includes methylsulfonyl group, ethylsulfonyl group, propylsulfonyl group, and isopropylsulfonyl group.

Example of "N oxide compound" includes a compound represented by formula (I-N1), a compound represented by formula (I-N2), a compound represented by formula (I-N3), and a compound represented by formula (I-N4).

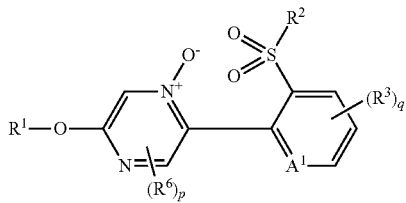
(I-N1)

[wherein the symbols are the same as defined above.]

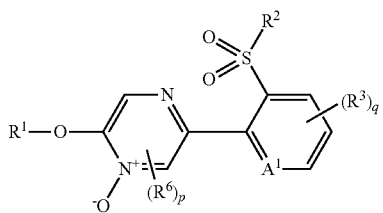
(I-N2)

[wherein the symbols are the same as defined above.]

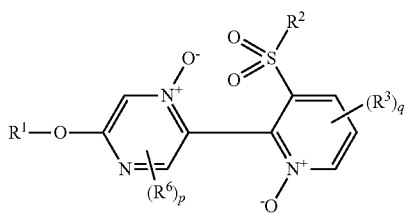
(I-N3)

[wherein the symbols are the same as defined above.]

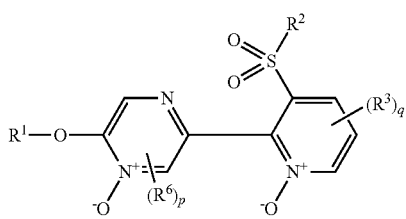
(I-N4)

[wherein the symbols are the same as defined above.]

Examples of the Present compound include the following compounds.

A compound of the present invention wherein $A^1$ represents a nitrogen atom or a $CR^4$, and $R^4$ represents a hydrogen atom or a halogen atom;

A compound of the present invention wherein $A^1$ represents a nitrogen atom or a CH;

A compound of the present invention wherein $R^1$ represents a C2-C10 haloalkyl group or a (C3-C7 cycloalkyl)C1-C3 alkyl group having one or more substituents selected from Group G;

A compound of the present invention wherein $R^1$ represents a C2-C10 haloalkyl group;

A compound of the present invention wherein $R^1$ represents a C2-C10 alkyl group having two or more fluoro atoms;

A compound of the present invention wherein $R^1$ represents a C2-C6 alkyl group having four or more fluoro atoms;

A compound of the present invention wherein $R^2$ represents a C1-C6 alkyl group optionally having one or more halogen atoms;

A compound of the present invention wherein $R^2$ represents a C1-C6 alkyl group;

A compound of the present invention wherein $R^2$ represents a methyl group or an ethyl group;

A compound of the present invention wherein $R^2$ represents an ethyl group;

A compound of the present invention wherein $R^3$ represents independently of each other a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $S(O)_yR^{15}$, or a halogen atom;

A compound of the present invention wherein q represents 0, 1 or 2, and $R^3$ represents independently of each other a C1-C6 chain hydrocarbon group optionally having one or more substituents selected from Group B, a phenyl group optionally having one or more substituents selected from Group D, a 6 membered aromatic heterocyclic group selected from any one of Group R (the 6 membered aromatic heterocyclic group may optionally have one or more substituents selected from Group D), a 5 membered aromatic heterocyclic group selected from any one of Group Q (the 5 membered aromatic heterocyclic group may optionally have one or more substituents selected from Group D), a $OR^{12}$, a $NR^{11}R^{12}$, a $NR^{11a}R^{12a}$, a $NR^{29}NR^{11}R^{12}$, a $S(O)_yR^{15}$, a $C(O)OR^{17}$ or a halogen atom, Group R:

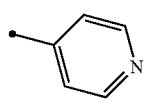
R-1

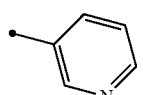
R-2

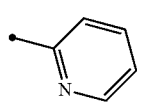
R-3

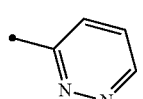
R-4

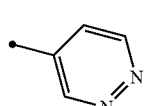
R-5

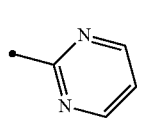
R-6

-continued

R-7
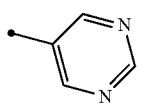

R-8
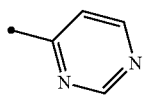

R-9
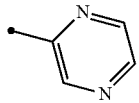

R-10
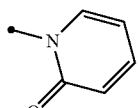

R-11
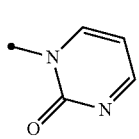

R-12
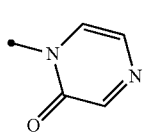

R-13
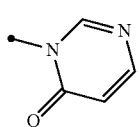

R-14
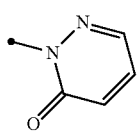

R-15
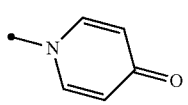

R-16
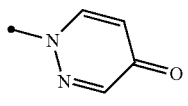

R-17
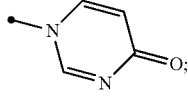

Group Q:

Q-1
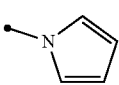

Q-2
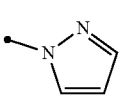

Q-3
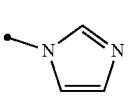

Q-4
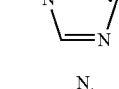

Q-5
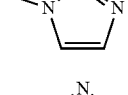

Q-6
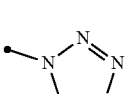

Q-7
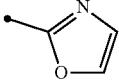

Q-8
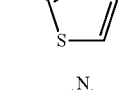

Q-9
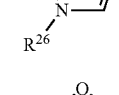

Q-10
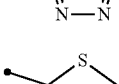

Q-11
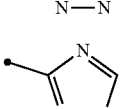

Q-12
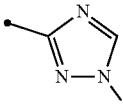

Q-13
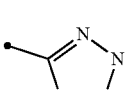

Q-14

Q-15

A compound of the present invention wherein q represents 0, 1 or 2, and $R^3$ represents independently of each other a C1-C6 chain hydrocarbon group optionally having one or more substituents selected from Group B, a 5 membered aromatic heterocyclic group selected from any one of Group Q (the 5 membered aromatic heterocyclic group may optionally have one or more substituents selected from Group D), a $OR^{12}$, a $NR^{11}R^{12}$, a $NR^{11a}R^{12a}$, a $NR^{29}NR^{11}R^{12}$, a $S(O)_y$ $R^{15}$, or a halogen atom, -continued

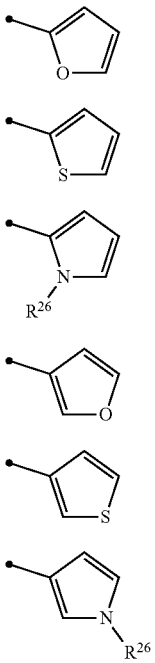

Q-16

Q-17

Q-18

Q-19

Q-20

Q-21

{In the above formulae, $R^{26}$ represents a C1-C6 alkyl group optionally having one or more halogen atoms};

A compound of the present invention wherein q represents 0, 1 or 2, and $R^3$ represents independently of each other a C1-C6 chain hydrocarbon group optionally having one or more halogen atoms, a phenyl group optionally having one or more substituents selected from Group D, a 6 membered aromatic heterocyclic group containing one to two nitrogen atoms (the 6 membered aromatic heterocyclic group may optionally have one or more substituents selected from Group D), a 5 membered aromatic heterocyclic group containing one to four nitrogen atoms (the 5 membered aromatic heterocyclic group may optionally have one or more substituents selected from Group D), a $OR^{12}$, a $NR^{11}R^{12}$, a $NR^{29}NR^{11}R^{12}$, a $S(O)_yR^{15}$, or a halogen atom;

A compound of the present invention wherein $R^4$ represents a hydrogen atom, or a halogen atom; $R^3$ represents independently of each other a C1-C6 chain hydrocarbon group optionally having one or more halogen atoms, a phenyl group optionally having one or more substituents selected from Group D, a 6 membered aromatic heterocyclic group containing one to two nitrogen atoms (the 6 membered aromatic heterocyclic group may optionally have one or more substituents selected from Group D), a 5 membered aromatic heterocyclic group containing one to four nitrogen atoms (the 5 membered aromatic heterocyclic group may optionally have one or more substituents selected from Group D), a $NR^{11}R^{12}$, or a halogen atom;

A compound of the present invention wherein $R^4$ represents a hydrogen atom, or a halogen atom; $R^3$ represents independently of each other a C1-C6 chain hydrocarbon group optionally having one or more halogen atoms, a phenyl group optionally having one or more substituents selected from Group D, a 6 membered aromatic heterocyclic group selected from any one of the above-mentioned R-1 to R-9 (the 6 membered aromatic heterocyclic group may optionally have one or more substituents selected from Group D), a 5 membered aromatic heterocyclic group selected from any one of the above-mentioned Q-1 to Q-7 (the 5 membered aromatic heterocyclic group may optionally have one or more substituents selected from Group D), a $OR^{12}$, a $NR^{11}R^{12}$, or a halogen atom;

A compound of the present invention wherein $R^4$ represents a hydrogen atom, or a halogen atom; $R^3$ represents independently of each other C1-C6 chain hydrocarbon group optionally having one or more halogen atoms, a phenyl group optionally having one or more substituents selected from Group D, a $OR^{12}$, or a halogen atom;

A compound of the present invention wherein $R^3$ represents independently of each other C1-C6 alkyl group optionally having one or more halogen atoms, a $NR^{11}R^{12}$, or a halogen atom; and $R^{11}$ and $R^{12}$ represent independently of each other a hydrogen atom or a C1-C3 alkyl group optionally having one or more halogen atoms;

A compound of the present invention wherein q represents 0, 1 or 2, and $R^3$ represents independently of each other a C1-C6 alkyl group optionally having one or more halogen atoms, or a halogen atom;

A compound of the present invention wherein q represents 0;

A compound of the present invention wherein $R^6$ represents independently of each other a C1-C6 alkyl group optionally having one or more halogen atoms, or a halogen atom;

A compound of the present invention wherein p represents 0 or 1, and $R^6$ represents a C1-C6 alkyl group optionally having one or more halogen atoms, a $OR^{12}$, a $NR^{18}R^{19}$, a cyano group, a nitro group or a halogen atom;

A compound of the present invention wherein p represents 0 or 1, and $R^6$ represents a C1-C6 alkyl group optionally having one or more halogen atoms, or a halogen atom;

A compound of the present invention wherein p represents 0;

A compound of the present invention wherein $R^4$ represents a hydrogen atom or a halogen atom, and $R^3$ represents independently of each other a C1-C6 chain hydrocarbon group optionally having one or more halogen atoms, a 5 membered aromatic heterocyclic group containing 1 to 4 nitrogen atoms, a $NR^{11}R^{12}$, or a halogen atom;

A compound of the present invention wherein $R^4$ represents a hydrogen atom or a halogen atom, $R^1$ represents a C2-C10 haloalkyl group, $R^2$ represents a C2-C6 alkyl group optionally having one or more halogen atoms, and q represents 0, 1 or 2;

A compound of the present invention wherein
$A^1$ represents a nitrogen atom or a CH,
$R^1$ represents a C2-C10 haloalkyl group,
$R^2$ represents an ethyl group,
q represents 0, 1 or 2, $R^3$ represents independently of each other a C1-C6 chain hydrocarbon group optionally having one or more substituents selected from Group B, a 5 or 6 membered aromatic heterocyclic group optionally having one or more substituents selected from Group D, a $OR^{12}$, a $NR^{11}R^{12}$, a $NR^{11a}R^{12a}$, a $S(O)_yR^{15}$, or a halogen atom, and
$R^6$ represents independently of each other a C1-C6 alkyl group optionally having one or more halogen atoms, or a halogen atom;

A compound of the present invention wherein
$A^1$ represents a nitrogen atom or a CH,
$R^1$ represents a C2-C10 haloalkyl group,
$R^2$ represents an ethyl group,
q represents 0, 1 or 2,
$R^3$ represents independently of each other a C1-C6 chain hydrocarbon group optionally having one or more halogen atoms, a phenyl group optionally having one or more substituents selected from Group D, a 6 membered aromatic heterocyclic group containing 1 to 2 nitrogen atoms (the 6 membered aromatic heterocyclic group may optionally have one or more substituents selected from Group D), a 5 membered aromatic heterocyclic group containing 1 to 4 nitrogen atoms (the 5 membered aromatic heterocyclic group may optionally have one or more substituents selected from Group D), a $OR^{12}$, a $NR^{11}R^{12}$, a $NR^{29}NR^{11}R^{12}$, a $S(O)_yR^{15}$, or a hydrogen atom, and $R^6$ represents independently of each other a C1-C6 alkyl group optionally having one or more halogen atoms, or a halogen atom;

A compound of the present invention wherein
$A^1$ represents a nitrogen atom or a CH;
$R^1$ represents a C2-C10 haloalkyl group;
$R^2$ represents an ethyl group;
q represents 0, 1 or 2, $R^3$ represents independently of each other a C1-C6 chain hydrocarbon group optionally having one or more halogen atoms, a phenyl group optionally having one or more substituents selected from Group D, a 6 membered aromatic heterocyclic group selected from any one of the above-mentioned R-1 to R-10 (the 6 membered aromatic heterocyclic group may optionally have one or more substituents selected from Group D), a 5 membered aromatic heterocyclic group selected from any one of the above-mentioned Q-1 to Q-15 (the 5 membered aromatic heterocyclic group may optionally have one or more substituents selected from Group D), a $OR^{12}$, a $NR^{11}R^{12}$, a $NR^{29}NR^{11}R^{12}$, a $S(O)_yR^{15}$, or a hydrogen atom, and $R^6$ represents independently of each other a C1-C6 alkyl group optionally having one or more halogen atoms, or a halogen atom;

A compound of the present invention wherein
$A^1$ represents a nitrogen atom or a CH;
$R^1$ represents a C2-C10 alkyl group containing two or more fluoro atoms;
$R^2$ represents an ethyl group;
q represents 0 or 1, $R^3$ represents a C1-C6 alkyl group optionally having one or more halogen atoms or a halogen atom; and
p represents 0;

A compound of the present invention wherein
$A^1$ represents a nitrogen atom or a CH;
$R^1$ represents a C3-C6 alkyl group containing four or more fluoro atoms,
$R^2$ represents an ethyl group;
q represents 0, 1 or 2, $R^3$ represents independently of each other a C1-C6 alkyl group optionally having one or more halogen atoms, a 5 membered aromatic heterocyclic group selected from any one of Group Q (the 5 membered aromatic heterocyclic group may optionally have one or more substituents selected from Group D), a $OR^{12}$, a $NR^{11}R^{12}$, a $NR^{11a}R^{12a}$ or a halogen atom; and $R^6$ represents of independently of each other a C1-C6 alkyl group optionally having one or more halogen atoms or a halogen atom;

A compound of the present invention wherein
$A^1$ represents a nitrogen atom or a CH;
$R^1$ represents a C3-C6 alkyl group containing four or more fluoro atoms,
$R^2$ represents an ethyl group;
q represents 0, 1 or 2, $R^3$ represents independently of each other a C1-C6 chain hydrocarbon group optionally having one or more halogen atoms, a phenyl group optionally having one or more substituents selected from Group D, a 6 membered aromatic heterocyclic group containing one to two nitrogen atoms (the 6 membered aromatic heterocyclic group may optionally have one or more substituents selected from Group D), a 5 membered aromatic heterocyclic group containing 1 to 4 nitrogen atoms (the a 5 membered aromatic heterocyclic group may optionally have one or more substituents selected from Group D), a $OR^{12}$, a $NR^{11}R^{12}$, a $NR^{29}NR^{11}R^{12}$, a $S(O)_yR^{15}$ or a halogen atom; and $R^6$ represents independently of each other a C1-C6 alkyl group optionally having one or more halogen atoms or a halogen atom;

A compound of the present invention wherein
$A^1$ represents a nitrogen atom or a CH;
$R^1$ represents a C3-C6 alkyl group containing four or more fluoro atoms;
$R^2$ represents an ethyl group;
q represents 0, 1 or 2, $R^3$ represents independently of each other a C1-C6 chain hydrocarbon group optionally having one or more halogen atoms, a phenyl group optionally having one or more substituents selected from Group D, a 6 membered aromatic heterocyclic group selected from any one of the above-mentioned R-1 to R-10 (the 6 membered aromatic heterocyclic group may optionally have one or more substituents selected from Group D), a 5 membered aromatic heterocyclic group selected from any one of the above-mentioned Q-1 to Q-15 (the 5 membered aromatic heterocyclic group may optionally have one or more substituents selected from Group D), a $OR^{12}$, a $NR^{11}R^{12}$, a $NR^{29}NR^{11}R^{12}$, a $S(O)_yR^{15}$, or a halogen atom; and $R^6$ represents independently of each other a C1-C6 alkyl group optionally having one or more halogen atoms or a halogen atom;

A compound of the present invention wherein
$A^1$ represents a nitrogen atom or a CH;
$R^1$ represents a C3-C6 haloalkyl group containing 4 or more fluoro atoms;
$R^2$ represents an ethyl group;
q represents 0; and
p represents 0;

A compound of the present invention wherein
$R^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms; $R^2$ represents a C1-C6 alkyl group, q represents 0 or 1; $R^3$ represents a C1-C6 alkyl group optionally having one or more halogen atoms; and p represents 0.

A compound represented by formula (I-A):

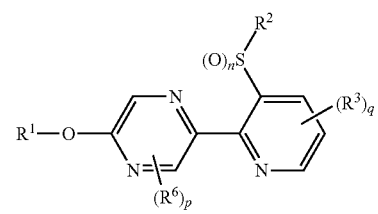

(hereinafter referred to as Present compound (I-A))
[wherein the symbols are the same as defined above].

A Present compound (I-A) wherein

R$^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms; R$^2$ represents a C1-C6 alkyl group, q represents 0 or 1; and R$^3$ represents independently of each other a C1-C6 chain hydrocarbon group optionally having one or more halogen atoms, a phenyl group optionally having one or more substituents selected from Group D, a 6 membered aromatic heterocyclic group selected from any one of the above-mentioned R-1 to R-9 (the 6 membered aromatic heterocyclic group may optionally have one or more substituents selected from Group D), a 5 membered aromatic heterocyclic group selected from any one of the above-mentioned Q-1 to Q-7 (the 5 membered aromatic heterocyclic group may optionally have one or more substituents selected from Group D), a OR$^{12}$, a NR$^{11}$R$^{12}$, or a halogen atom; and p represents 0;

A Present compound (I-A) wherein

R$^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms; R$^2$ represents a C1-C6 alkyl group, q represents 0 or 1; R$^3$ represents independently of each other a C1-C6 chain hydrocarbon group optionally having one or more halogen atoms, a phenyl group optionally having one or more substituents selected from Group D, a 6 membered aromatic heterocyclic group selected from any one of the above-mentioned R-1 to R-9 (the 6 membered aromatic heterocyclic group may optionally have one or more substituents selected from Group D), a 5 membered aromatic heterocyclic group selected from any one of the above-mentioned Q-1 to Q-7 (the 5 membered aromatic heterocyclic group may optionally have one or more substituents selected from Group D), a OR$^{12}$, a NR$^{11}$R$^{12}$, or a halogen atom; and p represents 0;

A Present compound (I-A) wherein

R$^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms; R$^2$ represents a C1-C6 alkyl group, q represents 0 or 1; R$^3$ represents independently of each other C1-C6 chain hydrocarbon group optionally having one or more halogen atoms, a phenyl group optionally having one or more substituents selected from Group D, a 6 membered aromatic heterocyclic group selected from any one of the above-mentioned R-1 to R-9 (the 6 membered aromatic heterocyclic group may optionally have one or more substituents selected from Group D), a OR$^{12}$, a NR$^{11}$R$^{12}$, or a halogen atom; and p represents 0;

A Present compound (I-A) wherein

R$^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms; R$^2$ represents a C1-C6 alkyl group, q represents 0 or 1, R$^3$ represents a C1-C6 alkyl group optionally having one or more halogen atoms; and p represents 0.

A Present compound (I-A) wherein

R$^1$ represents a C2-C10 haloalkyl group, and

R$^2$ represents a C1-C6 alkyl group optionally having one or more halogen atoms;

A Present compound (I-A) wherein

R$^1$ represents a C2-C10 haloalkyl group or a (C3-C7 cycloalkyl)C1-C3 alkyl group having one or more halogen atoms; R$^2$ represents a C1-C6 alkyl group; q represents 0 or 1; R$^3$ represents a C1-C6 alkyl group optionally having one or more halogen atoms; and p represents 0.

A Present compound (I-A) wherein

R$^1$ represents a C2-C10 haloalkyl group;

R$^2$ represents an ethyl group;

R$^3$ represents independently of each other a C1-C6 chain hydrocarbon group optionally having one or more substituents selected from Group B, a 5 or 6 membered aromatic heterocyclic group optionally having one or more substituents selected from Group D, a OR$^{12}$, a NR$^{11}$R$^{12}$, a NR$^{11a}$R$^{12a}$, a S(O)$_y$R$^{15}$, a halogen atom; and R$^6$ represents independently of each other a C1-C6 alkyl group optionally having one or more halogen atoms, or a halogen atom.

A Present compound (I-A) wherein

R$^1$ represents a C2-C10 haloalkyl group;

R$^2$ represents an ethyl group;

q represents 0, 1 or 2;

R$^3$ represents independently of each other a C1-C6 chain hydrocarbon group optionally having one or more halogen atoms, a phenyl group optionally having one or more substituents selected from Group D, a 6 membered aromatic heterocyclic group containing one to two nitrogen atoms (the 6 membered aromatic heterocyclic group may optionally have one or more substituents selected from Group D), a 5 membered aromatic heterocyclic group containing 1 to 4 nitrogen atoms (the 5 membered aromatic heterocyclic group may optionally have one or more substituents selected from Group D), a OR$^{12}$, a NR$^{11}$R$^{12}$, a NR$^{29}_{NR}{}^{11}$R$^{12}$, a S(O)$_y$R$^{15}$, or a halogen atom; and R$^6$ represents independently of each other a C1-C6 alkyl group optionally having one or more halogen atoms or a halogen atom.

A Present compound (I-A) wherein

R$^1$ represents a C2-C10 haloalkyl group;

R$^2$ represents an ethyl group;

q represents 0, 1 or 2, R$^3$ represents independently of each other a C1-C6 chain hydrocarbon group optionally having one or more halogen atoms, a phenyl group optionally having one or more substituents selected from Group D, a 6 membered aromatic heterocyclic group selected from any one of the above-mentioned R-1 to R-10 (the 6 membered aromatic heterocyclic group may optionally have one or more substituents selected from Group D), a 5 membered aromatic heterocyclic group selected from any one of the above-mentioned Q-1 to Q-15 (the 5 membered aromatic heterocyclic group may optionally have one or more substituents selected from Group D), a OR$^{12}$, a NR$^{11}$R$^{12}$, a NR$^{29}$NR$^{11}$R$^{12}$, a S(O)$_y$R$^{15}$, or a halogen atom; and R$^6$ represents independently of each other a C1-C6 alkyl group optionally having one or more halogen atoms or a halogen atom.

A Present compound (I-A) wherein
R$^1$ represents a C2-C10 alkyl group having two or more fluoro atoms,
R$^2$ represents an ethyl group;
R$^3$ represents independently of each other a C1-C6 alkyl group optionally having one or more halogen atoms or a halogen atom; and
p represents 0.

A Present compound (I-A) wherein
R$^1$ represents a C3-C6 alkyl group containing four or more fluoro atoms;
R$^2$ represents an ethyl group;
R$^3$ represents independently of each other a C1-C6 alkyl group optionally having one or more halogen atoms, a 5 membered aromatic heterocyclic group selected from any one of Group Q (the 5 membered aromatic heterocyclic group may optionally have one or more substituents selected from Group D), a OR$^{12}$, a NR$^{11}$R$^{12}$, a NR$^{11a}$R$^{12a}$, or a halogen atom; and
R$^6$ represents independently of each other a C1-C6 alkyl group optionally having one or more halogen atoms or a halogen atom.

A Present compound (I-A) wherein
R$^1$ represents a C3-C6 haloalkyl group containing 4 or more fluoro atoms, R$^2$ represents an ethyl group; q represents 0; and p represents 0.

A compound of the present invention wherein A$^1$ represents a CR$^4$; and R$^4$ represents a hydrogen atom or a halogen atom;

A compound of the present invention wherein A$^1$ represents a CH;

A compound represented by formula (I-B):

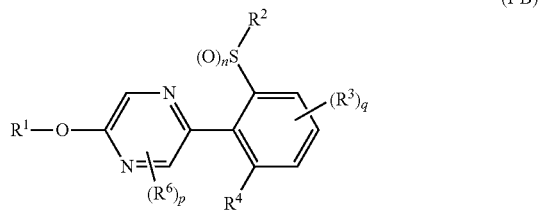

(I-B)

(hereinafter referred to as Present compound (I-B))
[wherein the symbols are the same as defined above.]

A Present compound (I-B) wherein
R$^4$ represents a hydrogen atom or a halogen atom; R$^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms; R$^2$ represents a C1-C6 alkyl group; q represents 0 or 1; R$^3$ represents independently of each other a C1-C6 chain hydrocarbon group optionally having one or more halogen atoms, a phenyl group optionally having one or more substituents selected from Group D, a 6 membered aromatic heterocyclic group selected from any one of the above-mentioned R-1 to R-9 (the 6 membered aromatic heterocyclic group may optionally have one or more substituents selected from Group D), a 5 membered aromatic heterocyclic group selected from any one of the above-mentioned Q-1 to Q-7 (the 5 membered aromatic heterocyclic group may optionally have one or more substituents selected from Group D), a OR$^{12}$, a NR$^{11}$R$^{12}$, or a halogen atom; and p represents 0;

A Present compound (I-B) wherein
R$^4$ represents a hydrogen atom or a halogen atom; R$^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms; R$^2$ represents a C1-C6 alkyl group; q represents 0 or 1; R$^3$ represents a C1-C6 alkyl group; q represents 0 or 1; R$^3$ represents independently of each other a C1-C6 chain hydrocarbon group optionally having one or more halogen atoms, a phenyl group optionally having one or more substituents selected from Group D, a 6 membered aromatic heterocyclic group selected from any one of the above-mentioned R-1 to R-9 (the 6 membered aromatic heterocyclic group may optionally have one or more substituents selected from Group D), a OR$^{12}$, a NR$^{11}$R$^{12}$, or a halogen atom; and p represents 0;

A Present compound (I-B) wherein
R$^4$ represents a hydrogen atom or a halogen atom; R$^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, or a (C3-C7 cycloalkyl)C1-C3 alkyl group having one or more halogen atoms; R$^2$ represents a C1-C6 alkyl group; q represents 0 or 1; R$^3$ represents a C1-C6 alkyl group optionally having one or more halogen atoms;
and p represents 0.

A Present compound (I-B) wherein
R$^4$ represents a hydrogen atom or a halogen atom;
R$^1$ represents a C2-C10 haloalkyl group; and
R$^2$ represents a C1-C6 alkyl group optionally having one or more halogen atoms.

A Present compound (I-B) wherein
R$^1$ represents a C2-C10 haloalkyl group; q represents 0 or 1; R$^3$ represents a C1-C6 alkyl group optionally having one or more halogen atoms; and p represents 0.

A Present compound (I-B) wherein
R$^4$ represents a hydrogen atom or a halogen atom;
R$^1$ represent a C2-C10 haloalkyl group;
R$^3$ represents independently of each other a C1-C6 chain hydrocarbon group optionally having one or more substituents selected from Group B, a 5 or 6 membered aromatic heterocyclic group optionally having one or more substituents selected from Group D, a OR$^{12}$, a NR$^{11}$R$^{12}$, a NR$^{11a}$R$^{12a}$, a S(O)$_y$R$^{15}$, or a halogen atom; and R$^6$ represents independently of each other a C1-C6 alkyl group optionally having one or more halogen atoms or a halogen atom.

A Present compound (I-B) wherein
$R^4$ represents a hydrogen atom or a halogen atom;
$R^1$ represents a C2-C10 haloalkyl group;
$R^2$ represents an ethyl group;
q represents 0, 1 or 2, $R^3$ represents independently of each other a C1-C6 chain hydrocarbon group optionally having one or more halogen atoms, a phenyl group optionally having one or more substituents selected from Group D, a 6 membered aromatic heterocyclic group containing one to two nitrogen atoms (the 6 membered aromatic heterocyclic group may optionally have one or more substituents selected from Group D), a 5 membered aromatic heterocyclic group containing 1 to 4 nitrogen atoms (the 5 membered aromatic heterocyclic group may optionally have one or more substituents selected from Group D), a $OR^{12}$, a $NR^{11}R^{12}$, a $NR^{29}R^{11}R^{12}$, a $S(O)_y R^{15}$, or a halogen atom; and
$R^6$ represents independently of each other a C1-C6 alkyl group optionally having one or more halogen atoms or a hydrogen atom.

A Present compound (I-B) wherein
$R^4$ represents a hydrogen atom or a halogen atom;
$R^1$ represents a C2-C10 haloalkyl group;
$R^2$ represents an ethyl group;
q represents 0, 1 or 2, $R^3$ represents independently of each other a C1-C6 chain hydrocarbon group optionally having one or more halogen atoms, a phenyl group optionally having one or more substituents selected from Group D, a 6 membered aromatic heterocyclic group selected from any one of the above-mentioned R-1 to R-10 (the 6 membered aromatic heterocyclic group may optionally have one or more substituents selected from Group D), a 5 membered aromatic heterocyclic group selected from any one of the above-mentioned Q-1 to Q-15 (the 5 membered aromatic heterocyclic group may optionally have one or more substituents selected from Group D), a $OR^{12}$, a $NR^{11}R^{12}$, a $NR^{29}R^{11}R^{12}$, a $S(O)_y R^{15}$, or a halogen atom; and
$R^6$ represents independently of each other a C1-C6 alkyl group optionally having one or more halogen atoms or a halogen atom.

A Present compound (I-B) wherein
$R^4$ represents a hydrogen atom;
$R^1$ represents a C2-C10 alkyl group having two or more fluoro atoms;
$R^2$ represents an ethyl group;
$R^3$ represents independently of each other a C1-C6 alkyl group optionally having one or more halogen atoms or a halogen atom; and p represents 0.

A Present compound (I-B) wherein
$R^4$ represents a hydrogen atom;
$R^1$ represents a C3-C6 alkyl group containing four or more fluoro atoms;
$R^2$ represents an ethyl group;
$R^3$ represents independently of each other a C1-C6 alkyl group optionally having one or more halogen atoms, a 5 membered aromatic heterocyclic group selected from any one of Group Q (the 5 membered aromatic heterocyclic group may optionally have one or more substituents selected from Group D), a $OR^{12}$, a $NR^{11}R^{12}$, a $NR^{11a}R^{12a}$, or a hydrogen atom; and
$R^6$ represents independently of each other a C1-C6 alkyl group optionally having one or more halogen atoms or a hydrogen atom.

A Present compound (I-B) wherein
$R^1$ represents a C3-C6 haloalkyl group containing 4 or more fluoro atoms;
$R^2$ represents an ethyl group;
q represents 1, $R^3$ represents a C1-C6 alkyl group optionally having one or more halogen atoms; and
p represents 0.

Next, a process for preparing the compound of the present invention is explained.

The compound of the present invention can be prepared, for example, according to the following processes.

Process 1

A compound represented by formula (Ib) (hereinafter, referred to as Present compound (Ib)) and a compound represented by formula (Ic) (hereinafter, referred to as Present compound (Ic)) may be prepared by reacting a compound represented by formula (Ia) (hereinafter, referred to as Present compound (Ia)) with an oxidizing agent.

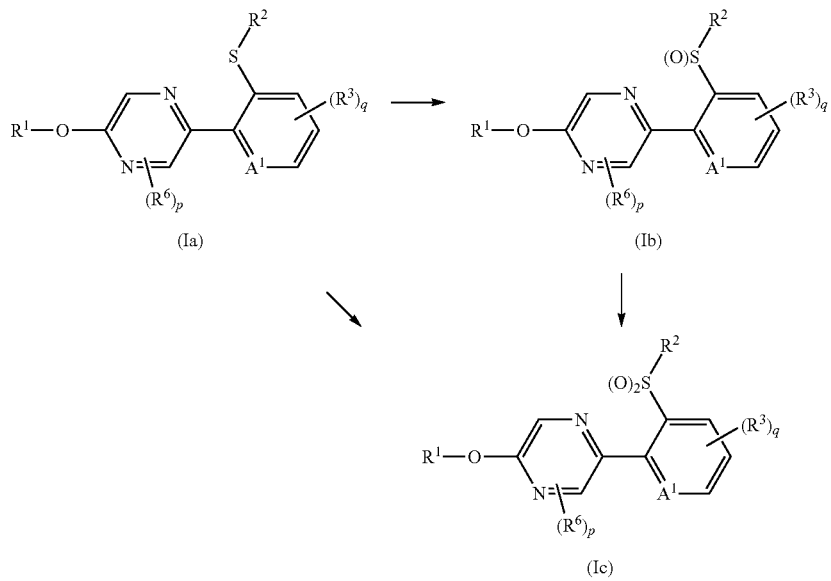

[wherein the symbols are the same as defined above]

First, a process for preparing the Present compound (Ib) from the Present compound (Ia) is described.

The reaction is usually carried out in a solvent. Examples of the solvent to be used in the reaction include halogenated aliphatic hydrocarbons such as dichloromethane and chloroform (hereinafter, collectively referred to as halogenated aliphatic hydrocarbons); nitriles such as acetonitrile (hereinafter collectively referred to nitriles); esters such as ethyl acetate (hereinafter collectively referred to esters); alcohols such as methanol and ethanol (hereinafter, collectively referred to as alcohols); acetic acid; water; and mixed solvents thereof.

Examples of the oxidizing agent to be used in the reaction includes sodium periodate, m-chloroperoxybenzoic acid (hereinafter referred to as mCPBA), and hydrogen peroxide.

When hydrogen peroxide is used as the oxidizing agent, sodium carbonate or a catalyst may be added as needed.

Examples of the catalyst to be used in the reaction include tungstic acid, and sodium tungstate.

In the reaction, the oxidizing agent is used usually within a range of 1 to 1.2 molar ratio(s), the sodium carbonate is used usually within a range of 0.01 to 1 molar ratio(s), and the catalyst is used usually within a range of 0.01 to 0.5 molar ratios, as opposed to 1 mole of the Present compound (Ia).

The reaction temperature of the reaction is usually within a range of −20 to 80° C. The reaction period of the reaction is usually within a range of 0.1 to 12 hours.

When the reaction is completed, to the reaction mixtures is added water, and the reaction mixtures are then extracted with organic solvent(s), and the organic layers are washed successively with an aqueous solution of a reducing agent (such as sodium sulfite, and sodium thiosulfate) and an aqueous solution of a base (such as sodium hydrogen carbonate). The resulting organic layers are dried and concentrated to give the Present compound (Ib).

Next, a process for preparing the Present compound (Ic) from the Present compound (Ib) is explained.

The reaction is usually carried out in a solvent. Examples of the solvent to be used in the reaction include halogenated aliphatic hydrocarbons, nitriles, alcohols, acetic acid, water, and mixed solvents thereof.

Examples of the oxidizing agent to be used in the reaction include mCPBA and hydrogen peroxide. When hydrogen peroxide is used as oxidizing agent, a base or a catalyst may be added as needed.

Examples of the base to be used include sodium carbonate.

Examples of the catalyst to be used include sodium tungstate.

In the reaction, the oxidizing agent is used usually within a range of 1 to 2 molar ratio(s), the base is used usually within a range of 0.01 to 1 molar ratio(s), and the catalyst is used usually within a range of 0.01 to 0.5 molar ratios, as opposed to 1 mole of the Present compound (Ib).

The reaction temperature of the reaction is usually within a range of −20 to 120° C. The reaction period of the reaction is usually within a range of 0.1 to 12 hours.

When the reaction is completed, to the reaction mixtures is added water, and the reaction mixtures are then extracted with organic solvent(s), and the organic layers are washed successively with an aqueous solution of a reducing agent (such as sodium sulfite, and sodium thiosulfate) and an aqueous solution of a base (such as sodium hydrogen carbonate). The resulting organic layers are dried and concentrated to give the Present compound (Ic).

Also, the Present compound (Ic) may be prepared in one step (one-spot) by reacting the Present compound (Ia) with an oxidizing agent.

The reaction may be carried out by using the oxidizing agent usually in 2.0 to 2.4 molar ratios as opposed to 1 mole of the Present compound (Ia) according to the method for preparing the Present compound (Ic) from the Present compound (Ib).

Process 2

The compound of the present invention represented by formula (I) (hereinafter referred to as Present compound (I)) may be prepared by reacting a compound represented by formula (M-3) (hereinafter referred to as Compound (M-3)) with a compound represented by formula (R-3) (hereinafter, referred to as Compound (R-3)) in the presence of a base.

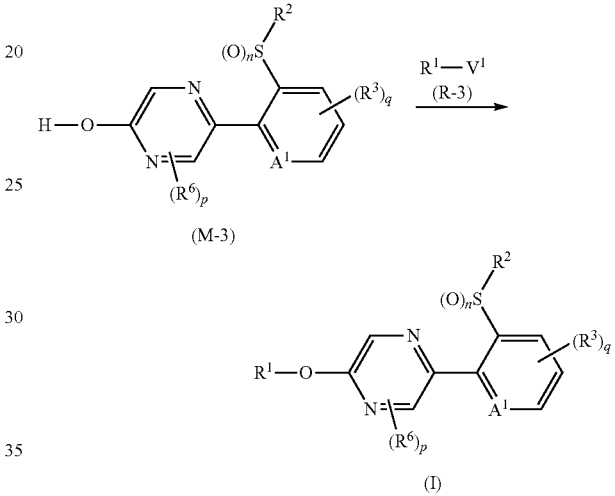

[wherein $V^1$ represents a halogen atom, a trifluoromethansulfonyloxy group, a nonafluorobutanesulfonyloxy group, or a tosyloxy group, and the other symbols are the same as defined above.]

The reaction is usually carried out in a solvent. Examples of the solvent to be used in the reaction include ethers such as tetrahydrofuran (hereinafter, referred to as THF), ethyleneglycol dimethyl ether, methyl tert-butyl ether, and 1,4-dioxane (hereinafter, collectively referred to as ethers); halogenated aliphatic hydrocarbons; aromatic hydrocarbons such as toluene and xylene (hereinafter, collectively referred to as aromatic hydrocarbons); polar aprotic solvents such as dimethylformamide (hereinafter, referred to as DMF), N-methyl pyrrolidone (hereinafter, referred to as NMP), dimethyl sulfoxide (hereinafter, referred to DMSO) (hereinafter, collectively referred to as polar aprotic solvent); and mixed solvents thereof.

Examples of the base to be used in the reaction include organic bases such as triethylamine, diisopropylethylamine, pyridine, 4-(dimethylamino)pyridine (hereinafter, collectively referred to as organic bases); alkali metal hydrides such as sodium hydride (hereinafter, collectively referred to as alkali metal hydrides); and alkali metal carbonates such as sodium carbonate and potassium carbonate (hereinafter, referred to as alkali metal carbonates).

In the reaction, the compound (R-3) is usually used within a range of in 1 to 10 molar ratio(s), and the base is usually used within a range of 0.1 to 5 molar ratio(s), as opposed to 1 mole of the compound (M-3).

The reaction temperature is usually within a range of −20 to 150° C. The reaction period of the reaction is usually within a range of 0.5 to 24 hours.

When the reaction is completed, to the reaction mixtures is added water, and the reaction mixtures are then extracted with organic solvents, and the resulting organic layers are worked up (for example, drying and concentration) to give the Present compound (I).

Process 3

The Present compound (Ia) may be prepared by reacting a compound represented by formula (M-1) (hereinafter, referred to Compound (M-1)) with a compound represented by formula (R-1) (hereinafter, referred to Compound (R-1)) in the presence of a base.

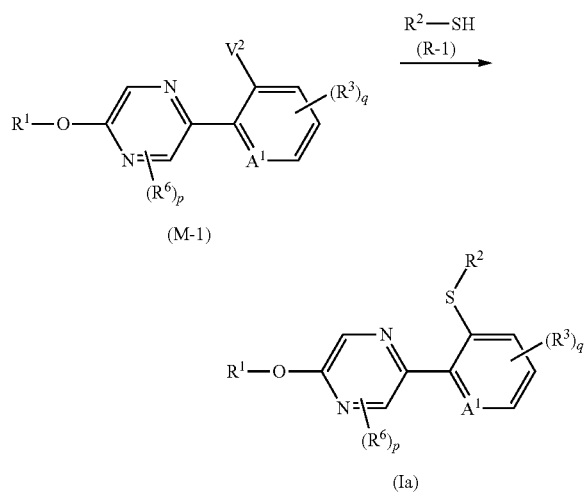

[wherein $V^2$ represents a halogen atom, and the other symbols are the same as defined above.]

The reaction is usually carried out in a solvent. Examples of the solvent to be used in the reaction include ethers, aromatic hydrocarbons, nitriles, polar aprotic solvents, and mixed solvents thereof.

Examples of the base to be used in the reaction include alkali metal carbonates and alkali metal hydrides.

In the reaction, the compound (R-1) is used usually within a range of 1 to 10 molar ratio(s), and the base is used usually within a range of 1 to 10 molar ratio(s), as opposed to 1 mole of the compound (M-1).

The reaction temperature is usually within a range of −20 to 150° C. The reaction period of the reaction is usually within a range of 0.5 to 24 hours.

When the reaction is completed, the reaction mixtures are extracted with organic solvents, and the resulting organic layers are worked up (for example, drying and concentration) to give the Present compound (Ia).

$V^2$ is preferably a fluorine atom or a chlorine atom.

Process 4

The Present compound (I) may be prepared by reacting a compound represented by formula (M-4) (hereinafter, referred to as Compound (M-4)) with a compound represented by formula (R-4) (hereinafter, referred to as Compound (R-4)) in the presence of a base.

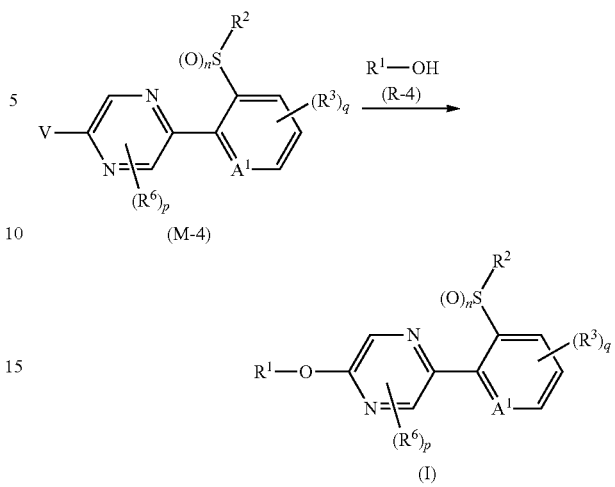

[wherein the symbols are the same as defined above.]

The reaction is usually carried out in a solvent. Examples of the solvent to be used in the reaction include ethers, aromatic hydrocarbons, nitriles, polar aprotic solvent, and mixed solvents thereof.

Examples of the base to be used in the reaction include alkali metal carbonates and alkali metal hydrides.

In the reaction, the compound (R-4) is usually used within a range of 1 to 10 molar ratio(s), and the base is usually used within a range of 1 to 10 molar ratio(s), as opposed to 1 mole of the compound (M-4).

The reaction temperature is usually within a range of −20 to 150° C. The reaction period of the reaction is usually within a range of 0.5 to 24 hours.

When the reaction is completed, to the reaction mixtures is added water, and the reaction mixtures are then extracted with organic solvents, and the resulting organic layers are worked up (for example, drying and concentration) to give the Present compound (I).

V is preferably a fluorine atom.

Process 5

A compound represented by formula (Ig) (hereinafter, referred to as Present compound (Ig)) may be prepared according to a method described below.

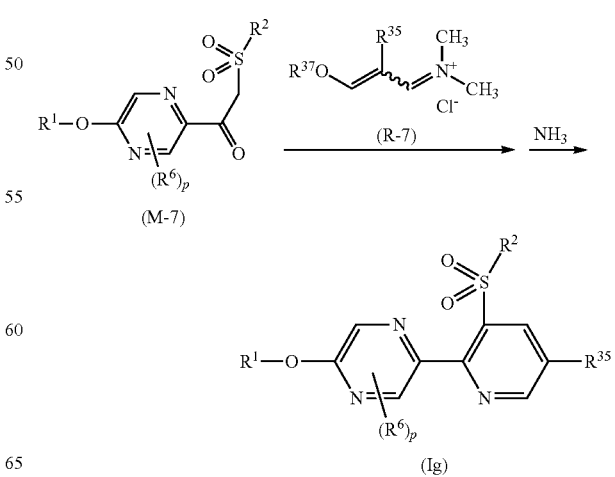

[wherein R$^{37}$ represents a C1-C6 alkyl group, R35 represents a hydrogen atom, a C1-C6 alkyl group optionally having one or more halogen atoms, a phenyl group optionally having one or more substituents selected from Group D, or a 5 or 6 membered aromatic heterocyclic group optionally having one or more substituents selected from Group D, and the other symbols are the same as defined above.]

First, Step 1 is explained.

In the Step 1, a compound represented by formula (M-7) (hereinafter, referred to as Compound (M-7)) and a compound represented by formula (R-7) (hereinafter, referred to as Compound (R-7)) are reacted.

The compound (R-7) may be prepared according to a similar method to that described in International Publication No. 2009/054742.

The reaction is usually carried out in a solvent. Examples of the solvent to be used in the reaction include ethers, aliphatic hydrocarbons, aromatic hydrocarbons, halogenated aliphatic hydrocarbons, alcohols, esters, nitriles, polar aprotic solvent, nitrogen-containing aromatic compounds such as pyridine and 2,6-lutidine (hereinafter, collectively referred to as nitrogen-containing aromatic compounds), and mixed solvents thereof.

A base may be added to the reaction, and examples of the base include organic bases.

In the reaction, the compound (R-7) is usually used within a range of 1 to 10 molar ratio(s), and the base is usually used within a range of 1 to 10 molar ratio(s), as opposed to 1 mole of the compound (M-7)).

The reaction temperature is usually within a range of −50 to 200° C. The reaction period of the reaction is usually within a range of 0.1 to 24 hours.

When the reaction is completed, the reaction mixtures are concentrated to obtain the residues, which are used as itself in the Step 2. Alternatively, to the reaction mixtures are added water and the mixtures are then extracted with organic solvents, and the organic layers are worked (for example, drying and concentration) to obtain the residues, which are used in the Step 2.

Next, Step 2 is explained.

In the Step 2, the residue obtained in the step 1 is reacted with ammonia to give the Present compound (Ig).

The reaction is usually carried out in a solvent.

Examples of the solvent to be used in the reaction include ethers, nitriles, alcohols, polar aprotic solvent, nitrogen-containing aromatic compounds, and mixed solvents thereof.

Examples of the ammonia to be used in the reaction include aqueous ammonia solution and solution of ammonia in methanol.

In the reaction, ammonia is usually used within a range of 1 to 100 molar ratio(s) as opposed to 1 mole of the compound (M-7).

The reaction temperature is usually within a range of 0 to 100° C. The reaction period of the reaction is usually within a range of 0.1 to 24 hours.

When the reaction is completed, to the reaction mixtures is added water, and the resulting mixtures are extracted with organic solvents, and the organic layers are worked up (for example, drying and concentration) to give the Present compound (Ig).

Process 6

A compound represented by formula (Id) (hereinafter, referred to as Present compound (Id)), a compound represented by formula (Ie) (hereinafter, referred to Present compound (Ie)), a compound represented by formula (If) (hereinafter, referred to Present compound (If)), and a compound represented by formula (Im) (hereinafter, referred to Present compound (Im)) may be prepared by reacting the Present compound (Ic) with an oxidizing agent.

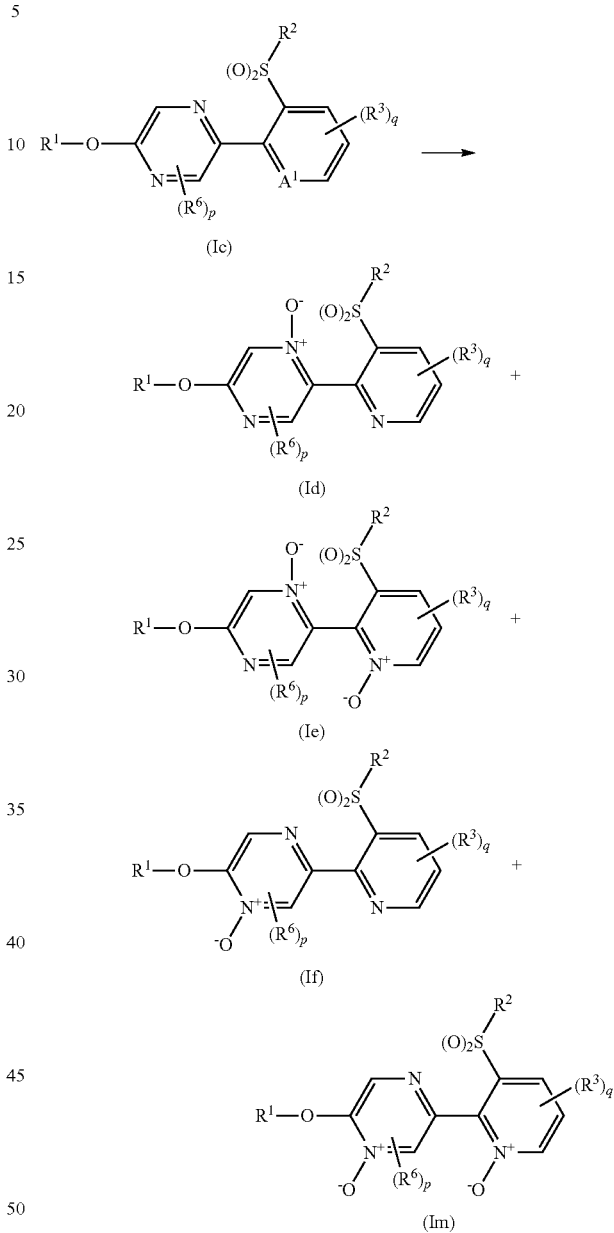

[wherein the symbols are the same as defined above.]

The reaction is usually carried out in a solvent. Examples of the solvent to be used in the reaction include halogenated aliphatic hydrocarbons; nitriles; esters such as ethyl acetate; alcohols; acetic acid; water; and mixed solvents thereof.

Examples of the oxidizing agent to be used in the reaction include mCPBA and hydrogen peroxide.

When hydrogen peroxide is used as the oxidizing agent, an acid, a base or a catalyst may be added as needed.

Examples of the acid to be used in the reaction include acetic acid, sulfuric acid, and trifluoroacetic acid.

Examples of the base to be used include sodium carbonate.

Examples of the catalyst to be used include tungstic acid and sodium tungstate.

In the reaction, the oxidizing agent is used usually within a range of 1 to 10 molar ratio(s), the acid is used usually within a range of 0.01 to 1 molar ratio(s), the base is used usually within a range of 0.01 to 1 molar ratio(s), and the catalyst is used usually within a range of 0.01 to 0.5 molar ratio(s), as opposed to 1 mole of the Present compound (Ic).

The reaction temperature of the reaction is usually within a range of −20 to 80° C. The reaction period of the reaction is usually within a range of 0.1 to 24 hours.

When the reaction is completed, to the reaction mixtures is added water, and the reaction mixtures are then extracted with organic solvent(s), and the organic layers are washed with an aqueous solution of a reducing agent (such as sodium sulfite, and sodium thiosulfate) and an aqueous solution of a base (such as sodium hydrogen carbonate). The resulting organic layers are dried and concentrated to give the residues, and the resulting residues are worked up (such as chromatography or recrystallization) to isolate the Present compound (Id), the Present compound (Ie) and the Present compound (If), or the Present compound (Im) respectively.

Process 7

The Present compound (Ia) may be prepared by reacting a compound represented by formula (M-2) (hereinafter, referred to as Compound (M-2)) with a compound represented by formula (R-2) (hereinafter, referred to as Compound (R-2)) in the presence of a base.

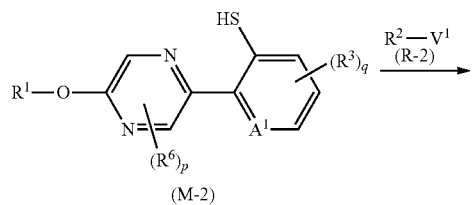

(M-2)

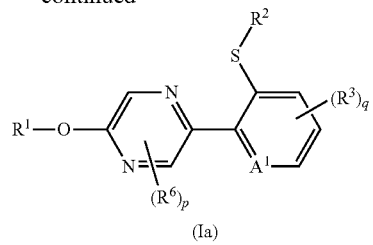

(Ia)

[wherein the symbols are the same as defined above.]

The reaction is usually carried out in a solvent. Examples of the solvent to be used in the reaction include ethers, aromatic hydrocarbons, nitriles, and polar aprotic solvent.

Examples of the base to be used in the reaction include alkali metal carbonates and alkali metal hydrides.

In the reaction, the compound (R-2) is usually used within a range of in 1 to 10 molar ratio(s), and the base is usually used within a range of 1 to 10 molar ratio(s), as opposed to 1 mole of the compound (M-2). Preferably, the compound (R-2) is usually used within a range of in 1.0 to 1.1 molar ratio(s), and the base is usually used within a range of 1 to 2 molar ratio(s), as opposed to 1 mole of the compound (M-2).

The reaction temperature is usually within a range of −20 to 150° C. The reaction period of the reaction is usually within a range of 0.5 to 24 hours.

When the reaction is completed, to the reaction mixtures is added water, and the reaction mixtures are then extracted with organic solvents, and the resulting organic layers are worked up (for example, drying and concentration) to give the Present compound (Ia).

Process 8

A compound represented by formula (Ik) (hereinafter, referred to as Present compound (Ik)) may be prepared according to a method described below.

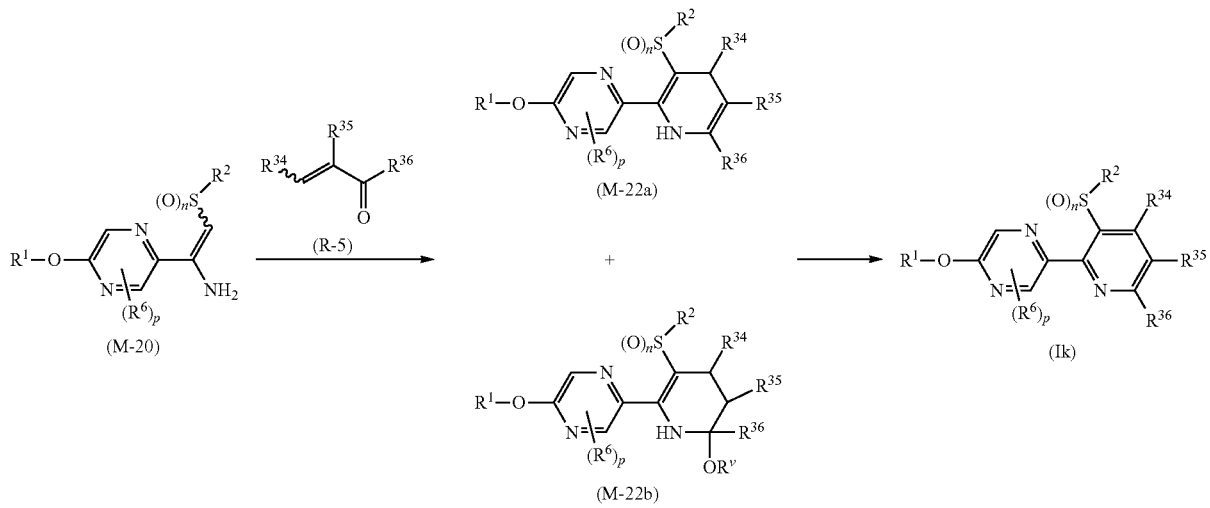

[wherein $R^{34}$ and $R^{36}$ represent independently of each other a hydrogen atom, a C1-C6 alkyl group optionally having one or more halogen atoms, a phenyl group optionally having one or more substituents selected from Group D, or a 5 or 6 membered aromatic heterocyclic group optionally having one or more substituents selected from Group D; $R^y$ represents a hydrogen atom, or a C1-C4 alkyl group; and the other symbols are the same as defined above.]

First, Step 1 is explained.

In the Step 1, a compound represented by formula (M-20) (hereinafter, referred to as Compound (M-20)) and a compound represented by formula (R-5) (hereinafter, referred to as Compound (R-5)) are reacted to give a compound represented by formula (M-22a) (hereinafter, referred to as Compound (M-22a)) and a compound represented by formula (M-22b) (hereinafter, referred to as Compound (M-22b)).

The reaction is usually carried out in a solvent. Examples of the solvent to be used in the reaction include ethers, aliphatic hydrocarbons, aromatic hydrocarbons, halogenated aliphatic hydrocarbons, alcohols, esters, nitriles, polar aprotic solvent, nitrogen-containing aromatic compounds, and mixed solvents thereof.

An acid or a base may be added to the reaction as needed. Examples of the acid to be used in the reaction include carbonic acids such as acetic acid; and sulfonic acids such as methanesulfonic acid and p-toluenesulfonic acid, and examples of the base to be used in the reaction include alkali metal carbonates, alkali metal hydrides, and organic bases.

In the reaction, the compound (R-5) is usually used within a range of 1 to 10 molar ratio(s), and the base is usually used within a range of 0.1 to 10 molar ratio(s), as opposed to 1 mole of the compound (M-20).

The reaction temperature is usually within a range of 0 to 200° C. The reaction period of the reaction is usually within a range of 0.1 to 24 hours.

When the reaction is completed, to the reaction mixtures is added water, and the reaction mixtures are then extracted with organic solvents, and the reaction mixtures are worked up (for example, drying and concentration) to give the Present compound (M-22a), the Present compound (M-22b), or a mixture thereof.

Next, Step 2 is described.

In the Step 2, the compound (M-22a), the compound (M-22b) or the mixture thereof is reacted with an oxidizing agent to give Present compound (Ik).

The reaction is usually carried out in a solvent. Examples of the solvent to be used in the reaction include ethers, aliphatic hydrocarbons, aromatic hydrocarbons, halogenated aliphatic hydrocarbons, nitriles, polar aprotic solvent, nitrogen-containing aromatic compounds, and mixed solvents thereof.

Examples of the oxidizing agent to be used in the reaction include manganese dioxide.

Instead of using the oxidizing agent, the compound (M-22a), the compound (M-22b) or the mixture thereof may be reacted with methanesulfonyl chloride and triethylamine successively, or the mixture of methanesulfonyl chloride and triethylamine.

Instead of using the oxidizing agent, the compound (M-22a), the compound (M-22b) or the mixture thereof may be reacted with Pd—C and olefins such as vinyl acetate successively, or the mixture of Pd—C and vinyl acetate.

In the reaction, the oxidizing agent is usually used within a range of 1 to 10 molar ratio(s) as opposed to 1 mole of the compound (M-22a) or the compound (M-22b).

In the reaction, when methanesulfonyl chloride and triethylamine are used instead of the oxidizing agent, the methanesulfonyl chloride is usually used within a range of 1 to 10 molar ratio(s), and the triethylamine is usually used within a range of 1 to 10 molar ratio(s), as opposed to 1 mole of the compound (M-22a) or the compound (M-22b).

In the reaction, when Pd—C and olefins such as vinyl acetate are used instead of the oxidizing agent, the Pd—C is usually used within a range of 0.001 to 1 molar ratio(s), and the olefins is usually used within a range of 1 to 10 molar ratio(s), as opposed to 1 mole of the compound (M-22a) or the compound (M-22b).

The reaction temperature is usually within a range of 0 to 200° C. The reaction period of the reaction is usually within a range of 0.1 to 24 hours.

When the reaction is completed, to the reaction mixtures is added water, and the reaction mixtures are then extracted with organic solvents, and the organic layers are worked up (for example, drying and concentration) to isolate the Present compound (Ik).

Process 9

A compound represented by formula (Ii) (hereinafter, referred to as Present compound (Ii)) may be prepared according to a method described below.

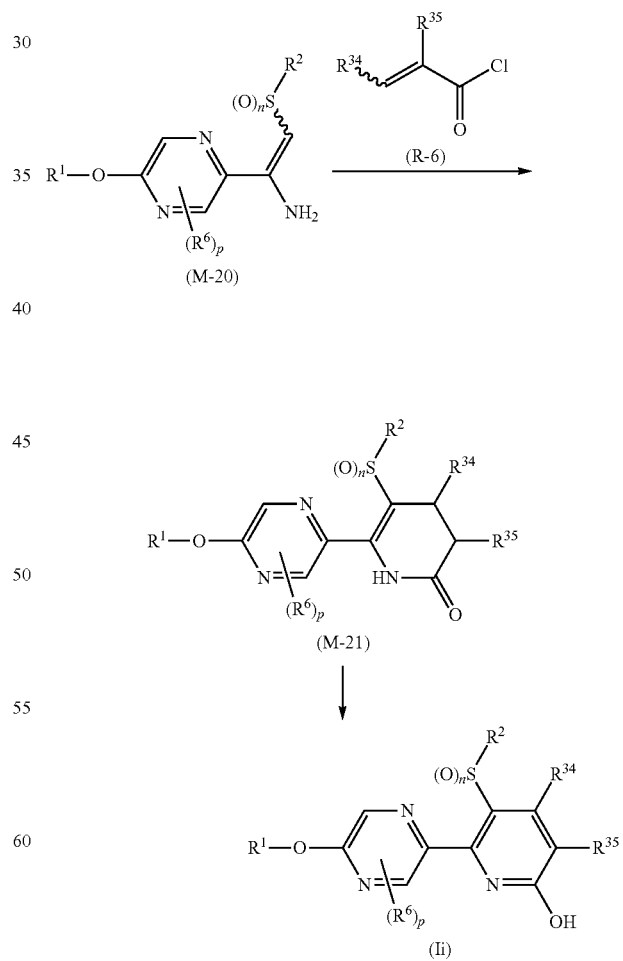

[wherein the symbols are the same as defined above.]

First, the process for preparing the compound represented by formula (M-21) (hereinafter, referred to as Compound (M-21)) from the compound (M-20) is described.

The compound (M-21) may be prepared by reacting the compound (M-20) with a compound represented by formula (R-6) (hereinafter, referred to as Compound (R-6)).

The reaction is usually carried out in a solvent. Examples of the solvent to be used in the reaction include ethers, aliphatic hydrocarbons, aromatic hydrocarbons, halogenated aliphatic hydrocarbons, nitriles, polar aprotic solvent, nitrogen-containing aromatic compounds, and mixed solvents thereof.

In the reaction, the compound (R-6) is usually used within a range of 1 to 10 molar ratio(s) as opposed to 1 mole of the compound (M-20).

The reaction temperature is usually within a range of 0 to 200° C. The reaction period of the reaction is usually within a range of 0.1 to 24 hours.

When the reaction is completed, to the reaction mixtures is added water, and the resulting mixtures are then extracted with organic solvents, and the organic layers are worked up (for example, drying and concentration) to isolate the compound (M-21).

Next, the process for preparing the Present compound (Ii) from the compound (M-21) is described.

The Present compound (Ii) may be prepared by reacting the compound (M-21) with a halogenating agent.

The reaction is usually carried out in a solvent. Examples of the solvent to be used in the reaction include ethers, aliphatic hydrocarbons, aromatic hydrocarbons, halogenated aliphatic hydrocarbons, nitriles, polar aprotic solvent, nitrogen-containing aromatic compounds, and mixed solvents thereof.

Examples of the halogenating agent to be used in the reaction include N-bromosuccinimide, N-chlorosuccinimide, sulfuryl chloride, and bromine.

A catalyst may be added to the reaction as needed. Examples of the catalyst to be used in the reaction include benzoyl peroxide.

In the reaction, a halogenating agent is usually used within a range of 1 to 10 molar ratio(s), and the catalyst is usually used within a range of 0.1 to 0.5 molar ratio(s), as opposed to 1 mole of the compound (M-21).

The reaction temperature is usually within a range of 0 to 200° C. The reaction period of the reaction is usually within a range of 0.1 to 24 hours.

When the reaction is completed, to the reaction mixtures is added water, and the resulting mixtures are then extracted with organic solvents, and the organic layers are worked up (for example, drying and concentration) to isolate the Present compound (Ii).

Process 10

A compound represented by formula (Ij) (hereinafter, referred to as Present compound (Ij)) may be prepared by reacting the compound (M-20) with a compound represented by formula (R-8) (hereinafter, referred to as Compound (R-8)).

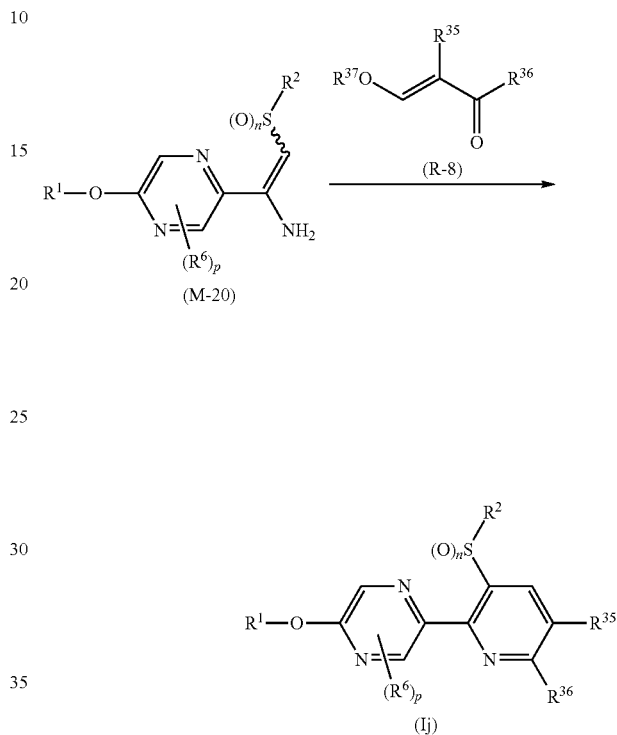

[wherein, the symbols are the same as defined above.]

The reaction is usually carried out in a solvent. Examples of the solvent to be used in the reaction include ethers, aliphatic hydrocarbons, aromatic hydrocarbons, halogenated aliphatic hydrocarbons, nitriles, alcohols, polar aprotic solvent, nitrogen-containing aromatic compounds, and mixed solvents thereof.

In the reaction, the compound (R-8) is usually used within a range of 1 to 10 molar ratio(s) as opposed to 1 mole of the compound (M-20)).

The reaction temperature is usually within a range of 0 to 200° C. The reaction period of the reaction is usually within a range of 0.1 to 24 hours.

When the reaction is completed, to the reaction mixtures is added water, and the resulting mixtures are then extracted with organic solvents, and the organic layers are worked up (for example, drying and concentration) to isolate the Present compound (Ij).

Process 11

A compound represented by formula (Ik) (hereinafter, referred to as Present compound (Ik)) may be prepared according to a method described below.

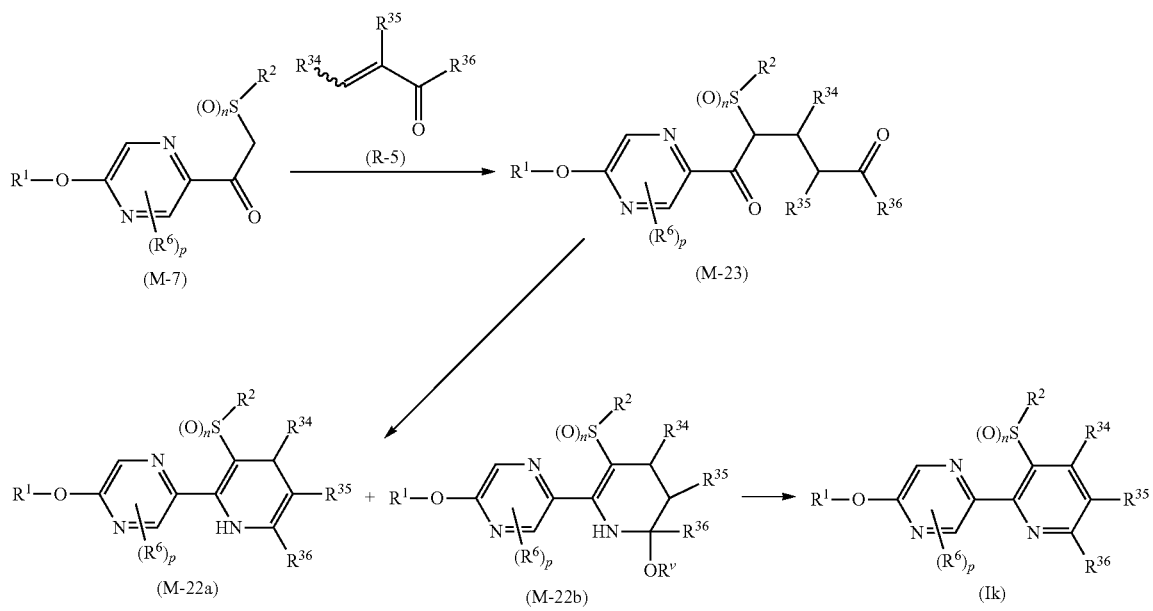

[wherein, the symbols are the same as defined above.]

First, Step 1 is explained.

In the Step 1, a compound represented by formula (M-7) (hereinafter, referred to as Compound (M-7)) and a compound represented by formula (R-5) (hereinafter, referred to as Compound (R-5)) are reacted to give a compound represented by formula (M-23) (hereinafter, referred to as Compound (M-23)).

The reaction is usually carried out in a solvent. Examples of the solvent to be used in the reaction include ethers, aliphatic hydrocarbons, aromatic hydrocarbons, halogenated aliphatic hydrocarbons, alcohols, esters, nitriles, polar aprotic solvent, nitrogen-containing aromatic compounds, and mixed solvents thereof.

In the reaction, the compound (R-5) is usually used within a range of 1 to 10 molar ratio(s) as opposed to 1 mole of the compound (M-7)).

The reaction temperature is usually within a range of 0 to 200° C. The reaction period of the reaction is usually within a range of 0.1 to 24 hours.

When the reaction is completed, the reaction mixtures are worked up (for example, drying and concentration) to isolate the compound (M-23). Alternatively, when the reaction is completed, the resulting compound (M-23) is not isolated and is used as itself in Step 2, or the reaction mixtures are concentrated to obtain the residues, which are used as itself in the Step 2.

Next, Step 2 is described.

In the Step 2, the compound (M-23) is reacted with ammonia to give the compound (M-22a) and the compound (M-22b).

The reaction is usually carried out in a solvent. Examples of the solvent to be used in the reaction include ethers, aliphatic hydrocarbons, aromatic hydrocarbons, halogenated aliphatic hydrocarbons, alcohols, esters, nitriles, polar aprotic solvent, nitrogen-containing aromatic compounds, and mixed solvents thereof.

Examples of the ammonia to be used in the reaction include aqueous ammonia solution and solution of ammonia in methanol.

The ammonia to be used in the reaction may be in the form of a gas, or may be in the form of an aqueous solution or an alcoholic solution. Alternatively, ammonium carboxylate such as ammonium acetate; ammonium phosphate such as ammonium dihydrogenphosphate; ammonium carbonate; ammonium halides such as ammonium chloride may be used.

In the reaction, ammonia is usually used within a range of 1 to 10 molar ratio(s) as opposed to 1 mole of the compound (M-7).

The reaction temperature is usually within a range of 0 to 200° C. The reaction period of the reaction is usually within a range of 0.1 to 24 hours.

When the reaction is completed, to the reaction mixtures is added water, and the reaction mixtures are then extracted with organic solvents, and the organic layers are worked up (for example, drying and concentration) to give the compound (M-22a), the compound (M-22b) or the mixture thereof. Alternatively, when the reaction is completed, the resulting compound (M-22a), the resulting compound (M-22b) or the resulting mixture thereof is not isolated and is used as itself in Step 3, or the reaction mixtures are concentrated to obtain the residues, which are used as itself in the Step 3.

Next, Step 3 is described.

In the Step 3, the compound (M-22a), the compound (M-22b), or the mixture thereof may be reacted with an oxidizing agent according to the method described in the Step 2 of the Process 8 to prepare the Present compound (Ik).

Hereinafter, a process for preparing each intermediate compound is described.

Reference Process 1

The compound (M-1) may be prepared by reacting a compound represented by formula (M-8) (hereinafter, referred to Compound (M-8)) with a compound represented by formula (M-9) (hereinafter, referred to Compound (M-9)) in the presence of a metal catalyst.

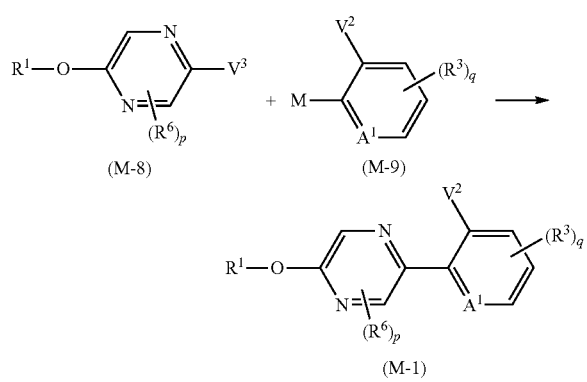

(M-8)        (M-9)

(M-1)

[wherein V³ represents a chlorine atom, a bromine atom or an iodine atom; M represents 9-borabicyclo[3.3.1]nona-9-yl group, —B(OH)$_2$, 4,4,5,5-tetramethyl-1,3,2-dioxaborolan-2-yl group, Sn(n-C$_4$H$_9$)$_3$, ZnCl, MgI, or MgBr; and the other symbols are the same as defined above.]

The compound (M-9) may be prepared according to a similar method to that described in International Publication 03/024961 or Organic Process Research & Development, 2004, 8, 192-200.

The compound (M-8) may be prepared according to a similar method to that described in International Publication 2010/016005.

The reaction is usually carried out in a solvent. Examples of the solvent to be used in the reaction include ethers, aromatic hydrocarbons, polar aprotic solvent, water, and mixed solvents thereof.

Examples of the metal catalyst to be used in the reaction include palladium catalysts such as tetrakis(triphenylphosphine)palladium(0), 1,1'-bis(diphenylphosphino)ferrocene palladium(II) dichloride, tris(dibenzylideneacetone)dipalladium(0), and palladium(II) acetate; nickel catalysts such as bis(cyclooctadiene)nickel(0) and nickel(II) chloride; and copper catalyst such as copper(I) iodide and copper(I) chloride.

A ligand, a base and/or an inorganic halogenated compound may be added to the reaction as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-(dicyclohexylphosphino)-2',4',6'-triisopropyl-1,1'-biphenyl, 2-dicyclohexylphosphino-2',6'-dimethoxybiphenyl, 1,2-bis(diphenylphosphino)ethane, 2,2'-bipyridine, 2-aminoethanol, 8-hydroquinoline, and 1,10-phenanthroline.

Examples of the base to be used in the reaction include alkali metal hydrides, alkali metal carbonates, and organic bases.

Examples of the inorganic halogenated compounds include alkali metal fluorides such as potassium fluoride, and sodium fluoride; and alkali metal chlorides such as lithium chloride, and sodium chloride.

In the reaction, the compound (M-9) is usually used within a range of 1 to 10 molar ratio(s), the metal catalyst is usually used within a range of 0.01 to 0.5 molar ratios, the ligand is usually used within a range of 0.01 to 1 molar ratio(s), the base is usually used within a range of 0.1 to 5 molar ratios, and the inorganic halogenated compound is usually used within a range of 0.1 to 5 molar ratios, as opposed to 1 mole of the compound (M-8).

The reaction temperature is usually within a range of −20 to 200° C. The reaction period of the reaction is usually within a range of 0.1 to 24 hours.

When the reaction is completed, to the reaction mixtures is added water, and the reaction mixtures are then extracted with organic solvent(s), and the organic solvents are worked up (for example, drying and concentration) to give the compound (M-1).

Reference Process 2

The compound (M-3) may be prepared by reacting a compound represented by formula (M-11) (hereinafter, referred to as Compound (M-11)) with an acid.

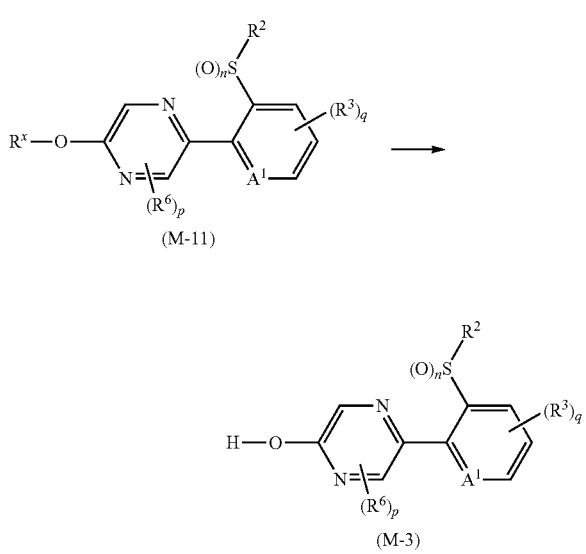

(M-11)

(M-3)

[wherein, RX represents a methyl group or an ethyl group; and the other symbols are the same as defined above.]

The reaction is usually carried out in a solvent. Examples of a solvent to be used in the reaction include halogenated aliphatic hydrocarbons, aromatic hydrocarbons, nitriles, alcohols, acetic acid, water, and mixed solvents thereof.

Examples of the acid to be used in the reaction include mineral acids such as hydrochloric acid; boron halides such as boron trichloride and boron tribromide; metal chlorides such as titanium chloride, and aluminium chloride.

In the reaction, the acid is usually used within a range of 0.1 to 10 molar ratio(s) as opposed to 1 mole of the compound (M-11). In the reaction, when the mineral acids are used as an acid, the mineral acid may be used also as a solvent.

The reaction temperature is usually within a range of −20 to 150° C. The reaction period of the reaction is usually within a range of 0.1 to 24 hours.

When the reaction is completed, to the reaction mixtures is added water, and the reaction mixtures are then extracted with organic solvents, and the organic layers are worked up (for example, drying and concentration) to give the compound (M-3).

Reference Process 3

The compound (M-11) wherein n is 0 (hereinafter, referred to as Compound (M-11a)), the compound (M-11) wherein n is 1 (hereinafter, referred to as Compound (M-11b)), and the compound (M-11) wherein n is 2 (hereinafter, referred to as Compound (M-11c)) may be prepared according to a method described below.

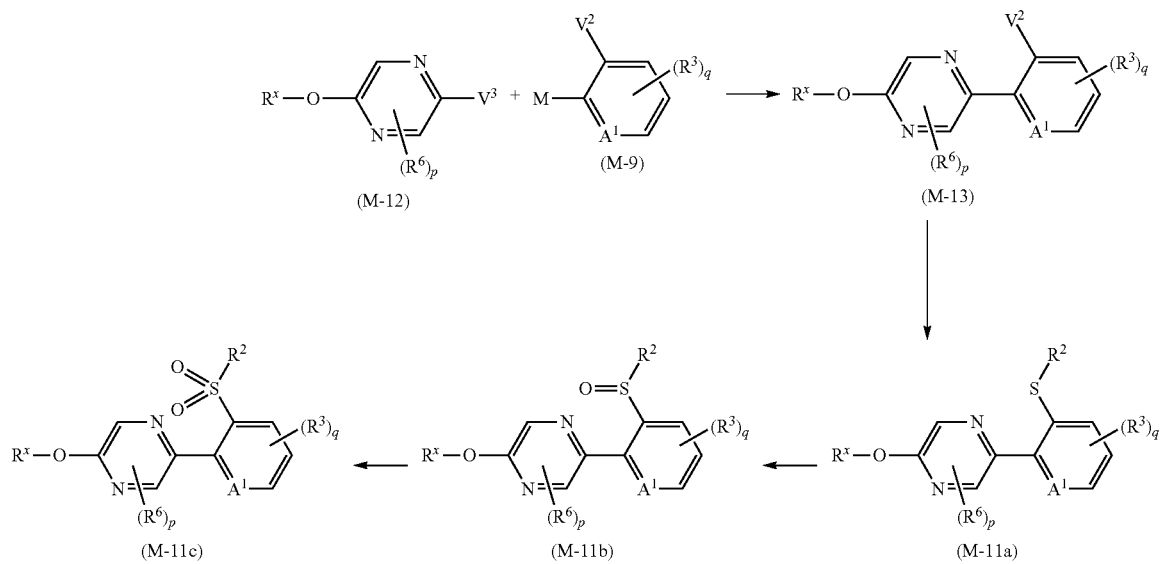

[wherein the symbols are the same as defined above.]

A compound represented by formula (M-13) (hereinafter, referred to as Compound (M-13)) may be prepared by using a compound represented by formula (M-12) (hereinafter, referred to as Compound (M-12)) instead of the compound (M-8) according to the similar method to that described in Reference Process 1.

The compound (M-12) is a commercially available compound, or may be prepared according to the similar method to a well-known method.

The compound (M-11a) may be prepared by using the compound (M-13) instead of the compound (M-1) according to a method described in Process 3.

The compound (M-11b) and the compound (M-11c) may be prepared by using the compound (M-11a) instead of the compound (Ia) according to the similar method to that described in Process 1.

Reference Process 4

A compound represented by formula (M-17) (hereinafter, referred to as Compound (M-17)) may be prepared by reacting a compound represented by formula (M-16) (hereinafter, referred to as Compound (M-16)) with the compound (R-12), followed by reacting the reaction mixtures with ammonia.

-continued

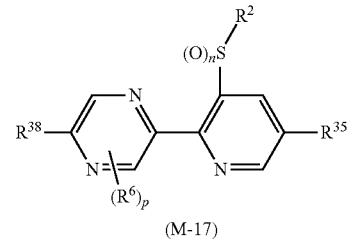

[wherein $R^{38}$ represents a halogen atom, or a C1-C4 alkoxy group, and the symbols are the same as defined above.]

The reaction may be carried out by using the compound (M-16) instead of the compound (M-7) according to the similar method to that described in Process 5.

Reference Process 5

The compound (M-16) may be prepared by reacting a compound represented by formula (M-15) (hereinafter, referred to as Compound (M-15)) with a compound represented by formula (R-16) (hereinafter, referred to as Compound (R-16)) in the presence of a base.

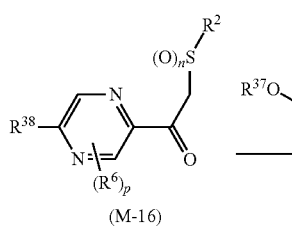 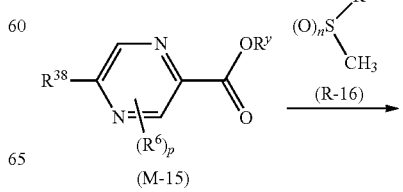

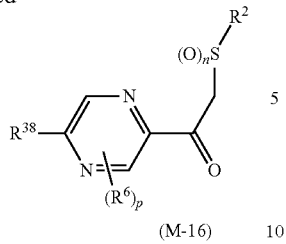

(M-16)

[wherein $R^y$ represents a methyl group, or an ethyl group, and the other symbols are the same as defined above.]

The compound (M-15) is a commercially available compound, or may be prepared according to the similar method to that described in International Publication No. 2014/204730.

The compound (R-16) is a commercially available compound, or may be prepared according to the method described in Journal of Molecular Catalysis A: Chemical, 2011, 341 (1-2), 57-62.

The reaction is usually carried out in a solvent. Examples of the solvent to be used in the reaction include alcohols, ethers, aromatic hydrocarbons, polar aprotic solvents, and mixed solvents thereof.

Examples of the base to be used in the reaction include n-butyl lithium, s-butyl lithium, t-butyl lithium, lithium diisopropylamide, sodium bis(trimethylsilyl)amide, potassium bis(trimethylsilyl)amide, potassium t-butoxide, sodium methoxide, sodium ethoxide, and alkali metal hydrides.

In the reaction, the compound (R-16) is usually used within a range of 1 to 5 molar ratio(s), and the base is usually used within a range of 1 to 5 molar ratio(s), as opposed to 1 mole of the compound (M-15). Preferably, the compound (R-16) is usually used within a range of 1 to 1.1 molar ratio(s), and the base is usually used within a range of 1 to 2 molar ratio(s), as opposed to 1 mole of the compound (M-15).

The reaction temperature is usually within a range of −78 to 100° C. The reaction period of the reaction is usually within a range of 0.5 to 12 hours.

When the reaction is completed, to the reaction mixtures is added water, and the reaction mixtures are then extracted with organic solvents, and the organic layers are worked up (for example, drying and concentration) to give the compound (M-16).

The compound (M-15) and the compound (M-16) are commercially available compounds or may be prepared by known methods.

Reference Process 6

A compound represented by formula (M-4a) (hereinafter, referred to as Compound (M-4a)) and a compound represented by formula (M-4b) (hereinafter, referred to as Compound (M-4b)) may be prepared according to a method described below.

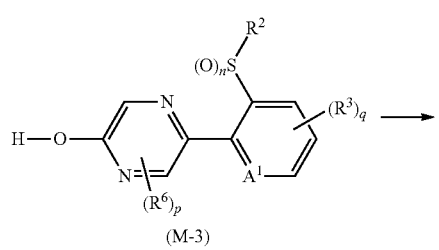

(M-3)

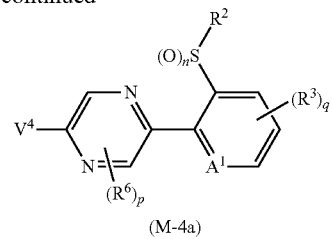

(M-4a)

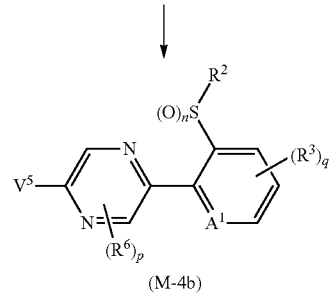

(M-4b)

[wherein, $V^4$ represents a chlorine atom or a bromine atom, $V^5$ represents a fluorine atom or an iodine atom, and the other symbols are the same as defined above]

First, a method for preparing the compound (M-4a) from the compound (M-3) is described.

The compound (M-4a) may be prepared by reacting the compound (M-3) with phosphoryl chloride or phosphoryl bromide.

The reaction is usually carried out in a solvent. Examples of the solvent to be used in the reaction include aromatic hydrocarbons.

When phosphoryl chloride is used, phosphoryl chloride may be used also as a solvent.

In the reaction, phosphoryl chloride or phosphoryl bromide is usually used within a range of 1 to 10 molar ratio(s) as opposed to 1 mole of the compound (M-3).

The reaction temperature is usually within a range of 0 to 150° C. The reaction period of the reaction is usually within a range of 0.5 to 24 hours.

When the reaction is completed, to the reaction mixtures is added water, and the reaction mixtures are then extracted with organic solvents, and the organic layers are worked up (for example, drying and concentration) to give the compound (M-4a).

Next, a method for preparing the compound (M-4b) from the compound (M-4a) is described.

The compound (4-b) may be prepared by reacting the compound (M-4a) with a inorganic fluoride compound or an inorganic iodide compound.

The reaction is usually carried out in a solvent. Examples of the solvents to be used in the reaction include nitriles, polar aprotic solvent, nitrogen-containing aromatic compounds, and mixed solvents thereof.

Examples of the inorganic fluoride compound to be used in the reaction include potassium fluoride, sodium fluoride and cesium fluoride.

Examples of the inorganic iodide compound to be used in the reaction include potassium iodide and sodium iodide.

When the compound (M-4b) wherein $V^5$ represents a fluorine atom is prepared, the inorganic fluoride compound is usually used within a range of 1 to 10 molar ratio(s) as opposed to 1 mole of the compound (M-4a).

When the compound (M-4b) wherein $V^5$ represents an iodine atom is prepared, the inorganic iodide compound is usually within a range of 1 to 10 molar ratio(s) as opposed to 1 mole of the compound (M-4a).

The reaction temperature is usually within a range of 0 to 250° C. The reaction period of the reaction is usually within a range of 0.5 to 24 hours.

When the reaction is completed, to the reaction mixtures is added water, and the reaction mixtures are then extracted with organic solvents, and the organic layers are worked up (for example, drying and concentration) to give the compound (M-4b).

Reference Process 7

A compound represented by formula (M-19) (hereinafter, referred to as Compound (M-19)) may be prepared according to a method described below.

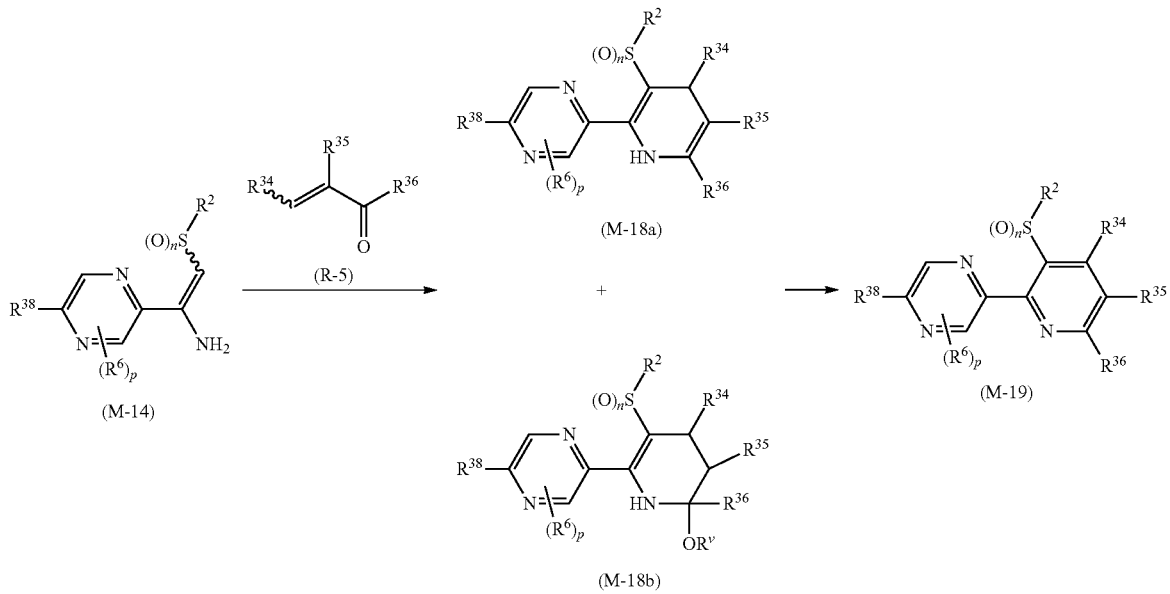

[wherein the symbols are the same as defined above.]

The reaction may be prepared by using a compound represented by formula (M-14) (hereinafter, referred to as Compound (M-14)) instead of the compound (M-20) according to the similar method to that described in Process 8.

Reference Process 8

The compound (M-19) may be prepared according to a method described below.

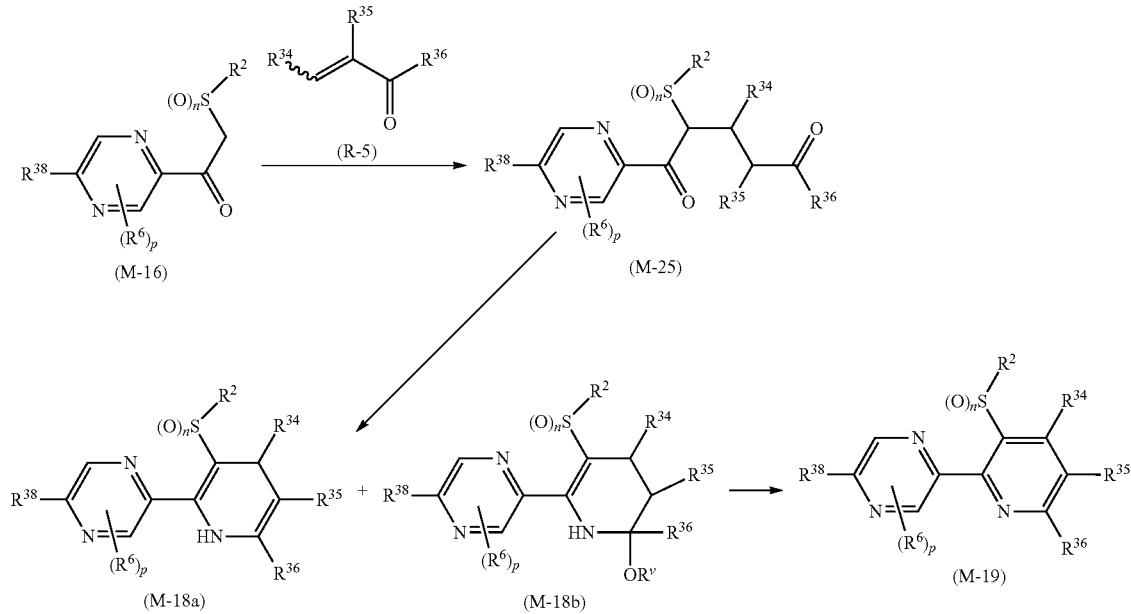

[wherein the symbols are the same as defined above.]

The reaction may be prepared by using a compound represented by formula (M-16) (hereinafter, referred to as Compound (M-16)) instead of the compound (M-7) according to the similar method to that described in Process 11.

Reference Process 9

A compound represented by formula (M-28) (hereinafter, referred to as Compound (M-28)) may be prepared by reacting a compound represented by formula (M-16) (hereinafter, referred to as Compound (M-16)) with the compound (R-12), followed by reacting the reaction mixtures with ammonia.

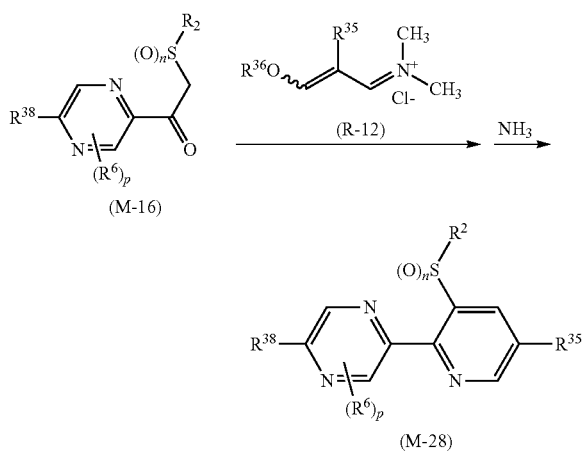

[wherein the symbols are the same as defined above.]

The reaction may be prepared by using the compound (M-16) instead of the compound (M-7) according to the similar method to that described in Process 5.

Reference Process 10

A compound represented by formula (M-29) (hereinafter, referred to as Compound (M-29)) may be prepared by reacting the compound (M-14) with the compound (R-8).

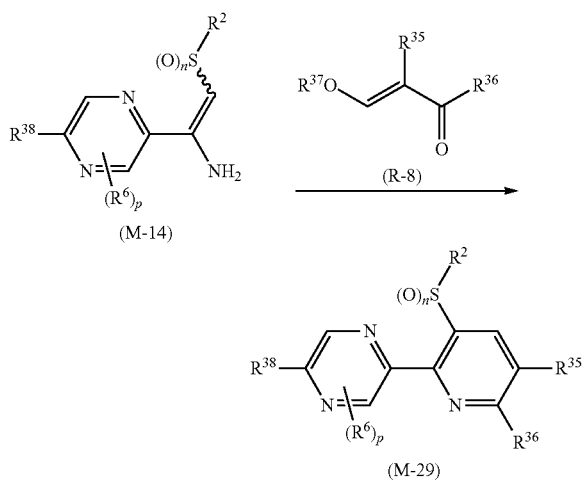

[wherein the symbols are the same as defined above.]

The reaction may be prepared by using the compound (M-14) instead of the compound (M-20) according to the similar method to that described in Process 10.

Reference Process 11

The compound (M-31) may be prepared by reacting the compound (M-30) with ammonia.

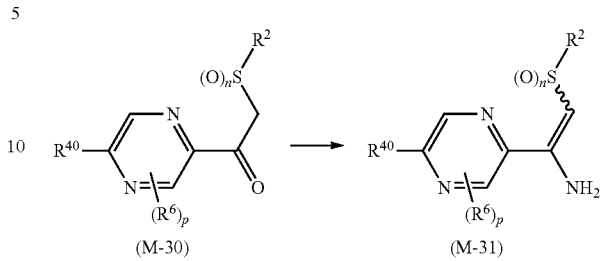

[wherein the symbols are the same as defined above.]

The reaction is usually carried out in a solvent. Examples of the solvent to be used in the reaction include ethers, aromatic hydrocarbons, nitriles, alcohols, polar aprotic solvents, water, and mixed solvents thereof.

The ammonia to be used in the reaction may be in the form of a gas, or may be in the form of an aqueous solution or an alcoholic solution. Alternatively, ammonium carboxylate such as ammonium acetate; ammonium phosphate such as ammonium dihydrogenphosphate; ammonium carbonate; ammonium halides such as ammonium chloride may be used.

In the reaction, the ammonia is usually used within a range of 0.1 to 100 molar ratio(s) as opposed to 1 mole of the compound (M-30).

The reaction temperature is usually within a range of 0 to 200° C. The reaction period of the reaction is usually within a range of 0.5 to 24 hours.

When the reaction is completed, to the reaction mixtures is added water, and the reaction mixtures are then extracted with organic solvents, and the organic layers are worked up (for example, drying and concentration) to give the compound (M-31).

Reference Process 12

The compound (M-2) may be prepared by reacting the compound (M-1) with a sulfating agent.

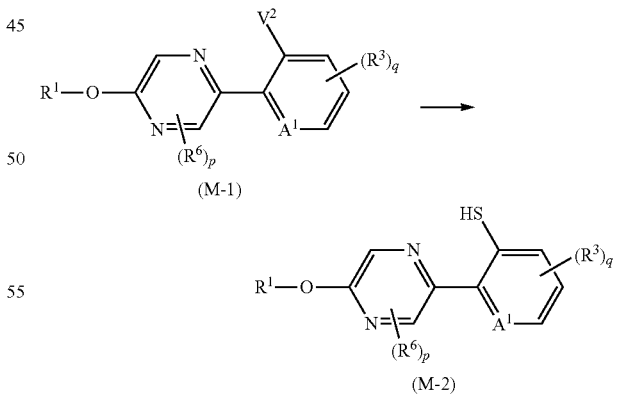

[wherein the symbols are the same as defined above.]

The reaction is usually carried out in a solvent. Examples of the solvents to be used in the reaction include ethers, aromatic hydrocarbons, nitriles, polar aprotic solvent, and mixed solvents thereof.

Examples of the sulfating agent to be used in the reaction include sodium sulfide and sodium hydrogen sulfide.

In the reaction, the sulfating agent is usually used within a range of 1 to 10 molar ratio(s) as opposed to 1 mole of the compound (M-1).

The reaction temperature is usually within a range of −20 to 150° C. The reaction period of the reaction is usually within a range of 0.5 to 24 hours.

When the reaction is completed, to the reaction mixtures is added water, and the reaction mixtures are then extracted with organic solvents, and the organic layers are worked up (for example, drying and concentration) to give the compound (M-2).

In the reaction, V is preferably a fluorine atom or a chlorine atom.

Examples of the compound (M-1) include the following compounds.

The compound (M-1) wherein $R^1$ represents a C2-C10 haloalkyl group, or a (C1-C5 alkoxy)C2-C5 alkyl group having one or more halogen atoms; and $R^3$ represents independently of each other a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{29}NR^{11}R^{12}$, or a halogen atom.

The compound (M-1) wherein $R^1$ represents a C2-C10 haloalkyl group, or a (C1-C5 alkoxy)C2-C5 alkyl group having one or more halogen atoms; and $R^3$ represents independently of each other a C1-C6 chain hydrocarbon group optionally having one or more substituents selected from Group B, a phenyl group optionally having one or more substituents selected from Group D, a 6 membered aromatic heterocyclic group having one to two nitrogen atoms (the 6 membered aromatic heterocyclic group may optionally have one or more substituents selected from Group D), a 5 membered aromatic heterocyclic group having one to four nitrogen atoms (the 5 membered aromatic heterocyclic group may optionally have one or more substituents selected from Group D), a $OR^{12}$, a $NR^{11}R^{12}$, a $NR^{29}NR^{11}R^{12}$, or a halogen atom.

The compound (M-1) wherein $A^1$ represents a nitrogen atom or a CH; $V^2$ represents a fluorine atom, or a chlorine atom; $R^1$ represents a C2-C10 haloalkyl group, or a (C1-C5 alkoxy)C2-C5 alkyl group having one or more halogen atoms; $R^3$ represents independently of each other a C1-C6 chain hydrocarbon group optionally having one or more halogen atoms, or a halogen atom; and $R^6$ represents independently of each other a C1-C6 alkyl group optionally having one or halogen atoms, or a halogen atom.

The compound (M-1) wherein $A^1$ represents a nitrogen atom or a CH; $V^2$ represents a fluorine atom, or a chlorine atom; $R^1$ represents a C2-C10 haloalkyl group having two or more fluorine atoms; $R^3$ represents independently of each other a C1-C6 chain hydrocarbon group optionally having one or more halogen atoms, or a halogen atom; and p represents 0.

The compound (M-1) wherein $A^1$ represents a nitrogen atom or a CH; $V^2$ represents a fluorine atom, or a chlorine atom; $R^1$ represents a C2-C10 haloalkyl group having two or more fluorine atoms; $R^3$ represents independently of each other a C1-C6 chain hydrocarbon group optionally having one or more halogen atoms, or a halogen atom; and p represents 0.

The compound (M-1) wherein $A^1$ represents a nitrogen atom or a CH; $V^2$ represents a fluorine atom, or a chlorine atom; $R^1$ represents a 2,2,2-trifluoroethyl group, a 2,2,3,3-tetrafluoropropyl group, a 2,2,3,3,3-pentafluoropropyl group, a 1,1,2,3,3,3-hexafluoropropyl group, a 1,1,2-trifluoro-2-(trifluoromethoxy)ethyl group, or a 2,2,3,4,4,4-hexafluorobutyl group; q represents 0 or 1; $R^3$ represents a trifluoromethyl group; and p represents 0.

Examples of the compound (M-2) include the following compounds.

The compound (M-2) wherein $R^1$ represents a C2-C10 haloalkyl group, or a (C1-C5 alkoxy)C2-C5 alkyl group having one or more halogen atom; and $R^3$ represents independently of each other a C1-C6 chain hydrocarbon group optionally having one or more halogen atoms, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{29}NR^{11}R^{12}$, or a halogen atom.

The compound (M-2) wherein $R^1$ represents a C2-C10 haloalkyl group, or a (C1-C5 alkoxy)C2-C5 alkyl group having one or more halogen atom; and $R^3$ represents independently of each other a C1-C6 chain hydrocarbon group optionally having one or more halogen atoms, a phenyl group optionally having one or more substituents selected from Group D, a 6 membered aromatic heterocyclic group having one to two nitrogen atoms (the 6 membered aromatic heterocyclic group may optionally have one or more substituents selected from Group D), a 5 membered aromatic heterocyclic group having one to four nitrogen atoms (the 5 membered aromatic heterocyclic group may optionally have one or more substituents selected from Group D), a $OR^{12}$, a $NR^{11}R^{12}$, a $NR^{29}NR^{11}R^{12}$, or a halogen atom.

The compound (M-2) wherein $A^1$ represents a nitrogen atom or a CH; $R^1$ represents a C2-C10 haloalkyl group or a (C1-C5 alkoxy)C2-C5 alkyl group having one or more halogen atom; $R^3$ represents independently of each other a C1-C6 chain hydrocarbon group optionally having one or more halogen atoms, or a halogen atom; and $R^6$ represents independently of each other a C1-C6 alkyl group optionally having one or halogen atoms or a halogen atom.

The compound (M-2) wherein $A^1$ represents a nitrogen atom or a CH; $R^1$ represents a C2-C10 alkyl group having two or more fluorine atoms; $R^3$ represents independently of each other a C1-C6 chain hydrocarbon group optionally having one or more halogen atoms, or a halogen atom; and p represents 0.

The compound (M-2) wherein $A^1$ represents a nitrogen atom or a CH; $R^1$ represents a C2-C10 alkyl group; q represents 0; and p represents 0.

The compound (M-2) wherein $A^1$ represents a nitrogen atom or a CH; $R^1$ represents a C2-C10 haloalkyl group having two or more fluorine atoms; $R^3$ represents independently of each other a C1-C6 chain hydrocarbon group optionally having one or more halogen atoms, or a halogen atom; and p represents 0.

The compound (M-2) wherein $A^1$ represents a nitrogen atom or a CH; $R^1$ represents a 2,2,2-trifluoroethyl group, a 2,2,3,3-tetrafluoropropyl group, a 2,2,3,3,3-pentafluoropropyl group, a 1,1,2,3,3,3-hexafluoropropyl group, a 1,1,2-trifluoro-2-(trifluoromethoxy)ethyl group, or a 2,2,3,4,4,4-hexafluorobutyl group; q represents 0 or 1; $R^3$ represents a trifluoromethyl group; and p represents 0.

Examples of the compound (M-3) include the following compounds.

The compound (M-3) wherein $R^2$ represents a C1-C6 alkyl group optionally having one or halogen atoms; and $R^3$ represents independently of each other a C1-C6 chain hydrocarbon group optionally having one or more halogen atoms, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{29}NR^{11}R^{12}$, or a halogen atom.

The compound (M-3) wherein $R^2$ represents a C1-C6 alkyl group optionally having one or halogen atoms; and $R^3$ represents independently of each other a C1-C6 chain hydrocarbon group optionally having one or more halogen atoms, a phenyl group optionally having one or more substituents selected from Group D, a 6 membered aromatic heterocyclic group having one to two nitrogen atoms (the 6 membered aromatic heterocyclic group may optionally have one or more substituents selected from Group D), a 5 membered aromatic heterocyclic group having one to four nitrogen atoms (the 5 membered aromatic heterocyclic group may optionally have one or more substituents selected from Group D), a $OR^{12}$, a $NR^{11}R^{12}$, or a halogen atom.

The compound (M-3) wherein $A^1$ represents a nitrogen atom, or a CH; $R^2$ represents an ethyl group; q represents 0, 1, 2, or 3; $R^3$ represents independently of each other a C1-C6 chain hydrocarbon group optionally having one or more halogen atoms, a 5 or 6 membered aromatic heterocyclic group optionally having one or more substituents selected from Group D, a $OR^{12}$, a $NR^{11}R^{12}$, a $NR^{29}NR^{11}R^{12}$, or a halogen atom; and $R^6$ represents independently of each other a C1-C6 alkyl group optionally having one or halogen atoms, or a halogen atom.

The compound (M-3) wherein $A^1$ represents a nitrogen atom, or a CH; $R^2$ represents an ethyl group; q represents 0, 1, 2, or 3; $R^3$ represents independently of each other a C1-C6 chain hydrocarbon group optionally having one or more halogen atoms, or a halogen atom; p represents 0, 1, 2, or 3; and $R^6$ represents independently of each other a C1-C6 alkyl group optionally having one or halogen atoms or a halogen atom.

Examples of the compound (M-4) include the following compounds.

The compound (M-4) wherein $R^2$ represents a C1-C6 alkyl group optionally having one or halogen atoms; and $R^3$ represents independently of each other a C1-C6 chain hydrocarbon group optionally having one or more halogen atoms, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{29}NR^{11}R^{12}$, or a halogen atom.

The compound (M-4) wherein $R^2$ represents a C1-C6 alkyl group optionally having one or halogen atoms; and $R^3$ represents independently of each other a C1-C6 chain hydrocarbon group optionally having one or more halogen atoms, a phenyl group optionally having one or more substituents selected from Group D, a 6 membered aromatic heterocyclic group having one to two nitrogen atoms (the 6 membered aromatic heterocyclic group may optionally have one or more substituents selected from Group D), a 5 membered aromatic heterocyclic group having one to four nitrogen atoms (the 5 membered aromatic heterocyclic group may optionally have one or more substituents selected from Group D), a $OR^{12}$, a $NR^{11}R^{12}$, or a halogen atom.

The compound (M-4) wherein $A^1$ represents a nitrogen atom, or a CH; V represents a fluorine atom, a chlorine atom, or an iodine atom; $R^2$ represents an ethyl group; $R^3$ represents independently of each other a C1-C6 chain hydrocarbon group optionally having one or more halogen atoms, or a halogen atom; and $R^6$ represents independently of each other a C1-C6 alkyl group optionally having one or halogen atoms, or a halogen atom.

Examples of the compound (M-30) include the following compounds.

The compound (M-30) wherein $R^1$ represents a C2-C10 haloalkyl group, or a (C1-C5 alkoxy)C2-C5 alkyl group having one or more halogen atom; and $R^2$ represents a C1-C6 alkyl group optionally having one or halogen atoms.

The compound (M-30) wherein $R^{40}$ represents a halogen atom, or a $OR^1$; $R^1$ represents a C2-C10 haloalkyl group, or a (C1-C5 alkoxy)C2-C5 alkyl group having one or more halogen atom; and $R^2$ represents a C1-C6 alkyl group optionally having one or halogen atoms.

The compound (M-30) wherein $R^{40}$ represents a halogen atom, or a $OR^1$; $R^1$ represents a C2-C10 haloalkyl group; and $R^2$ represents an ethyl group.

The compound (M-30) wherein $R^{40}$ represents a halogen atom, or a $OR^1$; $R^1$ represents a C2-C10 haloalkyl group; $R^2$ represents an ethyl group; and p represents 0.

The compound (M-30) wherein $R^{40}$ represents a halogen atom; and $R^2$ represents a C1-C6 alkyl group optionally having one or halogen atoms.

The compound (M-30) wherein $R^{40}$ represents a fluorine atom or a chlorine atom; and $R^2$ represents an ethyl group; n represents 2; and p represents 0.

The compound (M-23) wherein $R^{40}$ represents a $OR^4$; $R^4$ represents a C2-C10 haloalkyl group or a (C1-C5 alkoxy)C2-alkyl group having one or more halogen atom; and $R^2$ represents an ethyl group.

The compound (M-23) wherein $R^{40}$ represents a $OR^4$; $R^4$ represents a C2-C10 haloalkyl group having two or more fluorine atoms or a (C1-C5 alkoxy)C2-C5 alkyl group having one or more halogen atom; $R^2$ represents an ethyl group; n represents 2; and p represents 0.

The compound (M-30) wherein $R^{40}$ represents a $OR^1$; $R^1$ represents a 2,2,2-trifluoroethyl group, a 2,2,3,3-tetrafluoropropyl group, a 2,2,3,3,3-pentafluoropropyl group, a 1,1,2,3,3,3-hexafluoropropyl group, a 1,1,2-trifluoro-2-(trifluoromethoxy)ethyl group, or a 2,2,3,4,4,4-hexafluorobutyl group; $R^2$ represents an ethyl group; n represents 2; and p represents 0.

The compound (M-30) wherein $R^{40}$ represents a C1-C4 alkoxy group; $R^2$ represents an ethyl group; p represents 0, 1, 2, or 3; and $R^6$ represents independently of each other a C1-C6 alkyl group optionally having one or halogen atoms, a $NR^{18}R^{19}$, a $C(O)OR^{25}$, a $OC(O)OR^{20}$, a cyano group, a nitro group, or a halogen atom.

The compound (M-30) wherein $R^{40}$ represents a C1-C3 alkoxy group; $R^2$ represents an ethyl group; n represents 2; and p represents 0.

Examples of the compound (M-31) include the following compounds.

The compound (M-31) wherein $R^1$ represents a C2-C10 haloalkyl group, or a (C1-C5 alkoxy)C2-C5 alkyl group having one or more halogen atom; and $R^2$ represents a C1-C6 alkyl group optionally having one or halogen atoms.

The compound (M-31) wherein $R^{40}$ represents a halogen atom; and $R^2$ represents a C1-C6 alkyl group optionally having one or halogen atoms;

The compound (M-31) wherein $R^{40}$ represents a fluorine atom or a chlorine atom; $R^2$ represents an ethyl group; n represents 2; and p represents 0.

The compound (M-31) wherein $R^{40}$ represents a $OR^1$; $R^1$ represents a C2-C10 haloalkyl group, or a (C1-C5 alkoxy)C2-C5 alkyl group having one or more halogen atom; and $R^2$ represents an ethyl group.

The compound (M-31) wherein $R^{40}$ represents a $OR^1$; $R^1$ represents a C2-C10 haloalkyl group having two or more fluorine atoms, or a (C1-C5 alkoxy)C2-C5 alkyl group having one or more halogen atom; $R^2$ represents an ethyl group; n represents 2; and p represents 0.

The compound (M-31) wherein $R^{40}$ represents a $OR^1$; $R^1$ represents a 2,2,2-trifluoroethyl group, a 2,2,3,3-tetrafluoropropyl group, a 2,2,3,3,3-pentafluoropropyl group, a 1,1,2,3,3,3-hexafluoropropyl group, a 1,1,2-trifluoro-2-(trifluoromethoxy)ethyl group, or a 2,2,3,4,4,4-hexafluorobutyl group; $R^2$ represents an ethyl group; n represents 2; and p represents 0.

The compound (M-31) wherein $R^{40}$ represents a C1-C4 alkoxy group; and $R^2$ represents an ethyl group.

The compound (M-31) wherein $R^{40}$ represents a C1-C3 alkoxy group; $R^2$ represents an ethyl group; n represents 2; and p represents 0.

Next, specific examples of the compound of the present invention are shown below.

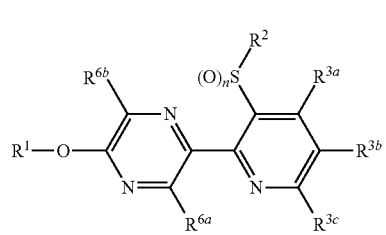

(I-C)

The compound represented by formula (I-C) of the present invention wherein n represents 2; $R^{3a}$, $R^{3b}$, $R^{3c}$, $R^{6a}$, and $R^{6b}$ represent a hydrogen atom; and $R^4$ and $R^2$ represent any combination indicated in Table 1 to Table 5 (hereinafter, referred to as Compound Group SX1).

TABLE 1

| $R^1$ | $R^2$ |
|---|---|
| $CF_2HCH_2$ | $CH_3CH_2$ |
| $CH_3CF_2$ | $CH_3CH_2$ |
| $CF_3CH_2$ | $CH_3CH_2$ |
| $CCl_3CH_2$ | $CH_3CH_2$ |
| $CF_2HCF_2$ | $CH_3CH_2$ |
| $CHClFCF_2$ | $CH_3CH_2$ |
| $CF_3CH_2CH_2$ | $CH_3CH_2$ |
| $CF_2HCF_2CH_2$ | $CH_3CH_2$ |
| $CF_3CF_2CH_2$ | $CH_3CH_2$ |
| $CBrF_2CF_2$ | $CH_3CH_2$ |
| $CF_3CFHCF_2$ | $CH_3CH_2$ |
| $CH_3CF_2CH_2$ | $CH_3CH_2$ |
| $CF_3CH(CH_3)$ | $CH_3CH_2$ |
| $CF_3C(CH_3)_2$ | $CH_3CH_2$ |
| $CH(CH_3)_2CH(CF_3)$ | $CH_3CH_2$ |
| $(CF_3)_2CH$ | $CH_3CH_2$ |
| $CH_3CH_2CH(CF_3)$ | $CH_3CH_2$ |
| $CF_3CCl_2CH_2$ | $CH_3CH_2$ |
| $CF_3CF_2CH(CH_3)$ | $CH_3CH_2$ |
| $CF_3CF_2CH(CH_2CH_3)$ | $CH_3CH_2$ |
| $C(CH_3)(CF_3)_2CH_2$ | $CH_3CH_2$ |
| $CF_3CFHCF_2CH_2$ | $CH_3CH_2$ |
| $CF_3(CF_2)_2CH_2$ | $CH_3CH_2$ |
| $CBrF_2CF_2CH_2CH_2$ | $CH_3CH_2$ |
| $CF_3CFHCF_2CH(CH_3)$ | $CH_3CH_2$ |

TABLE 2

| $R^1$ | $R^2$ |
|---|---|
| $CF_3CH=CHCH_2$ | $CH_3CH_2$ |
| $CF_3(CF_2)_3CH_2$ | $CH_3CH_2$ |
| $CF_3(CF_2)_4CH_2$ | $CH_3CH_2$ |

TABLE 2-continued

| $R^1$ | $R^2$ |
|---|---|
| $CF_3(CF_2)_3CH_2CH_2$ | $CH_3CH_2$ |
| $CF(CF_3)_2CF_2CF_2CH_2CH_2$ | $CH_3CH_2$ |
| $CF_2H(CF_2)_3CH_2$ | $CH_3CH_2$ |
| $CF_2H(CF_2)_5CH_2$ | $CH_3CH_2$ |
| $CF_3(CF_2)_3CH_2CH_2CH_2$ | $CH_3CH_2$ |
| $CF_3CF_2(CH_2)_5CH_2$ | $CH_3CH_2$ |
| $CF_3(CF_2)_5CH_2CH_2$ | $CH_3CH_2$ |
| $CF_3(CF_2)_3CH_2(CH_2)_4CH_2$ | $CH_3CH_2$ |
| $CF_3(CF_2)_5CH_2CH_2$ | $CH_3CH_2$ |
| $CF(CF_3)_2CH_2(CH_2)_4CH_2$ | $CH_3CH_2$ |
| $CF_3OCFHCF_2$ | $CH_3CH_2$ |
| $CH_3OCH_2CF_2CH_2$ | $CH_3CH_2$ |
| $CF_3CH_2OCH_2CF_2CH_2$ | $CH_3CH_2$ |
| $CH_2FCF_2CH_2$ | $CH_3CH_2$ |
| $CH_2ClCF_2CH_2$ | $CH_3CH_2$ |
| $CH_2BrCF_2CH_2$ | $CH_3CH_2$ |
| $CH_3OCH_2(CF_2)CH_2$ | $CH_3CH_2$ |
| $CF_3CH_2OCH_2(CF_2)_2CH_2$ | $CH_3CH_2$ |
| $CH_2F(CF_2)_2CH_2$ | $CH_3CH_2$ |
| $CH_2Cl(CF_2)_2CH_2$ | $CH_3CH_2$ |
| $CH_2Br(CF_2)_2CH_2$ | $CH_3CH_2$ |
| $CH_3OCH_2(CF_2)_3CH_2$ | $CH_3CH_2$ |

TABLE 3

| $R^1$ | $R^2$ |
|---|---|
| $CF_3CH_2OCH_2(CF_2)_3CH_2$ | $CH_3CH_2$ |
| $CH_3OCH_2(CF_2)_3CH_2$ | $CH_3CH_2$ |
| $CF_3CH_2OCH_2(CF_2)_3CH_2$ | $CH_3CH_2$ |
| $CH_2F(CF_2)_3CH_2$ | $CH_3CH_2$ |
| $CH_2Cl(CF_2)_3CH_2$ | $CH_3CH_2$ |
| $CH_2Br(CF_2)_3CH_2$ | $CH_3CH_2$ |
| $CH_3OCH_2(CF_2)_4CH_2$ | $CH_3CH_2$ |
| $CF_3CH_2OCH_2(CF_2)_4CH_2$ | $CH_3CH_2$ |
| $CH_2F(CF_2)_4CH_2$ | $CH_3CH_2$ |
| $CH_2Cl(CF_2)_4CH_2$ | $CH_3CH_2$ |
| $CH_2Br(CF_2)_4CH_2$ | $CH_3CH_2$ |
| $CF_3CF_2OCFHCF_2$ | $CH_3CH_2$ |
| $CF_3CF_2CF_2OCFHCF_2$ | $CH_3CH_2$ |
| $CF_3CF_2CF_2OCF(CF_3)CH_2$ | $CH_3CH_2$ |
| $CF_3CH_2OCH_2CH_2$ | $CH_3CH_2$ |

TABLE 4

| $R^1$ | $R^2$ |
|---|---|
| (fluorocyclopropyl-methyl structure) | $CH_3CH_2$ |
| (trifluoromethyl-cyclopropyl-methyl structure) | $CH_3CH_2$ |
| (perfluorocyclohexyl-methyl structure) | $CH_3CH_2$ |

TABLE 4-continued

| R¹ | R² |
|---|---|
| 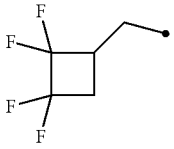 | CH₃CH₂ |
| 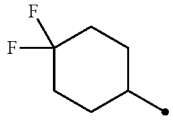 | CH₃CH₂ |
| 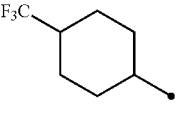 | CH₃CH₂ |
| 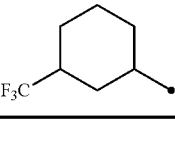 | CH₃CH₂ |

TABLE 5

| R² | R² |
|---|---|
| CH₃SCH₂CF₂CH₂ | CH₃CH₂ |
| CH₃S(O)CH₂CF₂CH₂ | CH₃CH₂ |
| CH₃S(O)₂CH₂CF₂CH₂ | CH₃CH₂ |
| CF₃CH₂SCH₂CF₂CH₂ | CH₃CH₂ |
| CF₃CH₂S(O)CH₂CF₂CH₂ | CH₃CH₂ |
| CF₃CH₂S(O)₂CH₂CF₂CH₂ | CH₃CH₂ |
| CF₃SCH₂CF₂CH₂ | CH₃CH₂ |
| CF₃S(O)CH₂CF₂CH₂ | CH₃CH₂ |
| CF₃S(O)₂CH₂CF₂CH₂ | CH₃CH₂ |
| CF₃SCH₂(CF₂)₂CH₂ | CH₃CH₂ |
| CF₃S(O)CH₂(CF₂)₂CH₂ | CH₃CH₂ |
| CF₃S(O)₂CH₂(CF₂)₂CH₂ | CH₃CH₂ |
| CF₃SCH₂(CF₂)₃CH₂ | CH₃CH₂ |
| CF₃S(O)CH₂(CF₂)₃CH₂ | CH₃CH₂ |
| CF₃S(O)₂CH₂(CF₂)₃CH₂ | CH₃CH₂ |
| CF₃SCH₂(CF₂)₄CH₂ | CH₃CH₂ |
| CF₃S(O)CH₂(CF₂)₄CH₂ | CH₃CH₂ |
| CF₃S(O)₂CH₂(CF₂)₄CH₂ | CH₃CH₂ |
| CF₃CH₂SCH₂CH₂ | CH₃CH₂ |
| CF₃CH₂S(O)CH₂CH₂ | CH₃CH₂ |
| CF₃CH₂S(O)₂CH₂CH₂ | CH₃CH₂ |
| CF₃SCH₂CH₂ | CH₃CH₂ |
| CF₃S(O)CH₂CH₂ | CH₃CH₂ |
| CF₃S(O)₂CH₂CH₂ | CH₃CH₂ |

The compound represented by formula (I-C) of the present invention wherein n represents 1; $R^{3a}$, $R^{3b}$, $R^{3c}$, $R^{6a}$, and $R^{6b}$ represent a hydrogen atom; and $R^1$ and $R^2$ represent any combination indicated in Table 1 to Table 5 (hereinafter, referred to as Compound Group SX2).

The compound represented by formula (I-C) of the present invention wherein n represents 0; $R^{3a}$, $R^{3b}$, $R^{3c}$, $R^{6a}$, and $R^{6b}$ represent a hydrogen atom; and $R^1$ and $R^2$ represent any combination indicated in Table 1 to Table 5 (hereinafter, referred to as Compound Group SX3).

The compound represented by formula (I-C) of the present invention wherein n represents 2; $R^{3a}$, $R^{3c}$, $R^{6a}$, and $R^{6b}$ represent a hydrogen atom; $R^{3b}$ represents a trifluoromethyl group; and $R^1$ and $R^2$ represent any combination indicated in Table 1 to Table 5 (hereinafter, referred to as Compound Group SX4).

The compound represented by formula (I-C) of the present invention wherein n represents 1; $R^{3a}$, $R^{3c}$, $R^{6a}$, and $R^{6b}$ represent a hydrogen atom; $R^{3b}$ represents a trifluoromethyl group; and $R^1$ and $R^2$ represent any combination indicated in Table 1 to Table 5 (hereinafter, referred to as Compound Group SX5).

The compound represented by formula (I-C) of the present invention wherein n represents 0; $R^{3a}$, $R^{3c}$, $R^{6a}$, and $R^{6b}$ represent a hydrogen atom; $R^{3b}$ represents a trifluoromethyl group; and $R^1$ and $R^2$ represent any combination indicated in Table 1 to Table 5 (hereinafter, referred to as Compound Group SX6).

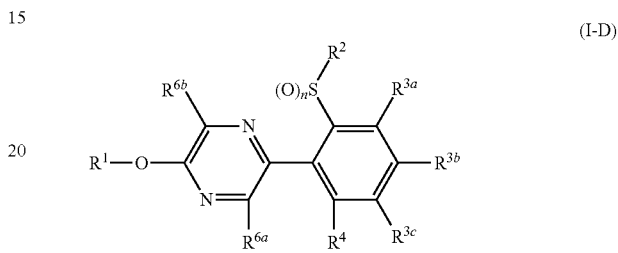

(I-D)

The compound represented by formula (I-D) of the present invention wherein $R^4$ represents a hydrogen atom; n represents 2; $R^{3a}$, $R^{3b}$, $R^{3c}$, $R^{6a}$, and $R^{6b}$ represent a hydrogen atom; and $R^1$ and $R^2$ represent any combination indicated in Table 1 to Table 5 (hereinafter, referred to as Compound Group SX7).

The compound represented by formula (I-D) of the present invention wherein $R^4$ represents a hydrogen atom; n represents 1; $R^{3a}$, $R^{3b}$, $R^{3c}$, $R^{6a}$, and $R^{6b}$ represent a hydrogen atom; and $R^1$ and $R^2$ represent any combination indicated in Table 1 to Table 5 (hereinafter, referred to as Compound Group SX8).

The compound represented by formula (I-D) of the present invention wherein $R^4$ represents a hydrogen atom; n represents 0; $R^{3a}$, $R^{3b}$, $R^{3c}$, $R^{6a}$, and $R^{6b}$ represent a hydrogen atom; and $R^1$ and $R^2$ represent any combination indicated in Table 1 to Table 5 (hereinafter, referred to as Compound Group SX9).

The compound represented by formula (I-D) of the present invention wherein $R^4$ represents a hydrogen atom; n represents 2; $R^{3a}$, $R^{3c}$, $R^{6a}$, and $R^{6b}$ represent a hydrogen atom; $R^{3b}$ represents a trifluoromethyl group; and $R^1$ and $R^2$ represent any combination indicated in Table 1 to Table 5 (hereinafter, referred to as Compound Group SX10).

The compound represented by formula (I-D) of the present invention wherein $R^4$ represents a hydrogen atom; n represents 1; $R^{3a}$, $R^{3c}$, $R^{6a}$, and $R^{6b}$ represent a hydrogen atom; $R^{3b}$ represents a trifluoromethyl group; and $R^1$ and $R^2$ represent any combination indicated in Table 1 to Table 5 (hereinafter, referred to as Compound Group SX11).

The compound represented by formula (I-D) of the present invention wherein $R^4$ represents a hydrogen atom; n represents 0; $R^{3a}$, $R^{3c}$, $R^{6a}$, and $R^{6b}$ represent a hydrogen atom; $R^{3b}$ represents a trifluoromethyl group; and $R^1$ and $R^2$ represent any combination indicated in Table 1 to Table 5 (hereinafter, referred to as Compound Group SX12).

The compound represented by formula (I-D) of the present invention wherein $R^4$ represents a fluorine atom; n represents 2; $R^{3a}$, $R^{3b}$, $R^{3c}$, $R^{6a}$, and $R^{6b}$ represent a hydrogen atom; and $R^1$ and $R^2$ represent any combination indicated in Table 1 to Table 5 (hereinafter, referred to as Compound Group SX13).

The compound represented by formula (I-D) of the present invention wherein R⁴ represents a fluorine atom; n represents 1; R³ᵃ, R³ᵇ, R³ᶜ, R⁶ᵃ, and R⁶ᵇ represent a hydrogen atom; and R¹ and R² represent any combination indicated in Table 1 to Table 5 (hereinafter, referred to as Compound Group SX14).

The compound represented by formula (I-D) of the present invention wherein R⁴ represents a fluorine atom; n represents 0; R³ᵃ, R³ᵇ, R³ᶜ, R⁶ᵃ, and R⁶ᵇ represent a hydrogen atom; and R¹ and R² represent any combination indicated in Table 1 to Table 5 (hereinafter, referred to as Compound Group SX15).

The compound represented by formula (I-D) of the present invention wherein R⁴ represents a fluorine atom; n represents 0; R³ᵃ, R³ᶜ, R⁶ᵃ, and R⁶ᵇ represent a hydrogen atom; R³ᵇ represents a trifluoromethyl group; and R¹ and R² represent any combination indicated in Table 1 to Table 5 (hereinafter, referred to as Compound Group SX16).

The compound represented by formula (I-D) of the present invention wherein R⁴ represents a fluorine atom; n represents 1; R³ᵃ, R³ᶜ, R⁶ᵃ, and R⁶ᵇ represent a hydrogen atom; R³ᵇ represents a trifluoromethyl group; and R¹ and R² represent any combination indicated in Table 1 to Table 5 (hereinafter, referred to as Compound Group SX17).

The compound represented by formula (I-D) of the present invention wherein R⁴ represents a fluorine atom; n represents 0; R³ᵃ, R³ᶜ, R⁶ᵃ, and R⁶ᵇ represent a hydrogen atom; R³ᵇ represents a trifluoromethyl group; and R¹ and R² represent any combination indicated in Table 1 to Table 5 (hereinafter, referred to as Compound Group SX18).

The compound of the present invention may be mixed or combined with one or more kinds of ingredients selected from a group consisting of the following Group (a), Group (b), Group (c), and Group (d) (hereinafter, referred to as Present active ingredient). Preferably, the present active ingredient includes one or more kinds of ingredients selected from a group consisting of sub group a-1, sub group a-2, sub group a-3, sub group a-4, sub group a-5, sub group a-6, sub group a-7, sub group a-8, sub group a-9, sub group b-1, sub group b-2, sub group b-3, sub group b-4, sub group b-5, sub group b-6, sub group b-7, sub group b-8, sub group b-9, sub group b-10, sub group b-11, sub group b-12, sub group b-13, sub group b-14, sub group b-15, sub group b-16, sub group c-1, sub group c-2, and Group (d). Particularly preferably, the present active ingredient includes one or more kinds of ingredients selected from a group consisting of sub group a-6, sub group a-9, sub group b-1, sub group b-3, sub group b-4, sub group b-5, sub group b-9, sub group b-11, and sub group b-13.

Group (a) represents a group of one or more kinds of insecticidal ingredients, miticidal ingredients, and nematicidal ingredients selected from the group consisting of the following sub group a-1 to a-10. The numerical number in bracket represents a CAS register number.

Sub Group a-1:
Carbamate acetylcholinesterase (AChE) inhibitor group selected from the group consisting of alanycarb, aldicarb, bendiocarb, benfuracarb, butocarboxim, butoxycarboxim, carbaryl: NAC, carbofuran, carbosulfan, ethiofencarb, fenobucarb: BPMC, formetanate, furathiocarb, isoprocarb: MIPC, methiocarb, methomyl, metolcarb, oxamyl, pirimicarb, propoxur: PHC, thiodicarb, thiofanox, triazamate, trimethacarb, XMC, and xylylcarb.

Sub Group a-2:
Organophosphorus acetylcholinesterase (AChE) inhibitor group selected from the group consisting of acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos: CYAP, demeton-S-methyl, diazinon, dichlorvos: DDVP, dicrotophos, dimethoate, dimethylvinphos, disulfoton, EPN, ethion, ethoprophos, famphur, fenamiphos, fenitrothion: MEP, fenthion: MPP, fosthiazate, heptenophos, imicyafos, isofenphos, isopropyl-O-(methoxyaminothiophosphoryl)salicylate, isoxathion, malathion, mecarbam, methamidophos, methidathion: DMTP, mevinphos, monocrotophos, naled: BRP, omethoate, oxydemeton-methyl, parathion, parathion-methyl, phenthoate: PAP, phorate, phosalone, phosmet: PMP, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon: DEP, and vamidothion.

Sub Group a-3:
GABA-gated chloride channel blockers group selected from the group consisting of ethiprole, fipronil, flufiprole, chlordane, endosulfan, and alpha-endosulfan.

Sub Group a-4:
GABA-gated chloride channel allosteric modulator group selected from the group consisting of afoxolaner, fluralaner, broflanilide, and fluxametamide.

Sub Group a-5:
Sodium channel modulator group selected from the group consisting of acrinathrin, allethrin, bifenthrin, kappa-bifenthrin, bioallethrin, bioresmethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, fluvalinate, tau-fluvalinate, halfenprox, heptafluthrin, imiprothrin, kadethrin, meperfluthrin, momfluorothrin, permethrin, phenothrin, prallethrin, pyrethrins, resmethrin, silafluofen, tefluthrin, kappa-tefluthrin, tetramethrin, tetramethylfluthrin, tralomethrin, transfluthrin, benfluthrin, flufenoprox, flumethrin, sigma-cypermethrin, furamethrin, metofluthrin, profluthrin, dimefluthrin, epsilon-metofluthrin, epsilon-momfluorothrin, and methoxychlor.

Sub Group a-6:
Nicotinic acetylcholine receptor (nAChR) competitive modulator group selected from the group consisting of acetamiprid, clothianidin, dinotefuran, imidacloprid, nitenpyram, thiacloprid, thiamethoxam, sulfoxaflor, flupyradifurone, triflumezopyrim, dicloromezotiaz, cycloxaprid, and a compound represented by the following formula:

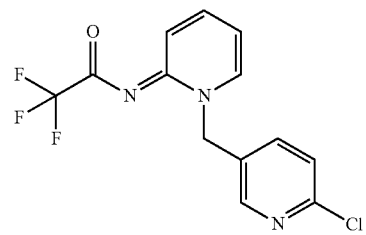 [SMILES: O=C(/N=c1\ccccn1Cc1ccc(Cl)nc1)C(F)(F)F]

(1363400-41-2, hereinafter, referred to as insecticidal compound α1).

Sub Group a-7:
Ryanodine receptor modulator group selected from the group consisting of chlorantraniliprole, cyantraniliprole, cycloniliprole, flubendiamide, tetraniliprole, cyhalodiamide, and a compound represented by the following formula:

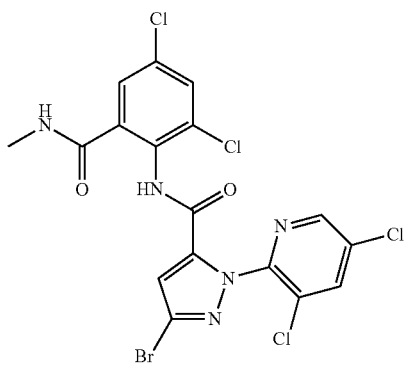 [SMILES: CNC(=O)c1cc(Cl)cc(Cl)c1NC(=O)c1cc(Br)nn1-c1ncc(Cl)cc1Cl]

(1104384-14-6, hereinafter, referred to as insecticidal compound α2).

Sub Group a-8:
Microbial material group selected from the group consisting of *Beauveria bassiana*, *Beauveria bassiana* strain GHA, *Beauveria brongniartii*, *Paecilomyces fumosoroseus*, *Paecilomyces lilacinus*, *Paecilomyces tenuipes*, *Verticillium lecani*, *Arthrobotrys dactyloides*, *Bacillus thuringiensis*, *Bacillus firmus*, *Bacillus firmus* strain CNCM 1-1582, *Bacillus megaterium*, *Hirsutella rhossiliensis*, *Hirsutella minnesotensis*, *Monacrosporium phymatopagus*, *Pasteuria nishizawae*, *Pasteuria penetrans*, *Pasteuria usgae*, and *Verticillium chlamydosporium*.

Sub Group a-9:
Nematicidal ingredients group selected from the group consisting of abamectin, fluazaindolizine, fluensulfone, fluopyram, and tioxazafen.

Sub Group a-10:
The other group as insecticides and miticides selected from the group consisting of spinetoram, spinosad, emamectin-benzoate, lepimectin, milbemectin, hydroprene, kinoprene, methoprene, fenoxycarb, pyriproxyfen, methyl bromide, chloropicrin, sulfuryl fluoride, sodium aluminium fluoride or chiolite, borax, boric acid, disodium octaborate, sodium borate, sodium metaborate, tartar emetic, dazomet, metam, pymetrozine, pyrifluquinazone, clofentezine, hexythiazox, diflovidazin, etoxazole, diafenthiuron, azocyclotin, cyhexatin, fenbutatin oxide, propargite, tetradifon, chlorfenapyr, DNOC, sulfluramid, bensultap, cartap, cartap hydrochloride, thiocyclam, thiosultap-disodium, thiosultap-monosodium, bistrifluron, chlorfluazuron, diflubenzuron, fluazuron, flucycloxuron, flufenoxuron, hexaflumuron, lufenuron, novaluron, noviflumuron, teflubenzuron, triflumuron, buprofezin, cyromazine, chromafenozide, halofenozide, methoxyfenozide, tebufenozide, amitraz, hydramethylnon, acequinocyl, fluacrypyrim, bifenazate, fenazaquin, fenpyroximate, pyridaben, pyrimidifen, tebufenpyrad, tolfenpyrad, rotenone, indoxacarb, metaflumizone, spirodiclofen, spiromesifen, spirotetramat, aluminium phosphide, calcium phosphide, phosphine, zinc phosphide, calcium cyanide, potassium cyanide, sodium cyanide, cyenopyrafen, cyflumetofen, pyflubumide, flonicamid, azadirachtin, benzoximate, bromopropylate, chinomethionat, dicofol, pyridalyl, lime sulfur, sulfur, machine oil, nicotine, nicotine-sulfate, afidopyropen, flometoquin, metoxadiazone, pyriminostrobin, a compound represented by the following formula:

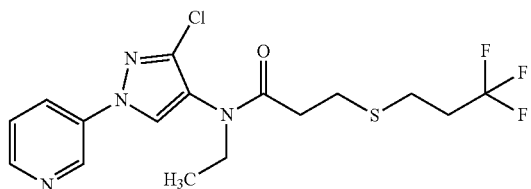 [SMILES: CCN(C(=O)CCSCCC(F)(F)F)c1cn(-c2cccnc2)nc1Cl]

(1477919-27-9, hereinafter, referred to as fungicide compound α3), a compound represented by the following formula:

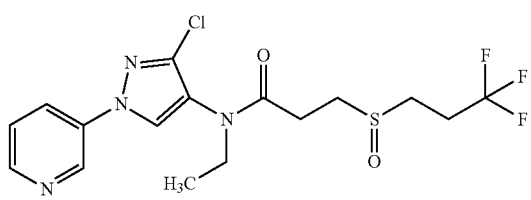 [SMILES: CCN(C(=O)CCS(=O)CCC(F)(F)F)c1cn(-c2cccnc2)nc1Cl]

(1477923-37-7, hereinafter, referred to as fungicide compound α4), and a compound represented by the following formula:

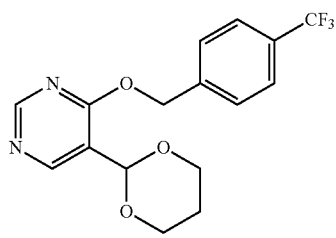 [SMILES: FC(F)(F)c1ccc(COc2ncncc2C2OCCCO2)cc1]

(1449021-97-9, hereinafter, referred to as fungicide compound α5).

Group (b) represents a fungicidal ingredient group selected from the group consisting of the following sub group b-1 to sub group b-18.

Sub Group b-1
PA fungicide (Phenyl amide) selected from the group consisting of benalaxyl, benalaxyl-M, furalaxyl, metalaxyl, metalaxyl-M, oxadixyl, and ofurace.

Sub Group b-2
MBC fungicide (methyl benzimidazole carbamate) group selected from the group consisting of benomyl, carbendazim, fuberidazole, thiabendazole, thiophanate, and thiophanate-methyl.

Sub Group b-3
Thiazole carboxamide group selected from the group consisting of ethaboxam.

Sub Group b-4
SDHI (Succinate dehydrogenase inhibitor) group selected from the group consisting of benodanil, flutolanil, mepronil, isofetamid, fenfuram, carboxin, oxycarboxin, thifluzamide, benzovindiflupyr, bixafen, fluxapyroxad, furametpyr, isopyrazam, penflufen, penthiopyrad, sedaxane, pydiflumetofen, boscalid, pyraziflumid, 3-difluoromethyl-1-methyl-N-(1,1,3-trimethylindan)-4-yl)pyrazole-4-carboxamide (141573-94-6, hereinafter, referred to as fungicide compound β1), 3-difluoromethyl-1-methyl-N-[(3R)-1,1,3-trimethylindan-4-yl]pyrazole-4-carboxamide (1352994-67-2, hereinafter, referred to as fungicide compound β2), 3-difluoromethyl- N-(7-fluoro-1,1,3-trimethylindan-4-yl)-1-methylpyrazole-4-carboxamide (1383809-87-7, hereinafter, referred to as fungicide compound β3), 3-difluoromethyl-N-[(3R)-7-fluoro-1,1,3-trimethylindan-4-yl)-1-methylpyrazole-4-carboxamide (1513466-73-3, hereinafter, referred to as fungicide compound β4), and N-cyclopropyl-3-(difluoromethyl)-5-fluoro-N-(5-chloro-2-isopropylbenzyl)-1-methyl-1H-pyrazole-4-carboxamide (1255734-28-1, hereinafter, referred to as fungicide compound β5).

Sub Group b-5
QoI fungicide (Qo Inhibitor) group selected from the group consisting of azoxystrobin, coumoxystrobin, enoxastrobin, flufenoxystrobin, picoxystrobin, pyraoxystrobin, mandestrobin, pyraclostrobin, pyrametostrobin, triclopyricarb, kresoxim-methyl, trifloxystrobin, dimoxystrobin, fenaminstrobin, metominostrobin, orysastrobin, famoxadone, fluoxastrobin, fenamidone, and pyribencarb.

Sub Group b-6
QiI fungicide (Qi Inhibitor) group selected from the group consisting of cyazofamid, amisulbrom, binapacryl, meptyldinocap, dinocap, and fluazinam.

Sub Group b-7
Thiophanate carboxamide group selected from the group consisting of silthiofam.

Sub Group b-8
AP fungicide (Anilinopyrimidine) group selected from the group consisting of cyprodinil, mepanipyrim, and pyrimethanil.

Sub Group b-9
PP fungicide (Phenylpyrrole) group selected from the group consisting of fenpiclonil and fludioxonil.

Sub Group b-10
AH fungicide (Aromaic hydrocarbons) group selected from the group consisting of biphenyl, chloroneb, dicloran, quintozene, tecnazene, and tolclofos-methyl.

Sub Group b-11
DMI fungicide (Demethylation inhibitor) group selected from the group consisting of azaconazole, bitertanol, bromuconazole, cyproconazole, difenoconazole, diniconazole, diniconazole-M, fenbuconazole, fluquinconazole, flusilazole, flutriafol, hexaconazole, imibenconazole, ipconazole, ipfentrifluconazole, mefentrifluconazole, metconazole, myclobutanil, penconazole, propiconazole, simeconazole, tebuconazole, tetraconazole, triadimefon, triadimenol, triticonazole, prothioconazole, triforine, pyrifenox, pyrisoxazole, fenarimol, nuarimol, imazalil, oxpoconazole, oxpoconazole fumarate, pefurazoate, prochloraz, and triflumizole.

Sub Group b-12
CCA fungicide (Carboxylic acid amide) group selected from the group consisting of dimethomorph, flumorph, pyrimorph, benthiavalicarb, benthivalicarb-isopropyl, iprovalicarb, valifenalate, and mandipropamid.

Sub Group b-13
Piperidinyl thiazole isoxazoline group selected from the group consisting of oxathiapiprolin.

Sub Group b-14
Tetrazolyl oxime group selected from the group consisting of picarbutrazox.

Sub Group b-15
Dithiocarbamate group selected from the group consisting of ferbam, mancozeb, maneb, metiram, propineb, thiram, zineb, and ziram.

Sub Group b-16
Phthalimide group selected from the group consisting of captan, captafol, and folpet.

Sub Group b-17
Microbial fungicide group selected from the group consisting of *Agrobacterium radiobactor, Bacillus amyloliquefaciens, Bacillus amyloliquefaciens* strain QST713, *Bacillus amyloliquefaciens* strain FZB24, *Bacillus amyloliquefaciens* strain MBI600, *Bacillus amyloliquefaciens* strain D747, *Bacillus amyloliquefaciens* strain AT-332, *Bacillus pumilus, Bacillus pumilus* strain GB34, *Bacillus pumilus* strain QST2808, *Bacillus subtilis, Erwinia carotovora* (CGE234M403 strain and so on), *Pseudomonas fluorescens* (G7090 strain and so on), *Talaromyces flavus* (SAY-Y-94-01 strain and so on), *Trichoderma atroviride* (SKT-1 strain and so on), *Trichoderma harzianum*, and Harpin protein.

Sub Group b-18
Other fungicide group selected from the group consisting of bupirimate, dimethirimol, ethirimol, hymexazole, octhilinone, oxolinic acid, diethofencarb, zoxamide, pencycuron, fluopicolide, phenamacril, diflumetorim, tolfenpyrad, fentin acetate, fentin chloride, fentin hydroxide, ametoctradin, blasticidin-S, kasugamycin, streptomycin, oxytetracycline, quinoxyfen, proquinazid, chlozolinate, dimethachlone, iprodione, procymidone, vinclozolin, edifenphos, iprobenfos, pyrazophos, isoprothiolane, etridiazole, iodocarb, propamocarb, prothiocarb, aldimorph, dodemorph, fenpropidin, fenpropimorph, piperalin, spiroxamine, tridemorph, fenhexamid, fenpyrazamine, pyributicarb, naftifine, terbinafine, polyoxins, phthalide, pyroquilon, tricyclazole, carpropamid, diclocymet, fenoxanil, tolprocarb, acibenzolar-S-methyl, probenazole, tiadinil, isotianil, laminarin, cymoxanil, fosetyl, teclofthalam, triazoxide, flusulfamide, diclomezine, methasulfocarb, cyflufenamid, metrafenone, pyriofenone, dodine, flutianil, ferimzone, tebufloquin, validamycin, basic copper chloride, copper(II) hydroxide, basic copper sulfate, Dodecylbenzenesulphonic acid bisethylenediamine copper [II] salt (DBEDC), organocopper, sulfur, chlorothalonil, dichlofluanid, tolylfluanid, guazatine, iminoctadine, anilazine, dithianon, chinomethionat, fluoroimide, dipymetitrone, quinofumelin, dichlobentiazox, 3-chloro-5-phenyl-6-methyl-4-(2,6-difluorophenyl)pyridadine (1358061-55-8; hereinafter, referred to as fungicide compound β6), a compound represented by the following formula:

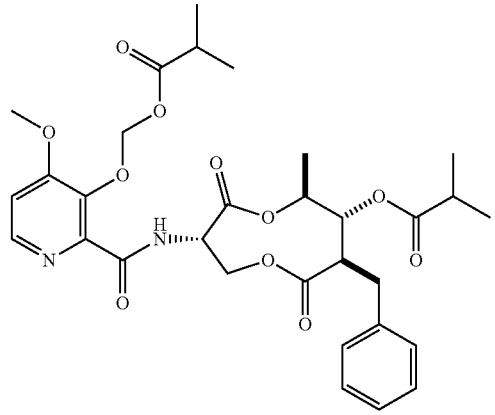 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

(517875-34-2; hereinafter, referred to as fungicide compound β7), N'-[4-({3-[(4-chlorophenyl)methyl]-1,2,4-thiadiazol-5-yl}oxy)-2,5-dimethylphenyl]-N-ethyl-N-methyl-methaneimidamide (1202781-91-6; hereinafter, referred to as fungicide compound β8), 4-(2-bromo-4-fluorophenyl)-N-(2-chloro-6-fluorophenyl)-1,3-dimethyl-1H-pyrazole-5-amine (1362477-26-6; hereinafter, referred to as fungicide compound β9), 2,2-dimethy-9-fluoro-5-(quinolin-3-yl)-2,3- dihydrobenzo[f][1,4]oxazepine (1207749-50-5; hereinafter, referred to as fungicide compound β10), 2-[6-(3-fluoro-4-methoxyphenyl)-4-methylpyridin-2-yl]quinazoline (1257056-97-5; hereinafter, referred to as fungicide compound β11), 5-fluoro-2-[(4-methylphenyl)methoxy]-4-pyrimidineamine (1174376-25-0; hereinafter, referred to as fungicide compound β12), 5-fluoro-4-imino-3-methyl-1-tosyl-3,4-dihydropyrimidine-2(1H)-one (1616664-98-2; hereinafter, referred to as fungicide compound β13), N'-(2,5-dimethyl-4-phenoxyphenyl)-N-ethyl-N-methylmethaneimideamide (1052688-31-9; hereinafter, referred to as fungicide compound β14), N'-{4-[(4,5-dichlorothiazol-2-yl)oxy]-2,5-dimethylphenyl}-N-ethyl-N-methylmethaneimideamide (929908-57-6; hereinafter, referred to as fungicide compound β15), ethyl (2Z)-3-amino-2-cyano-3-phenylacrylate (39491-78-6; hereinafter, referred to as fungicide compound β16), N-[(2-chlorothiazol-5-yl)methyl]-N-ethyl-6-methoxy-3-nitropyridine-2-amine (1446247-98-8; hereinafter, referred to as fungicide compound β17), and 1-[2-({[1-(4-chlorophenyl)-1H-pyrazol-3-yl]oxy}methyl)-3-methylpenyl]-4-methyl-5-oxo-4,5-dihydro-1H-tetrazole (1472649-01-6, hereinafter, referred to as fungicide compound β18).

Group (c) represents a plant growth modulating ingredients group selected from the group consisting of the following sub group c-1, sub group c-2, and sub group c-3.

Sub Group c-1:
Plant growth modulating ingredients group selected from the group consisting of ethephon, chlormequat, chlormequat-chloride, mepiquat, mepiquat-chloride, Gibberellin A3, abscisic acid, Kinetin, benzyladenine, forchlorfenuron, and thidiazuron.

Sub Group c-2:
Mycorrhizal fungi group selected from the group consisting of *Glomus* spp., *Glomus intraradices*, *Glomus mosseae*, *Glomus aggregatum*, and *Glomus etunicatum*.

Sub Group c-3:
Root nodule bacteria group selected from the group consisting of *Bradyrhizobium elkani*, *Bradyrhizobium japonicum*, *Bradyrhizobium lupini*, *Rhizobium leguminosarum* bv. *trifolii*, *Rhizobium leguminosarum* bv. *phaseoli*, *Rhizobium leguminosarum* bv. *viciae*, *Sinorhizobium meliloti*, and *Rhizobium* spp.

Group (d):
Phytotoxicity-reducing ingredient group selected from the group consisting of benoxacor, cloquintocet-mexyl, cyometrinil, dichlormid, fenchlorazole-ethyl, fenclorim, flurazole, furilazole, mefenpyr-diethyl, MG191 (2-(dichloromethyl)-2-methyl-1,3-dioxolane), oxabetrinil, allidochlor, isoxadifen-ethyl, cyprosulfamide, fluxofenim, 1,8-naphthalic anhydride, and AD-67 (4-(dichloroacetyl)-1-oxa-4-azaspiro [4.5] decane).

Examples of the combination of the present active ingresient and the Present compound in the present composition are described below. The symbol of "SX" represents any one of the Present compound selected from the compound group SX1 to the compound group SX18. Also, all the below-mentioned present active ingredient are known active ingredients, and are commercially available, may be produced by the known method, or are available from the bacterial authority depository.

alanycarb+SX, aldicarb+SX, bendiocarb+SXbenfuracarb+SX, butocarboxim+SX, butoxycarboxim+SX, carbaryl: NAC+SX, carbofuran+SX, carbosulfan+SX, ethiofencarb+SX, fenobucarb: BPMC+SX, formetanate+SX, furathiocarb+SX, isoprocarb: MIPC+SX, methiocarb+SX, methomyl+SX, metolcarb+SX, oxamyl+SX, pirimicarb+SX, propoxur: PHC+SX, thiodicarb+SX, thiofanox+SX, triazamate+SX, trimethacarb+SX, XMC+SX, xylylcarb+SX;

acephate+SX, azamethiphos+SX, azinphos-ethyl+SX, azinphos-methyl+SX, cadusafos+SX, chlorethoxyfos+SX, chlorfenvinphos+SX, chlormephos+SX, chlorpyrifos+SX, chlorpyrifos-methyl+SX, coumaphos+SX, cyanophos: CYAP+SX, demeton-S-methyl+SX, diazinon+SX, dichlorvos: DDVP+SX, dicrotophos+SX, dimethoate+SX, dimethylvinphos+SX, disulfoton+SX, EPN+SX, ethion+SX, ethoprophos+SX, famphur+SX, fenamiphos+SX, fenitrothion: MEP+SX, fenthion: MPP+SX, fosthiazate+SX, heptenophos+SX, imicyafos+SX, isofenphos+SX, isopropyl-O-(methoxyaminothiophosphoryl)salicylate+SX, isoxathion+SX, malathion+SX, mecarbam+SX, methamidophos+SX, methidathion: DMTP+SX, mevinphos+SX, monocrotophos+SX, naled: BRP+SX, omethoate+SX, oxydemeton-methyl+SX, parathion+SX, parathion-methyl+SX, phenthoate: PAP+SX, phorate+SX, phosalone+SX, phosmet: PMP+SX, phosphamidon+SX, phoxim+SX, pirimiphos-methyl+SX, profenofos+SX, propetamphos+SX, prothiofos+SX, pyraclofos+SX, pyridaphenthion+SX, quinalphos+SX, sulfotep+SX, tebupirimfos+SX, temephos+SX, terbufos+SX, tetrachlorvinphos+SX, thiometon+SX, triazophos+SX, trichlorfon: DEP+SX, vamidothion+SX;
ethiprole+SX, fipronil+SX, flufiprole+SX, chlordane+SX, endosulfan+SX, alpha-endosulfan+SX;
afoxolaner+SX, fluralaner+SX, broflanilide+SX, fluxametamide+SX;
acrinathrin+SX, allethrin+SX, bifenthrin+SX, kappa-bifenthrin+SX, bioallethrin+SX, bioresmethrin+SX, cycloprothrin+SX, cyfluthrin+SX, beta-cyfluthrin+SX, cyhalothrin+SX, gamma-cyhalothrin+SX, lambda-cyhalothrin+SX, cypermethrin+SX, alpha-cypermethrin+SX, beta-cypermethrin+SX, theta-cypermethrin+SX, zeta-cypermethrin+SX, cyphenothrin+SX, deltamethrin+SX, empenthrin+SX, esfenvalerate+SX, etofenprox+SX, fenpropathrin+SX, fenvalerate+SX, flucythrinate+SX, flumethrin+SX, fluvalinate+SX, tau-fluvalinate+SX, halfenprox+SX, heptafluthrin+SX, imiprothrin+SX, kadethrin+SX, meperfluthrin+SX, momfluorothrin+SX, permethrin+SX, phenothrin+SX, prallethrin+SX, pyrethrins+SX, resmethrin+SX, silafluofen+SX, tefluthrin+SX, kappa-tefluthrin+SX, tetramethrin+SX, tetramethylfluthrin+SX, tralomethrin+SX, transfluthrin+SX, benfluthrin+SX, flufenoprox+SX, flumethrin+SX, sigma-cypermethrin+SX, furamethrin+SX, metofluthrin+SX, profluthrin+SX, dimefluthrin+SX, epsilon-metofluthrin+SX, epsilon-momfluorothrin+SX, methoxychlor+SX;
acetamiprid+SX, clothianidin+SX, dinotefuran+SX, imidacloprid+SX, nitenpyram+SX, thiacloprid+SX, thiamethoxam+SX, sulfoxaflor+SX, flupyradifurone+SX, triflumezopyrim+SX, dicloromezotiaz+SX, cycloxaprid+SX, insecticidal compound α1+SX;
chlorantraniliprole SX, cyantraniliprole SX, cycloniliprole+SX, flubendiamide+SX, tetraniliprole+SX, cyhalodiamide+SX, insecticidal compound α2+SX;
*Beauveria bassiana*+SX, *Beauveria bassiana* strain GHA+SX, *Beauveria brongniartii*+SX, *Paecilomyces fumosoroseus*+SX, *Paecilomyces lilacinus*+SX, *Paecilomyces tenuipes*+SX, *Verticillium lecani*+SX, *Arthrobotrys dactyloides*+SX, *Bacillus thuringiensis*+SX, *Bacillus firmus*+SX, *Bacillus firmus* strain CNCM 1-1582+SX, *Bacillus megaterium*+SX, *Hirsutella rhossiliensis*+SX, *Hirsutella minnesotensis*+SX, *Monacrosporium phymatopagus*+SX, *Pasteuria nishizawae*+SX, *Pasteuria penetrans*+SX, *Pasteuria usgae*+SX, *Verticillium chlamydosporium*+SX;

abamectin+SX, fluazaindolizine+SX, fluensulfone+SX, fluopyram+SX, tioxazafen+SX;
spinetoram+SX, spinosad+SX, emamectin-benzoate+SX, lepimectin+SX, milbemectin+SX, hydroprene+SX, kinoprene+SX, methoprene+SX, fenoxycarb+SX, pyriproxyfen+SX, methyl bromide+SX, chloropicrin+SX, sulfuryl fluoride+SX, sodium aluminium fluoride or chiolite+SX, borax+SX, boric acid+SX, disodium octaborate+SX, sodium borate+SX, sodium metaborate+SX, tartar emetic+SX, dazomet+SX, metam+SX, pymetrozine+SX, pyrifluquinazone+SX, clofentezine+SX, hexythiazox+SX, diflovidazin+SX, etoxazole+SX, diafenthiuron+SX, azocyclotin+SX, cyhexatin+SX, fenbutatin oxide+SX, propargite+SX, tetradifon+SX, chlorfenapyr+SX, DNOC+SX, sulfluramid+SX, bensultap+SX, cartap+SX, cartap hydrochloride+SX, thiocyclam+SX, thiosultap-disodium+SX, thiosultap-monosodium+SX, bistrifluron+SX, chlorfluazuron+SX, diflubenzuron+SX, fluazuron+SX, flucycloxuron+SX, flufenoxuron+SX, hexaflumuron+SX, lufenuron+SX, novaluron+SX, noviflumuron+SX, teflubenzuron+SX, triflumuron+SX, buprofezin+SX, cyromazine+SX, chromafenozide+SX, halofenozide+SX, methoxyfenozide+SX, tebufenozide+SX, amitraz+SX, hydramethylnon+SX, acequinocyl+SX, fluacrypyrim+SX, bifenazate+SX, fenazaquin+SX, fenpyroximate+SX, pyridaben+SX, pyrimidifen+SX, tebufenpyrad+SX, tolfenpyrad+SX, rotenone+SX, indoxacarb+SX, metaflumizone+SX, spirodiclofen+SX, spiromesifen+SX, spirotetramat+SX, aluminium phosphide+SX, calcium phosphide+SX, phosphine+SX, zinc phosphide+SX, calcium cyanide+SX, potassium cyanide+SX, sodium cyanide+SX, cyenopyrafen+SX, cyflumetofen+SX, pyflubumide+SX, flonicamid+SX, azadirachtin+SX, benzoximate+SX, bromopropylate+SX, chinomethionat+SX, dicofol+SX, pyridalyl+SX, lime sulfur+SX, sulfur+SX, machine oil+SX, nicotine+SX, nicotine-sulfate+SX, afidopyropen+SX, flometoquin+SX, metoxadiazone+SX, pyriminostrobin+SX, insecticidal compound α3+SX, insecticidal compound α4+SX, insecticidal compound α5+SX;
benalaxyl+SX, benalaxyl-M+SX, furalaxyl+SX, metalaxyl+SX, metalaxyl-M+SX, oxadixyl+SX, ofurace+SX;
benomyl+SX, carbendazim+SX, fuberidazole+SX, thiabendazole+SX, thiophanate+SX, thiophanate-methyl+SX;
ethaboxam+SX;
benodanil+SX, flutolanil+SX, mepronil+SX, isofetamid+SX, fenfuram+SX, carboxin+SX, oxycarboxin+SX, thifluzamide+SX, benzovindiflupyr+SX, bixafen+SX, fluxapyroxad+SX, furametpyr+SX, isopyrazam+SX, penflufen+SX, penthiopyrad+SX, sedaxane+SX, pydiflumetofen+SX, boscalid+SX, pyraziflumid+SX, fungicide compound β1+SX, fungicide compound β2+SX, fungicide compound β3+SX, fungicide compound β4+SX, fungicide compound β5+SX;
azoxystrobin+SX, coumoxystrobin+SX, enoxastrobin+SX, flufenoxystrobin+SX, picoxystrobin+SX, pyraoxystrobin+SX, mandestrobin+SX, pyraclostrobin+SX, pyrametostrobin+SX, triclopyricarb+SX, kresoxim-methyl+SX, trifloxystrobin+SX, dimoxystrobin+SX, fenaminstrobin+SX, metominostrobin+SX, orysastrobin+SX, famoxadone+SX, fluoxastrobin+SX, fenamidone+SX, pyribencarb+SX;
cyazofamid+SX, amisulbrom+SX, binapacryl+SX, meptyldinocap+SX, dinocap+SX, fluazinam+SX;
silthiofam+SX;
cyprodinil+SX, mepanipyrim+SX, pyrimethanil+SX;
fenpiclonil+SX, fludioxonil+SX;
biphenyl+SX, chloroneb+SX, dicloran+SX, quintozene+SX, tecnazene+SX, tolclofos-methyl+SX;
azaconazole+SX, bitertanol+SX, bromuconazole+SX, cyproconazole+SX, difenoconazole+SX, diniconazole+SX, diniconazole-M+SX, epoxiconazole+SX, etaconazole+SX, fenbuconazole+SX, fluquinconazole+SX, flusilazole+SX, flutriafol+SX, hexaconazole+SX, imibenconazole+SX, ipconazole+SX, ipfentrifluconazole+SX, mefentrifluconazole+SX, metconazole+SX, myclobutanil+SX, penconazole+SX, propiconazole+SX, simeconazole+SX, tebuconazole+SX, tetraconazole+SX, triadimefon+SX, triadimenol+SX, triticonazole+SX, prothioconazole+SX, triforine+SX, pyrifenox+SX, pyrisoxazole+SX, fenarimol+SX, nuarimol+SX, imazalil+SX, oxpoconazole+SX, oxpoconazole fumarate+SX, pefurazoate+SX, prochloraz+SX, triflumizole+SX;
dimethomorph+SX, flumorph+SX, pyrimorph+SX, benthiavalicarb+SX, benthivalicarb-isopropyl+SX, iprovalicarb+SX, valifenalate+SX, mandipropamid+SX;
oxathiapiprolin+SX;
picarbutrazox+SX;
ferbam+SX, mancozeb+SX, maneb+SX, metiram+SX, propineb+SX, thiram+SX, zineb+SX, ziram+SX;
captan+SX, captafol+SX, folpet+SX;
*Agrobacterium radiobactor*+SX, *Bacillus amyloliquefaciens*+SX, *Bacillus amyloliquefaciens* strain QST713+SX, *Bacillus amyloliquefaciens* strain FZB24+SX, *Bacillus amyloliquefaciens* strain MBI600+SX, *Bacillus amyloliquefaciens* strain D747+SX, *Bacillus amyloliquefaciens* strain AT-332+SX, *Bacillus pumilus*+SX, *Bacillus pumilus* strain GB34+SX, *Bacillus pumilus* strain QST2808+SX, *Bacillus subtilis*+SX, *Erwinia carotovora* (such as CGE234M403 stain)+SX, *Pseudomonas fluorescens* (such as G7090 strain)+SX, *Talaromyces flavus* (such as SAY-Y-94-01 strain)+SX, *Trichoderma atroviride* (such as SKT-1 strain)+SX, *Trichoderma harzianum*+SX, Harpin protein+SX;
bupirimate+SX, dimethirimol+SX, ethirimol+SX, hymexazole+SX, octhilinone+SX, oxolinic acid+SX, diethofencarb+SX, zoxamide+SX, pencycuron+SX, fluopicolide+SX, phenamacril+SX, diflumetorim+SX, tolfenpyrad+SX, fentin acetate+SX, fentin chloride+SX, fentin hydroxide+SX, ametoctradin+SX, blasticidin-S+SX, kasugamycin+SX, streptomycin+SX, oxytetracycline+SX, quinoxyfen+SX, proquinazid+SX, chlozolinate+SX, dimethachlone+SX, iprodione+SX, procymidone+SX, vinclozolin+SX, edifenphos+SX, iprobenfos+SX, pyrazophos+SX, isoprothiolane+SX, etridiazole+SX, iodocarb+SX, propamocarb+SX, prothiocarb+SX, aldimorph+SX, dodemorph+SX, fenpropidin+SX, fenpropimorph+SX, piperalin+SX, spiroxamine+SX, tridemorph+SX, fenhexamid+SX, fenpyrazamine+SX, pyributicarb+SX, naftifine+SX, terbinafine+SX, polyoxins+SX, phthalide+SX, pyroquilon+SX, tricyclazole+SX, carpropamid+SX, diclocymet+SX, fenoxanil+SX, tolprocarb+SX, acibenzolar-S-methyl+SX, probenazole+SX, tiadinil+SX, isotianil+SX, laminarin+SX, cymoxanil+SX, fosetyl+SX, teclofthalam+SX, triazoxide+SX, flusulfamide+SX, diclomezine+SX, methasulfocarb+SX, cyflufenamid+SX, metrafenone+SX, pyriofenone+SX, dodine+SX, flutianil+SX, ferimzone+SX, tebufloquin+SX, validamycin+SX, basic copper chloride+SX, copper(II) hydroxide+SX, basic copper sulphate+SX, Dodecylbenzenesulphonic acid bisethylenediamine copper [II] salt (DBEDC)+SX, organocopper+SX, sulfur+SX, chlorothalonil+SX, dichlofluanid+SX, tolylfluanid+SX, guazatine+SX, iminoctadine+SX, anilazine+SX, dithianon+SX, chinomethionat+SX, fluoroimide+SX, dipymetitrone+SX, quinofumelin+SX, dichlobentiazox+SX, fungicide compound β6+SX, fungicide compound β7+SX, fungicide compound β8+SX, fungicide compound β9+SX, fungicide compound β10+SX, fungicide compound β11+SX, fungicide compound β12+SX, fungicide compound β13+SX, fungicide compound β14+SX, fungicide compound β15+SX, fungicide compound β16+SX, fungicide compound β17+SX, fungicide compound β18+SX;

ethephon+SX, chlormequat+SX, chlormequat-chloride+SX, mepiquat+SX, mepiquat-chloride+SX, Gibberellin A3+SX, abscisic acid+SX, Kinetin+SX, benzyladenine+SX, forchlorfenuron+SX, thidiazuron+SX;

Glomus spp.+SX, Glomus intraradices+SX, Glomus mosseae+SX, Glomus aggregatum+SX, Glomus etunicatum+SX;

Bradyrhizobium elkani+SX, Bradyrhizobium japonicum+SX, Bradyrhizobium lupini+SX, Rhizobium leguminosarum bv. trifolii+SX, Rhizobium leguminosarum bv. phaseoli+SX, Rhizobium leguminosarum bv. viciae+SX, Sinorhizobium meliloti+SX, Rhizobium spp.+SX;

benoxacor+SX, cloquintocet-mexyl+SX, cyometrinil+SX, dichlormid+SX, fenchlorazole-ethyl+SX, fenclorim+SX, flurazole+SX, furilazole+SX, mefenpyr-diethyl+SX, MG191 (2-(dichloromethyl)-2-methyl-1,3-dioxolane)+SX, oxabetrinil+SX, allidochlor+SX, isoxadifen-ethyl+SX, cyprosulfamide+SX, fluxofenim+SX, 1,8-naphthalic anhydride+SX, AD-67 4-(dichloroacetyl)-1-oxa-4-azaspiro [4.5] decane)+SX.

In the composition of the present invention, the weight ratio of the Present compound to the present active ingredient includes, for example, usually within a range of 100:1 to 1:100, and preferably within a range of 10:1 to 1:10, when the present active ingredient is selected from the above-mentioned Group (a), Group (c) or Group (d). When the present active ingredient is selected from the above-mentioned Group (b), the weight ratio of the Present compound to the present active ingredient includes, for example, usually within a range of 10,000:1 to 1:100, and preferably within a range of 1,000:1 to 1:10.

The compound of the present invention and the composition of the present invention can be used to control harmful arthropod. Examples of the harmful arthropod are as follows.

Hemiptera pests:
Delphacidae (for example, *Laodelphax striatellus, Nilaparvata lugens, Sogatella furcifera*, or *Peregrinus maidis*), Deltocephalidae (for example, *Nephotettix cincticeps, Nephotettix virescens, Nephotettix nigropictus* (Rice green leafhopper), *Recilia dorsalis, Empoasca onukii, Empoasca fabae, Dalbulus maidis, Mahanarva posticata* (Sugarcane froghopper), *Mahanarva fimbriolota* (Sugarcane root spittlebug), *Cofana spectra*, or *Nephotettix nigropictus, Recilia dorsalis*), Aphididae (for example, *Aphis gossypii, Myzus persicae, Brevicoryne brassicae, Aphis spiraecola, Macrosiphum euphorbiae, Aulacorthum solani, Rhopalosiphum padi, Toxoptera citricidus, Hyalopterus pruni, Aphis glycines Matsumura, Rhopalosiphum maidis, Tetraneura nigriabdominalis, Viteus vitifoliae, Daktulosphaira vitifoliae* (Grape Phylloxera), *Phylloxera devastatrix Pergande* (Pecan *phylloxera*), *Phylloxera notabilis pergande* (Pecan leaf *phylloxera*), or *Phylloxera russellae Stoetzel* (Southern pecan leaf *phylloxera*), Pentatomidae (for example, *Scotinophara lurida, Scotinophara coarctata* (Malayan rice black bug), *Nezara antennata, Eysarcoris parvus, Halyomorpha mista, Nezara viridula, Euschistus heros* (Brown stink bug), *Nezara viridula* (Southern green stink bug), *Piezodorus guildinii* (Red banded stink bug), *Scaptocoris castanea* (Burrower brown bug), *Oebalus pugnax*, or *Dichelops melacanthus*), Alydidae (for example, *Riptortus clavetus, Leptocorisa chinensis, Leptocorisa aceta*, or *Leptocorisa* spp.), Miridae (for example, *Trigonotylus caelestialium, Stenotus rubrovittatus, Lygus lineolaris*, or *Blissus leucopterus leucopterus* (Chinchi bug)), Aleyrodidae (for example, *Trialeurodes vaporariorum, Bemisia tabaci, Dialeurodes citri*, or *Aleurocanthus spiniferus*), Coccoidea (for example, *Aonidiella aurantii, Comstockaspis perniciosa, Unaspis citri, Ceroplastes rubens, Icerya purchasi, Planococcus Kraunhiae, Pseudococcus longispinis, Pseudaulacaspis Pentagona*, or *Brevennia rehi*), Psyllidae (for example, *Diaphorina citri, Psylla pyrisuga, Bactericerca cockerelli*), Tingidae (for example, *Stephanitis nasi*), Cimicoidea (for example, *Cimex lectularius*),

*Quesada gigas* (Giant Cicada);

and the others.

Lepidoptera pests:
Pyralidae (for example, *Chilo suppressalis, Chilo polychrysus* (Darkheaded stm borer), *Tryporyza incertulas, Chilo polychrysus, Scirpophaga innotata, Scirpophaga incertulas* (Yellow stem borer), *Sesamia inferens* (Pink borer), *Rupela albinella, Cnaphalocrocis medinalis, Marasmia patnalis, Marasmia exigna, Notarcha derogata, Plodia interpunctella, Ostrinia furnacalis, Hellula undalis, Pediasia teterrellus, Nymphula depunctalis, Marasmia* spp., *Hydraecia immanis* (Hop vine borer), *Ostrinia nubilalis* (European corn borer), *Elasmopalpus lignosellus* (Lesser cornstalk borer), *Epinotia aporema* (Bean Shoot Borer), *Diatraea saccharalis* (Sugarcane borer), *Telchin licus* (Giant Sugarcane borer)), Noctuidae (for example, *Spodoptera litura, Spodoptera exigua, Pseudaletia separata, Mamestra brassicae, Sesamia inferens, Spodoptera mauritia, Spodoptera frugiperda, Spodoptera exempta, Agrotis ipsilon, Plusia nigrisigna, Pseudoplusia includens* (Soybean looper), *Trichoplusia* spp., *Heliothis* spp. (for example, *Heliothis virescens*), *Helicoverpa* spp. (for example, *Helicoverpa armigera*), *Anticarsia gammatalis* (Velvetbean caterpillar), or *Alabama argillacea* (Cotton leafworm)), Pieridae (for example, *Pieris rapae*), Adokisofiesu genus, Tortricidae (for example, *Grapholita molesta, Leguminivora glycinivorella, Matsumuraeses azukivora, Adoxophyes orana fasciata, Adoxophyes honmai, Homona magnanima, Archips fuscocupreanus*, or *Cydia pomonella*), Gracillariidae (for example, *Caloptilia theivora*, or *Phyllonorycter ringoneella*), Carposinidae (for example, *Carposina niponensis, Ecdytolopha aurantiana* (Citrus fruit borer)), Lyonetiidae (for example, *Leucoptera coffeela* (Coffee Leaf miner), or *Lyonetia* spp.)), Lymantriidae (for example, *Lymantria* spp., or *Euproctis* spp.), Yponomeutidae (for example, *Plutella xylostella*), Gelechiidae (for example, *Pectinophora gossypiella*, or *Phthorimaea operculella*), Arctiidae (for example, *Hyphantria cunea*);

and the others.

Thysanoptera pests:
Thysanopterae (for example, *Frankliniella occidentalis, Thrips parmi, Scirtothrips dorsalis, Thrips tabaci, Frankliniella intonsa, Frankliniella occidentalis, Haplothrips aculeatus, Stenchaetothrips biformis*);

and the others.

Diptera pests:
Diptera:
  House mosquitoes (*Culex* spp.) (for example, *Culex pipiens pallens*, *Culex tritaeniorhynchus*, or *Culex quinquefasciatus*),
  *Aedes* spp. (for example, *Aedes aegypti*, or *Aedes albopictus*),
  *Anopheles* spp. (for example, *Anopheles sinensis*),
  Chironomidae,
  Muscidae (for example, *Musca domestica*, or *Muscina stabulans*),
  Anthomyiidae (for example, *Delia platura*, *Delia antiqua*, or *Tetanops myopaeformis*),
  Agromyzidae (for example, *Agromyza oryzae*, *Hydrellia griseola*, *Liriomyza sativae*, *Liriomyza trifolii*, or *Chromatomyia horticola*),
  Chloropidae (for example, *Chlorops oryzae*),
  Tephritidae (for example, *Dacus cucurbitae*, or *Ceratitis capitata*),
  Ephydridae (for example, *Hydrellia philippina*, or *Hydrellia sasakii*),
  Drosophilidae,
  Phoridae (for example, *Megaselia spiracularis*),
  Psychodidae (for example, *Clogmia albipunctata*),
  Sciaridae,
  Cecidomyiidae (for example, *Mayetiola destructor*, or *Orseolia oryzae*),
  Diopsidae (for example, *Diopsis macrophthalma*),
  Tipulidae (for example, *Tipula oleracea* (Common cranefly), or *Tipula paludosa* (European cranefly));
  and the others.
Coleoptera pests:
  Chrysomelidae (for example, *Diabrotica virgifera virgifera*, *Diabrotica undecimpunctata howardi*, *Diabrotica barberi*, *Diabrotica virgifera zeae*, *Diabrotica balteata LeConte*, *Diabrotica speciosa*, *Diabrotica speciosa* (Cucurbit Beetle), *Cerotoma trifurcata*, *Oulema melanopus*, *Aulacophora femoralis*, *Phyllotreta striolata*, *Leptinotarsa decemlineata*, *Oulema oryzae*, *Colaspis brunnea*, *Chaetocnema pulicaria*, *Epitrix cucumeris*, *Dicladispa armigera*, *Stenolophus lecontei* (Seedcorn beetle), or *Clivinia impressifrons* (Slender seedcorn beetle)),
  Scarabaeidae (for example, *Anomala cuprea*, *Anomala rufocuprea*, *Popillia japonica*, *Rhizotrogus majalis* (European Chafer), *Bothynus gibbosus* (Carrot beetle), *Colaspis brunnea* (Grape *Colaspis*), *Myochrous denticollis* (southern Corn leaf beetle), *Holotrichia* spp., or *Phyllophaga* spp. (for example, *Phyllophaga crinita*)),
  Erirhinidae (for example, *Sitophilus zeamais*, *Echinocnemus squameus*, *Lissorhoptrus oryzophilus*, or *Sphenophorus venatus*),
  Curculionidae (for example, *Anthonomus grandis*, *Sphenophorus callosus* (Southern Corn Billbug), *Sternechus subsignatus* (Soybean stalk weevil), or *Sphenophorus* spp. (for example, *Sphenophorus levis*)),
  *Epilachna* (for example, *Epilachna vigintioctopunctata*),
  Scolytidae (for example, *Lyctus brunneus*, or *Tomicus piniperda*),
  Bostrichidae,
  Ptinidae,
  Cerambycidae (for example, *Anoplophora malasiaca*, or *Migdolus fryanus*),
  Elateridae (*Agriotes* sp., *Aelous* sp., *Anchastus* sp., *Melanotus* sp., *Limonius* sp., *Conoderus* sp., *Ctenicera* sp.) (for example, *Melanotus okinawensis*, *Agriotes ogurae fuscicollis*, or *Melanotus legatus*),
  Staphylinidae (for example, *Paederus fuscipes*),
  *Hypothenemus hampei* (Coffee Barry Borer);
  and the others.
Orthoptera pests:
  *Locusta migratoria*, *Gryllotalpa africana*, *Dociostaurus maroccanus*, *Chortoicetes terminifera*, *Nomadacris septemfasciata*, *Locustana pardalina* (Brown Locust), *Anacridium melanorhodon* (Tree Locust), *Calliptamus italicus* (Italian Locust), *Melanoplus differentialis* (Differential grasshopper), *Melanoplus bivittatus* (Twostriped grasshopper), *Melanoplus sanguinipes* (Migratory grasshopper), *Melanoplus femurrubrum* (Red-Legged grasshopper), *Camnula pellucida* (Clearwinged grasshopper), *Schistocerca gregaria*, *Gastrimargus musicus* (Yellow-winged locust), *Austracris guttulosa* (Spur-throated locust), *Oxya yezoensis*, *Oxya japonica*, *Patanga succincta*, Grylloidea (for example, *Acheta domesticus*, *Teleogryllus emma*, or *Anabrus simplex* (Mormon cricket));
  and the others.
Hymenoptera pests:
  Tenthredinidae (for example, *Athalia rosae*, or *Athalia japonica*),
  *Solenopsis* spp.,
  *Acromyrmex* spp. (for example, *Atta capiguara* (Brown leaf-cutting ant));
  and the others.
Blattariae pests:
  *Blattella germanica*, *Periplaneta fuliginosa*, *Periplaneta americana*, *Periplaneta brunnea*, *Blatta orientalis*, and the others.
Isoptera pests:
  *Reticulitermes speratus*, *Coptotermes formosanus*, *Incisitermes minor* (*Coptotermes formosanus*), *Cryptotermes domesticus*, *Odontotermes formosanus*, *Neotermes koshunensis*, *Glyptotermes Satsumensis*, *Glyptotermes Nakajimai*, *Glyptotermes Fuscus*, *Glyptotermes Kodamai*, *Glyptotermes Kushimensis*, *Hodotermopsis Sjostedti*, *Coptotermes guangzhoensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, or *Cornitermes cumulans*);
  and the others.
Acarina pests:
  Tetranychidae (for example, *Tetranychus urticae*, *Tetranychus kanzawai*, *Panonychus citri*, *Panonychus ulmi*, *Oligonychus* spp., or *Brevipalpus phoenicis* (Southern Turkey spider mites)),
  Eriophyidae (for example, *Aculops pelekassi*, *Phyllocoptruta citri*, *Aculops lycopersici*, *Calacarus carinatus*, *Acaphylla theavagrans*, *Eriophyes chibaensis*, or *Aculus schlechtendali*),
  Tarsonemidae (for example, *Polyphagotarsonemus latus*),
  Tenuipalpidae (for Example, *Brevipalpus phoenicis*),
  Tuckerellidae;
  Ixodidae (for Example, *Haemaphysalis longicornis*, *Haemaphysalis flava*, *Dermacentor taiwanicus*, *Dermacentor variabilis*, *Ixodes ovatus*, *Ixodes persulcatus*, *Ixodes scapularis*, *Amblyomma americanum*, *Boophilus microplus*, or *Rhipicephalus sanguineus*),
  Acaridae (for example, *Tyrophagus putrescentiae*, or *Tyrophagus similis*),
  Pyroglyphidae (for example, *Dermatophagoides farinae*, or *Dermatophagoides ptrenyssnus*);
  Cheyletidae (for example, *Cheyletus eruditus*, *Cheyletus malaccensis*, or *Cheyletus moorei*);
  Sarcoptidae (for example, *Octodectes cynotis*, or *Sacroptes scabiei*),

*Demodex folliculorum* (for example, *Demodex canis*),
Listrophoridae,
Oribatid mites,
Dermanyssidae (for example, *Ornithonyssus bacoti*, *Ornithonyssus sylvairum*, or *Dermanyssus gallinae*),
Trombiculid mites (for example, *Leptotrombidium akamushi*),
and the others.
Araneae:
*Chiracanthium japonicum*, or *Latrodectus hasseltii*, and the others.
Chilopoda:
*Thereuonema hilgendorfi*, or *Scolopendra subspinipes*, and the others.
Diplopoda:
*Oxidus gracilis*, or *Nedyopus tambanus*, and the others,
Isopoda:
*Armadillidium vulgare*, and the others.
Gastropoda:
*Limax marginates*, or *Limax flavus*, *Pomacea canaliculata*, and the others.

For example, when the present active ingredient is an ingredient selected from the sub group a-9, the composition of the present invention can be used to control harmful nematodes. Also, for example, when the present active ingredient is an ingredient selected from the sub group (b), the composition of the present invention can be used to control phytopathogenic fungus.

Examples of the harmful nematodes and the phytopathogenic fungus include the followings.

Harmful nematodes:
*Aphelenchoides* sp. (for example, *Aphelenchoides basseyi*); *Pratylenchus* sp. (for example, *Pratylenchus coffeae*, *Pratylenchus brachyurus*, *Pratylenchus neglectus*); *Meloidogyne* sp. (for example, *Meloidogyne javanica*, *Meloidogyne incognita*, *Meloidogyne hapla*); *Heterodera* sp. (for example, *Heterodera glycines*); *Globodera* sp. (for example, *Globodera rostochiensis*); *Bursaphelenchus* sp. (for example, *Rotylenchulus reniformis*, *Nothotylenchus acris*, *Radopholus similis*, *Ditylenchus dipsaci*, *Tylenchulus semipenetrans*, *Longidorus* sp., *Xiphinema* sp., *Trichodorus* sp., *Bursaphelenchus xylophilus*);

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (*Erysiphe graminis*), fusarium blight (*Fusarium gaminearum*, *F. avenaceum*, *F. culmorum*, *Microdochium nivale*), rust (*Puccinia striiformis*, *P. graminis*, *P. recondita*), snow mould (*Micronectriella nivale*, *M. majus*), typhulasnow blight (*Typhula* sp.), loose smut (*Ustilago tritici*), stinking smut (*Tilletia caries*, *T. controversa*), eyespot (*Pseudocercosporella herpotrichoides*), leaf blotch (*Septoria tritici*), glume blotch (*Stagonospora nodorum*), tan spot (*Pyrenophora tritici-repentis*), rhizoctonia seeding blight (*Rhizoctonia solani*), and take-all disease (*Gaeumannomyces graminis*);

Barly diseases: powdery mildew (*Erysiphe graminis*), fusarium blight (*Fusarium gaminearum*, *F. avenaceum*, *F. culmorum*, *Microdochium nivale*), rust (*Puccinia striiformis*, *P. graminis*, *P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and rhizoctonia seeding blight (*Rhizoctonia solani*);

Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum gfaminicola*), gray leaf spot (*Cercospora zeae-maydis*), eyespot (*Kabatiella zeae*), *phaeosphaeria* leaf spot (*Phaeosphaeria maydis*), diplomat over Deer disease (*Stenocarpella maydis*, *Stenocarpella macrospora*), Stalk Rot (*Fusarium graminearum*, *Fusarium verticilioides*, *Colletotrichum graminicola*), corn smut (*Ustilago maydis*);

Cotton diseases: anthracnose (*Colletotrichum gossypii*), grey mildew (*Ramuraria areola*), alternaria leaf spot (*Alternaria macrospora*, *A. gossypii*), Black root rot due to *Thielaviopsis* spp. (*Thielaviopsis basicola*);

Coffee diseases: rust (*Hemileia vastatrix*), leaf spot (*Cercospora coffeicola*);

Rape seed diseases: *sclerotinia* rot (*Sclerotinia sclerotiorum*), black spot (*Alternaria brassicae*), and black leg (*Phoma lingam*);

Sugarcane diseases: rust (*Puccinia melanocephela*, *Puccinia kuehnii*), and smut (*Ustilago scitaminea*);

Sunflower diseases: rust (*Puccinia helianthi*), and downy mildew (*Plasmopara halstedii*);

Citrus diseases: melanose (*Diaporthe citri*), scab (*Elsinoe fawcetti*), fruit rot (*Penicillium digitatum*, *P. italicum*), and epidemics (*Phytophthora parasitica*, *Phytophthora citrophthora*);

Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), anthracnose (*Glomerella cingulata*), brown spot (*Diplocarpon mali*), ring spot (*Botryosphaeria berengeriana*), and epidemics (*Phytophtora cactorum*);

Pear diseases: scab (*Venturia nashicola*, *V. pirina*), black spot (*Alternaria alternata* Japanese pear pathotype) and rust (*Gymnosporangium haraeanum*);

Peach diseases: brown rot (*Monilinia fructicola*), scab (*Cladosporium carpophilum*) and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*) and leaf spot (*Cercospora kaki*, *Mycosphaerella nawae*);

Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), *fusarium* wilt (*Fusarium oxysporum*), downy mildew (*Pseudoperonospora cubensis*), epidemics (*Phytophthora* sp.) and damping-off (*Pythium* sp.);

Tomato diseases: early blight (*Alternaria solani*), leaf mold (*Cladosporium fulvum*), leaf mold (*Pseudocercospora fuligena*), late blight (*Phytophthora infestans*), and powdery mildew (*Leveillula taurica*);

Eggplant disease: brown spot (*Phomopsis vexans*) and powdery mildew (*Erysiphe cichoracearum*);

Diseases of Cruciferous Vegetables: alternaria leaf spot (*Alternaria japonica*), white spot (*Cercosporella brassicae*), clubroot (*Plasmodiophora parasitica*), downy mildew (*Peronospora parasitica*);

Welsh onion diseases: rust (*Puccinia allii*);

Soybean diseases: purple stain (*Cercospora kikuchii*), *sphaceloma* scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrithum glycines*, *C. truncatum*), Rhizoctonia aerial blight (*Rhizoctonia solani*), septoria brown spot (*Septoria glycines*), frog eye leaf spot (*Cercospora sojina*), sclerotal disease (*Sclerotinia sclerotiorum*), Powdery mildew (*Microsphaera diffusa*), Stem plague (*Phytophthora sojae*), downy mildew (*Peronospora manshurica*), sudden death (*Fusarium virguliforme*);

Kindney bean diseases: Crown rot (*Sclerotinia sclerotiorum*), rust (*Uromyces appendiculatus*), angular leaf spot (*Phaeoisariopsis griseola*), and anthracnose (*Colletotrichum lindemthianum*);

Peanut diseases: early leaf spot (*Cercospora personata*), late leaf spot (*Cercospora arachidicola*) and southern blight (*Sclerotium rolfsii*);

Garden pea diseases: powdery mildew (*Erysiphe pisi*);

Potato diseases: early blight (*Alternaria solani*), late blight (*Phytophthora infestans*), Pink rot (*Phytophthora erythroseptica*), powdery scab (*Spongospora subterranean* f. sp. *subterranea*), and *verticillium* wilt (*verticillium alboatrum, V. dahliae, V. nigrescens*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.) and anthracnose (*Colletotrichum theae-sinensis*);

Tabacco diseases: brown spot (*Alternaria longipes*), powdery mildew (*Erysiphe cichoracearum*), anthracnose (*Colletotrichum tabacum*), downy mildew (*Peronospora tabacina*), and epidemics (*Phytophthora nicotianae*);

Sugar beet diseases: *cercospora* leaf spot (*Cercospora beticola*), leaf blight (*Thanatephorus cucumeris*), root rot (*Thanatephorus cucumeris*) and *aphanomyces* root rot (*Aphanomyces cochlioides*);

Rose diseases: black spot (*Diplocarpon rosae*) and powdery mildew (*Sphaerotheca pannosa*);

Diseases of *Chrysanthemum*: leaf blight (*Septoria chrysanthemi-indici*) and white rust (*Puccinia horiana*);

Onion diseases: *botrytis* leaf blight (*Botrytis cinerea, B. byssoidea, B. squamosa*), gray-mold neck rot (*Botrytis alli*), and small sclerotial rot (*Botrytis squamosa*);

Various crops diseases: gray mold (*Botrytis cinerea*), and *sclerotinia* rot (*Sclerotinia sclerotiorum*);

Diseases of Japanese radish: *alternaria* leaf spot (*Alternaria brassicicola*);

Turfgrass diseases: dollar spot (*Sclerotinia homeocarpa*), brown patch and large patch (*Rhizoctonia solani*); and Banana diseases: Sigatoka disease (*Mycosphaerella fijiensis, Mycosphaerella musicola*);

Seed diseases or diseases in the early stages of the growth of various plants caused by bacteria of *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp., and *Diplodia* spp.; and Viral diseases of various plants mediated by *Polymixa* genus or *Olpidium* genus.

*Burkholderia plantarii* of rice (*Burkholderia plantarii*); Angular Leaf Spot of Cucumber (*Pseudomonas syringae* pv. *Lachrymans*); wilt disease of eggplant (*Ralstonia solanacearum*); Citrus Canker (*Xanthomonas citiri*); and Sof rot of white cabbage (*Erwinia carotovora*).

The harmful arthropods, harmful nematodes and phytopathogenic fungus may be harmful arthropods, harmful nematodes or phytopathogenic fungus whose the sensitivity to any of the present active ingredient is lowered or whose the resistance against the present active ingredient is developed.

The compound of the present invention or the composition of the present invention can be used to protect plants from the plant diseases caused by insect-mediated viruses.

Examples of the plant diseases caused by the insect-mediated viruses on which the compound of the present invention or the composition of the present invention has a control efficacy include as follows.

Rice dwarf disease (Rice waika virus), Rice tungro disease (Rice tungro spherical virus, Rice tungro baciliform virus), Rice grassy stunt disease (Rice grassy stunt virus), Rice ragged stunt disease (Rice ragged stunt virus), Rice stripe disease (Rice stripe virus), Rice black streaked dwarf disease (Rice black streaked dwarf virus), Southern rice black-streaked dwarf disease (Southern rice black-streaked dwarf virus), Rice gall dwarf disease (Rice gall dwarf virus), Rice hoja blanca disease (Rice hoja blanca virus), White leaf desease of rice (Rice white leaf virus), Yellow dwarf disease (Yellow dwarf virus), Red disease (Rice penyakit merah virus), Rice yellow stunt disease (Rice yellow stunt virus), Rice transitory yellowing disease (Rice transitory yellowing virus), Rice Yellow Mottle disease (Rice Yellow Mottle Virus), Rice necrosis mosaic disease (Rice necrosis mosaic virus), Rice dwarf stunt disease (Rice dwarf stunt virus), Wheat northern cereal mosaic disease (Northern Cereal Mosaic Virus), Barley Yellow Dwarf disease (Barley Yellow Dwarf Virus), Wheat yellow dwarf disease (Wheat yellow dwarf virus), Oat sterile dwarf disease (Oat sterile dwarf virus), Wheat streak mosaic disease (Wheat streak mosaic virus);

Maize dwarf mosaic disease (Maize dwarf mosaic virus), Maize stripe disease (maize stripe tenuivirus), Maize chlorotic dwarf disease (Maize chlorotic dwarf virus), Maize chlorotic mottle disease (maize chlorotic mottle virus), Maize rayado fino disease (maize rayado fino marafivirus), Corn stunt disease (Corn stunt spiroplasma), Maize bushy stunt disease (Maize bushy stunt phytoplasma);

Sugarcane mosaic disease (Sugarcane mosaic virus);

Soybean mild mosaic disease (Soybean mild mosaic virus), Mosaic disease (Alfalfa Mosaic Virus, Bean yellow-spot mosaic virus, Soybean mosaic virus, Bean yellow mosaic virus, Cowpea severe mosaic virus), bean virus disease (Broad bean wilt virus, Bean common mosaic virus, Peanut stunt virus, Southern bean mosaic virus), Soybean dwarf disease (Soybean dwarf luteovirus, Milk-vetch dwarf luteovirus), Bean-pod mottle disease (Bean-pod mottle virus), Brazilian bud blight disease (Tobbaco streak virus), Cowpea chlorotic mottle disease (Cowpea chlorotic mottle), Mung bean yellow mosaic disease (Mung bean yellow mosaic virus), Peanut stripe disease (Peanut stripe mottle), Soybean crinkle leaf disease (Soybean crinkle leaf virus), Soybean severe stunt disease (Soybean severe stunt virus);

Tomato yellow leaf disease (Tomato chlorosis virus), Tomato spotted wilt disease (Tomato spotted wilt virus), Tomato yellow leaf curl disease (Tomato yellow leaf curl virus), Melon spotted wilt disease (Melon yellow spot virus), Watermelon mosaic disease (Watermelon mosaic virus), Dwarf disease (Cucumber mosaic virus), Zucchini yellow mosaic disease (Zucchini yellow mosaic virus), Turnip mosaic disease (Turnip mosaic virus), Cucurbit chlorotic yellow disease (Cucurbit chlorotic yellows virus), *Capsicum* chlorosis disease (*Capsicum* chlorosis virus), Beet pseudo yellow disease (Beet pseudo yellows virus);

*chrysanthemum* stem necrosis disease (*chrysanthemum* stem necrosis virus), *Impatiens* necrotic spot disease (*Impatiens* necrotic spot virus), Iris yellow spot disease (Iris yellow spot virus);

Sweet potato mottle mosaic disease (Sweet potato internal cork virus), Sweet potato shukuyo mosaic disease (Sweet potato shukuyo mosaic virus); and Mosaic virus diseases of various plants mediated by *Polymixa* spp. or *Olpidium* spp.

The agent for controlling harmful arthropods of the present invention comprises the compound of the present invention or the composition of the present invention and an inert active carrier. The agent for controlling harmful arthropods is usually prepared by mixing the compound of the present invention or the composition of the present invention with an inert active carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations and tablets and the others. Such formulations may be processed into mosquito repellent coils, electric mosquito repellent mats, liquid mosquito formulations, smoking agents, fumigants, sheet formulations, spot-on formulations or formulations for oral treatment. Also, the agent for controlling harmful arthropods of the present invention may be mixed with other pesticides, miticides, nematicides, fungicides, plant growth regulators, herbicides, and synergists.

The agent for controlling harmful arthropods of the present invention comprises usually 0.01 to 95% by weight of the compound of the present invention or the composition of the present invention.

The formulation comprising the compound of the present invention and the formulation comprising the active ingredient of the present invention can be mixed, and then used as a mixture thereof.

Examples of the solid carrier to be used in the formulation include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate or hydrated silica) or chemical fertilizers (for example, ammonium sulfate, ammonium phosphate, ammonium nitrate, urea or ammonium chloride) and the others; as well as synthetic resins (for Example, polyester resins such as polypropylene, polyacrylonitrile, polymethylmethacrylate and polyethylene terephthalate; nylon resins (for Example, nylon-6, nylon-11 and nylon-66); polyamide resins; polyvinyl chloride, polyvinylidene chloride, vinyl chloride-propylene copolymers, and the others).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for Example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles (for Example, acetonitrile or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether or 3-methoxy-3-methyl-1-butanol); acid amides (for example, dimethylformamide or dimethylacetamide); halogenated hydrocarbons (for example, dichloromethane, trichloroethane or carbon tetrachloride); sulfoxides (for example, dimethyl sulfoxide); propylene carbonate; and vegetable oils (for example, soybean oil or cottonseed oil).

Examples of the above-mentioned gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol).

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The method for controlling harmful arthropods of the present invention is conducted by applying an effective amount of the compound of the present invention or the composition of the present invention to a harmful arthropod directly and/or a habitat thereof (for example, plant bodies, soil, an interior of a house, animal bodies). In the method for controlling harmful arthropods of the present invention, the Present compound is usually used in the form of a harmful arthropod controlling agent.

When an agent for controlling harmful arthropods of the present invention is used for controlling harmful arthropods in an agricultural field, the application dose as an amount of the compound of the present invention or a total amount of the compound of the present invention and the active ingredient of the present invention is usually within a range from 1 to 10,000 g per 10,000 $m^2$. The emulsifiable concentrate, the wettable powder, or the flowable formulation etc. of an agent for controlling harmful arthropods of the present invention is usually applied by diluting it with water in such a way that a concentration of the compound of the present invention or a total concentration of the compound of the present invention and the active ingredient of the present invention is within a range from 0.01 to 10,000 ppm. The granular formulation, or the dust formulation etc., is usually applied as itself without diluting it.

When the agent for controlling harmful arthropods of the present invention is used to control harmful arthropods that live inside a house, the application dose as an amount of the Present compound is usually within a range from 0.01 to 1,000 mg per 1 $m^2$ of an area to be treated, in the case of using it on a planar area. In the case of using it spatially, the application dose as an amount of the Present compound is usually within a range from 0.01 to 500 mg per $m^3$ of the space to be treated. When the agent for controlling harmful arthropods of the present invention is formulated into emulsifiable concentrates, wettable powders, flowables or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits and the others, such formulations are used as itself without diluting it.

When the agent for controlling harmful arthropods of the present invention is sued for controlling external parasites of livestock such as cows, horses, pigs, sheep, goats and chickens and small animals such as dogs, cats, rats and mice, the pest control agent of the present invention can be applied to the animals by a known method in the veterinary field. Specifically, when systemic control is intended, the pest control agent of the present invention is administered to the animals as a tablet, a mixture with feed or a suppository, or by injection (including intramuscular, subcutaneous, intravenous and intraperitoneal injections). On the other hand, when non-systemic control is intended, the pest control agent of the present invention is applied to the animals by means of spraying of the oil solution or aqueous solution, pour-on or spot-on treatment, or washing of the animal with a shampoo formulation, or by putting a collar or ear tag made of the resin formulations to the animal. In the case of administering to an animal body, the dose of the Present compound is usually within a range from 0.1 to 1,000 mg per 1 kg of an animal body weight.

The method for controlling harmful arthropods of the present invention is carried out by applying an effective amount of the compound of the present invention or the composition of the present invention directly to harmful arthropods, and/or habitats of harmful arthropods. Examples of the habitats of harmful arthropods include plants, soils for cultivating plants, houses, and animals.

Examples of applying an effective amount of the compound of the present invention or the composition of the present invention to plant or soils for cultivating plants include a method of applying an effective amount of the compound of the present invention or the composition of the present invention to a stem and leaf, a flower, a seedling, an ear of a plant; a method of applying an effective amount of the compound of the present invention or the composition of the present invention to a seed or a bulb such as seed tuber (for example, a seed disinfection, a seed soaking, or a seed coating), or a method of applying an effective amount of the compound of the present invention or the composition of the present invention to soils before planting plants or soils after planting plants.

Specific examples of applying an effective amount of the compound of the present invention or the composition of the present invention to a stem and leaf, a flower, a seedling, an ear of a plant include a method for applying an effective amount of the compound of the present invention or the composition of the present invention to a surface of a plant (for example, foliage application, and trunk application), a method for applying an effective amount of the compound of the present invention or the composition of the present invention to a flower or a whole plant at flowering times including before flowering, during flowering, and after flowering, and a method for applying an effective amount of the compound of the present invention or the composition of the present invention to an ear or a whole grain at sprouting season of grain.

Examples of a method of controlling harmful arthropods by applying an effective amount of the compound of the present invention or the composition of the present invention soils before planting plants or after planting plants include a method of applying an effective amount of a composition of the present invention to a root part of a crop to be protected from damage such as ingestion by harmful arthropods, and a method of controlling harmful arthropods that ingest a plant by permeating and transferring an effective amount of the composition of the present invention from a root into the interior of the plant body.

Examples of the method of applying an effective amount of the compound of the present invention or the composition of the present invention to soils before planting plants or after planting plants include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of sowing (planting row spraying at the time of sowing, soil mixing after planting row treatment at the time of sowing), broadcast treatment (overall soil surface spraying, soil mixing after broadcast treatment), side-article treatment, treatment of water surface (application to water surface, application to water surface after flooding), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at a seedling raising stage, drug solution injection treatment, irrigation of a plant part just above the ground, drug solution drip irrigation, chemigation), seedling raising box treatment (spraying into a seedling raising box, irrigation of a seedling raising box, flooding into a seedling raising box with drug solution), seedling raising tray treatment (spraying on a seedling raising tray, irrigation of a seedling raising tray, flooding into a seedling raising tray with drug solution), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing, spraying at sowing before covering with soils, spraying at sowing after covering with soils, mixing with covering soil, and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

In a step of applying to a seed or a bulb, a seed described herein represents a seed of a plant at the state before seeding to a soil or a culture medium for cultivating a seed, and a bulb described herein represents discoid stems, corms, rhizomes, tubers, tuberous, seed tubers, and tuberous roots of a plant at the state before planting in a soil or a culture medium for cultivating. A method for controlling harmful arthropods by applying an effective amount of the compound of the present invention or the composition of the present invention into a seed or a bulb include a method of applying an effective amount of the compound of the present invention or the composition of the present invention directly into a seed or a bulb of a plant to be protected from damage such as ingestion by harmful arthropods; and a method for controlling harmful arthropods that ingest a seed by applying an effective amount of the compound of the present invention or the composition of the present invention in the vicinity of a seed or a bulb; and a method for controlling harmful arthropods that ingest a plant by permeating and transferring an effective amount of the compound of the present invention or the composition of the present invention from a seed or a bulb into the interior of the plant body. Examples of a method of applying an effective amount of the compound of the present invention or the composition of the present invention to a seed or a bulb include spraying treatment, spray coating treatment, immersion treatment, impregnation treatment, coating treatment, film coating treatment, and pellet coating treatment, and these methods can provide a preparation of a seed or a bulb that retain an effective amount of the composition of the present invention or the composition of the present invention on the surface and/or into the interior thereof.

When the compound of the present invention or the composition of the present invention are applied to a seed or a bulb, an effective amount of the compound of the present invention is usually within a range of 0.001 to 100 g, preferably within a range of 0.02 to 20 g, based on 1 kg of the seed or the bulb. Also an effective amount of the composition of the present invention is usually within a range of 0.000001 to 50 g, preferably within a range of 0.0001 to 30 g of a total amount of the compound of the present invention and the active ingredient of the present invention, based on 1 kg of the seed or the bulb.

The plants to which the compound of the present invention and the composition of the present invention can be applied include the followings.

Crops:
corn, rice, wheat, barley, rye, triticale, oat, sorghum, cotton, soybean, peanut, *arachis*, common bean (kidney bean), lima bean, adzuki bean, cowpea, mung bean, urd bean, scarlet runner bean, rice bean, moth bean, tepary bean, broad bean, pea, chick pea, lentils, lupin, pigeon pea, alfalfa, buckwheat, beet, rape, sunflower, sugarcane, tobacco, and the others;

Vegetables:
solanaceous vegetables (for example, eggplant, tomato, pimento, pepper, bell pepper and potato),
cucurbitaceous vegetables (for example, cucumber, pumpkin, zucchini, water melon, melon, and squash),
cruciferous vegetables (for example, Japanese radish, white turnip, horseradish, kohlrabi, Chinese cabbage, cabbage, leaf mustard, broccoli and cauliflower),
asteraceous vegetables (for example, burdock, crown daisy, artichoke and lettuce),
liliaceous vegetables (for example, green onion, onion, garlic and asparagus),
ammiaceous vegetables (for example, carrot, parsley, celery and parsnip),
chenopodiaceous vegetables (for example, spinach and Swiss chard),
lamiaceous vegetables (for example, *Perilla frutescens*, mint, basil, and lavender),
strawberry, sweet potato, *Dioscorea japonica, colocasia*, and the others;

Fruits:
pomaceous fruits (for example, apple, pear, Japanese pear, Chinese quince and quince),
stone fleshy fruits (for example, peach, plum, nectarine, *Prunus* mume, cherry fruit, apricot and prune),
citrus fruits (for example, Citrus unshiu, orange, lemon, lime and grapefruit),
nuts (for example, chestnut, walnuts, hazelnuts, almond, pistachio, cashew nuts and macadamia nuts),
berry fruits (for example, blueberry, cranberry, blackberry and raspberry),
grape, kaki persimmon, olive, Japanese plum, banana, coffee, date palm, coconuts,
and the others;
tea, mulberry,
flowering plant,
roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate),
flowers,
ornamental foliage plants,
sods, and
grasses.

The plants described above are not limited specifically, as long as they are breeds that are usually cultivated.

The plant described above may be plants that are bred by a hybrid technology.

the plants that are bred by a hybrid technology is a first-generation hybrid that is produced by breeding two kinds of different lines of breed variety, and generally speaking, are plants having a heterosis having superior characters to those of both parents breeds (in general, for example, it leads to enhancement of yield potential and improvement of resistance to biological and abiotic stress factors).

The plants described above may include genetically-modified crop.

For example, the genetically-modified crop described above include also plants having resistance to herbicides including HPPD (that is, 4-hydroxyphenylpyruvate dioxygenase) inhibitors such as isoxaflutole; ALS (that is, acetoacetate synthase) inhibitors such as imazethapyr and thifensulfuron methyl; EPSP (that is, 5-enolpyruvoylshikimate-3-phosphate synthase) inhibitors; glutamine synthetase inhibitors; PPO (that is, protoporphyrinogen oxidase) inhibitors; bromoxynil; dicamba, and the like, which resistance has been imparted by a classical breeding method or gene recombination technology.

The plants described above may include plants that have become capable of synthesizing selective toxins and the like (for example, genus *Bacillus* such as *Bacillus thuringiensis*) produced by using a gene recombination technology; and the plants being capable of synthesizing a gene segment that match partially an endogenous gene derived from a harmful insect and also impart with specific insecticidal activity by inducing a gene silencing (RNAi; RNA interference) in a target harmful insect.

In addition, the plants described above include lines having two or more types of characters related to herbicide resistance, pest resistance, disease resistance, and the like as described above, which characters are imparted using a classical breeding technology or gene recombination technology, and lines having two or more types of properties possessed by parent lines, which properties are imparted by crossing genetically-engineered plants having the same or different types of properties. Examples of such plants include Smart stax (registered trademark).

EXAMPLES

The following Examples including Preparation examples, Formulation examples and Test examples, serve to illustrate the present invention in more detail, which should not intend to limit the present invention.

First, regarding the preparation of the compound of the present invention, the Preparation Examples are shown below.

Preparation Example 1

To a mixture of 2,5-dichloropyrazine 3.0 g, sodium hydride (60%, oily) 880 mg, and NMP 50 mL was added benzyl alcohol 2.3 g under ice-cooling. The reaction mixtures were raised to room temperature, and the resulting mixtures stirred at room temperature for 5 hours. To the resulting reaction mixtures was added water, and the mixtures were extracted with ethyl acetate. The resulting organic mixtures were washed with saturated brine, and dried over anhydrous sodium sulfate, and concentrated under reduced pressure. The resulting residues were subjected to a silica gel column chromatography to give an intermediate compound 1 represented by the following formula 3.1 g.

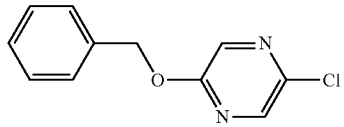 [SMILES: Clc1cnc(OCc2ccccc2)cn1]

Intermediate Compound 1
$^1$H-NMR (CDCl$_3$) δ: 8.12 (1H, d), 8.06 (1H, d), 7.46-7.33 (5H, m), 5.37 (2H, s).

Preparation Example 2

The mixture of the intermediate compound 1,3.1 g 2-[2-fluoro-4-(trifluoromethyl)phenyl]-4,4,5,5-tetramethyl-1,3,2-dioxaborolane 4.1 g, tetrakis(triphenylphosphine)palladium(0) 820 mg, and 2M aqueous sodium carbonate solution 18 mL and dimethoxyethane 60 mL was heated at 80° C. with stirring for 3 hours. The resulting reaction mixtures were allowed to stand to room temperature, and to the mixtures was added water, and the mixtures were extracted with ethyl acetate. The resulting organic layers were washed with saturated brine, dried over anhydrous sodium sulfate and concentrated under reduced pressure. The resulting residues were subjected to a silica gel column chromatography to give an intermediate compound 2 represented by the following formula 3.2 g.

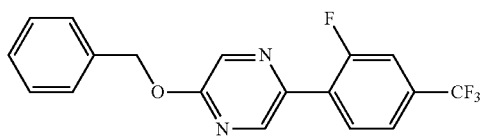 [SMILES: Fc1cc(C(F)(F)F)ccc1-c1cnc(OCc2ccccc2)cn1]

Intermediate Compound 2
$^1$H-NMR (CDCl$_3$) δ: 8.69 (1H, dd), 8.40 (1H, d), 8.15 (1H, d), 7.56-7.33 (7H, m), 5.46 (2H, s).

Preparation Example 3

The mixture of the intermediate compound 2 3.2 g, ethanethiol 680 mg, sodium hydride (60%, oily) 440 mg, and NMP 40 mL was stirred at room temperature for 4 fours. To the resulting reaction mixtures was added water, and the mixtures were extracted with ethyl acetate. The resulting organic layers were washed with saturated brine, dried over anhydrous sodium sulfate, and concentrated under reduced pressure. The resulting residues were dissolved into chloroform 50 mL, and to the mixtures was added mCPA (75%) 4.6 g under ice-cooling, and the mixtures were stirred for three hours under ice-cooling. To the resulting reaction mixtures was added saturated aqueous sodium thiosulfate solution, and the mixtures were extracted with chloroform. The resulting organic layers were washed successively with saturated aqueous sodium hydrocarbonate solution and saturated brine, dried over anhydrous sodium sulfate, and concentrated under reduced pressure. The resulting residues were subjected to a silica gel column chromatography to give an intermediate compound 3 represented by the following formula 2.8 g.

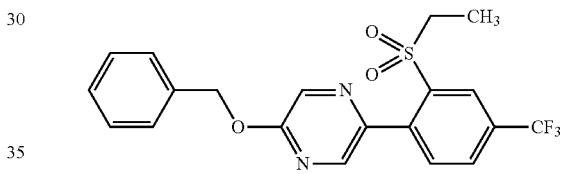

Intermediate Compound 3
$^1$H-NMR (CDCl$_3$) δ: 8.45 (1H, d), 8.29 (1H, d), 8.28 (1H, d), 7.98 (1H, dd), 7.64 (1H, d), 7.51-7.38 (5H, m), 5.45 (2H, s), 3.55 (2H, q), 1.32 (3H, t).

Preparation Example 4

The mixture of the intermediate compound 3 2.8 g, boron tribromide (2M dichloromethane solution) 11 mL, and chloroform 60 mL was stirred for 2 hours under ice-cooling. To the resulting reaction mixtures was added water, and the mixtures were extracted with chloroform. The resulting organic layers were washed successively with saturated aqueous sodium hydrocarbon solution and saturated brine, dried over anhydrous sodium sulfate, and concentrated under reduced pressure. The resulting residues were subjected to a silica gel column chromatography to give an intermediate compound c-16 represented by the following formula 20 g.

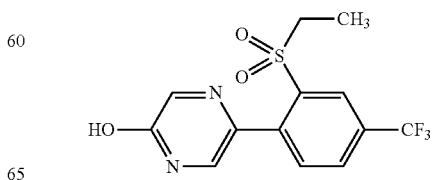

Intermediate compound c-16

$^1$H-NMR (DMSO-D$_6$) δ: 8.24 (1H, s), 8.21 (1H, d), 8.09 (1H, d), 7.88 (1H, d), 7.86 (1H, br s), 3.67 (2H, q), 1.17 (3H, t).

Preparation Example 5

The mixture of the intermediate compound c-16 300 mg, cesium carbonate 350 mg, 2,2,2-trifluoroethyl=trifluoromethanesulfonate 230 mg, and NMP 4 mL was stirred at room temperature for 2.5 hours. To the resulting reaction mixtures was added water, and the mixtures were extracted with ethyl acetate. The resulting organic layers were washed with saturated brine, dried over anhydrous sodium sulfate, and concentrated under reduced pressure. The resulting residues were subjected to a silica gel column chromatography to give the Present compound 1 represented by the following formula 220 mg and the side product 1 100 mg.

The Present compounds that are prepared according to the Preparation example 5 and their physical properties are shown below.

A compound represented by formula (I-1)

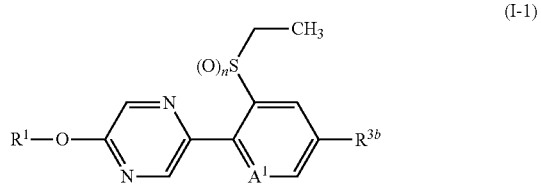
(I-1)

wherein A$^1$, R$^1$, R$^{3b}$, and n are indicated in Table 6.

TABLE 6

| Present compound | A$^1$ | R$^1$ | R$^{3b}$ | n |
|---|---|---|---|---|
| 1 | CH | CF$_3$CH$_2$ | CF$_3$ | 2 |
| 2 | CH | CF$_2$HCF$_2$CH$_2$ | CF$_3$ | 2 |
| 3 | CH | CF$_3$CFHCF$_2$CH$_2$ | CF$_3$ | 2 |

Present Compound 1

$^1$H-NMR (CDCl$_3$) δ: 8.45 (1H, d), 8.38 (1H, d), 8.27 (1H, d), 8.01-7.98 (1H, m), 7.63 (1H, d), 4.83 (2H, q), 3.52 (2H, q), 1.32 (3H, t).

Present Compound 2

$^1$H-NMR (CDCl$_3$) δ: 8.45 (1H, s), 8.35 (1H, t), 8.28 (1H, t), 7.99 (1H, dd), 7.63 (1H, d), 6.18-5.89 (1H, m), 4.82 (2H, td), 3.52 (2H, q), 1.32 (3H, t).

Present Compound 3

$^1$H-NMR (CDCl$_3$) δ: 8.45 (1H, d), 8.36 (1H, d), 8.29 (1H, d), 8.00 (1H, dd), 7.63 (1H, d), 5.26-504 (1H, m), 4.87-4.76 (2H, m), 3.52 (2H, q), 1.33 (3H, t).

The side products that are prepared according to Preparation example 5 and their physical properties are shown below.

A compound represented by formula (B-1)

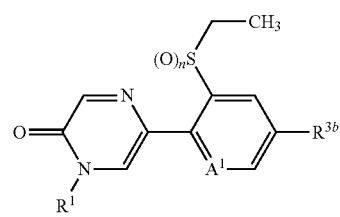
(B-1)

wherein A$^1$, R$^1$, R$^{3b}$, and n are indicated in Table 7.

TABLE 7

| Side product | A$^1$ | R$^1$ | R$^{3b}$ | n |
|---|---|---|---|---|
| 1 | CH | CF$_3$CH$_2$ | CF$_3$ | 2 |
| 2 | CH | CF$_2$HCF$_2$CH$_2$ | CF$_3$ | 2 |
| 3 | CH | CF$_3$CFHCF$_2$CH$_2$ | CF$_3$ | 2 |

Side Product 1

$^1$H-NMR (CDCl$_3$) δ: 8.43 (1H, s), 8.25 (1H, d), 7.97 (1H, dd), 7.63 (1H, d), 7.42 (1H, s), 4.62 (2H, q), 3.41 (2H, q), 1.30 (3H, t).

Side Product 2

$^1$H-NMR (CDCl$_3$) δ: 8.43 (1H, d), 8.24 (1H, d), 7.96 (1H, dd), 7.63 (1H, d), 7.43 (1H, d), 5.96 (1H, tt), 4.58 (2H, t), 3.42 (2H, q), 1.30 (3H, t).

Side Product 3

$^1$H-NMR (CDCl$_3$) δ: 8.43 (1H, d), 8.25 (1H, d), 7.96 (1H, dd), 7.63 (1H, d), 7.43 (1H, d), 5.17-4.95 (1H, m), 4.71-4.49 (2H, m), 3.41 (2H, q), 1.30 (3H, t).

Preparation Example 6(1)

The mixture of methyl 5-chloro-2-pyridine carboxylate 10 g, sodium methoxide (28% methanol solution) 28 mL, and THF 100 mL was stirred for 3 hours under ice-cooling. To the resulting reaction mixtures was added ethyl methyl sulfone 18 mL under ice-cooling. The reaction mixtures were raised to 80° C., and heated with stirring for 24 hours. The resulting reaction mixtures were allowed to cool to room temperature and to the mixtures was added 2N hydrochloric acid and the mixtures were extracted with ethyl acetate. The resulting organic layers were dried over anhydrous sodium sulfate and concentrated. The resulting residues were subjected to a silica gel column chromatography to give the intermediate compound e-18 represented by the following formula 11 g.

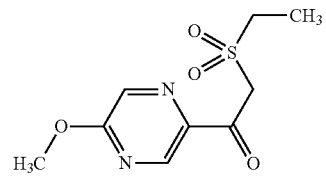 [SMILES: CCS(=O)(=O)CC(=O)c1cnc(OC)cn1]

$^1$H-NMR (CDCl$_3$) δ: 8.91 (1H, d), 8.25 (1H, d), 4.87 (2H, s), 4.08 (3H, s), 3.29 (2H, q), 1.47 (3H, t).

Preparation Example 6(2)

The mixture of the intermediate compound e-18 5.0 g, ammonium acetate 7.89 g, and methanol 15.0 g was heated at 70° C. with stirring for 4 hours. The reaction mixtures were concentrated under reduced pressure to obtain the crude product 12.9 g, and thereto was added ethyl acetate 25 g to dissolve it. The mixtures were washed with water 15 g three times. The resulting organic layers were concentrated under reduced pressure to give the intermediate compound 18 represented by the following formula 4.5 g.

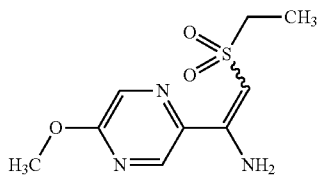

Intermediate Compound 18

$^1$H-NMR (CDCl$_3$) δ: 8.52 (1H, d), 8.21 (1H, d), 6.69 (2H, br), 5.31 (1H, s), 4.03 (3H, s), 3.11 (2H, q), 1.41 (3H, t)

Preparation Example 7

To a mixture of DMF 19 mL and chloroform 600 mL was added oxalyl chloride 21 mL under ice-cooling. The reaction mixtures were raised to room temperature, and stirred for 2 hours. To the resulting reaction mixtures was added butyl vinyl ether 64 mL under ice-cooling and the mixtures were stirred for 3 hours. To the resulting reaction mixtures were added the intermediate compound e-18 20 g and triethylamine 68 mL. The reaction mixtures were stirred for 6 hours, and then concentrated under reduced pressure. To the resulting residues were added ethanol 300 mL and 28% aqueous ammonia solution 30 mL. The reaction mixtures were heated with stirring at 60° C. for 12 hours. The reaction mixtures were concentrated under reduced pressure. To the resulting residues was added water, and the mixtures were extracted with ethyl acetate. The resulting organic layers were dried over anhydrous sodium sulfate, and concentrated under reduced pressure. The resulting residues were subjected to a silica gel column chromatography to give the intermediate compound 6 represented by the following formula 11.4 g.

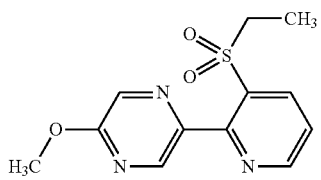

Intermediate Compound 6

$^1$H-NMR (CDCl$_3$) δ: 8.74 (1H, dd), 8.66 (1H, dd), 8.49 (1H, d), 8.20 (1H, d), 7.55 (1H, dd), 4.05 (3H, s), 3.85 (2H, q), 1.38 (3H, t).

Preparation Example 8

The mixture of the intermediate compound 6 4.5 g, and 12N hydrochloric acid 20 mL was heated at 100° C. with stirring for 1 hour. The reaction mixtures were allowed to cool to room temperature, and thereto was added ice water 100 mL. The solution was alkalified with saturated aqueous sodium hydrocarbon solution, and the mixtures were extracted with ethyl acetate. The resulting organic layers were dried over anhydrous sodium sulfate, and concentrated under reduced pressure. The resulting residues were subjected to a silica gel column chromatography to give the intermediate compound c-2 represented by the following formula 4.3 g.

The compounds that prepared according to the method described in Preparation example 8 and their physical properties are shown below.

A compound represented by formula (M-3-1)

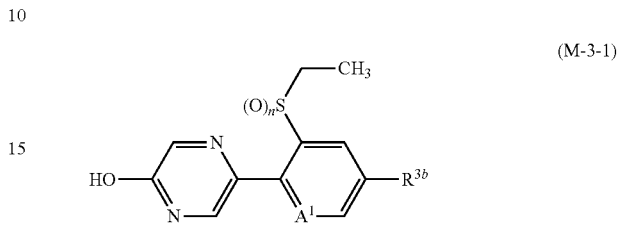

wherein $A^1$, $R^{3b}$, and n are indicated in Table 8.

TABLE 8

| Intermediate compound | $A^1$ | $R^{3b}$ | n |
|---|---|---|---|
| c-2 | N | H | 2 |
| 11 | N | H | 0 |

Intermediate Compound c-2

$^1$H-NMR (CDCl$_3$) δ: 8.81 (1H, dd), 8.47 (1H, dd), 8.21 (1H, d), 7.97 (1H, d), 7.52 (1H, dd), 3.83 (2H, q), 1.39 (3H, t).

Intermediate Compound 11

$^1$H-NMR (CDCl$_3$) δ: 8.40 (1H, dd), 8.34 (1H, d), 8.04 (1H, br s), 7.69 (1H, dd), 7.24 (1H, dd), 2.94 (2H, q), 1.34 (3H, t).

Preparation Example 9

The mixture of the intermediate compound c-2 4.3 g, phosphorus oxychloride 12 mL, and toluene 60 mL was heated at 100° C. with stirring for 2 hours. The resulting reaction mixtures were allowed to cool to room temperature, and concentrated under reduced pressure. To the resulting residues was added water, and the mixtures were extracted with chloroform. The resulting organic layers were dried over anhydrous sodium sulfate and concentrated under reduced pressure to give the intermediate compound d-2 represented by the following formula 4.6 g.

The compounds that prepared according to the method described in Preparation example 9 and their physical properties are shown below.

A compound represented by formula (M-4-1)

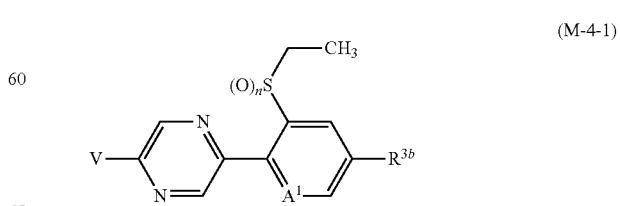

wherein V, $A^1$, $R^{3b}$ and n are indicated in Table 9.

TABLE 9

| Intermediate compound | V | A$^1$ | R$^{3b}$ | n |
|---|---|---|---|---|
| d-2 | Cl | N | H | 2 |
| 12 | Cl | N | H | 0 |
| 13 | Br | N | H | 2 |

Intermediate Compound d-2
$^1$H-NMR (CDCl$_3$) δ: 8.94 (1H, dd), 8.90 (1H, dd), 8.59 (1H, d), 8.52 (1H, d), 7.65 (1H, dd), 3.81 (2H, q), 1.39 (3H, t).
Intermediate Compound 12
$^1$H-NMR (CDCl$_3$) δ: 9.10 (1H, d), 8.68 (1H, d), 8.49 (1H, dd), 7.75 (1H, dd), 7.33 (1H, dd), 2.94 (2H, q), 1.33 (3H, t).
Intermediate Compound 13
$^1$H-NMR (CDCl$_3$) δ: 8.91 (1H, d), 8.87 (1H, s), 8.67 (1H, s), 8.50 (1H, d), 7.62 (1H, q), 3.78 (2H, q), 1.37 (3H, t)

Preparation Example 10

The mixture of the intermediate compound d-2 300 mg, cesium carbonate 480 mg, 2,2,3,3-tetrafluoropropanol 210 mg, and NMP 4 mL was heated at 70° C. with stirring for 2 hours. The resulting reaction mixtures were allowed to cool to room temperature, and thereto was added water, and the mixtures were extracted with ethyl acetate. The resulting organic layers were washed successively with saturated brine, dried over anhydrous sodium sulfate and concentrated. The resulting residues were subjected to a silica gel column chromatography to give the Present compound 4 represented by the following formula 300 mg.
The compounds that prepared according to the method described in Preparation example 10 and their physical properties are shown below.
A compound represented by formula (I-1)

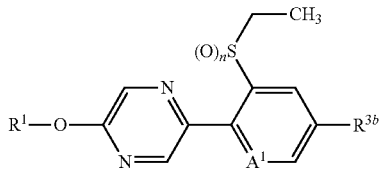

wherein A$^1$, R$^1$, R$^{3b}$ and n are indicated in Table 10.

TABLE 10

| Present compound | A$^1$ | R$^1$ | R$^{3b}$ | n |
|---|---|---|---|---|
| 4 | N | CF$_2$HCF$_2$CH$_2$ | H | 2 |
| 5 | N | CF$_3$CF$_2$CH$_2$ | H | 2 |
| 6 | N | CF$_3$CFHCF$_2$CH$_2$ | H | 2 |
| 7 | N | ![F,F-cyclopropyl-CH2] | H | 2 |
| 8 | N | CF$_3$CH$_2$ | H | 2 |
| 9 | N | CF$_2$HCH$_2$ | H | 2 |
| 10 | N | CH$_3$CF$_2$CH$_2$ | H | 2 |
| 11 | N | CF$_3$CH(CH$_3$) | H | 2 |
| 12 | N | CF$_3$CF$_2$CH(CH$_3$) | H | 2 |
| 13 | N | CF$_3$CF$_2$CH$_2$CH$_2$ | H | 2 |
| 14 | N | CF$_3$-CH-cyclopropyl | H | 2 |
| 15 | N | CF$_3$CF$_2$CF$_2$CF$_2$CH$_2$ | H | 2 |
| 16 | N | CF$_3$CF$_2$CF$_2$CH(CH$_3$) | H | 2 |
| 17 | N | F,F-cyclohexyl | H | 2 |
| 18 | N | CCl$_3$CH$_2$ | H | 2 |
| 19 | N | CF$_3$CH=CHCH$_2$ | H | 2 |
| 20 | N | CF$_3$SCH$_2$CH$_2$ | H | 2 |
| 21 | N | CF$_3$OCH$_2$CH$_2$ | H | 2 |
| 22 | N | CF$_3$CCl$_2$CH$_2$ | H | 2 |
| 23 | N | CF3C≡CCH$_2$ | H | 2 |
| 24 | N | F$_3$C-cyclopropyl-CH2 | H | 2 |
| 25 | N | CF$_3$CH=CFCH$_2$ | H | 2 |
| 26 | N | CF$_3$CF$_2$CH$_2$ | CF$_3$ | 2 |
| 27 | N | CF$_2$HCF$_2$CH$_2$ | CF$_3$ | 2 |
| 28 | N | CF$_3$CFHCF$_2$CH$_2$ | CF$_3$ | 2 |
| 29 | N | CF$_3$CF$_2$CF$_2$CH$_2$ | CF$_3$ | 2 |
| 30 | N | CF$_3$CH(CH$_3$) | CF$_3$ | 2 |
| 31 | N | CF$_3$CF$_2$CH(CH$_3$) | CF$_3$ | 2 |
| 32 | N | CF$_3$CF$_2$CF$_2$CH(CH$_3$) | CF$_3$ | 2 |

Present Compound 4
$^1$H-NMR (CDCl$_3$) δ: 8.90 (1H, dd), 8.66 (1H, d), 8.50 (1H, dd), 8.31 (1H, d), 7.59 (1H, dd), 6.03 (1H, tt), 4.83 (2H, tt), 3.83 (2H, q), 1.38 (3H, t).
Present Compound 5
$^1$H-NMR (CDCl$_3$) δ: 8.90 (1H, dd), 8.66 (1H, d), 8.50 (1H, dd), 8.33 (1H, d), 7.59 (1H, dd), 4.91 (2H, td), 3.83 (2H, q), 1.38 (3H, t).
Present Compound 6
$^1$H-NMR (CDCl$_3$) δ: 8.91 (1H, dd), 8.67 (1H, d), 8.50 (1H, dd), 8.32 (1H, d), 7.59 (1H, dd), 5.27-5.03 (1H, m), 4.89-4.78 (2H, m), 3.83 (2H, q), 1.39 (3H, t).
Present Compound 7
$^1$H-NMR (CDCl$_3$) δ: 8.91-8.88 (1H, m), 8.63 (1H, d), 8.49 (1H, dd), 8.22 (1H, d), 7.56 (1H, dd), 4.59-4.39 (2H, m), 3.85 (2H, q), 2.25-2.12 (1H, m), 1.41-1.29 (5H, m).
Present Compound 8
$^1$H-NMR (CDCl$_3$) δ: 8.89 (1H, d), 8.64 (1H, s), 8.49 (1H, d), 8.32 (1H,$), 7.57 (1H, dd), 4.83 (2H, q), 3.82 (2H, q), 1.37 (3H, t),
Present Compound 9
$^1$H-NMR (CDCl$_3$) δ: 8.89 (1H, d), 8.63 (1H, s), 8.48 (1H, d), 8.28 (1H, s), 7.56 (1H, dd), 6.16 (1H, tt), 4.62 (2H, td), 3.82 (2H, q), 1.37 (3H, t)
Present Compound 10
$^1$H-NMR (CDCl$_3$) δ: 8.89 (1H, d), 8.63 (1H, s), 8.48 (1H, d), 8.28 (1H, s), 7.54-7.58 (1H, m), 4.58 (2H, t), 3.83 (2H, q), 1.77 (3H, t), 1.37 (3H, t)
Present Compound 11
$^1$H-NMR (CDCl$_3$) δ: 8.90 (1H, dd), 8.64 (1H, d), 8.50 (1H, dd), 8.27 (1H, dd), 7.58 (1H, dd), 5.84-5.74 (1H, m), 3.84 (2H, m), 1.56 (3H, d), 1.39 (3H, t).

Present Compound 12

$^1$H-NMR (CDCl$_3$) δ: 8.90 (1H, dd), 8.65 (1H, d), 8.51 (1H, dd), 8.26 (1H, d), 7.58 (1H, dd), 5.90 (1H, dq), 3.85 (2H, m), 1.58 (3H, d), 1.39 (3H, t).

Present Compound 13

$^1$H-NMR (CDCl$_3$) δ: 8.88 (1H, dd), 8.64 (1H, d), 8.48 (1H, dd), 8.31 (1H, d), 7.57 (1H, dd), 4.93 (2H, t), 3.81 (2H, q), 1.36 (3H, t).

Present Compound 14

$^1$H-NMR (CDCl$_3$) δ: 8.89 (1H, dd), 8.61 (1H, d), 8.50 (1H, dd), 8.28 (1H, d), 7.57 (1H, dd), 5.28 (1H, m), 3.92-3.79 (2H, m), 1.39 (3H, t), 1.34-1.28 (1H, m), 0.82-0.62 (4H, m).

Present Compound 15

$^1$H-NMR (CDCl$_3$) δ: 1.38 (3H, q), 3.82 (2H, q), 4.96 (2H, t), 7.57 (1H, dd), 8.32 (1H, s), 8.49 (1H, d), 8.65 (1H, s), 8.89 (1H, d)

Present Compound 16

$^1$H-NMR (CDCl$_3$) δ: 1.37 (3H, m), 1.54 (3H, m), 3.80-3.88 (2H, m), 5.88-6.00 (1H, m), 7.57 (1H, dd), 8.24 (1H, s), 8.50 (1H, d), 8.65 (1H, s), 8.88 (1H, d)

Present Compound 18

$^1$H-NMR (CDCl$_3$) δ: 1.38 (3H, t), 3.83 (2H, q), 5.11 (2H, s), 7.53-7.63 (1H, m), 8.37 (1H, s), 8.49 (1H, d), 8.65 (1H, s), 8.89 (1H, d)

Present Compound 19

$^1$H-NMR (CDCl$_3$) δ: 1.38 (3H, t), 3.06-3.18 (2H, m), 3.82 (2H, d), 4.99-5.09 (1H, m), 7.53-7.66 (2H, m), 8.32 (1H, s), 8.49 (1H, d), 8.65 (1H, d), 8.89 (1H, s)

Present Compound 24

$^1$H-NMR (CDCl$_3$) δ 0.92 (2H, s), 1.18 (2H, s), 1.36 (3H, t), 3.82 (2H, q), 4.51 (2H, s), 7.53-7.56 (1H, m), 8.22 (1H, s), 8.47 (1H, d), 8.60 (1H, s), 8.87 (1H, d)

Preparation Example 11

The mixture of 2-bromo-5-methoxypyradine 4.9 g, (3-fluoropyridin-2-yl)tributyltin 14 g, tetrakis(triphenylphosphine)palladium(0) 0.60 g, and copper(I) iodide 1.0 g, lithium chloride 1.7 g, and toluene 60 mL was heated under reflux with stirring for 10 hours. The resulting reaction mixtures were allowed to cool to room temperature, and thereto was added water, and the mixtures were extracted with ethyl acetate. The resulting organic layers were washed with saturated brine, dried over anhydrous sodium sulfate, and concentrated. The resulting residues were subjected to a silica gel column chromatography to give the intermediate compound 9 represented by the following formula 5.2 g.

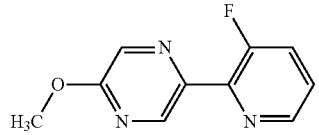

Intermediate Compound 9

$^1$H-NMR (CDCl$_3$) δ: 8.80 (1H, s), 8.61-8.58 (1H, m), 8.41 (1H, d), 7.59-7.53 (1H, m), 7.39-7.33 (1H, m), 4.05 (3H, s).

Preparation Example 12

To the mixture of the intermediate compound 9 5.2 g, sodium hydride (60%, oily), and DMF 85 mL was added ethanethiol 1.7 g under ice-cooling. The resulting mixtures were stirred at room temperature for 3 hours. To the resulting reaction mixtures was added water, and the mixtures were extracted with ethyl acetate. The resulting organic layers were washed with saturated brine, dried over anhydrous sodium sulfate, and concentrated. The resulting residues were subjected to a silica gel column chromatography to give the intermediate compound 10 represented by the following formula 4.4 g.

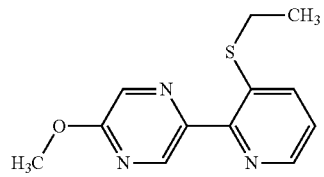 [SMILES: CCSc1cccnc1-c1cnc(OC)cn1]

Intermediate Compound 10

$^1$H-NMR (CDCl$_3$) δ: 8.75 (1H, d), 8.46 (1H, dd), 8.32 (1H, d), 7.71 (1H, dd), 7.27 (1H, dd), 4.04 (3H, s), 2.92 (2H, q), 1.31 (3H, t).

Preparation Example 13

The mixture of the intermediate compound 12 2.9 g, mCPBA (75%) 5.6 g, and chloroform 40 mL was stirred under ice-cooling for 4 hours. To the resulting reaction mixtures was added saturated aqueous sodium thiosulfate solution, and the mixtures were extracted with chloroform. The resulting organic layers were washed successively with saturated aqueous sodium hydrocarbon solution, water, and saturated brine, dried over anhydrous sodium sulfate, and concentrated under reduced pressure. The resulting residues were subjected to a silica gel column chromatography to give the intermediate compound d-2 2.8 g.

Preparation Example 14-1

To the mixture of magnesium chloride 5.16 g, triethylamine 9.15 g and THF 24 g was added 1-ethanesulfonyl-2-propanone 8.15 g at room temperature and the mixtures were stirred for 1 hour. To the mixtures was added dropwise a mixture of 5-chloro-2-pyradine carboxylic acid chloride 8.0 g and ThF 8 g over 30 minutes, and the mixtures were stirred at room temperature for 3 hours. To the mixtures was added 13% hydrochloric acid 25 g, and the mixtures were stirred for another 17 hours. The resulting mixtures were extracted with toluene 40 g, and the organic layers were washed with water twice (water 16 g, water 8 g, successively). The resulting organic layers were concentrated under reduced pressure. The resulting residues were recrystallized from toluene 8 g to give the intermediate compound e-16 represented by the following formula 9.16 g.

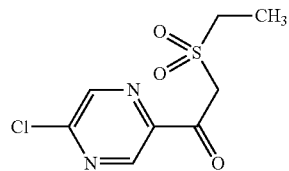

Intermediate Compound e-16

$^1$H-NMR (CDCl$_3$) δ: 9.08 (1H, d), 8.70 (1H, d), 4.89 (2H, s), 3.29 (2H, q), 1.48 (3H, t)

Preparation Example 14-2

The compounds that prepared according to the method described in Preparation example 14-1 and their physical properties are shown below.

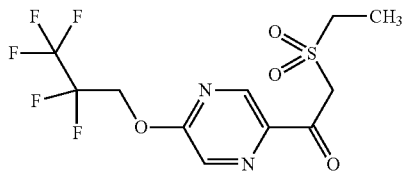 [SMILES: CCS(=O)(=O)CC(=O)c1cnc(OCC(F)(F)C(F)(F)F)cn1]

Intermediate Compound e-24
$^1$H-NMR (CDCl$_3$) δ: 8.90 (1H, d), 8.40 (1H, d), 4.95 (2H, td), 4.88 (2H, s), 3.29 (2H, q), 1.47 (3H, t).

Preparation Example 15-1

The mixture of the intermediate compound e-16 2.2 g, ammonium acetate 3.4 g and methanol 10 g was stirred at 70° C. for 3 hours. The mixtures were cooled to room temperature, and thereto was added water, and the mixtures were extracted with ethyl acetate. The resulting organic layers were washed with water 10 g, dried over anhydrous sodium sulfate, and concentrated under reduced pressure to give the intermediate compound f-16 represented by the following formula 1.6 g.

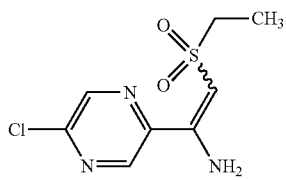

Intermediate Compound f-16
$^1$H-NMR (DMSO-d6) δ: 9.05 (1H, d), 8.89 (1H, d), 7.01 (2H, br), 5.67 (1H, s), 3.09 (2H, q), 1.23 (3H, t)

The compounds that prepared according to the method described in Preparation example 15-1 and their physical properties are shown below.

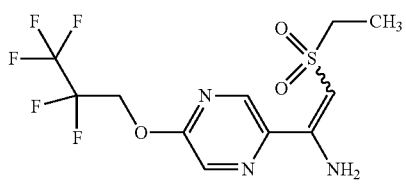

$^1$H-NMR (CDCl$_3$) δ: 8.52 (1H, d), 8.35 (1H, d), 6.68 (1H, s), 5.34 (1H, s), 4.91 (2H, td), 3.11 (2H, q), 1.41 (3H, t).

Preparation Example 16(1)

To the mixtures of the intermediate compound f-16 1.0 g, acetic acid 0.27 g, and methanol 3.0 g was added acrolein 0.27 g at 60° C., and the mixtures were stirred for 5 hours. To the mixtures was added acrolein 0.045 g, and the mixtures were stirred for another 3 hours. The mixtures were concentrated under reduced pressure to give the intermediate compound 16 represented by the following formula 1.3 g.

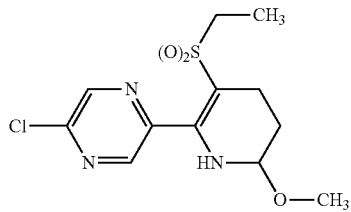

Intermediate Compound 16
$^1$H-NMR (CDCl$_3$) δ: 8.54 (2H, m), 5.12 (1H, s), 4.60 (1H, q), 3.41 (3H, s), 2.95 (2H, m), 2.67 (1H, m), 2.53 (1H, m), 2.22 (1H, m), 1.77 (1H, m), 1.24 (3H, t)

Preparation Example 16(2)

The intermediate compound 19 represented by the following formula was obtained by using the intermediate compound 18 instead of the intermediate compound f-16 according to the method described in Preparation example 16(1).

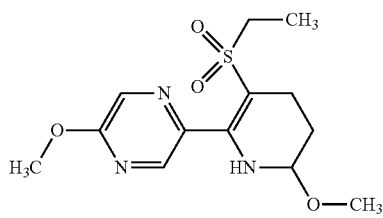

Intermediate Compound 19
$^1$H-NMR (CDCl$_3$) δ: 8.31 (1H, d), 8.15 (1H, d), 5.21 (1H, br), 4.59 (1H, m), 4.00 (3H, s), 3.37 (3H, s), 2.94 (2H, m), 2.67 (1H, m), 2.52 (1H, m), 2.19 (1H, m), 1.75 (1H, m), 1.22 (3H, t)

Preparation Example 17

The intermediate compound 16 0.10 g, vinyl acetate 0.16 g and acetic acid 1.0 g and 5% Pd—C 0.010 g were mixed, and the reaction vessel was replaced with nitrogen gas, and the mixtures were heated at 60° C. with stirring for 3 hours, and heated at 100° C. with stirring for 2 hours. The resulting reaction mixtures were analyzed by a high performance liquid chromatography and confirmed that contained 21% area percentage of the intermediate compound d-2.

Preparation Example 18

To the mixtures of the intermediate compound e-16 50 g, triethylamine 0.41 g, methanol 12.5 g, and toluene 12.5 g was added acrolein 1.35 g at room temperature, and the mixtures were stirred for 1 hour. It was confirmed by $^1$H-NMR that the mixtures contained the intermediate compound 17.

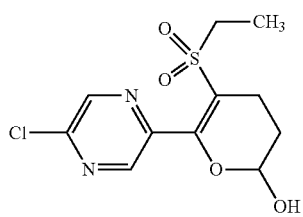 [SMILES: CCS(=O)(=O)C1=C(c2cnc(Cl)cn2)OC(O)CC1]

Intermediate Compound 17

$^1$H-NMR (CDCl$_3$) δ: 9.73 (1H, s), 9.08 (1H, d), 8.66 (1H, d), 5.83 (1H, dd), 3.17 (2H, m), 2.60 (2H, m), 2.50 (2H, m), 1.41 (3H, t)

Without isolating the intermediate compound 17, to the resulting reaction mixtures was added ammonium acetate 1.86 g, and the mixtures were stirred at room temperature for 7 hours. To the resulting reaction mixtures were added water 10 g, and the mixtures were extracted with ethyl acetate 250 g. The resulting organic layers were washed with water 10 g, and concentrated under reduced pressure to give the intermediate compound 16 6.0 g.

Preparation Example 19

The mixture of the intermediate compound 19 50 g, THF 10.0 g and methanesulfonyl chloride 0.50 g was stirred at 60° C. for 3 hours. The resulting reaction mixtures were analyzed by a high performance liquid chromatography and confirmed that the mixtures contained 29% area percentage of the intermediate compound 6.

Preparation Example 20

The mixtures of the intermediate compound 20 20 g, 2,2,3,3,3-hexafluoropropanol 0.61 mL, cesium carbonate 20 g and DMF 20 mL was stirred at 40° C. for 3 hours. The reaction mixtures were added to 1N hydrochloric acid and the mixtures were extracted with ethyl acetate. The resulting organic layers were dried over anhydrous sodium sulfate, and concentrated under reduced pressure. The resulting residues were subjected to a silica gel column chromatography to give the Present compound 343 1.9 g as a crude product.

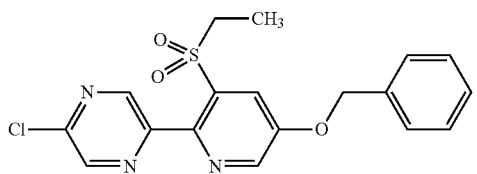 [SMILES: CCS(=O)(=O)c1cc(OCc2ccccc2)cnc1-c1cnc(Cl)cn1]

Intermediate Compound 20

$^1$H-NMR (CDCl$_3$) δ: 8.84 (1H, d), 8.63 (1H, d), 8.55 (1H, d), 8.03 (1H, d), 7.48-7.30 (5H, m), 5.27 (2H, s), 3.84-3.77 (2H, m), 1.32 (3H, t).

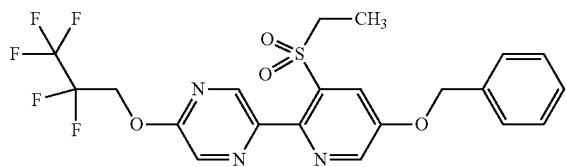 [SMILES: CCS(=O)(=O)c1cc(OCc2ccccc2)cnc1-c1cnc(OCC(F)(F)C(F)(F)F)cn1]

Present Compound 343

$^1$H-NMR (CDCl$_3$) δ: 8.61 (1H, d), 8.58 (1H, d), 8.30 (1H, d), 8.03 (1H, d), 7.48-7.36 (5H, m), 5.26 (2H, s), 4.89 (2H, td), 3.80 (2H, q), 1.31 (3H, t).

Preparation Example 21

The mixtures of the Present compound 343 1.9 g as crude product, and HBr in acetic acid 4 mL was stirred at 70° C. for 2 hours. To the reaction mixtures was added water, and the mixtures were extracted with ethyl acetate. The resulting organic layers were dried over anhydrous sodium sulfate, and concentrated under reduced pressure. The resulting residues were subjected to a silica gel column chromatography to give the Present compound 344 1.0 g.

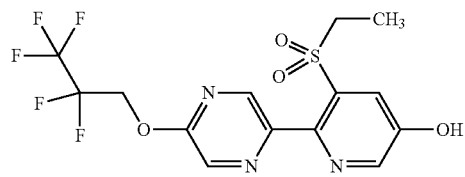 [SMILES: CCS(=O)(=O)c1cc(O)cnc1-c1cnc(OCC(F)(F)C(F)(F)F)cn1]

Present Compound 344

$^1$H-NMR (CDCl$_3$) δ: 8.59 (1H, d), 8.53 (1H, d), 8.30 (1H, d), 7.99 (1H, d), 4.90 (2H, dd), 3.85 (2H, q), 1.39 (3H, t).

Preparation Example 22

The mixture of the Present compound 344 0.33 g, isopropyl iodide 0.12 mL, cesium carbonate 390 mg, and DMF 2 mL was stirred at room temperature for 1 hour. To the reaction mixtures was added water, and the mixtures were extracted with MTBE. The resulting organic layers were dried over anhydrous sodium sulfate, and concentrated under reduced pressure. The resulting residues were subjected to a silica gel column chromatography to give the Present compound 279 0.26 g.

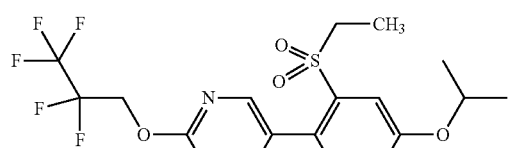

Present Compound 279

$^1$H-NMR (CDCl$_3$) δ: 8.57 (1H, d), 8.51 (1H, d), 8.30 (1H, d), 7.93 (1H, d), 4.89 (2H, t), 4.78-4.72 (1H, m), 3.82 (2H, q), 1.43 (6H, d), 1.38 (3H, t).

Preparation Example 23

The compounds that prepared according to the method described in Preparation example 22 and their physical properties are show below.

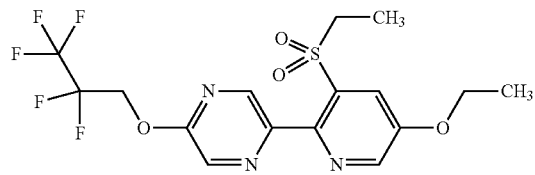 [SMILES: CCOc1cnc(-c2cnc(OCC(F)(F)C(F)(F)F)cn2)c(S(=O)(=O)CC)c1]

Present Compound 274

$^1$H-NMR (CDCl$_3$) δ: 8.58 (1H, d), 8.55 (1H, d), 8.30 (1H, d), 7.94 (1H, d), 4.90 (2H, t), 4.23 (2H, q), 3.82 (2H, q), 1.51 (3H, t), 1.38 (3H, t).

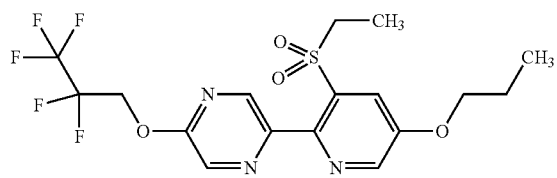 [SMILES: CCCOc1cnc(-c2cnc(OCC(F)(F)C(F)(F)F)cn2)c(S(=O)(=O)CC)c1]

Present Compound 339

¹H-NMR (CDCl₃) δ: 8.57 (1H, d), 8.55 (1H, d), 8.30 (1H, d), 7.94 (1H, d), 4.89 (2H, t), 4.11 (2H, t), 3.82 (2H, q), 1.92-1.88 (2H, m), 1.38 (3H, t), 1.10 (3H, t).

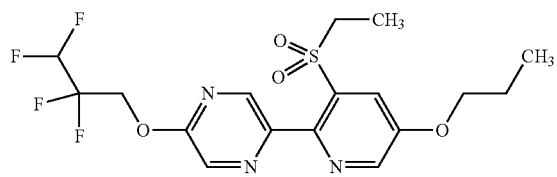

Present Compound 340

¹H-NMR (CDCl₃) δ: 8.58 (1H, d), 8.55 (1H, d), 8.28 (1H, d), 7.94 (1H, d), 6.02 (1H, tt), 4.81 (2H, tt), 4.11 (2H, t), 3.82 (2H, q), 1.90 (2H, td), 1.38 (3H, t), 1.09 (3H, t).

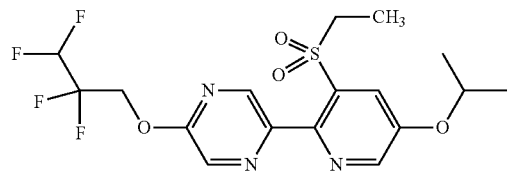 [SMILES: CCS(=O)(=O)c1cc(OC(C)C)cnc1-c1cnc(OCC(F)(F)C(F)F)cn1]

Present Compound 280

¹H-NMR (CDCl₃) δ: 8.58 (1H, d), 8.51 (1H, d), 8.28 (1H, d), 7.93 (1H, d), 6.02 (1H, tt), 4.85-4.70 (3H, m), 3.82 (2H, q), 1.43 (6H, d), 1.38 (3H, t).

Preparation Example 24

The mixture of the Present compound 345 1.4 g, N-bromosuccinimide 680 mg, and acetic acid 7 mL was heated under reflux with stirring for 24 hours. The resulting mixtures were made pH 11 with 1N sodium hydroxide. To the mixtures was added saturated aqueous sodium sulfite solution, and the precipitated solids were filtered and washed with water to give the Present compound 346 860 mg.

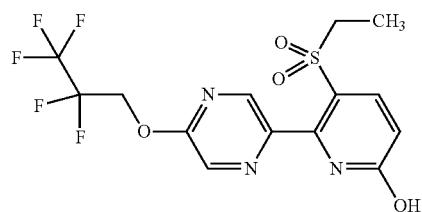 [SMILES: CCS(=O)(=O)c1ccc(O)nc1-c1cnc(OCC(F)(F)C(F)(F)F)cn1]

Present Compound 345

¹H-NMR (CDCl₃) δ: 8.52 (1H, d), 8.40 (1H, d), 8.01 (1H, d), 6.63 (1H, d), 4.93 (2H, t), 3.39 (2H, q), 1.31 (3H, t).

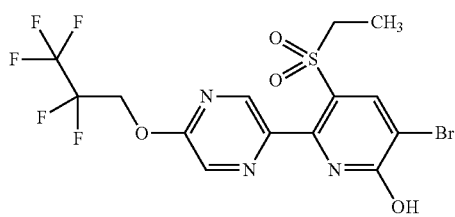 [SMILES: CCS(=O)(=O)c1cc(Br)c(O)nc1-c1cnc(OCC(F)(F)C(F)(F)F)cn1]

Present Compound 346

¹H-NMR (CDCl₃) δ: 8.63 (1H, s), 8.42 (1H, s), 8.38 (1H, s), 4.93 (2H, t), 3.36-3.27 (2H, m), 1.32 (3H, t).

Preparation Example 25

The mixtures of the Present compound 346 860 mg, 4-fluorophenyl boronic acid 270 mg, tetrakis(triphenylphosphine)palladium(0) 32 mg, 2-dicyclohexylphosphino-2'-6'-dimethoxybiphenyl 57 mg, tripotassium phosphate 1.5 g, and dimethoxyethane 4.5 mL and was heated under reflux with stirring for 10 hours. To the resulting mixtures was added water, and the mixtures were extracted with ethyl acetate. The resulting organic layers were dried over anhydrous sodium sulfate, and concentrated under reduced pressure. The resulting residues were subjected to a silica gel column chromatography to give the Present compound 347 280 mg.

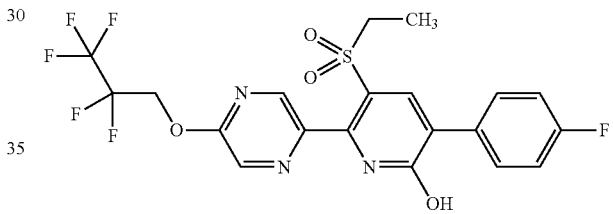

Present Compound 347

¹H-NMR (DMSO-D₆) δ: 8.64 (1H, d), 8.60 (1H, d), 7.95 (1H, s), 7.85 (2H, dd), 7.33-7.28 (2H, m), 5.27 (2H, t), 3.50-3.39 (2H, m), 1.23-1.15 (3H, m).

Preparation Example 26

The mixtures of the Present compound 347 280 mg, and phosphorus oxychloride 5 mL was heated under reflux with stirring for 72 hours. The resulting reaction mixtures were concentrated under reduced pressure. To the resulting residues were added saturated aqueous sodium hydrocarbon solution under ice-cooling and the mixtures were extracted with ethyl acetate. The resulting organic layers were dried over anhydrous sodium sulfate, and concentrated under reduced pressure. The resulting residues were subjected to a silica gel column chromatography to give the Present compound 348 130 mg.

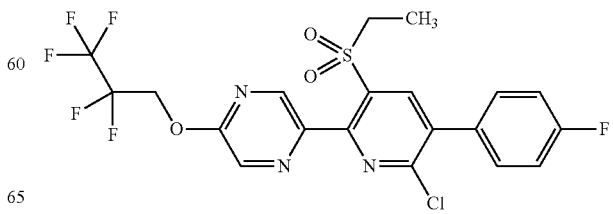

Present Compound 348

¹H-NMR (CDCl₃) δ: 8.75 (1H, d), 8.43 (1H, s), 8.35 (1H, d), 7.57-7.51 (2H, m), 7.26-7.19 (2H, m), 4.93 (2H, t), 3.89 (2H, q), 1.42 (3H, t).

Preparation Example 27

The mixtures of the intermediate compound e-24 390 mg, the intermediate compound 21 200 mg, sodium hydride (60%, oily) 95 mg, and THF 5 mL was stirred under ice-cooling for 24 hours. To the resulting reaction mixtures were added ammonium acetate 830 mg and ethanol 5 mL under ice-cooling. The resulting reaction mixtures were stirred at 80° C. for 24 hours. The resulting reaction mixtures were concentrated under reduced pressure, and the resulting residues were subjected to a silica gel column chromatography to give the Present compound 194 120 mg.

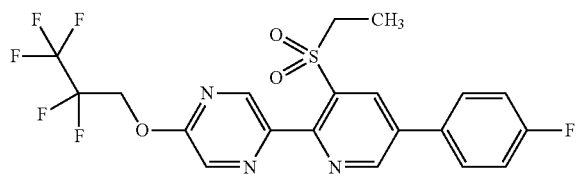 [SMILES: CCS(=O)(=O)c1cc(-c2ccc(F)cc2)cnc1-c1cnc(OCC(F)(F)C(F)(F)F)cn1]

Present Compound 194

¹H-NMR (CDCl₃) δ: 9.07 (1H, d), 8.71 (1H, d), 8.63 (1H, d), 8.35 (1H, d), 7.69-7.66 (2H, m), 7.28-7.25 (2H, m), 4.92 (2H, td), 3.89 (2H, q), 1.45-1.40 (3H, m).

The compounds represented by formula (100)

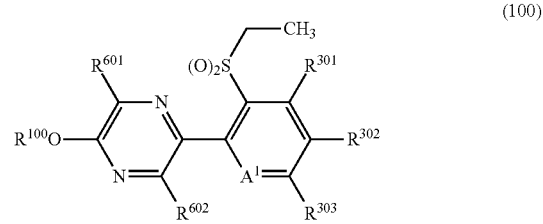

[wherein, $R^{301}$, $R^{302}$, $R^{303}$, $R^{601}$, $R^{602}$, $R^{100}$, and $A^1$ represent any one of the combination indicated in the following Table 11 to Table 36]

can be prepared according to the processes described above.

TABLE 11

| Present compound | $A^1$ | $R^{100}$ | $R^{301}$ | $R^{302}$ | $R^{303}$ | $R^{601}$ | $R^{602}$ |
|---|---|---|---|---|---|---|---|
| 33 | N | CF₂HCH₂ | H | H | NH₂ | H | H |
| 34 | N | CF₃CF₂CH₂ | H | H | NH₂ | H | H |
| 35 | N | CF₂HCF₂CH₂ | H | H | NH₂ | H | H |
| 36 | N | CF₃CF₂CF₂CH₂ | H | H | NH₂ | H | H |
| 37 | N | CF₃CFHCF₂CH₂ | H | H | NH₂ | H | H |
| 38 | N | CF₂HCH₂ | H | H | NHCH₃ | H | H |
| 39 | N | CF₃CF₂CH₂ | H | H | NHCH₃ | H | H |
| 40 | N | CF₂HCF₂CH₂ | H | H | NHCH₃ | H | H |
| 41 | N | CF₃CF₂CF₂CH₂ | H | H | NHCH₃ | H | H |
| 42 | N | CF₃CFHCF₂CH₂ | H | H | NHCH₃ | H | H |
| 43 | N | CF₂HCH₂ | H | H | N(CH₃)₂ | H | H |
| 44 | N | CF₃CF₂CH₂ | H | H | N(CH₃)₂ | H | H |
| 45 | N | CF₂HCF₂CH₂ | H | H | N(CH₃)₂ | H | H |
| 46 | N | CF₃CF₂CF₂CH₂ | H | H | N(CH₃)₂ | H | H |
| 47 | N | CF₃CFHCF₂CH₂ | H | H | N(CH₃)₂ | H | H |
| 48 | N | CF₂HCH₂ | H | H | N(CH₂CH₃)₂ | H | H |
| 49 | N | CF₃CF₂CH₂ | H | H | N(CH₂CH₃)₂ | H | H |
| 50 | N | CF₂HCF₂CH₂ | H | H | N(CH₂CH₃)₂ | H | H |
| 51 | N | CF₃CF₂CF₂CH₂ | H | H | N(CH₂CH₃)₂ | H | H |
| 52 | N | CF₃CFHCF₂CH₂ | H | H | N(CH₂CH₃)₂ | H | H |
| 53 | N | CF₂HCH₂ | H | H | NHCH₂CF₃ | H | H |
| 54 | N | CF₃CF₂CH₂ | H | H | NHCH₂CF₃ | H | H |
| 55 | N | CF₂HCF₂CH₂ | H | H | NHCH₂CF₃ | H | H |
| 56 | N | CF₃CF₂CF₂CH₂ | H | H | NHCH₂CF₃ | H | H |
| 57 | N | CF₃CFHCF₂CH₂ | H | H | NHCH₂CF₃ | H | H |

TABLE 12

| Present compound | $A^1$ | $R^{100}$ | $R^{301}$ | $R^{302}$ | $R^{303}$ | $R^{601}$ | $R^{602}$ |
|---|---|---|---|---|---|---|---|
| 58 | N | $CF_2HCH_2$ | H | H | Cl | H | H |
| 59 | N | $CF_3CF_2CH_2$ | H | H | Cl | H | H |
| 60 | N | $CF_2HCF_2CH_2$ | H | H | Cl | H | H |
| 61 | N | $CF_3CF_2CF_2CH_2$ | H | H | Cl | H | H |
| 62 | N | $CF_3CFHCF_2CH_2$ | H | H | Cl | H | H |
| 63 | N | $CF_2HCH_2$ | H | Cl | H | H | H |
| 64 | N | $CF_3CF_2CH_2$ | H | Cl | H | H | H |
| 65 | N | $CF_2HCF_2CH_2$ | H | Cl | H | H | H |
| 66 | N | $CF_3CF_2CF_2CH_2$ | H | Cl | H | H | H |
| 67 | N | $CF_3CFHCF_2CH_2$ | H | Cl | H | H | H |
| 68 | N | $CF_2HCH_2$ | H | H | $OCH_3$ | H | H |
| 69 | N | $CF_3CF_2CH_2$ | H | H | $OCH_3$ | H | H |
| 70 | N | $CF_2HCF_2CH_2$ | H | H | $OCH_3$ | H | H |
| 71 | N | $CF_3CF_2CF_2CH_2$ | H | H | $OCH_3$ | H | H |
| 72 | N | $CF_3CFHCF_2CH_2$ | H | H | $OCH_3$ | H | H |

TABLE 13

| Present compound | $A^1$ | $R^{100}$ | $R^{301}$ | $R^{302}$ | $R^{303}$ | $R^{601}$ | $R^{602}$ |
|---|---|---|---|---|---|---|---|
| 73 | N | $CF_2HCH_2$ | H | H | 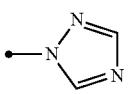 | H | H |
| 74 | N | $CF_3CF_2CH_2$ | H | H | 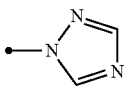 | H | H |
| 75 | N | $CF_2HCF_2CH_2$ | H | H | 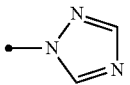 | H | H |
| 76 | N | $CF_3CF_2CF_2CH_2$ | H | H | 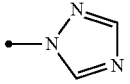 | H | H |
| 77 | N | $CF_3CFHCF_2CH_2$ | H | H | 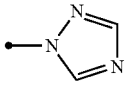 | H | H |
| 78 | N | $CF_2HCH_2$ | H | H | 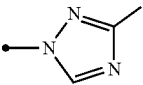 | H | H |
| 79 | N | $CF_3CF_2CH_2$ | H | H | 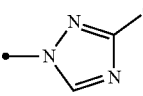 | H | H |
| 80 | N | $CF_2HCF_2CH_2$ | H | H | 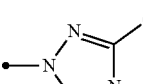 | H | H |
| 81 | N | $CF_3CF_2CF_2CH_2$ | H | H | 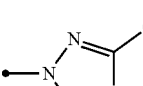 | H | H |
| 82 | N | $CF_3CFHCF_2CH_2$ | H | H | 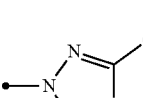 | H | H |

TABLE 14
| Present compound | A¹ | R¹⁰⁰ | R³⁰¹ | R³⁰² | R³⁰³ | R⁶⁰¹ | R⁶⁰² |
|---|---|---|---|---|---|---|---|
| 83 | N | CF₂HCH₂ | H | H | 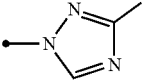 | H | H |
| 84 | N | CF₃CF₂CH₂ | H | H | 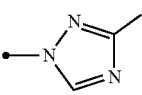 | H | H |
| 85 | N | CF₂HCF₂CH₂ | H | H | 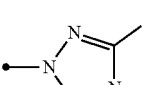 | H | H |
| 86 | N | CF₃CF₂CF₂CH₂ | H | H | 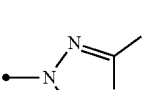 | H | H |
| 87 | N | CF₃CFHCF₂CH₂ | H | H | 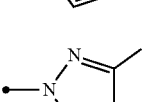 | H | H |
| 88 | N | CF₂HCH₂ | H | H | 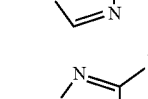 | H | H |
| 89 | N | CF₃CF₂CH₂ | H | H | 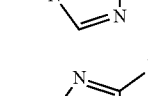 | H | H |
| 90 | N | CF₂HCF₂CH₂ | H | H | 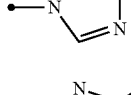 | H | H |
| 91 | N | CF₃CF₂CF₂CH₂ | H | H | 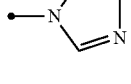 | H | H |
| 92 | N | CF₃CFHCF₂CH₂ | H | H | 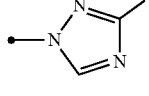 | H | H |
TABLE 15
| Present compound | A¹ | R¹⁰⁰ | R³⁰¹ | R³⁰² | R³⁰³ | R⁶⁰¹ | R⁶⁰² |
|---|---|---|---|---|---|---|---|
| 93 | N | CF₂HCH₂ | H | H | 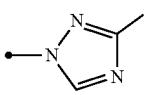 | H | H |
| 94 | N | CF₃CF₂CH₂ | H | H | 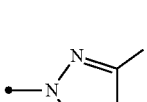 | H | H |

TABLE 15-continued
| Present compound A¹ | R¹⁰⁰ | R³⁰¹ | R³⁰² | R³⁰³ | R⁶⁰¹ | R⁶⁰² |
|---|---|---|---|---|---|---|
| 95 | N | CF₂HCF₂CH₂ | H | H | 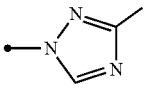 | H | H |
| 96 | N | CF₃CF₂CF₂CH₂ | H | H | 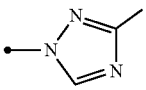 | H | H |
| 97 | N | CF₃CFHCF₂CH₂ | H | H | 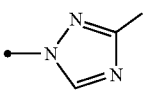 | H | H |
| 98 | N | CF₂HCH₂ | H | H | 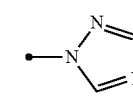 | H | H |
| 99 | N | CF₃CF₂CH₂ | H | H | 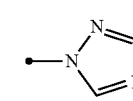 | H | H |
| 100 | N | CF₂HCF₂CH₂ | H | H | 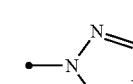 | H | H |
| 101 | N | CF₃CF₂CF₂CH₂ | H | H | 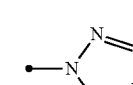 | H | H |
| 102 | N | CF₃CFHCF₂CH₂ | H | H | 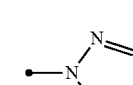 | H | H |
TABLE 16
| Present Compound A¹ | R¹⁰⁰ | R³⁰¹ | R³⁰² | R³⁰³ | R⁶⁰¹ | R⁶⁰² |
|---|---|---|---|---|---|---|
| 103 | N | CF₂HCH₂ | H | H | 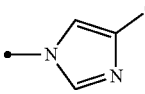 | H | H |
| 104 | N | CF₃CF₂CH₂ | H | H | 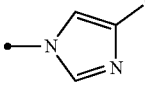 | H | H |
| 105 | N | CF₂HCF₂CH₂ | H | H | 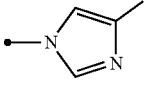 | H | H |
| 106 | N | CF₃CF₂CF₂CH₂ | H | H | 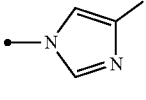 | H | H |

TABLE 16-continued

| Present Compound A¹ | | R¹⁰⁰ | R³⁰¹ | R³⁰² | R³⁰³ | | R⁶⁰¹ | R⁶⁰² |
|---|---|---|---|---|---|---|---|---|
| 107 | N | CF₃CFHCF₂CH₂ | H | H | 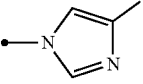 | CF₃ | H | H |
| 108 | N | CF₂HCH₂ | H | H | 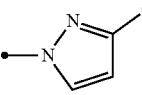 | CF₃ | H | H |
| 109 | N | CF₃CF₂CH₂ | H | H | 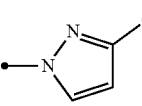 | CF₃ | H | H |
| 110 | N | CF₂HCF₂CH₂ | H | H | 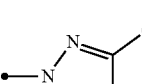 | CF₃ | H | H |
| 111 | N | CF₃CF₂CF₂CH₂ | H | H | 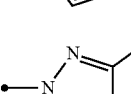 | CF₃ | H | H |
| 112 | N | CF₃CFHCF₂CH₂ | H | H | 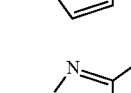 | CF₃ | H | H |

TABLE 17

| Present compound A¹ | | R¹⁰⁰ | R³⁰¹ | R³⁰² | R³⁰³ | R⁶⁰¹ | R⁶⁰² |
|---|---|---|---|---|---|---|---|
| 113 | N | CF₂HCH₂ | H | H | 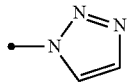 | H | H |
| 114 | N | CF₃CF₂CH₂ | H | H | 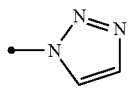 | H | H |
| 115 | N | CF₂HCF₂CH₂ | H | H | 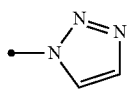 | H | H |
| 116 | N | CF₃CF₂CF₂CH₂ | H | H | 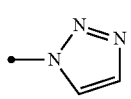 | H | H |
| 117 | N | CF₃CFHCF₂CH₂ | H | H | 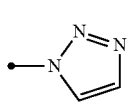 | H | H |
| 118 | N | CF₂HCH₂ | H | H | 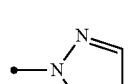 | H | H |
| 119 | N | CF₃CF₂CH₂ | H | H | 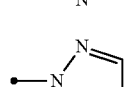 | H | H |

TABLE 17-continued
| Present compound | A¹ | R¹⁰⁰ | R³⁰¹ | R³⁰² | R³⁰³ | R⁶⁰¹ | R⁶⁰² |
|---|---|---|---|---|---|---|---|
| 120 | N | CF₂HCF₂CH₂ | H | H | 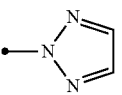 | H | H |
| 121 | N | CF₃CF₂CF₂CH₂ | H | H | 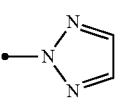 | H | H |
| 122 | N | CF₃CFHCF₂CH₂ | H | H | 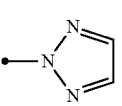 | H | H |
TABLE 18
| Present compound | A¹ | R¹⁰⁰ | R³⁰¹ | R³⁰² | R³⁰³ | R⁶⁰¹ | R⁶⁰² |
|---|---|---|---|---|---|---|---|
| 123 | N | CF₂HCH₂ | H | H | 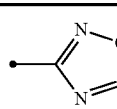 | H | H |
| 124 | N | CF₃CF₂CH₂ | H | H | 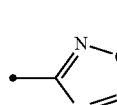 | H | H |
| 125 | N | CF₂HCF₂CH₂ | H | H | 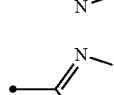 | H | H |
| 126 | N | CF₃CF₂CF₂CH₂ | H | H | 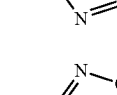 | H | H |
| 127 | N | CF₃CFHCF₂CH₂ | H | H | 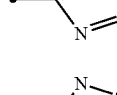 | H | H |
| 128 | N | CF₂HCH₂ | H | H | 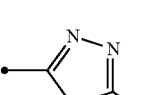 | H | H |
| 129 | N | CF₃CF₂CH₂ | H | H | 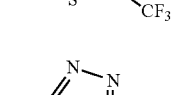 | H | H |
| 130 | N | CF₂HCF₂CH₂ | H | H | 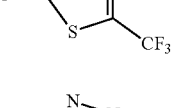 | H | H |
| 131 | N | CF₃CF₂CF₂CH₂ | H | H | 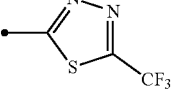 | H | H |

TABLE 18-continued

| Present compound A¹ | R¹⁰⁰ | R³⁰¹ | R³⁰² | R³⁰³ | R⁶⁰¹ | R⁶⁰² |
|---|---|---|---|---|---|---|
| 132 | N | CF₃CFHCF₂CH₂ | H | H | ![2-CF3-1,3,4-thiadiazol-5-yl] | H | H |

TABLE 19

| Present compound A¹ | R¹⁰⁰ | R³⁰¹ | R³⁰² | R³⁰³ | R⁶⁰¹ | R⁶⁰² |
|---|---|---|---|---|---|---|
| 133 | N | CF₂HCH₂ | H | 1,2,4-triazol-1-yl | H | H | H |
| 134 | N | CF₃CF₂CH₂ | H | 1,2,4-triazol-1-yl | H | H | H |
| 135 | N | CF₂HCF₂CH₂ | H | 1,2,4-triazol-1-yl | H | H | H |
| 136 | N | CF₃CF₂CF₂CH₂ | H | 1,2,4-triazol-1-yl | H | H | H |
| 137 | N | CF₃CFHCF₂CH₂ | H | 1,2,4-triazol-1-yl | H | H | H |
| 138 | N | CF₂HCH₂ | H | 3-Cl-1,2,4-triazol-1-yl | H | H | H |
| 139 | N | CF₃CF₂CH₂ | H | 3-Cl-1,2,4-triazol-1-yl | H | H | H |
| 140 | N | CF₂HCF₂CH₂ | H | 3-Cl-1,2,4-triazol-1-yl | H | H | H |
| 141 | N | CF₃CF₂CF₂CH₂ | H | 3-Cl-1,2,4-triazol-1-yl | H | H | H |
| 142 | N | CF₃CFHCF₂CH₂ | H | 3-Cl-1,2,4-triazol-1-yl | H | H | H |

TABLE 20

| Present compound | A¹ | R¹⁰⁰ | R³⁰¹ | R³⁰² | R³⁰³ | R⁶⁰¹ | R⁶⁰² |
|---|---|---|---|---|---|---|---|
| 143 | N | CF₂HCH₂ | H | triazole-OCH₃ | H | H | H |
| 144 | N | CF₃CF₂CH₂ | H | triazole-OCH₃ | H | H | H |
| 145 | N | CF₂HCF₂CH₂ | H | triazole-OCH₃ | H | H | H |
| 146 | N | CF₃CF₂CF₂CH₂ | H | triazole-OCH₃ | H | H | H |
| 147 | N | CF₃CFHCF₂CH₂ | H | triazole-OCH₃ | H | H | H |
| 148 | N | CF₂HCH₂ | H | triazole-NH₂ | H | H | H |
| 149 | N | CF₃CF₂CH₂ | H | triazole-NH₂ | H | H | H |
| 150 | N | CF₂HCF₂CH₂ | H | triazole-NH₂ | H | H | H |
| 151 | N | CF₃CF₂CF₂CH₂ | H | triazole-NH₂ | H | H | H |
| 152 | N | CF₃CFHCF₂CH₂ | H | triazole-NH₂ | H | H | H |

TABLE 21

| Present compound | A¹ | R¹⁰⁰ | R³⁰¹ | R³⁰² | R³⁰³ | R⁶⁰¹ | R⁶⁰² |
|---|---|---|---|---|---|---|---|
| 153 | N | CF₂HCH₂ | H | triazole-S(O)₂CH₃ | H | H | H |
| 154 | N | CF₃CF₂CH₂ | H | triazole-S(O)₂CH₃ | H | H | H |

TABLE 21-continued

| Present compound | A¹ | R¹⁰⁰ | R³⁰¹ | R³⁰² | R³⁰³ | R⁶⁰¹ | R⁶⁰² |
|---|---|---|---|---|---|---|---|
| 155 | N | CF₂HCF₂CH₂ | H | 1,2,4-triazol-1-yl-3-S(O)₂CH₃ | H | H | H |
| 156 | N | CF₃CF₂CF₂CH₂ | H | 1,2,4-triazol-1-yl-3-S(O)₂CH₃ | H | H | H |
| 157 | N | CF₃CFHCF₂CH₂ | H | 1,2,4-triazol-1-yl-3-S(O)₂CH₃ | H | H | H |
| 158 | N | CF₂HCH₂ | H | 1,2,4-triazol-1-yl-3-CN | H | H | H |
| 159 | N | CF₃CF₂CH₂ | H | 1,2,4-triazol-1-yl-3-CN | H | H | H |
| 160 | N | CF₂HCF₂CH₂ | H | 1,2,4-triazol-1-yl-3-CN | H | H | H |
| 161 | N | CF₃CF₂CF₂CH₂ | H | 1,2,4-triazol-1-yl-3-CN | H | H | H |
| 162 | N | CF₃CFHCF₂CH₂ | H | 1,2,4-triazol-1-yl-3-CN | H | H | H |

TABLE 22

| Present compound | A¹ | R¹⁰⁰ | R³⁰¹ | R³⁰² | R³⁰³ | R⁶⁰¹ | R⁶⁰² |
|---|---|---|---|---|---|---|---|
| 163 | N | CF₂HCH₂ | H | imidazol-1-yl-4-CF₃ | H | H | H |
| 164 | N | CF₃CF₂CH₂ | H | imidazol-1-yl-4-CF₃ | H | H | H |
| 165 | N | CF₂HCF₂CH₂ | H | imidazol-1-yl-4-CF₃ | H | H | H |
| 166 | N | CF₃CF₂CF₂CH₂ | H | imidazol-1-yl-4-CF₃ | H | H | H |

TABLE 22-continued

| Present compound | A¹ | R¹⁰⁰ | R³⁰¹ | R³⁰² | R³⁰³ | R⁶⁰¹ | R⁶⁰² |
|---|---|---|---|---|---|---|---|
| 167 | N | CF₃CFHCF₂CH₂ | H | 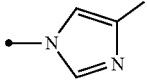 CF₃ | H | H | H |
| 168 | N | CF₂HCH₂ | H | 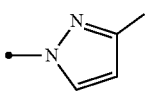 CF₃ | H | H | H |
| 169 | N | CF₃CF₂CH₂ | H | 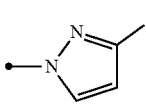 CF₃ | H | H | H |
| 170 | N | CF₂HCF₂CH₂ | H | 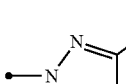 CF₃ | H | H | H |
| 171 | N | CF₃CF₂CF₂CH₂ | H | 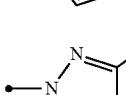 CF₃ | H | H | H |
| 172 | N | CF₃CFHCF₂CH₂ | H | 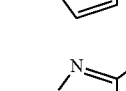 CF₃ | H | H | H |

TABLE 23

| Present compound | A¹ | R¹⁰⁰ | R³⁰¹ | R³⁰² | R³⁰³ | R⁶⁰¹ | R⁶⁰² |
|---|---|---|---|---|---|---|---|
| 173 | N | CF₂HCH₂ | H | 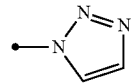 | H | H | H |
| 174 | N | CF₃CF₂CH₂ | H | 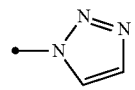 | H | H | H |
| 175 | N | CF₂HCF₂CH₂ | H | 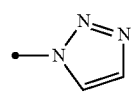 | H | H | H |
| 176 | N | CF₃CF₂CF₂CH₂ | H | 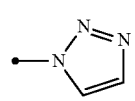 | H | H | H |
| 177 | N | CF₃CFHCF₂CH₂ | H | 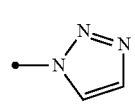 | H | H | H |
| 178 | N | CF₂HCH₂ | H | 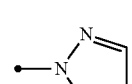 | H | H | H |
| 179 | N | CF₃CF₂CH₂ | H | 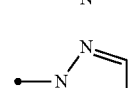 | H | H | H |

TABLE 23-continued

| Present compound A¹ | R¹⁰⁰ | R³⁰¹ | R³⁰² | R³⁰³ | R⁶⁰¹ | R⁶⁰² |
|---|---|---|---|---|---|---|
| 180 | N | CF$_2$HCF$_2$CH$_2$ | H | 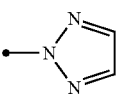 | H | H | H |
| 181 | N | CF$_3$CF$_2$CF$_2$CH$_2$ | H | 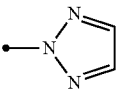 | H | H | H |
| 182 | N | CF$_3$CFHCF$_2$CH$_2$ | H | 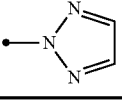 | H | H | H |

TABLE 24

| Present compound A¹ | R¹⁰⁰ | R³⁰¹ | R³⁰² | R³⁰³ | R⁶⁰¹ | R⁶⁰² |
|---|---|---|---|---|---|---|
| 183 | N | CF$_2$HCH$_2$ | H | 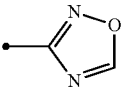 | H | H | H |
| 184 | N | CF$_3$CF$_2$CH$_2$ | H | 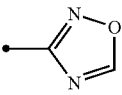 | H | H | H |
| 185 | N | CF$_2$HCF$_2$CH$_2$ | H | 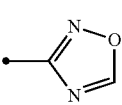 | H | H | H |
| 186 | N | CF$_3$CF$_2$CF$_2$CH$_2$ | H | 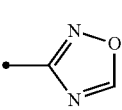 | H | H | H |
| 187 | N | CF$_3$CFHCF$_2$CH$_2$ | H | 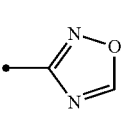 | H | H | H |
| 188 | N | CF$_2$HCH$_2$ | H | 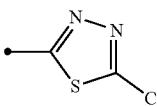 | H | H | H |
| 189 | N | CF$_3$CF$_2$CH$_2$ | H | 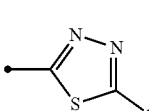 | H | H | H |
| 190 | N | CF$_2$HCF$_2$CH$_2$ | H | 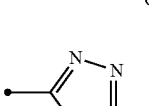 | H | H | H |
| 191 | N | CF$_3$CF$_2$CF$_2$CH$_2$ | H | 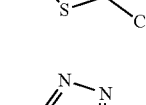 | H | H | H |

TABLE 24-continued

| Present compound | A¹ | R$^{100}$ | R$^{301}$ | R$^{302}$ | R$^{303}$ | R$^{601}$ | R$^{602}$ |
|---|---|---|---|---|---|---|---|
| 192 | N | CF$_3$CFHCF$_2$CH$_2$ | H | 2-CF$_3$-1,3,4-thiadiazol-5-yl | H | H | H |

TABLE 25

| Present compound | A¹ | R$^{100}$ | R$^{301}$ | R$^{302}$ | R$^{303}$ | R$^{601}$ | R$^{602}$ |
|---|---|---|---|---|---|---|---|
| 193 | N | CF$_2$HCH$_2$ | H | 4-F-C$_6$H$_4$ | H | H | H |
| 194 | N | CF$_3$CF$_2$CH$_2$ | H | 4-F-C$_6$H$_4$ | H | H | H |
| 195 | N | CF$_2$HCF$_2$CH$_2$ | H | 4-F-C$_6$H$_4$ | H | H | H |
| 196 | N | CF$_3$CF$_2$CF$_2$CH$_2$ | H | 4-F-C$_6$H$_4$ | H | H | H |
| 197 | N | CF$_3$CFHCF$_2$CH$_2$ | H | 4-F-C$_6$H$_4$ | H | H | H |
| 198 | N | CF$_2$HCH$_2$ | H |  | H | H | H |
| 199 | N | CF$_3$CF$_2$CH$_2$ | H |  | H | H | H |
| 200 | N | CF$_2$HCF$_2$CH$_2$ | H |  | H | H | H |
| 201 | N | CF$_3$CF$_2$CF$_2$CH$_2$ | H |  | H | H | H |
| 202 | N | CF$_3$CFHCF$_2$CH$_2$ | H |  | H | H | H |

TABLE 26

| Present compound | A¹ | R$^{100}$ | R$^{301}$ | R$^{302}$ | R$^{303}$ | R$^{601}$ | R$^{602}$ |
|---|---|---|---|---|---|---|---|
| 203 | N | CF$_2$HCH$_2$ | H | 4-CN-C$_6$H$_4$ | H | H | H |
| 204 | N | CF$_3$CF$_2$CH$_2$ | H | 4-CN-C$_6$H$_4$ | H | H | H |
| 205 | N | CF$_2$HCF$_2$CH$_2$ | H | 4-CN-C$_6$H$_4$ | H | H | H |
| 206 | N | CF$_3$CF$_2$CF$_2$CH$_2$ | H | 4-CN-C$_6$H$_4$ | H | H | H |

TABLE 26-continued

| Present compound | A¹ | R¹⁰⁰ | R³⁰¹ | R³⁰² | R³⁰³ | R⁶⁰¹ | R⁶⁰² |
|---|---|---|---|---|---|---|---|
| 207 | N | CF₃CFHCF₂CH₂ | H | 4-CN-phenyl | H | H | H |
| 208 | N | CF₂HCH₂ | H | 4-CF₃-phenyl | H | H | H |
| 209 | N | CF₃CF₂CH₂ | H | 4-CF₃-phenyl | H | H | H |
| 210 | N | CF₂HCF₂CH₂ | H | 4-CF₃-phenyl | H | H | H |
| 211 | N | CF₃CF₂CF₂CH₂ | H | 4-CF₃-phenyl | H | H | H |
| 212 | N | CF₃CFHCF₂CH₂ | H | 4-CF₃-phenyl | H | H | H |

TABLE 27

| Present compound | A¹ | R¹⁰⁰ | R³⁰¹ | R³⁰² | R³⁰³ | R⁶⁰¹ | R⁶⁰² |
|---|---|---|---|---|---|---|---|
| 213 | N | CF₂HCH₂ | H | 3-F-phenyl | H | H | H |
| 214 | N | CF₃CF₂CH₂ | H | 3-F-phenyl | H | H | H |
| 215 | N | CF₂HCF₂CH₂ | H | 3-F-phenyl | H | H | H |
| 216 | N | CF₃CF₂CF₂CH₂ | H | 3-F-phenyl | H | H | H |
| 217 | N | CF₃CFHCF₂CH₂ | H | 3-F-phenyl | H | H | H |

TABLE 27-continued

| Present compound | A¹ | R$^{100}$ | R$^{301}$ | R$^{302}$ | R$^{303}$ | R$^{601}$ | R$^{602}$ |
|---|---|---|---|---|---|---|---|
| 218 | N | CF$_2$HCH$_2$ | H | 3-cyanophenyl | H | H | H |
| 219 | N | CF$_3$CF$_2$CH$_2$ | H | 3-cyanophenyl | H | H | H |
| 220 | N | CF$_2$HCF$_2$CH$_2$ | H | 3-cyanophenyl | H | H | H |
| 221 | N | CF$_3$CF$_2$CF$_2$CH$_2$ | H | 3-cyanophenyl | H | H | H |
| 222 | N | CF$_3$CFHCF$_2$CH$_2$ | H | 3-cyanophenyl | H | H | H |

TABLE 28

| Present compound | A¹ | R$^{100}$ | R$^{301}$ | R$^{302}$ | R$^{303}$ | R$^{601}$ | R$^{602}$ |
|---|---|---|---|---|---|---|---|
| 223 | N | CF$_2$HCH$_2$ | H | pyridin-2-yl | H | H | H |
| 224 | N | CF$_3$CF$_2$CH$_2$ | H | pyridin-2-yl | H | H | H |
| 225 | N | CF$_2$HCF$_2$CH$_2$ | H | pyridin-2-yl | H | H | H |
| 226 | N | CF$_3$CF$_2$CF$_2$CH$_2$ | H | pyridin-2-yl | H | H | H |
| 227 | N | CF$_3$CFHCF$_2$CH$_2$ | H | pyridin-2-yl | H | H | H |
| 228 | N | CF$_2$HCH$_2$ | H | pyrazin-2-yl | H | H | H |

TABLE 28-continued
| Present compound | A¹ | R¹⁰⁰ | R³⁰¹ | R³⁰² | R³⁰³ | R⁶⁰¹ | R⁶⁰² |
|---|---|---|---|---|---|---|---|
| 229 | N | CF₃CF₂CH₂ | H | 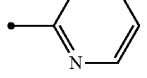 | H | H | H |
| 230 | N | CF₂HCF₂CH₂ | H | 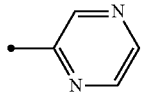 | H | H | H |
| 231 | N | CF₃CF₂CF₂CH₂ | H | 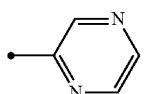 | H | H | H |
| 232 | N | CF₃CFHCF₂CH₂ | H | 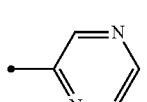 | H | H | H |
TABLE 29
| Present compound | A¹ | R¹⁰⁰ | R³⁰¹ | R³⁰² | R³⁰³ | R⁶⁰¹ | R⁶⁰² |
|---|---|---|---|---|---|---|---|
| 233 | N | CF₂HCH₂ | H | 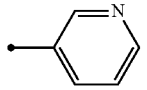 | H | H | H |
| 234 | N | CF₃CF₂CH₂ | H | 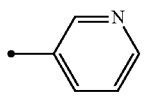 | H | H | H |
| 235 | N | CF₂HCF₂CH₂ | H | 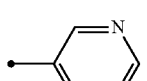 | H | H | H |
| 236 | N | CF₃CF₂CF₂CH₂ | H | 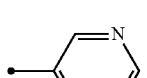 | H | H | H |
| 237 | N | CF₃CFHCF₂CH₂ | H | 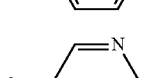 | H | H | H |
| 238 | N | CF₂HCH₂ | H | 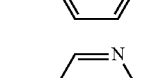 | H | H | H |
| 239 | N | CF₃CF₂CH₂ | H | 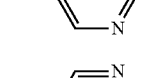 | H | H | H |
| 240 | N | CF₂HCF₂CH₂ | H | 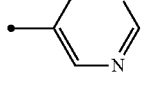 | H | H | H |
| 241 | N | CF₃CF₂CF₂CH₂ | H | 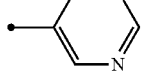 | H | H | H |

TABLE 29-continued

| Present compound | $A^1$ | $R^{100}$ | $R^{301}$ | $R^{302}$ | $R^{303}$ | $R^{601}$ | $R^{602}$ |
|---|---|---|---|---|---|---|---|
| 242 | N | $CF_3CFHCF_2CH_2$ | H | 5-pyrimidinyl | H | H | H |

TABLE 30

| Present compound | $A^1$ | $R^{100}$ | $R^{301}$ | $R^{302}$ | $R^{303}$ | $R^{601}$ | $R^{602}$ |
|---|---|---|---|---|---|---|---|
| 243 | N | $CF_2HCH_2$ | H | 4-($CF_3$)-pyridin-2-yl | H | H | H |
| 244 | N | $CF_3CF_2CH_2$ | H | 4-($CF_3$)-pyridin-2-yl | H | H | H |
| 245 | N | $CF_2HCF_2CH_2$ | H | 4-($CF_3$)-pyridin-2-yl | H | H | H |
| 246 | N | $CF_3CF_2CF_2CH_2$ | H | 4-($CF_3$)-pyridin-2-yl | H | H | H |
| 247 | N | $CF_3CFHCF_2CH_2$ | H | 4-($CF_3$)-pyridin-2-yl | H | H | H |
| 248 | N | $CF_2HCH_2$ | H | 6-($CF_3$)-pyridin-3-yl | H | H | H |
| 249 | N | $CF_3CF_2CH_2$ | H | 6-($CF_3$)-pyridin-3-yl | H | H | H |
| 250 | N | $CF_2HCF_2CH_2$ | H | 6-($CF_3$)-pyridin-3-yl | H | H | H |
| 251 | N | $CF_3CF_2CF_2CH_2$ | H | 6-($CF_3$)-pyridin-3-yl | H | H | H |
| 252 | N | $CF_3CFHCF_2CH_2$ | H | 6-($CF_3$)-pyridin-3-yl | H | H | H |

TABLE 31

| Present compound | A¹ | R¹⁰⁰ | R³⁰¹ | R³⁰² | R³⁰³ | R⁶⁰¹ | R⁶⁰² |
|---|---|---|---|---|---|---|---|
| 253 | N | CF₂HCH₂ | H | 2-F-pyrimidin-5-yl | H | H | H |
| 254 | N | CF₃CF₂CH₂ | H | 2-F-pyrimidin-5-yl | H | H | H |
| 255 | N | CF₂HCF₂CH₂ | H | 2-F-pyrimidin-5-yl | H | H | H |
| 256 | N | CF₃CF₂CF₂CH₂ | H | 2-F-pyrimidin-5-yl | H | H | H |
| 257 | N | CF₃CFHCF₂CH₂ | H | 2-F-pyrimidin-5-yl | H | H | H |
| 258 | N | CF₂HCH₂ | H | pyrimidin-2-yl | H | H | H |
| 259 | N | CF₃CF₂CH₂ | H | pyrimidin-2-yl | H | H | H |
| 260 | N | CF₂HCF₂CH₂ | H | pyrimidin-2-yl | H | H | H |
| 261 | N | CF₃CF₂CF₂CH₂ | H | pyrimidin-2-yl | H | H | H |
| 262 | N | CF₃CFHCF₂CH₂ | H | pyrimidin-2-yl | H | H | H |

TABLE 32

| Present compound | A¹ | R¹⁰⁰ | R³⁰¹ | R³⁰² | R³⁰³ | R⁶⁰¹ | R⁶⁰² |
|---|---|---|---|---|---|---|---|
| 263 | N | CF₂HCH₂ | H | 5-CF₃-2-oxopyridin-1-yl | H | H | H |

TABLE 32-continued

| Present compound | A¹ | R¹⁰⁰ | R³⁰¹ | R³⁰² | R³⁰³ | R⁶⁰¹ | R⁶⁰² |
|---|---|---|---|---|---|---|---|
| 264 | N | CF₃CF₂CH₂ | H | 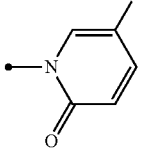 | H | H | H |
| 265 | N | CF₂HCF₂CH₂ | H | 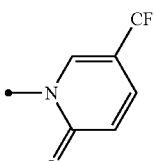 | H | H | H |
| 266 | N | CF₃CF₂CF₂CH₂ | H | 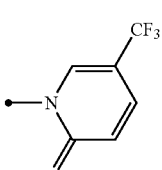 | H | H | H |
| 267 | N | CF₃CFHCF₂CH₂ | H | 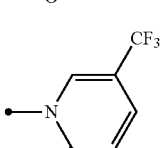 | H | H | H |

TABLE 33

| Present compound | A¹ | R¹⁰⁰ | R³⁰¹ | R³⁰² | R³⁰³ | R⁶⁰¹ | R⁶⁰² |
|---|---|---|---|---|---|---|---|
| 268 | N | CF₂HCH₂ | H | OCH₃ | H | H | H |
| 269 | N | CF₃CF₂CH₂ | H | OCH₃ | H | H | H |
| 270 | N | CF₂HCF₂CH₂ | H | OCH₃ | H | H | H |
| 271 | N | CF₃CF₂CF₂CH₂ | H | OCH₃ | H | H | H |
| 272 | N | CF₃CFHCF₂CH₂ | H | OCH₃ | H | H | H |
| 273 | N | CF₂HCH₂ | H | OCH₂CH₃ | H | H | H |
| 274 | N | CF₃CF₂CH₂ | H | OCH₂CH₃ | H | H | H |
| 275 | N | CF₂HCF₂CH₂ | H | OCH₂CH₃ | H | H | H |
| 276 | N | CF₃CF₂CF₂CH₂ | H | OCH₂CH₃ | H | H | H |
| 277 | N | CF₃CFHCF₂CH₂ | H | OCH₂CH₃ | H | H | H |
| 278 | N | CF₂HCH₂ | H | OCH(CH₃)₂ | H | H | H |
| 279 | N | CF₃CF₂CH₂ | H | OCH(CH₃)₂ | H | H | H |
| 280 | N | CF₂HCF₂CH₂ | H | OCH(CH₃)₂ | H | H | H |
| 281 | N | CF₃CF₂CF₂CH₂ | H | OCH(CH₃)₂ | H | H | H |
| 282 | N | CF₃CFHCF₂CH₂ | H | OCH(CH₃)₂ | H | H | H |
| 283 | N | CF₂HCH₂ | H | OCH₂CH₂N(CH₃)₂ | H | H | H |
| 284 | N | CF₃CF₂CH₂ | H | OCH₂CH₂N(CH₃)₂ | H | H | H |
| 285 | N | CF₂HCF₂CH₂ | H | OCH₂CH₂N(CH₃)₂ | H | H | H |
| 286 | N | CF₃CF₂CF₂CH₂ | H | OCH₂CH₂N(CH₃)₂ | H | H | H |
| 287 | N | CF₃CFHCF₂CH₂ | H | OCH₂CH₂N(CH₃)₂ | H | H | H |
| 288 | N | CF₂HCH₂ | H | OCH₂CF₃ | H | H | H |
| 289 | N | CF₃CF₂CH₂ | H | OCH₂CF₃ | H | H | H |
| 290 | N | CF₂HCF₂CH₂ | H | OCH₂CF₃ | H | H | H |
| 291 | N | CF₃CF₂CF₂CH₂ | H | OCH₂CF₃ | H | H | H |
| 292 | N | CF₃CFHCF₂CH₂ | H | OCH₂CF₃ | H | H | H |

TABLE 34

| Present compound | A¹ | R¹⁰⁰ | R³⁰¹ | R³⁰² | R³⁰³ | R⁶⁰¹ | R⁶⁰² |
|---|---|---|---|---|---|---|---|
| 293 | N | CF₂HCH₂ | H | OCH₂CF₃ | H | H | H |
| 294 | N | CF₃CF₂CH₂ | H | OCH₂CF₃ | H | H | H |
| 295 | N | CF₂HCF₂CH₂ | H | OCH₂CF₃ | H | H | H |
| 296 | N | CF₃CF₂CF₂CH₂ | H | OCH₂CF₃ | H | H | H |
| 297 | N | CF₃CFHCF₂CH₂ | H | OCH₂CF₃ | H | H | H |
| 298 | N | CF₂HCH₂ | H | OCH₂CF₂CF₂H | H | H | H |
| 299 | N | CF₃CF₂CH₂ | H | OCH₂CF₂CF₂H | H | H | H |
| 300 | N | CF₂HCF₂CH₂ | H | OCH₂CF₂CF₂H | H | H | H |
| 301 | N | CF₃CF₂CF₂CH₂ | H | OCH₂CF₂CF₂H | H | H | H |
| 302 | N | CF₃CFHCF₂CH₂ | H | OCH₂CF₂CF₂H | H | H | H |
| 303 | N | CF₂HCH₂ | H | OCH₂CF₂CF₃ | H | H | H |
| 304 | N | CF₃CF₂CH₂ | H | OCH₂CF₂CF₃ | H | H | H |
| 305 | N | CF₂HCF₂CH₂ | H | OCH₂CF₂CF₃ | H | H | H |
| 306 | N | CF₃CF₂CF₂CH₂ | H | OCH₂CF₂CF₃ | H | H | H |
| 307 | N | CF₃CFHCF₂CH₂ | H | OCH₂CF₂CF₃ | H | H | H |
| 308 | N | CF₂HCH₂ | H | NHC(O)CH₃ | H | H | H |
| 309 | N | CF₃CF₂CH₂ | H | NHC(O)CH₃ | H | H | H |
| 310 | N | CF₂HCF₂CH₂ | H | NHC(O)CH₃ | H | H | H |
| 311 | N | CF₃CF₂CF₂CH₂ | H | NHC(O)CH₃ | H | H | H |
| 312 | N | CF₃CFHCF₂CH₂ | H | NHC(O)CH₃ | H | H | H |
| 313 | N | CF₂HCH₂ | H | NHC(O)CH₂CH₃ | H | H | H |
| 314 | N | CF₃CF₂CH₂ | H | NHC(O)CH₂CH₃ | H | H | H |
| 315 | N | CF₂HCF₂CH₂ | H | NHC(O)CH₂CH₃ | H | H | H |
| 316 | N | CF₃CF₂CF₂CH₂ | H | NHC(O)CH₂CH₃ | H | H | H |
| 317 | N | CF₃CFHCF₂CH₂ | H | NHC(O)CH₂CH₃ | H | H | H |

TABLE 35

| Present compound | A¹ | R¹⁰⁰ | R³⁰¹ | R³⁰² | R³⁰³ | R⁶⁰¹ | R⁶⁰² |
|---|---|---|---|---|---|---|---|
| 318 | N | CF₂HCH₂ | H | —NH—C(O)—cyclopropyl | H | H | H |
| 319 | N | CF₃CF₂CH₂ | H | —NH—C(O)—cyclopropyl | H | H | H |
| 320 | N | CF₂HCF₂CH₂ | H | —NH—C(O)—cyclopropyl | H | H | H |
| 321 | N | CF₃CF₂CF₂CH₂ | H | —NH—C(O)—cyclopropyl | H | H | H |
| 322 | N | CF₃CFHCF₂CH₂ | H | —NH—C(O)—cyclopropyl | H | H | H |
| 323 | N | CF₂HCH₂ | H | —N(CH₃)—C(O)—cyclopropyl | H | H | H |
| 324 | N | CF₃CF₂CH₂ | H | —N(CH₃)—C(O)—cyclopropyl | H | H | H |

TABLE 35-continued

| Present compound | $A^1$ | $R^{100}$ | $R^{301}$ | $R^{302}$ | $R^{303}$ | $R^{601}$ | $R^{602}$ |
|---|---|---|---|---|---|---|---|
| 325 | N | $CF_2HCF_2CH_2$ | H | ![N(CH3)C(O)cyclopropyl] | H | H | H |
| 326 | N | $CF_3CF_2CF_2CH_2$ | H | ![N(CH3)C(O)cyclopropyl] | H | H | H |
| 327 | N | $CF_3CFHCF_2CH_2$ | H | ![N(CH3)C(O)cyclopropyl] | H | H | H |

TABLE 36

| Present compound | $A^1$ | $R^{100}$ | $R^{301}$ | $R^{302}$ | $R^{303}$ | $R^{601}$ | $R^{602}$ |
|---|---|---|---|---|---|---|---|
| 328 | N | $CF_2HCH_2$ | H | NHC (O) $OCH_3$ | H | H | H |
| 329 | N | $CF_3CF_2CH_2$ | H | NHC (O) $OCH_3$ | H | H | H |
| 330 | N | $CF_2HCF_2CH_2$ | H | NHC (O) $OCH_3$ | H | H | H |
| 331 | N | $CF_3CF_2CF_2CH_2$ | H | NHC (O) $OCH_3$ | H | H | H |
| 332 | N | $CF_3CFHCF_2CH_2$ | H | NHC (O) $OCH_3$ | H | H | H |
| 333 | N | $CF_2HCH_2$ | H | NHC (O) $OCH_2CH_3$ | H | H | H |
| 334 | N | $CF_3CF_2CH_2$ | H | NHC (O) $OCH_2CH_3$ | H | H | H |
| 335 | N | $CF_2HCF_2CH_2$ | H | NHC (O) $OCH_2CH_3$ | H | H | H |
| 336 | N | $CF_3CF_2CF_2CH_2$ | H | NHC (O) $OCH_2CH_3$ | H | H | H |
| 337 | N | $CF_3CFHCF_2CH_2$ | H | NHC (O) $OCH_2CH_3$ | H | H | H |
| 338 | N | $CF_2HCH_2$ | H | $OCH_2CH_2CH_3$ | H | H | H |
| 339 | N | $CF_3CF_2CH_2$ | H | $OCH_2CH_2CH_3$ | H | H | H |
| 340 | N | $CF_2HCF_2CH_2$ | H | $OCH_2CH_2CH_3$ | H | H | H |
| 341 | N | $CF_3CF_2CF_2CH_2$ | H | $OCH_2CH_2CH_3$ | H | H | H |
| 342 | N | $CF_3CFHCF_2CH_2$ | H | $OCH_2CH_2CH_3$ | H | H | H |

A compound represented by formula (M-100)

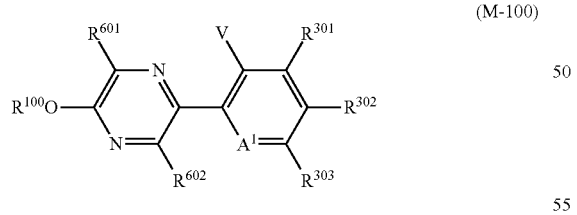

(M-100)

[wherein, $R^{301}$, $R^{302}$, $R^{303}$, $R^{601}$, $R^{602}$, $R^{100}$, $A^1$, and V represent any combination indicated in the Table 37 below.] can be prepared according to the processes described above.

TABLE 37

| Intermediate compound | $A^1$ | V | $R^{100}$ | $R^{301}$ | $R^{302}$ | $R^{303}$ | $r^{601}$ | $R^{602}$ |
|---|---|---|---|---|---|---|---|---|
| a-1 | N | F | $CF_3CH_2$ | H | H | H | H | H |
| a-2 | N | F | $CF_2HCH_2$ | H | H | H | H | H |
| a-3 | N | F | $CF_3CF_2CH_2$ | H | H | H | H | H |

TABLE 37-continued

| Intermediate compound | $A^1$ | V | $R^{100}$ | $R^{301}$ | $R^{302}$ | $R^{303}$ | $r^{601}$ | $R^{602}$ |
|---|---|---|---|---|---|---|---|---|
| a-4 | N | F | $CF_2HCF_2CH_2$ | H | H | H | H | H |
| a-5 | N | F | $CF_3CF_2CF_2CH_2$ | H | H | H | H | H |
| a-6 | N | F | $CF_3CFHCF_2CH_2$ | H | H | H | H | H |
| a-7 | N | F | $CF_2HCF_2CF_2CF_2CH_2$ | H | H | H | H | H |
| a-8 | N | Cl | $CF_3CH_2$ | H | $CF_3$ | H | H | H |
| a-9 | N | Cl | $CF_2HCH_2$ | H | $CF_3$ | H | H | H |
| a-10 | N | Cl | $CF_3CF_2CH_2$ | H | $CF_3$ | H | H | H |
| a-11 | N | Cl | $CF_2HCF_2CH_2$ | H | $CF_3$ | H | H | H |
| a-12 | N | Cl | $CF_3CF_2CF_2CH_2$ | H | $CF_3$ | H | H | H |
| a-13 | N | Cl | $CF_3CFHCF_2CH_2$ | H | $CF_3$ | H | H | H |
| a-14 | N | Cl | $CF_2HCF_2CF_2CF_2CH_2$ | H | $CF_3$ | H | H | H |
| a-15 | CH | F | $CF_3CH_2$ | H | $CF_3$ | H | H | H |
| a-16 | CH | F | $CF_2HCH_2$ | H | $CF_3$ | H | H | H |
| a-17 | CH | F | $CF_3CF_2CH_2$ | H | $CF_3$ | H | H | H |
| a-18 | CH | F | $CF_2HCF_2CH_2$ | H | $CF_3$ | H | H | H |
| a-19 | CH | F | $CF_3CF_2CF_2CH_2$ | H | $CF_3$ | H | H | H |
| a-20 | CH | F | $CF_3CFHCF_2CH_2$ | H | $CF_3$ | H | H | H |
| a-21 | CH | F | $CF_2HCF_2CF_2CF_2CH_2$ | H | $CF_3$ | H | H | H |

A compound represented by formula (M-200)

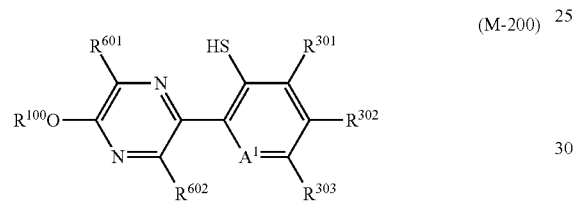

(M-200)

[wherein, $R^{301}$, $R^{302}$, $R^{303}$, $R^{601}$, $R^{602}$, $R^{100}$, and $A^1$ represent any combination indicated in the Table 38 below.] can be prepared according to the processes described above.

TABLE 38

| Intermediate compound | $A^1$ | $R^{100}$ | $R^{301}$ | $R^{302}$ | $R^{303}$ | $R^{601}$ | $R^{602}$ |
|---|---|---|---|---|---|---|---|
| b-1 | N | $CF_3CH_2$ | H | H | H | H | H |
| b-2 | N | $CF_2HCH_2$ | H | H | H | H | H |
| b-3 | N | $CF_3CF_2CH_2$ | H | H | H | H | H |
| b-4 | N | $CF_2HCF_2CH_2$ | H | H | H | H | H |
| b-5 | N | $CF_3CF_2CF_2CH_2$ | H | H | H | H | H |
| b-6 | N | $CF_3CFHCF_2CH_2$ | H | H | H | H | H |
| b-7 | N | $CF_2HCF_2CF_2CF_2CH_2$ | H | H | H | H | H |
| b-8 | N | $CF_3CH_2$ | H | $CF_3$ | H | H | H |
| b-9 | N | $CF_2HCH_2$ | H | $CF_3$ | H | H | H |
| b-10 | N | $CF_3CF_2CH_2$ | H | $CF_3$ | H | H | H |
| b-11 | N | $CF_2HCF_2CH_2$ | H | $CF_3$ | H | H | H |
| b-12 | N | $CF_3CF_2CF_2CH_2$ | H | $CF_3$ | H | H | H |
| b-13 | N | $CF_3CFHCF_2CH_2$ | H | $CF_3$ | H | H | H |
| b-14 | N | $CF_2HCF_2CF_2CF_2CH_2$ | H | $CF_3$ | H | H | H |
| b-15 | CH | $CF_3CH_2$ | H | $CF_3$ | H | H | H |
| b-16 | CH | $CF_2HCH_2$ | H | $CF_3$ | H | H | H |
| b-17 | CH | $CF_3CF_2CH_2$ | H | $CF_3$ | H | H | H |
| b-18 | CH | $CF_2HCF_2CH_2$ | H | $CF_3$ | H | H | H |
| b-19 | CH | $CF_3CF_2CF_2CH_2$ | H | $CF_3$ | H | H | H |
| b-20 | CH | $CF_3CFHCF_2CH_2$ | H | $CF_3$ | H | H | H |
| b-21 | CH | $CF_2HCF_2CF_2CF_2CH_2$ | H | $CF_3$ | H | H | H |

A compound represented by formula (M300)

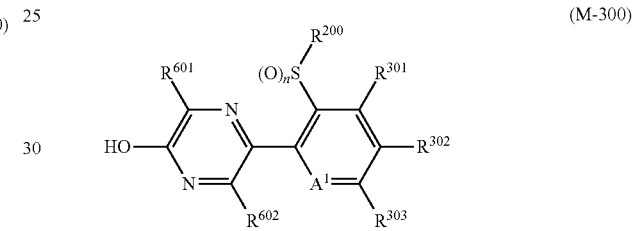

(M-300)

[wherein, $R^{301}$, $R^{302}$, $R^{303}$, $R^{601}$, $R^{602}$, $R^{100}$, and $A^1$ represent any combination indicated in the Table 39 below.] can be prepared according to the processes described above.

TABLE 39

| Intermediate compound | $A^1$ | $R^{200}$ | n | $R^{301}$ | $R^{302}$ | $R^{303}$ | $R^{601}$ | $R^{602}$ |
|---|---|---|---|---|---|---|---|---|
| c-1 | N | $CH_3$ | 2 | H | H | H | H | H |
| c-2 | N | $CH_3CH_2$ | 2 | H | H | H | H | H |
| c-3 | N | $CH_3CH_2CH_2$ | 2 | H | H | H | H | H |
| c-4 | N | $CH(CH_3)_2$ | 2 | H | H | H | H | H |
| c-5 | N | $CF_3CH_2$ | 2 | H | H | H | H | H |
| c-6 | N | cyclopropyl | 2 | H | H | H | H | H |
| c-7 | N | cyclopropyl-CH₂ | 2 | H | H | H | H | H |
| c-8 | N | $CH_3$ | 2 | H | $CF_3$ | H | H | H |
| c-9 | N | $CH_3CH_2$ | 2 | H | $CF_3$ | H | H | H |
| c-10 | N | $CH_3CH_2CH_2$ | 2 | H | $CF_3$ | H | H | H |
| c-11 | N | $CH(CH_3)_2$ | 2 | H | $CF_3$ | H | H | H |
| c-12 | N | $CF_3CH_2$ | 2 | H | $CF_3$ | H | H | H |
| c-13 | N | cyclopropyl | 2 | H | $CF_3$ | H | H | H |
| c-14 | N | cyclopropyl-CH₂ | 2 | H | $CF_3$ | H | H | H |

TABLE 39-continued

| Intermediate compound | A¹ | R²⁰⁰ | n | R³⁰¹ | R³⁰² | R³⁰³ | R⁶⁰¹ | R⁶⁰² |
|---|---|---|---|---|---|---|---|---|
| c-15 | CH | CH₃ | 2 | H | CF₃ | H | H | H |
| c-16 | CH | CH₃CH₂ | 2 | H | CF₃ | H | H | H |
| c-17 | CH | CH₃CH₂CH₂ | 2 | H | CF₃ | H | H | H |
| c-18 | CH | CH(CH₃)₂ | 2 | H | CF₃ | H | H | H |
| c-19 | CH | CF₃CH₂ | 2 | H | CF₃ | H | H | H |
| c-20 | CH | ▵ | 2 | H | CF₃ | H | H | H |
| c-21 | CH | ▵CH₂ | 2 | H | CF₃ | H | H | H |

A compound represented by formula (M400)

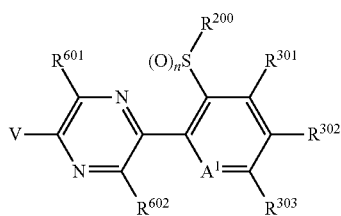

(M-400)

[wherein, R³⁰¹, R³⁰², R³⁰³, R⁶⁰¹, R⁶⁰², R²⁰⁰, V and A¹ represent any combination indicated in the Table 40 below.] can be prepared according to the processes described above.

TABLE 40

| Intermediate compound | A¹ | V | R²⁰⁰ | n | R³⁰¹ | R³⁰² | R³⁰³ | R⁶⁰¹ | R⁶⁰² |
|---|---|---|---|---|---|---|---|---|---|
| d-1 | N | Cl | CH₃ | 2 | H | H | H | H | H |
| d-2 | N | Cl | CH₃CH₂ | 2 | H | H | H | H | H |
| d-3 | N | Cl | CH₃CH₂CH₂ | 2 | H | H | H | H | H |
| d-4 | N | Cl | CH(CH₃)₂ | 2 | H | H | H | H | H |
| d-5 | N | Cl | CF₃CH₂ | 2 | H | H | H | H | H |
| d-6 | N | Cl | ▵ | 2 | H | H | H | H | H |
| d-7 | N | Cl | ▵CH₂ | 2 | H | H | H | H | H |
| d-8 | N | Cl | CH₃ | 2 | H | CF₃ | H | H | H |
| d-9 | N | Cl | CH₃CH₂ | 2 | H | CF₃ | H | H | H |
| d-10 | N | Cl | CH₃CH₂CH₂ | 2 | H | CF₃ | H | H | H |
| d-11 | N | Cl | CH(CH₃)₂ | 2 | H | CF₃ | H | H | H |
| d-12 | N | Cl | CF₃CH₂ | 2 | H | CF₃ | H | H | H |
| d-13 | N | Cl | ▵ | 2 | H | CF₃ | H | H | H |
| d-14 | N | Cl | ▵CH₂ | 2 | H | CF₃ | H | H | H |
| d-15 | CH | Cl | CH₃ | 2 | H | CF₃ | H | H | H |
| d-16 | CH | Cl | CH₃CH₂ | 2 | H | CF₃ | H | H | H |
| d-17 | CH | Cl | CH₃CH₂CH₂ | 2 | H | CF₃ | H | H | H |
| d-18 | CH | Cl | CH(CH₃)₂ | 2 | H | CF₃ | H | H | H |
| d-19 | CH | Cl | CF₃CH₂ | 2 | H | CF₃ | H | H | H |
| d-20 | CH | Cl | ▵ | 2 | H | CF₃ | H | H | H |
| d-21 | CH | Cl | ▵CH₂ | 2 | H | CF₃ | H | H | H |

A compound represented by formula (M330)

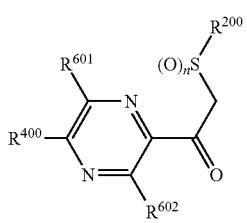

(M-330)

[wherein, R⁶⁰¹, R⁶⁰², R²⁰⁰ and R⁴⁰⁰ represent any combination indicated in the Table 41 to Table 43 below.] can be prepared according to the processes described above.

TABLE 41

| Intermediate compound | R⁴⁰⁰ | R²⁰⁰ | n | R⁶⁰¹ | R⁶⁰² |
|---|---|---|---|---|---|
| e-1 | F | CH₃ | 2 | H | H |
| e-2 | Cl | CH₃ | 2 | H | H |
| e-3 | Br | CH₃ | 2 | H | H |
| e-4 | CH₃O | CH₃ | 2 | H | H |
| e-5 | CH₃CH₂O | CH₃ | 2 | H | H |
| e-6 | CF₃CH(CH₃) | CH₃ | 2 | H | H |
| e-7 | CF₃CF₂CH(CH₃) | CH₃ | 2 | H | H |
| e-8 | CF₃CH₂ | CH₃ | 2 | H | H |
| e-9 | CF₂HCH₂ | CH₃ | 2 | H | H |
| e-10 | CF₃CF₂CH₂ | CH₃ | 2 | H | H |
| e-11 | CF₂HCF₂CH₂ | CH₃ | 2 | H | H |
| e-12 | CF₃CF₂CF₂CH₂ | CH₃ | 2 | H | H |
| e-13 | CF₃CFHCF₂CH₂ | CH₃ | 2 | H | H |
| e-14 | CF₂HCF₂CF₂CF₂CH₂ | CH₃ | 2 | H | H |
| e-15 | F | CH₃CH₂ | 2 | H | H |
| e-16 | Cl | CH₃CH₂ | 2 | H | H |
| e-17 | Br | CH₃CH₂ | 2 | H | H |
| e-18 | CH₃O | CH₃CH₂ | 2 | H | H |
| e-19 | CH₃CH₂O | CH₃CH₂ | 2 | H | H |
| e-20 | CF₃CH(CH₃) | CH₃CH₂ | 2 | H | H |
| e-21 | CF₃CF₂CH(CH₃) | CH₃CH₂ | 2 | H | H |
| e-22 | CF₃CH₂ | CH₃CH₂ | 2 | H | H |
| e-23 | CF₂HCH₂ | CH₃CH₂ | 2 | H | H |
| e-24 | CF₃CF₂CH₂ | CH₃CH₂ | 2 | H | H |
| e-25 | CF₂HCF₂CH₂ | CH₃CH₂ | 2 | H | H |
| e-26 | CF₃CF₂CF₂CH₂ | CH₃CH₂ | 2 | H | H |
| e-27 | CF₃CFHCF₂CH₂ | CH₃CH₂ | 2 | H | H |
| e-28 | CF₂HCF₂CF₂CF₂CH₂ | CH₃CH₂ | 2 | H | H |

TABLE 42

| Intermediate compound | R400 | R200 | n | R601 | R602 |
|---|---|---|---|---|---|
| e-29 | F | cyclopropyl | 2 | H | H |
| e-30 | Cl | cyclopropyl | 2 | H | H |
| e-31 | Br | cyclopropyl | 2 | H | H |
| e-32 | $CH_3O$ | cyclopropyl | 2 | H | H |
| e-33 | $CH_3CH_2O$ | cyclopropyl | 2 | H | H |
| e-34 | $CF_3CH(CH_3)$ | cyclopropyl | 2 | H | H |
| e-35 | $CF_3CF_2CH(CH_3)$ | cyclopropyl | 2 | H | H |
| e-36 | $CF_3CH_2$ | cyclopropyl | 2 | H | H |
| e-37 | $CF_2HCH_2$ | cyclopropyl | 2 | H | H |
| e-38 | $CF_3CF_2CH_2$ | cyclopropyl | 2 | H | H |
| e-39 | $CF_2HCF_2CH_2$ | cyclopropyl | 2 | H | H |
| e-40 | $CF_3CF_2CF_2CH_2$ | cyclopropyl | 2 | H | H |
| e-41 | $CF_3CFHCF_2CH_2$ | cyclopropyl | 2 | H | H |
| e-42 | $CF_2HCF_2CF_2CF_2CH_2$ | cyclopropyl | 2 | H | H |

Table 43

TABLE 43

| Intermediate compound | R400 | R200 | n | R601 | R602 |
|---|---|---|---|---|---|
| e-43 | F | cyclopropylmethyl | 2 | H | H |
| e-44 | Cl | cyclopropylmethyl | 2 | H | H |

TABLE 43-continued

| Intermediate compound | R400 | R200 | n | R601 | R602 |
|---|---|---|---|---|---|
| e-45 | Br | cyclopropylmethyl | 2 | H | H |
| e-46 | $CH_3O$ | cyclopropylmethyl | 2 | H | H |
| e-47 | $CH_3CH_2O$ | cyclopropylmethyl | 2 | H | H |
| e-48 | $CF_3CH(CH_3)$ | cyclopropylmethyl | 2 | H | H |
| e-49 | $CF_3CF_2CH(CH_3)$ | cyclopropylmethyl | 2 | H | H |
| e-50 | $CF_3CH_2$ | cyclopropylmethyl | 2 | H | H |
| e-51 | $CF_2HCH_2$ | cyclopropylmethyl | 2 | H | H |
| e-52 | $CF_3CF_2CH_2$ | cyclopropylmethyl | 2 | H | H |
| e-53 | $CF_2HCF_2CH_2$ | cyclopropylmethyl | 2 | H | H |
| e-54 | $CF_3CF_2CF_2CH_2$ | cyclopropylmethyl | 2 | H | H |
| e-55 | $CF_3CFHCF_2CH_2$ | cyclopropylmethyl | 2 | H | H |
| e-56 | $CF_2HCF_2CF_2CF_2CH_2$ | cyclopropylmethyl | 2 | H | H |

A compound represented by formula (M331)

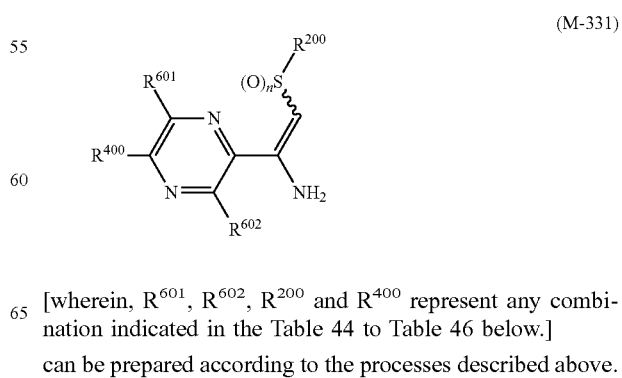

(M-331)

[wherein, $R^{601}$, $R^{602}$, $R^{200}$ and $R^{400}$ represent any combination indicated in the Table 44 to Table 46 below.]

can be prepared according to the processes described above.

TABLE 44

| Intermediate compound | $R^{400}$ | $R^{200}$ | n | $R^{601}$ | $R^{602}$ |
|---|---|---|---|---|---|
| f-1 | F | $CH_3$ | 2 | H | H |
| f-2 | Cl | $CH_3$ | 2 | H | H |
| f-3 | Br | $CH_3$ | 2 | H | H |
| f-4 | $CH_3O$ | $CH_3$ | 2 | H | H |
| f-5 | $CH_3CH_2O$ | $CH_3$ | 2 | H | H |
| f-6 | $CF_3CH(CH_3)$ | $CH_3$ | 2 | H | H |
| f-7 | $CF_3CF_2CH(CH_3)$ | $CH_3$ | 2 | H | H |
| f-8 | $CF_3CH_2$ | $CH_3$ | 2 | H | H |
| f-9 | $CF_2HCH_2$ | $CH_3$ | 2 | H | H |
| f-10 | $CF_3CF_2CH_2$ | $CH_3$ | 2 | H | H |
| f-11 | $CF_2HCF_2CH_2$ | $CH_3$ | 2 | H | H |
| f-12 | $CF_3CF_2CF_2CH_2$ | $CH_3$ | 2 | H | H |
| f-13 | $CF_3CFHCF_2CH_2$ | $CH_3$ | 2 | H | H |
| f-14 | $CF_2HCF_2CF_2CF_2CH_2$ | $CH_3$ | 2 | H | H |
| f-15 | F | $CH_3CH_2$ | 2 | H | H |
| f-16 | Cl | $CH_3CH_2$ | 2 | H | H |
| f-17 | Br | $CH_3CH_2$ | 2 | H | H |
| f-18 | $CH_3O$ | $CH_3CH_2$ | 2 | H | H |
| f-19 | $CH_3CH_2O$ | $CH_3CH_2$ | 2 | H | H |
| f-20 | $CF_3CH(CH_3)$ | $CH_3CH_2$ | 2 | H | H |
| f-21 | $CF_3CF_2CH(CH_3)$ | $CH_3CH_2$ | 2 | H | H |
| f-22 | $CF_3CH_2$ | $CH_3CH_2$ | 2 | H | H |
| f-23 | $CF_2HCH_2$ | $CH_3CH_2$ | 2 | H | H |
| f-24 | $CF_3CF_2CH_2$ | $CH_3CH_2$ | 2 | H | H |
| f-25 | $CF_2HCF_2CH_2$ | $CH_3CH_2$ | 2 | H | H |
| f-26 | $CF_3CF_2CF_2CH_2$ | $CH_3CH_2$ | 2 | H | H |
| f-27 | $CF_3CFHCF_2CH_2$ | $CH_3CH_2$ | 2 | H | H |
| f-28 | $CF_2HCF_2CF_2CF_2CH_2$ | $CH_3CH_2$ | 2 | H | H |

TABLE 45

| Intermediate compound | $R^{400}$ | $R^{200}$ | n | $R^{601}$ | $R^{602}$ |
|---|---|---|---|---|---|
| f-29 | F |  | 2 | H | H |
| f-30 | Cl |  | 2 | H | H |
| f-31 | Br |  | 2 | H | H |
| f-32 | $CH_3O$ |  | 2 | H | H |
| f-33 | $CH_3CH_2O$ |  | 2 | H | H |
| f-34 | $CF_3CH(CH_3)$ |  | 2 | H | H |
| f-35 | $CF_3CF_2CH(CH_3)$ |  | 2 | H | H |
| f-36 | $CF_3CH_2$ |  | 2 | H | H |
| f-37 | $CF_2HCH_2$ |  | 2 | H | H |
| f-38 | $CF_3CF_2CH_2$ | 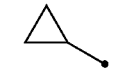 | 2 | H | H |
| f-39 | $CF_2HCF_2CH_2$ |  | 2 | H | H |
| f-40 | $CF_3CF_2CF_2CH_2$ |  | 2 | H | H |
| f-41 | $CF_3CFHCF_2CH_2$ |  | 2 | H | H |
| f-42 | $CF_2HCF_2CF_2CF_2CH_2$ | 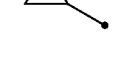 | 2 | H | H |

TABLE 46

| Intermediate compound | $R^{400}$ | $R^{200}$ | n | $R^{601}$ | $R^{602}$ |
|---|---|---|---|---|---|
| f-43 | F |  | 2 | H | H |
| f-44 | Cl | 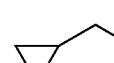 | 2 | H | H |
| f-45 | Br | 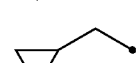 | 2 | H | H |
| f-46 | $CH_3O$ | 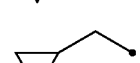 | 2 | H | H |
| f-47 | $CH_3CH_2O$ | 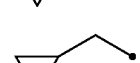 | 2 | H | H |
| f-48 | $CF_3CH(CH_3)$ | 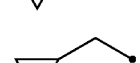 | 2 | H | H |
| f-49 | $CF_3CF_2CH(CH_3)$ | 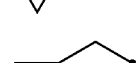 | 2 | H | H |
| f-50 | $CF_3CH_2$ | 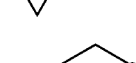 | 2 | H | H |
| f-51 | $CF_2HCH_2$ | 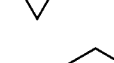 | 2 | H | H |
| f-52 | $CF_3CF_2CH_2$ | 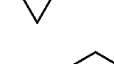 | 2 | H | H |
| f-53 | $CF_2HCF_2CH_2$ |  | 2 | H | H |

TABLE 46-continued

| Intermediate compound | $R^{400}$ | $R^{200}$ | n | $R^{601}$ | $R^{602}$ |
|---|---|---|---|---|---|
| f-54 | $CF_3CF_2CF_2CH_2$ | (cyclopropyl-CH=) | 2 | H | H |
| f-55 | $CF_3CFHCF_2CH_2$ | (cyclopropyl-CH=) | 2 | H | H |
| f-56 | $CF_2HCF_2CF_2CF_2CH_2$ | (cyclopropyl-CH=) | 2 | H | H |

Next, the formulation examples of the Present compound are shown below. The "parts" represents "part by weight" unless otherwise specified.

Formulation Example 1

Into a mixture of 35 parts of xylene and 35 parts of DMF, 10 parts of each of the Present compounds 1 to 348 is dissolved, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of synthetic hydrated silicon oxide fine powder and 54 parts of diatomaceous earth are mixed, and further 20 parts of each of the Present compounds 1 to 348 is added, followed by mixing them to obtain each wettable powders.

Formulation Example 3

To 2 parts of each of the Present compounds 1 to 348, 1 part of synthetic hydrated silicon oxide fine powder, 2 parts of calcium lignin sulfonate, 30 parts of bentonite and 65 parts of kaolin clay are added, followed by mixing, granulation with a granulator and forced-air drying to obtain each granular formulation.

Formulation Example 4

Into an appropriate amount of acetone, 1 part of each the Present compounds 1 to 348 is mixed, and then 5 parts of synthetic hydrous silicon oxide fine powder, 0.3 parts of isopropyl acid phosphate and 93.7 parts of kaolin clay are added, followed by mixing with stirring thoroughly and removal of acetone from the mixture by evaporation to obtain each of powder formulation.

Formulation Example 5

A mixture of 35 parts of polyoxyethylene alkyl ether sulfate ammonium salt and white carbon (weight ratio of 1:1), 10 parts of each of the Present compounds 1 to 348, and 55 parts of water are mixed, followed by finely grounding by a wet grinding method to obtain each flowable formulation.

Formulation Example 6

Into a mixture of 5 parts of xylene and 5 parts of trichloroethane, 0.1 parts of each of the Present compounds 1 to 348 is dissolved, and the resulting mixture is then mixed with 89.9 parts of kerosene to obtain each oil solution.

Formulation Example 7

Into 0.5 mL of acetone, 10 mg of each of the Present compounds 1 to 348 is dissolved and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 8

Into an aerosol can, 0.1 part of each of the Present compound 1 to 348 and 49.9 parts of Neothiozole (Chuo Kasei Co., Ltd.) are placed. After mounting an aerosol valve, 25 parts of dimethylether and 25 parts of LPG are filled, followed by shaking and further mounting an actuator to obtain an oily aerosol.

Formulation Example 9

A mixture of 0.6 part of each of the Present compounds to 348, 0.01 part of BHT (2,6-di-tert-butyl-4-methylphenol), 5 parts of xylene, 3.39 parts of deodorized kerosine and 1 part of an emulsifier {Rheodol MO-60 (registered trademark of Kao Corporation)} and 50 parts of distilled water are filled into an aerosol container, and a valve part is attached. Then, 40 parts of a propellant (LPG) is filled therein through the valve under pressure to obtain an aqueous aerosol.

Formulation Example 10

Zero point one (0.1) parts of each of the Present compounds 1 to 348 are mixed into 2 mL of propylene glycol, and the resulting solution is impregnated into a ceramic plate having a size of 4.0 cm×4.0 cm and a thickness of 1.2 cm, to obtain thermal fumigants.

Formulation Example 11

Five (5) parts of each of the Present compounds 1 to 348, and 95 parts of ethylene-methyl methacrylate copolymer (the ratio of the methyl methacrylate in the copolymer: 10 weight %), Acryft (registered by trademark) WD 301, manufactured by Sumitomo Chemical Co. Ltd.) are melted and kneaded with a closed type pressure kneader, and the resulting kneaded product is extruded from an extrusion molding machine through a molding die to obtain a rod-shaped molded product having a length of 15 cm and a diameter of 3 mm.

Formulation Example 12

Five (5) parts of each of the Present compounds 1 to 348, and 95 parts of plasticized polyvinyl chloride resin are melted and kneaded with a closed type pressure kneader, and the resulting kneaded product is extruded from an extrusion molding machine through a molding die to obtain a rod-shaped molded product having a length of 15 cm and a diameter of 3 mm.

Formulation Example 13

One hundred (100) mg of each of the Present compounds 1 to 348, 68.75 mg of lactose, 237.5 mg of corn starch, 43.75 mg of microcrystalline cellulose, 18.75 mg of polyvinylpyrrolidone, 28.75 mg of sodium carbomethyl starch and 25 mg of magnesium stearate are mixed, and the resulting mixture was compressed to an appropriate size to obtain a tablet.

Formulation Example 14

Twenty five (25) mg of each of the Present compounds 1 to 348, 60 mg of lactose, 25 mg of corn starch, 6 mg of carmellose calcium and an appropriate amount of 5% of hydroxypropyl methylcellulose are mixed, and the resulting mixture are filled into a hard shell gelatin capsule or a hydroxypropyl methylcellulose capsule to obtain capsules.

Formulation Example 15

To 100 mg of each of the Present compounds 1 to 348, 500 mg of fumaric acid, 2000 mg of granulated sugar, 13,000 mg of sorbitol (70% solution), 100 mg of Veegum K (manufactured by Vanderbilt Co.), 35 mg of perfume and 500 mg of coloring agent, a distilled water is added so that a final volume is set to be 100 mL, followed by mixing them to obtain a suspension for oral administration.

Formulation Example 16

Into a mixture of 5% by weight of an emulsifier, 3% by weight of benzyl alcohol and 30% by weight of propylene glycol, 5% by weight of each of the Present compounds 1 to 348 is dissolved, and phosphate buffer is added thereto so that a pH of the solution is set to be 6.0 to 6.5, and water is added as the rest parts to obtain the solution for oral administration.

Formulation Example 17

To a mixture of 57% by weight of fractional distilled palm oil and 3% by weight of polysorbate 85, 5% by weight of aluminum distearate is added, and heated to disperse it. The resulting mixture is cooled to room temperature, and 25% by weight of saccharin is dispersed in an oil vehicle. Ten (10) % by weight of each of the Present compounds 1 to 348 is divided thereto to obtain a paste for oral administration.

Formulation Example 18

Five (5) % by weight of each of the Present compounds 1 to 348 is mixed with 95% by weight of limestone filler, followed by a wet granulation of the resulting mixture to obtain a granule for oral administration.

Formulation Example 19

Into 80 parts of diethylene glycol monomethyl ether, 5 parts of each of the Present compounds 1 to 348 is dissolved, and 15 parts of propylene carbonate is added thereto, and the resulting mixture is mixed to obtain a spot-on solution.

Formulation Example 20

Into 70 parts of diethylene glycol monomethyl ether, parts of each of the Present compounds 1 to 348 is dissolved, and 20 parts of 2-octyldodecanol is added thereto, and the resulting mixture is mixed to obtain a pour-on solution.

Formulation Example 21

To 0.5 parts of each of the Present compounds 1 to 348, parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly, and 19.5 parts of water is then added thereto and the resulting mixture is further mixed with stirring thoroughly to obtain a hydrogenous solution of shampoo formulation.

Formulation Example 22

Zero point fifteen (0.15)% by weight of each of the Present compounds 1 to 348, 95% by weight of animal feed, as well as 4.85% by weight of a mixture of dibasic calcium phosphate, diatomaceous earth, aerosol and carbonate (or chalk) are mixed with stirring thoroughly to obtain a premix for animal feed.

Formulation Example 23

Seven point two (7.2) g of each of the Present compounds 1 to 348, and 92.8 g of Hosco (registered trademark) S-55 (manufactured by Maruishi Pharmaceuticals) are melted and mixed at 100° C., and the resulting mixture was poured into a suppository mold, followed by performing a cooling solidification to obtain a suppository.

Next, Test Examples are used to show an efficacy of the Present compound on controlling harmful arthropods.

The following test examples were carried out at 25° C.

Test Example 1

The test compounds are made to a formulation according to a similar method to that described in the Formulation Example 5, and thereto is added water containing 0.03 v/v % of a spreader to prepare a diluted solution containing a prescribed concentration of the test compound.

Cucumber (*Cucumis sativus*) seedling (on the developmental stage of the second true leaf) is planted in a polyethylene cup and approximately 30 heads of cotton aphid (*Aphis gossypii*) (all stages of life) are released onto the leaves of the cucumber. After 1 day, the diluted solutions are sprayed into the seedling in a ratio of 10 mL/seedling. After 5 days, the number of the surviving insects was examined and the controlling value was calculated by the following equation.

$$\text{Controlling value (\%)} = \{1-(Cb \times Tai)/(Cai \times Tb)\} \times 100$$

wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;
Here the "untreated group" represents a group where the similar treatment procedure to that of the treated group except not using the test compound is done.

The results of the test that was done according to the Test example 1 are shown below.

When the prescribed concentration was 500 ppm, the treated group that was treated with each of the below-mentioned Present compounds showed 90% or greater as the controlling value.

Present compound number: 1, 2, 3, 4, 5, 6, 7, 8, 9, 10, 11, 12, 13, 14, 15, 16, 18, 19, and 24

The results of the test that was done according to the Test example 1 are shown below.

When the prescribed concentration was 200 ppm, the treated group that was treated with each of the below-mentioned Present compounds showed 90% or greater as the controlling value.

Present compound number: 2, 4, 5, 6, 7, 8, 9, 10, 11, 12, 13, 16, 18, and 24

Test Example 2

The test compounds are made to a formulation according to a similar method to that described in the Formulation Example 5, and thereto is added water to prepare a diluted solution containing a prescribed concentration of the test compound.

Cucumber seedling (on the developmental stage of the second true leaf) is planted in a polyethylene cup, and the diluted solutions in the ratio on 5 mL/seedling were irrigated into the plant foot. After 7 days, approximately heads of cotton aphid (all stages of life) were inoculated onto the cucumber leaves. After additional 6 days, the number of the surviving insects was examined, and the controlling value was calculated by the following equation.

Controlling value (%)={1−($Cb$×$Tai$)/($Cai$×$Tb$)}×100 wherein the symbols in the formula represent the following descriptions.

$Cb$: Number of the test insects in untreated group;
$Cai$: Number of the surviving insects at the time of the investigation in untreated group;
$Tb$: Number of the test insects in treated group;
$Tai$: Number of the surviving insects at the time of the investigation in treated group;

Here the "untreated group" represents a group where the similar treatment procedure to that of the treated group except not using the test compound is done.

The results of the test that was done according to the Test example 2 are shown below.

When the prescribed concentration was 200 ppm, the treated group that was treated with each of the below-mentioned Present compounds showed 90% or greater as the controlling value.

Present compound number: 4, 5, 6, 8, 9, 10, 11, 12, 13, 16, 18, and 24

Test Example 3

The test compounds are made to a formulation according to a similar method to that described in the Formulation Example 5, and thereto is added water containing 0.03 v/v % of a spreader to prepare a diluted solution containing a prescribed concentration of the test compound.

Rice (*Oryza sativa*) seedling (on the developmental stage of the second true leaf) is planted in a polyethylene cup, and the diluted solutions are sprayed into the seedling in a ratio of 10 mL/seedling. Thereafter, 20 heads of 3rd instar larvae of brown planthopper (*Nilaparvata lugens*) were released onto the rice leaves. After 6 days, the number of the surviving insects was examined, and the mortality was calculated by the following equation.

Mortality (%)={1−the number of the surviving insects/20}×100

The results of the test that was done according to the Test example 3 are shown below.

When the prescribed concentration was 500 ppm, each of the below-mentioned Present compounds showed 90% or greater as the controlling value.

Present compound number: 2, 4, 5, 6, 7, 8, 9, 10, 11, 12, 13, 14, 16, 18, 19, 21, and 24

The results of the test that was done according to the Test example 3 are shown below.

When the prescribed concentration was 200 ppm, each of the below-mentioned Present compounds showed 90% or greater as the controlling value.

Present compound number: 1, 2, 4, 5, 6, 7, 8, 9, 10, 11, 12, 13, 15, 16, 18, and 24

Test Example 4

The test compounds are made to a formulation according to a similar method to that described in the Formulation Example 5, and thereto is added water to prepare a diluted solution containing a prescribed concentration of the test compound.

The diluted solutions described above were added to the polyethylene cup, and therein was installed Rice seedling (on the developmental stage of the second true leaf) that had been planted in a polyethylene cup having a hole in the bottom. After 7 days, 20 heads of 3rd instar larvae of brown planthopper (*Nilaparvata lugens*) were released. After additional 6 days, the number of the surviving insects was examined, and the mortality was calculated by the following equation.

Mortality (%)={1−the number of the surviving insects/20}×100

The results of the test that was done according to the Test example 4 are shown below.

When the prescribed concentration was 200 ppm, each of the below-mentioned Present compounds showed 90% or greater as the mortality of insects.

Present compound number: 2, 4, 5, 6, 7, 8, 10, 11, 12, 13, 14, 18, and 24

Test Example 5

The test compounds are made to a formulation according to a similar method to that described in the Formulation Example 5, and thereto is added water to prepare a diluted solution containing a prescribed concentration of the test compound.

In the polyethylene cup, 7.7 g of Insecta LF (manufactured by NOSAN CORPORATION), an artificial diet was placed, and thereto is irrigated 2 mL of the diluted solution. Five (5) heads of fourth instar larvae of tobacco cutworm (*Spodoptera litura*) are released onto the artificial diet, and the cup was sealed with a lid. After days, the number of the surviving tobacco cutworm (*Spodoptela litura*) was examined, and the mortality was calculated by the following equation.

Mortality (%)={1−the number of the surviving insects/5}×100

The results of the test that was done according to the Test example 5 are shown below.

When the prescribed concentration was 500 ppm, each of the below-mentioned Present compounds showed 80% or greater as the mortality of insects.

Present compound number: 1, 2, 3, 4, 5, 6, 12, 13, 15, and 18

Test Example 6

The test compounds are made to a formulation according to a similar method to that described in the Formulation Example 5, and thereto is added water containing 0.03 v/v % of a spreader to prepare a diluted solution containing a prescribed concentration of the test compound.

The diluted solutions are sprayed into the cabbage (*Brassicae oleracea*) seedling (on the developmental stage of the second to third true leaf) that is planted in the polyethylene cup in a ratio of 20 mL/seedling. Thereafter, the stem and leaf thereof was cut out and then is installed into the polyethylene cup that is covered with the filter paper. Five heads of cabbage moth (*Plutella xylostella*) at the second instar larval stages were released into the cup and the cup was covered with the lid. After 5 days, the surviving insects were counted, and the mortality of insects was calculated by the following equation.

$$\text{Mortality (\%)} = \{1 - \text{the number of the surviving insects}/5\} \times 100$$

The results of the test that was done according to the Test example 6 are shown below.

When the prescribed concentration was 500 ppm, each of the below-mentioned Present compounds showed 80% or greater as the mortality of insects.
Present compound number: 1, 2, 3, 4, 5, 6, 7, 8, 9, 10, 11, 12, 13, 14, 15, 16, 18, 19, 21, and 24

Test Example 7

The test compounds are made to a formulation according to a similar method to that described in the Formulation Example 5, and thereto is added water containing 0.03 v/v % of a spreader to prepare a diluted solution containing a prescribed concentration of the test compound. The diluted solutions are sprayed into the cabbage seedling (on the developmental stage of the third to fourth true leaf) that is planted in the polyethylene cup in a ratio of 20 mL/seedling. Thereafter, 10 heads of cabbage moth (*Plutella xylostella*) at the third instar larval stages were released into the cup, and the insects are held in the polyethylene cup that was covered with a net. After 5 days, the surviving insects are counted, and the mortality of insects was calculated by the following equation.

$$\text{Mortality (\%)} = \{1 - \text{the number of the surviving insects}/10\} \times 100$$

The results of the test that was done according to the Test example 7 are shown below.

When the prescribed concentration was 200 ppm, each of the below-mentioned Present compounds showed 90% or greater as the mortality of insects.
Present compound number: 1, 2, 3, 4, 5, 6, 7, 8, 9, 10, 11, 12, 13, 14, 15, 16, 18, 19, and 24

Test Example 8

The test compounds are dissolved into a mixed solution of polyoxyethylene sorbitan mono-cocoate and acetone (acetone and polyoxyethylene sorbitan mono-cocoate=5:95 (v/v ratio)) in a ratio of 50 μL of the mixed solution per 1 mg of the test compound. Thereto is added water containing 0.03% by volume of a spreader to prepare a diluted solution containing a prescribed concentration of the test compound.

Corns (*Zea mays*) are sown on a tray overlaid with damped KimWipes (registered trademark). After corns were grown for 5 days, the entire seedling of the corn is immersed into the diluted solution for 30 seconds. Thereafter, each two grains of the seedling are installed in a plastic petri dish (90 mm radius), and 10 heads of western corn rootworm (*Diabrotica virgifera virgifera*) at the second instar larval stages are released onto the cup and the cup is covered with a lid. After 5 days, the number of the died insects is counted and the mortality of insects is calculated by the following equation.

$$\text{Mortality (\%)} = \{1 - \text{the number of the surviving insects}/10\} \times 100$$

The results of the test that was done according to the Test example 8 are shown below.

When the prescribed concentration was 500 ppm, each of the below-mentioned Present compounds showed 80% or greater as the mortality of insects.
Present compound number: 3, 4, 5, 6, 7, 8, 9, 10, 11, 12, 14, 16, and 18

Test Example 9

The test compounds are dissolved into a mixed solution of xylene, DMF and surfactants (xylene, DMF and surfactants=4:4:1 (v/v ratio)) in a ratio of 10 μL of the mixed solution per 1 mg of the test compound. Thereto is added water containing 0.03% by volume of a spreader to prepare a diluted solution containing a prescribed concentration of the test compound. The diluted solutions are sprayed into the cucumber seedling (on the developmental stage of the second to third true leaf) that is planted in the polyethylene cup in a ratio of 10 mL/seedling. Thereafter, the second leaf is cut out, and then installed into the polyethylene cup, and ten heads of cucurbit leaf beetle (*Aulacophora femoralis*) at the second instar larval stages were released into the cup and the cup was covered with the lid. After 5 days, the number of died insects is counted and the mortality of insects is calculated by the following equation.

$$\text{Mortality of insects (\%)} = (\text{Number of dead insects}/10) \times 100$$

The results of the test that was done according to the Test example 9 are shown below.

When the prescribed concentration was 50 ppm, each the below-mentioned Present compounds showed 80% or greater as the mortality of insects.
Present compound number: 2 and 3

Test Example 10

The test compounds are made to a formulation according to a similar method to that described in the Formulation Example 5, and thereto is added water to prepare a diluted solution containing a prescribed concentration of the test compound.

The bottom of the polyethylene cup having 5.5 cm diameter is matted with the same size of a filter paper, and 0.7 mL of the diluted solution is added dropwise to the filter paper, and 30 mg sucrose as bait is placed in the cup uniformly. Ten (10) heads of female adult housefly (*Musca domestica*) are released into the polyethylene cup, and the cup was covered with the lid. After 24 hours, the life and death of housefly is examined and the number of died insects is counted and the mortality of insects is calculated by the following equation.

$$\text{Mortality of insects (\%)} = (\text{Number of dead insects}/\text{Number of test insects}) \times 100$$

The results of the test that was done according to the Test example 10 are shown below.

When the prescribed concentration was 500 ppm, each the below-mentioned Present compounds showed 100% as the mortality of insects.

Present compound number: 4, 5, and 6

Next, Test Examples are used to show an efficacy of the present composition on controlling harmful arthropods.

Test Example 11

Each 1 mg of the Present compound is dissolved into a 10 μL of the mixed solution of xylene, DMF and surfactants (xylene, DMF and surfactants=4:4:1 (v/v ratio)). Thereto is added water containing 0.02% by volume of a spreader to prepare a diluted solution containing a prescribed concentration of the Present compound.

When the commercially available formulation of the present active ingredient is used, each of the commercially available formulation is diluted with water containing 0.02 v/v % of the spreader to prepare the prescribed concentration of the diluted solution of the present active ingredient.

Whereas, when the commercially available formulation of the present active ingredient is not used, each 1 mg of the present active ingredient is dissolved into a 10 μL of the mixed solution of xylene, DMF and surfactants (xylene, DMF and surfactants=4:4:1 (v/v ratio)). Thereto is added water containing 0.02% by volume of a spreader to prepare a diluted solution containing a prescribed concentration of the present active ingredient.

The above prepared diluted solution of the Present compound and the above prepared diluted solution of the present active ingredient are mixed to prepare the test chemical solution of the composition comprising the Present compound and the present active ingredient.

A leaf disk (length 1.5 cm) of the seed leaf of cucumber (*Cucumis sativus*) is placed into each well in a 24 well microplate, and 2 wingless adults of a cotton aphid (*Aphis gossypii*) and 8 nymphs of a cotton aphid are released per 1 well, and the test chemical solution is sprayed in a ratio of 20 μL per 1 well, which is referred to as a treated group.

Whereas, 20 μL water containing 0.02 v/v % of the spreader is sprayed into a well instead of the test chemical solution, which is referred to as an untreated group.

After the test chemical solution is dried, the upper part of a microplate is covered with the gas permeable film sheet (Product Name: AeraSal, manufactured by Excel Scientific Inc.), and 5 days after the release, the number of the surviving insects of each well is examined.

The controlling value is calculated by the following equation.

$$\text{Controlling value (\%)} = \{1-(Tai)/(Cai)\} \times 100$$

wherein the symbols in the formula represent the following descriptions.

Cai: Number of the surviving insects at the time of the investigation in untreated group;

Tai: Number of the surviving insects at the time of the investigation in treated group;

The composition that is examined according to a method of Test example 11 is shown in Table 47. As a result, the composition described in Table 47 show an excellent efficacy on controlling harmful arthropods.

TABLE 47

| Composition | Concentration (ppm) (Present compound + Present active ingredient) |
|---|---|
| any one kind of Present compounds 1 to 348 + Clothianidin | 200 + 2000 |
| any one kind of Present compounds 1 to 348 + Clothianidin | 200 + 200 |
| any one kind of Present compounds 1 to 348 + Clothianidin | 500 + 50 |
| any one kind of Present compounds 1 to 348 + Thiamethoxam | 200 + 2000 |
| any one kind of Present compounds 1 to 348 + Thiamethoxam | 200 + 200 |
| any one kind of Present compounds 1 to 348 + Thiamethoxam | 500 + 50 |
| any one kind of Present compounds 1 to 348 + Imidacloprid | 200 + 2000 |
| any one kind of Present compounds 1 to 348 + Imidacloprid | 200 + 200 |
| any one kind of Present compounds 1 to 348 + Imidacloprid | 500 + 50 |
| any one kind of Present compounds 1 to 348 + Thiacloprid | 200 + 2000 |
| any one kind of Present compounds 1 to 348 + Thiacloprid | 200 + 200 |
| any one kind of Present compounds 1 to 348 + Thiacloprid | 500 + 50 |
| any one kind of Present compounds 1 to 348 + Flupyradifurone | 200 + 2000 |
| any one kind of Present compounds 1 to 348 + Flupyradifurone | 200 + 200 |
| any one kind of Present compounds 1 to 348 + Flupyradifurone | 500 + 50 |
| any one kind of Present compounds 1 to 348 + Sulfoxaflor | 200 + 2000 |
| any one kind of Present compounds 1 to 348 + Sulfoxaflor | 200 + 200 |
| any one kind of Present compounds 1 to 348 + Sulfoxaflor | 500 + 50 |
| any one kind of Present compounds 1 to 348 + Triflumezopyrim | 200 + 2000 |
| any one kind of Present compounds 1 to 348 + Triflumezopyrim | 200 + 200 |
| any one kind of Present compounds 1 to 348 + Triflumezopyrim | 500 + 50 |
| any one kind of Present compounds 1 to 348 + Dicloromezotiaz | 200 + 2000 |
| any one kind of Present compounds 1 to 348 + Dicloromezotiaz | 200 + 200 |
| any one kind of Present compounds 1 to 348 + Dicloromezotiaz | 500 + 50 |

TABLE 47-continued

| Composition | Concentration (ppm) (Present compound + Present active ingredient) |
|---|---|
| any one kind of Present compounds 1 to 348 + Beta-cyfluthrin | 200 + 2000 |
| any one kind of Present compounds 1 to 348 + Beta-cyfluthrin | 200 + 200 |
| any one kind of Present compounds 1 to 348 + Beta-cyfluthrin | 500 + 50 |
| any one kind of Present compounds 1 to 348 + Tefluthrin | 200 + 2000 |
| any one kind of Present compounds 1 to 348 + Tefluthrin | 200 + 200 |
| any one kind of Present compounds 1 to 348 + Tefluthrin | 500 + 50 |
| any one kind of Present compounds 1 to 348 + Fipronil | 200 + 2000 |
| any one kind of Present compounds 1 to 348 + Fipronil | 200 + 200 |
| any one kind of Present compounds 1 to 348 + Fipronil | 500 + 50 |
| any one kind of Present compounds 1 to 348 + Chlorantraniliprole | 200 + 2000 |
| any one kind of Present compounds 1 to 348 + Chlorantraniliprole | 200 + 200 |
| any one kind of Present compounds 1 to 348 + Chlorantraniliprole | 500 + 50 |
| any one kind of Present compounds 1 to 348 + Cyantraniliprole | 200 + 2000 |
| any one kind of Present compounds 1 to 348 + Cyantraniliprole | 200 + 200 |
| any one kind of Present compounds 1 to 348 + Cyantraniliprole | 500 + 50 |
| any one kind of Present compounds 1 to 348 + Tetraniliprole | 200 + 2000 |
| any one kind of Present compounds 1 to 348 + Tetraniliprole | 200 + 200 |
| any one kind of Present compounds 1 to 348 + Tetraniliprole | 500 + 50 |
| any one kind of Present compounds 1 to 348 + Thiodicarb | 200 + 2000 |
| any one kind of Present compounds 1 to 348 + Thiodicarb | 200 + 200 |
| any one kind of Present compounds 1 to 348 + Thiodicarb | 500 + 50 |
| any one kind of Present compounds 1 to 348 + Carbofuran | 200 + 2000 |
| any one kind of Present compounds 1 to 348 + Carbofuran | 200 + 200 |
| any one kind of Present compounds 1 to 348 + Carbofuran | 500 + 50 |
| any one kind of Present compounds 1 to 348 + fluxametamide | 200 + 2000 |
| any one kind of Present compounds 1 to 348 + fluxametamide | 200 + 200 |
| any one kind of Present compounds 1 to 348 + fluxametamide | 500 + 50 |
| any one kind of Present compounds 1 to 348 + Afoxolaner | 200 + 2000 |
| any one kind of Present compounds 1 to 348 + Afoxolaner | 200 + 200 |
| any one kind of Present compounds 1 to 348 + Afoxolaner | 500 + 50 |
| any one kind of Present compounds 1 to 348 + fluralaner | 200 + 2000 |
| any one kind of Present compounds 1 to 348 + fluralaner | 200 + 200 |
| any one kind of Present compounds 1 to 348 + fluralaner | 500 + 50 |
| any one kind of Present compounds 1 to 348 + broflanilide | 200 + 2000 |
| any one kind of Present compounds 1 to 348 + broflanilide | 200 + 200 |
| any one kind of Present compounds 1 to 348 + broflanilide | 500 + 50 |
| any one kind of Present compounds 1 to 348 + Abamectin | 200 + 2000 |
| any one kind of Present compounds 1 to 348 + Abamectin | 200 + 200 |
| any one kind of Present compounds 1 to 348 + Abamectin | 500 + 5 |
| any one kind of Present compounds 1 to 348 + Fluopyram | 200 + 2000 |
| any one kind of Present compounds 1 to 348 + Fluopyram | 200 + 20 |
| any one kind of Present compounds 1 to 348 + Fluopyram | 500 + 0.5 |
| any one kind of Present compounds 1 to 348 + Fluensulfone | 200 + 2000 |
| any one kind of Present compounds 1 to 348 + Fluensulfone | 200 + 200 |
| any one kind of Present compounds 1 to 348 + Fluensulfone | 500 + 5 |
| any one kind of Present compounds 1 to 348 + Fluazaindolizine | 200 + 2000 |
| any one kind of Present compounds 1 to 348 + Fluazaindolizine | 200 + 200 |
| any one kind of Present compounds 1 to 348 + Fluazaindolizine | 500 + 5 |

TABLE 47-continued

| Composition | Concentration (ppm) (Present compound + Present active ingredient) |
|---|---|
| any one kind of Present compounds 1 to 348 + Tioxazafen | 200 + 2000 |
| any one kind of Present compounds 1 to 348 + Tioxazafen | 200 + 200 |
| any one kind of Present compounds 1 to 348 + Tioxazafen | 500 + 5 |
| any one kind of Present compounds 1 to 348 + Insecticide compound α1 | 200 + 2000 |
| any one kind of Present compounds 1 to 348 + Insecticide compound α1 | 200 + 200 |
| any one kind of Present compounds 1 to 348 + Insecticide compound α1 | 500 + 50 |
| any one kind of Present compounds 1 to 348 + Mycorrhizal fungi | 200 + 2000 |
| any one kind of Present compounds 1 to 348 + Mycorrhizal fungi | 200 + 200 |
| any one kind of Present compounds 1 to 348 + Mycorrhizal fungi | 500 + 5 |
| any one kind of Present compounds 1 to 348 + Bacillus firmus | 200 + 2000 |
| any one kind of Present compounds 1 to 348 + Bacillus firmus | 200 + 200 |
| any one kind of Present compounds 1 to 348 + Bacillus firmus | 500 + 5 |
| any one kind of Present compounds 1 to 348 + Bacillus amyloliquefaciens | 200 + 2000 |
| any one kind of Present compounds 1 to 348 + Bacillus amyloliquefaciens | 200 + 200 |
| any one kind of Present compounds 1 to 348 + Bacillus amyloliquefaciens | 500 + 5 |
| any one kind of Present compounds 1 to 348 + Pasteuria nishizawae | 200 + 2000 |
| any one kind of Present compounds 1 to 348 + Pasteuria nishizawae | 200 + 200 |
| any one kind of Present compounds 1 to 348 + Pasteuria nishizawae | 500 + 5 |
| any one kind of Present compounds 1 to 348 + Pasteuria penetrans | 200 + 2000 |
| any one kind of Present compounds 1 to 348 + Pasteuria penetrans | 200 + 200 |
| any one kind of Present compounds 1 to 348 + Pasteuria penetrans | 500 + 5 |
| any one kind of Present compounds 1 to 348 + Tebuconazole | 200 + 2000 |
| any one kind of Present compounds 1 to 348 + Tebuconazole | 200 + 20 |
| any one kind of Present compounds 1 to 348 + Tebuconazole | 500 + 0.5 |
| any one kind of Present compounds 1 to 348 + Prothioconazole | 200 + 2000 |
| any one kind of Present compounds 1 to 348 + Prothioconazole | 200 + 20 |
| any one kind of Present compounds 1 to 348 + Prothioconazole | 500 + 0.5 |
| any one kind of Present compounds 1 to 348 + Metconazole | 200 + 2000 |
| any one kind of Present compounds 1 to 348 + Metconazole | 200 + 20 |
| any one kind of Present compounds 1 to 348 + Metconazole | 500 + 0.5 |
| any one kind of Present compounds 1 to 348 + Ipconazole | 200 + 2000 |
| any one kind of Present compounds 1 to 348 + Ipconazole | 200 + 20 |
| any one kind of Present compounds 1 to 348 + Ipconazole | 500 + 0.5 |
| any one kind of Present compounds 1 to 348 + Triticonazole | 200 + 2000 |
| any one kind of Present compounds 1 to 348 + Triticonazole | 200 + 20 |
| any one kind of Present compounds 1 to 348 + Triticonazole | 500 + 0.5 |
| any one kind of Present compounds 1 to 348 + Difenoconazole | 200 + 2000 |
| any one kind of Present compounds 1 to 348 + Difenoconazole | 200 + 20 |
| any one kind of Present compounds 1 to 348 + Difenoconazole | 500 + 0.5 |
| any one kind of Present compounds 1 to 348 + Imazalil | 200 + 2000 |
| any one kind of Present compounds 1 to 348 + Imazalil | 200 + 20 |
| any one kind of Present compounds 1 to 348 + Imazalil | 500 + 0.5 |
| any one kind of Present compounds 1 to 348 + Triadimenol | 200 + 2000 |
| any one kind of Present compounds 1 to 348 + Triadimenol | 200 + 20 |
| any one kind of Present compounds 1 to 348 + Triadimenol | 500 + 0.5 |
| any one kind of Present compounds 1 to 348 + Tetraconazole | 200 + 2000 |
| any one kind of Present compounds 1 to 348 + Tetraconazole | 200 + 20 |
| any one kind of Present compounds 1 to 348 + Tetraconazole | 500 + 0.5 |

TABLE 47-continued

| Composition | Concentration (ppm) (Present compound + Present active ingredient) |
|---|---|
| any one kind of Present compounds 1 to 348 + Flutriafol | 200 + 2000 |
| any one kind of Present compounds 1 to 348 + Flutriafol | 200 + 20 |
| any one kind of Present compounds 1 to 348 + Flutriafol | 500 + 0.5 |
| any one kind of Present compounds 1 to 348 + Mandestrobin | 200 + 2000 |
| any one kind of Present compounds 1 to 348 + Mandestrobin | 200 + 20 |
| any one kind of Present compounds 1 to 348 + Mandestrobin | 500 + 0.5 |
| any one kind of Present compounds 1 to 348 + Azoxystrobin | 200 + 2000 |
| any one kind of Present compounds 1 to 348 + Azoxystrobin | 200 + 20 |
| any one kind of Present compounds 1 to 348 + Azoxystrobin | 500 + 0.5 |
| any one kind of Present compounds 1 to 348 + Pyraclostrobin | 200 + 2000 |
| any one kind of Present compounds 1 to 348 + Pyraclostrobin | 200 + 20 |
| any one kind of Present compounds 1 to 348 + Pyraclostrobin | 500 + 0.5 |
| any one kind of Present compounds 1 to 348 + Trifloxystrobin | 200 + 2000 |
| any one kind of Present compounds 1 to 348 + Trifloxystrobin | 200 + 20 |
| any one kind of Present compounds 1 to 348 + Trifloxystrobin | 500 + 0.5 |
| any one kind of Present compounds 1 to 348 + Fluoxastrobin | 200 + 2000 |
| any one kind of Present compounds 1 to 348 + Fluoxastrobin | 200 + 20 |
| any one kind of Present compounds 1 to 348 + Fluoxastrobin | 500 + 0.5 |
| any one kind of Present compounds 1 to 348 + Picoxystrobin | 200 + 2000 |
| any one kind of Present compounds 1 to 348 + Picoxystrobin | 200 + 20 |
| any one kind of Present compounds 1 to 348 + Picoxystrobin | 500 + 0.5 |
| any one kind of Present compounds 1 to 348 + Fenamidone | 200 + 2000 |
| any one kind of Present compounds 1 to 348 + Fenamidone | 200 + 20 |
| any one kind of Present compounds 1 to 348 + Fenamidone | 500 + 0.5 |
| any one kind of Present compounds 1 to 348 + Metalaxyl | 200 + 2000 |
| any one kind of Present compounds 1 to 348 + Metalaxyl | 200 + 20 |
| any one kind of Present compounds 1 to 348 + Metalaxyl | 500 + 0.5 |
| any one kind of Present compounds 1 to 348 + Metalaxyl M | 200 + 2000 |
| any one kind of Present compounds 1 to 348 + Metalaxyl M | 200 + 20 |
| any one kind of Present compounds 1 to 348 + Metalaxyl M | 500 + 0.5 |
| any one kind of Present compounds 1 to 348 + Fludioxonil | 200 + 2000 |
| any one kind of Present compounds 1 to 348 + Fludioxonil | 200 + 20 |
| any one kind of Present compounds 1 to 348 + Fludioxonil | 500 + 0.5 |
| any one kind of Present compounds 1 to 348 + Sedaxane | 200 + 2000 |
| any one kind of Present compounds 1 to 348 + Sedaxane | 200 + 20 |
| any one kind of Present compounds 1 to 348 + Sedaxane | 500 + 0.5 |
| any one kind of Present compounds 1 to 348 + Penfurufen | 200 + 2000 |
| any one kind of Present compounds 1 to 348 + Penfurufen | 200 + 20 |
| any one kind of Present compounds 1 to 348 + Penfurufen | 500 + 0.5 |
| any one kind of Present compounds 1 to 348 + Fluxapyroxad | 200 + 2000 |
| any one kind of Present compounds 1 to 348 + Fluxapyroxad | 200 + 20 |
| any one kind of Present compounds 1 to 348 + Fluxapyroxad | 500 + 0.5 |
| any one kind of Present compounds 1 to 348 + Benzovindiflupyr | 200 + 2000 |
| any one kind of Present compounds 1 to 348 + Benzovindiflupyr | 200 + 20 |
| any one kind of Present compounds 1 to 348 + Benzovindiflupyr | 500 + 0.5 |
| any one kind of Present compounds 1 to 348 + Boscalid | 200 + 2000 |
| any one kind of Present compounds 1 to 348 + Boscalid | 200 + 20 |
| any one kind of Present compounds 1 to 348 + Boscalid | 500 + 0.5 |

TABLE 47-continued

| Composition | Concentration (ppm) (Present compound + Present active ingredient) |
|---|---|
| any one kind of Present compounds 1 to 348 + Carboxin | 200 + 2000 |
| any one kind of Present compounds 1 to 348 + Carboxin | 200 + 20 |
| any one kind of Present compounds 1 to 348 + Carboxin | 500 + 0.5 |
| any one kind of Present compounds 1 to 348 + Penthiopyrad | 200 + 2000 |
| any one kind of Present compounds 1 to 348 + Penthiopyrad | 200 + 20 |
| any one kind of Present compounds 1 to 348 + Penthiopyrad | 500 + 0.5 |
| any one kind of Present compounds 1 to 348 + Flutolanil | 200 + 2000 |
| any one kind of Present compounds 1 to 348 + Flutolanil | 200 + 20 |
| any one kind of Present compounds 1 to 348 + Flutolanil | 500 + 0.5 |
| any one kind of Present compounds 1 to 348 + Captan | 200 + 2000 |
| any one kind of Present compounds 1 to 348 + Captan | 200 + 20 |
| any one kind of Present compounds 1 to 348 + Captan | 500 + 0.5 |
| any one kind of Present compounds 1 to 348 + Thiuram | 200 + 2000 |
| any one kind of Present compounds 1 to 348 + Thiuram | 200 + 20 |
| any one kind of Present compounds 1 to 348 + Thiuram | 500 + 0.5 |
| any one kind of Present compounds 1 to 348 + Tolclofos-methyl | 200 + 2000 |
| any one kind of Present compounds 1 to 348 + Tolclofos-methyl | 200 + 20 |
| any one kind of Present compounds 1 to 348 + Tolclofos-methyl | 500 + 0.5 |
| any one kind of Present compounds 1 to 348 + Thiabendazole | 200 + 2000 |
| any one kind of Present compounds 1 to 348 + Thiabendazole | 200 + 20 |
| any one kind of Present compounds 1 to 348 + Thiabendazole | 500 + 0.5 |
| any one kind of Present compounds 1 to 348 + Ethaboxam | 200 + 2000 |
| any one kind of Present compounds 1 to 348 + Ethaboxam | 200 + 20 |
| any one kind of Present compounds 1 to 348 + Ethaboxam | 500 + 0.5 |
| any one kind of Present compounds 1 to 348 + Mancozeb | 200 + 2000 |
| any one kind of Present compounds 1 to 348 + Mancozeb | 200 + 20 |
| any one kind of Present compounds 1 to 348 + Mancozeb | 500 + 0.5 |
| any one kind of Present compounds 1 to 348 + Picarbutrazox | 200 + 2000 |
| any one kind of Present compounds 1 to 348 + Picarbutrazox | 200 + 20 |
| any one kind of Present compounds 1 to 348 + Picarbutrazox | 500 + 0.5 |
| any one kind of Present compounds 1 to 348 + Oxathiapiprolin | 200 + 2000 |
| any one kind of Present compounds 1 to 348 + Oxathiapiprolin | 200 + 20 |
| any one kind of Present compounds 1 to 348 + Oxathiapiprolin | 500 + 0.5 |
| any one kind of Present compounds 1 to 348 + Silthiofam | 200 + 2000 |
| any one kind of Present compounds 1 to 348 + Silthiofam | 200 + 20 |
| any one kind of Present compounds 1 to 348 + Silthiofam | 500 + 0.5 |
| any one kind of Present compounds 1 to 348 + Fungicide compound β1 | 200 + 2000 |
| any one kind of Present compounds 1 to 348 + Fungicide compound β1 | 200 + 20 |
| any one kind of Present compounds 1 to 348 + Fungicide compound β1 | 500 + 0.5 |
| any one kind of Present compounds 1 to 348 + Fungicide compound β2 | 200 + 2000 |
| any one kind of Present compounds 1 to 348 + Fungicide compound β2 | 200 + 20 |
| any one kind of Present compounds 1 to 348 + Fungicide compound β2 | 500 + 0.5 |

Next, the Test example is used to show an efficacy of the present composition on controlling harmful arthropods.

Test Example 12

Each 1 mg of the Present compound was dissolved into a 10 μL of the mixed solution of xylene:DMF:surfactants (Trade name: Sorpol 3005X, manufactured by TOHO CHEMICAL INDUSTRY CO. LTD) (xylene:DMF:surfactants=4:4:1 (v/v ratio)). Thereto was added water containing 0.02% (v/v) of the spreading agent (Trade name: Sindain, manufactured by Sumitomo Chemical Company, Limited) so as to give a diluted solution containing the prescribed concentration of the Present compound.

When the commercially available formulation of the present active ingredient was used, each of the commercially available formulation was diluted with water containing 0.02 v/v % of the spreader to prepare the prescribed concentration of the diluted solution of the present active ingredient.

Whereas, when the commercially available formulation of the present active ingredient was not used, each 1 mg of the present active ingredient was dissolved into a 10 μL of the mixed solution of xylene, DMF and surfactants (xylene, DMF and surfactants=4:4:1 (v/v ratio)). Thereto was added water containing 0.02% by volume of a spreader (Trade name: Sindain, manufactured by Sumitomo Chemical Company, Limited) to prepare a diluted solution containing a prescribed concentration of the present active ingredient.

The above prepared diluted solution of the Present compound and the above prepared diluted solution of the present active ingredient were mixed to prepare the test chemical solution of the composition comprising the Present compound and the present active ingredient.

A leaf disk (length 1.5 cm) of the seed leaf of cucumber (*Cucumis sativus*) was placed into each well in a 24 well microplate, and 2 wingless adults of a cotton aphid (*Aphis gossypii*) and 8 nymphs were released per 1 well, and the test chemical solution was sprayed in a ratio of 20 μL per 1 well, which is referred to as a treated group.

Whereas, 20 μl of water containing 0.02 v/v % of the spreader (Trade name: Sindain, manufactured by Sumitomo Chemical Company, Limited) was sprayed into a well instead of the test drug solution, which was referred to as an untreated group.

After the test chemical solution was dried, the upper part of a microplate was covered with the gas permeable film sheet (Product Name: AeraSeal, manufactured by Excel Scientific Inc.), and 5 days after the release, the number of the surviving insects of each well was examined.

The controlling value was calculated by the following equation.

Controlling value (%)={1−(*Tai*)/(*Cai*)}×100 wherein the symbols in the formula represent the following descriptions.

Cai: Number of the surviving insects at the time of the investigation in untreated group;

Tai: Number of the surviving insects at the time of the investigation in treated group;

The result of the test that was done according to Test example 12 is shown below.

Any the present composition wherein the respective concentration of the Present compound and the present active ingredient is indicated in the following Tables 48 to 61 showed 90% or greater as a controlling value against harmful arthropods.

Table 48

TABLE 48

| Composition | Concentration (ppm) |
|---|---|
| Present compound 2 + Clothianidin | 200 + 2000 |
| Present compound 2 + Clothianidin | 500 + 50 |
| Present compound 2 + Imidacloprid | 200 + 2000 |
| Present compound 2 + Imidacloprid | 500 + 50 |
| Present compound 2 + Thiamethoxam | 200 + 2000 |
| Present compound 2 + Thiamethoxam | 500 + 50 |
| Present compound 2 + Azoxystrobin | 200 + 200 |
| Present compound 2 + Azoxystrobin | 500 + 0.5 |
| Present compound 2 + Difenoconazole | 200 + 200 |
| Present compound 2 + Difenoconazole | 500 + 0.5 |
| Present compound 2 + Ethaboxam | 200 + 200 |

TABLE 48-continued

| Composition | Concentration (ppm) |
|---|---|
| Present compound 2 + Ethaboxam | 500 + 0.5 |
| Present compound 2 + Fludioxonil | 200 + 200 |
| Present compound 2 + Fludioxonil | 500 + 0.5 |
| Present compound 2 + Fluopyram | 200 + 2000 |
| Present compound 2 + Fluopyram | 500 + 0.5 |
| Present compound 2 + Fluoxastrobin | 200 + 200 |
| Present compound 2 + Fluoxastrobin | 500 + 0.5 |
| Present compound 2 + Flutolanil | 200 + 200 |
| Present compound 2 + Flutolanil | 500 + 0.5 |
| Present compound 2 + Flutriafol | 200 + 200 |
| Present compound 2 + Flutriafol | 500 + 0.5 |
| Present compound 2 + Fluxapyroxad | 200 + 200 |
| Present compound 2 + Fluxapyroxad | 500 + 0.5 |
| Present compound 2 + Ipconazole | 200 + 200 |
| Present compound 2 + Ipconazole | 500 + 0.5 |
| Present compound 2 + Mandestrobin | 200 + 200 |
| Present compound 2 + Mandestrobin | 500 + 0.5 |
| Present compound 2 + Metalaxyl M | 200 + 200 |
| Present compound 2 + Metalaxyl M | 500 + 0.5 |
| Present compound 2 + Metalaxyl | 200 + 200 |
| Present compound 2 + Metalaxyl | 500 + 0.5 |
| Present compound 2 + Metconazole | 200 + 200 |
| Present compound 2 + Metconazole | 500 + 0.5 |
| Present compound 2 + Oxathiapiprolin | 200 + 200 |
| Present compound 2 + Oxathiapiprolin | 500 + 0.5 |
| Present compound 2 + Penfurufen | 200 + 200 |
| Present compound 2 + Penfurufen | 500 + 0.5 |
| Present compound 2 + Penthiopyrad | 200 + 200 |
| Present compound 2 + Penthiopyrad | 500 + 0.5 |
| Present compound 2 + Picoxystrobin | 200 + 200 |
| Present compound 2 + Picoxystrobin | 500 + 0.5 |
| Present compound 2 + Prothioconazole | 200 + 200 |
| Present compound 2 + Prothioconazole | 500 + 0.5 |
| Present compound 2 + Pyraclostrobin | 200 + 200 |
| Present compound 2 + Pyraclostrobin | 500 + 0.5 |
| Present compound 2 + Fungicide compound β2 | 200 + 200 |
| Present compound 2 + Fungicide compound β2 | 500 + 0.5 |
| Present compound 2 + Sedaxane | 200 + 200 |
| Present compound 2 + Sedaxane | 500 + 0.5 |
| Present compound 2 + Tebuconazole | 200 + 200 |
| Present compound 2 + Tebuconazole | 500 + 0.5 |
| Present compound 2 + Triadimenol | 200 + 200 |
| Present compound 2 + Triadimenol | 500 + 0.5 |
| Present compound 2 + Trifloxystrobin | 200 + 200 |
| Present compound 2 + Trifloxystrobin | 500 + 0.5 |
| Present compound 2 + Triticonazole | 200 + 200 |
| Present compound 2 + Triticonazole | 500 + 0.5 |

TABLE 49

| Composition | Concentration (ppm) |
|---|---|
| Present compound 4 + Clothianidin | 200 + 2000 |
| Present compound 4 + Clothianidin | 500 + 50 |
| Present compound 4 + Imidacloprid | 200 + 2000 |
| Present compound 4 + Imidacloprid | 500 + 50 |
| Present compound 4 + Thiamethoxam | 200 + 2000 |
| Present compound 4 + Thiamethoxam | 500 + 50 |
| Present compound 4 + Azoxystrobin | 200 + 200 |
| Present compound 4 + Azoxystrobin | 500 + 0.5 |
| Present compound 4 + Difenoconazole | 200 + 200 |
| Present compound 4 + Difenoconazole | 500 + 0.5 |
| Present compound 4 + Ethaboxam | 200 + 200 |
| Present compound 4 + Ethaboxam | 500 + 0.5 |
| Present compound 4 + Fludioxonil | 200 + 200 |
| Present compound 4 + Fludioxonil | 500 + 0.5 |
| Present compound 4 + Fluopyram | 200 + 2000 |
| Present compound 4 + Fluopyram | 500 + 0.5 |
| Present compound 4 + Fluoxastrobin | 200 + 200 |
| Present compound 4 + Fluoxastrobin | 500 + 0.5 |
| Present compound 4 + Flutolanil | 200 + 200 |
| Present compound 4 + Flutolanil | 500 + 0.5 |
| Present compound 4 + Flutriafol | 200 + 200 |

TABLE 49-continued

| Composition | Concentration (ppm) |
| --- | --- |
| Present compound 4 + Flutriafol | 500 + 0.5 |
| Present compound 4 + Fluxapyroxad | 200 + 200 |
| Present compound 4 + Fluxapyroxad | 500 + 0.5 |
| Present compound 4 + Ipconazole | 200 + 200 |
| Present compound 4 + Ipconazole | 500 + 0.5 |
| Present compound 4 + Mandestrobin | 200 + 200 |
| Present compound 4 + Mandestrobin | 500 + 0.5 |
| Present compound 4 + Metalaxyl M | 200 + 200 |
| Present compound 4 + Metalaxyl M | 500 + 0.5 |
| Present compound 4 + Metalaxyl | 200 + 200 |
| Present compound 4 + Metalaxyl | 500 + 0.5 |
| Present compound 4 + Metconazole | 200 + 200 |
| Present compound 4 + Metconazole | 500 + 0.5 |
| Present compound 4 + Oxathiapiprolin | 200 + 200 |
| Present compound 4 + Oxathiapiprolin | 500 + 0.5 |
| Present compound 4 + Penfurufen | 200 + 200 |
| Present compound 4 + Penfurufen | 500 + 0.5 |
| Present compound 4 + Penthiopyrad | 200 + 200 |
| Present compound 4 + Penthiopyrad | 500 + 0.5 |
| Present compound 4 + Picoxystrobin | 200 + 200 |
| Present compound 4 + Picoxystrobin | 500 + 0.5 |
| Present compound 4 + Prothioconazole | 200 + 200 |
| Present compound 4 + Prothioconazole | 500 + 0.5 |
| Present compound 4 + Pyraclostrobin | 200 + 200 |
| Present compound 4 + Pyraclostrobin | 500 + 0.5 |
| Present compound 4 + Fungicide compound β2 | 200 + 200 |
| Present compound 4 + Fungicide compound β2 | 500 + 0.5 |
| Present compound 4 + Sedaxane | 200 + 200 |
| Present compound 4 + Sedaxane | 500 + 0.5 |
| Present compound 4 + Tebuconazole | 200 + 200 |
| Present compound 4 + Tebuconazole | 500 + 0.5 |
| Present compound 4 + Triadimenol | 200 + 200 |
| Present compound 4 + Triadimenol | 500 + 0.5 |
| Present compound 4 + Trifloxystrobin | 200 + 200 |
| Present compound 4 + Trifloxystrobin | 500 + 0.5 |
| Present compound 4 + Triticonazole | 200 + 200 |
| Present compound 4 + Triticonazole | 500 + 0.5 |

TABLE 50

| Composition | Concentration (ppm) |
| --- | --- |
| Present compound 5 + Clothianidin | 200 + 2000 |
| Present compound 5 + Clothianidin | 500 + 50 |
| Present compound 5 + Imidacloprid | 200 + 2000 |
| Present compound 5 + Imidacloprid | 500 + 50 |
| Present compound 5 + Thiamethoxam | 200 + 2000 |
| Present compound 5 + Thiamethoxam | 500 + 50 |
| Present compound 5 + Azoxystrobin | 200 + 200 |
| Present compound 5 + Azoxystrobin | 500 + 0.5 |
| Present compound 5 + Difenoconazole | 200 + 200 |
| Present compound 5 + Difenoconazole | 500 + 0.5 |
| Present compound 5 + Ethaboxam | 200 + 200 |
| Present compound 5 + Ethaboxam | 500 + 0.5 |
| Present compound 5 + Fludioxonil | 200 + 200 |
| Present compound 5 + Fludioxonil | 500 + 0.5 |
| Present compound 5 + Fluopyram | 200 + 2000 |
| Present compound 5 + Fluopyram | 500 + 0.5 |
| Present compound 5 + Fluoxastrobin | 200 + 200 |
| Present compound 5 + Fluoxastrobin | 500 + 0.5 |
| Present compound 5 + Flutolanil | 200 + 200 |
| Present compound 5 + Flutolanil | 500 + 0.5 |
| Present compound 5 + Flutriafol | 200 + 200 |
| Present compound 5 + Flutriafol | 500 + 0.5 |
| Present compound 5 + Fluxapyroxad | 200 + 200 |
| Present compound 5 + Fluxapyroxad | 500 + 0.5 |
| Present compound 5 + Ipconazole | 200 + 200 |
| Present compound 5 + Ipconazole | 500 + 0.5 |
| Present compound 5 + Mandestrobin | 200 + 200 |
| Present compound 5 + Mandestrobin | 500 + 0.5 |
| Present compound 5 + Metalaxyl M | 200 + 200 |
| Present compound 5 + Metalaxyl M | 500 + 0.5 |
| Present compound 5 + Metalaxyl | 200 + 200 |

TABLE 50-continued

| Composition | Concentration (ppm) |
| --- | --- |
| Present compound 5 + Metalaxyl | 500 + 0.5 |
| Present compound 5 + Metconazole | 200 + 200 |
| Present compound 5 + Metconazole | 500 + 0.5 |
| Present compound 5 + Oxathiapiprolin | 200 + 200 |
| Present compound 5 + Oxathiapiprolin | 500 + 0.5 |
| Present compound 5 + Penfurufen | 200 + 200 |
| Present compound 5 + Penfurufen | 500 + 0.5 |
| Present compound 5 + Penthiopyrad | 200 + 200 |
| Present compound 5 + Penthiopyrad | 500 + 0.5 |
| Present compound 5 + Picoxystrobin | 200 + 200 |
| Present compound 5 + Picoxystrobin | 500 + 0.5 |
| Present compound 5 + Prothioconazole | 200 + 200 |
| Present compound 5 + Prothioconazole | 500 + 0.5 |
| Present compound 5 + Pyraclostrobin | 200 + 200 |
| Present compound 5 + Pyraclostrobin | 500 + 0.5 |
| Present compound 5 + Fungicide compound β2 | 200 + 200 |
| Present compound 5 + Fungicide compound β2 | 500 + 0.5 |
| Present compound 5 + Sedaxane | 200 + 200 |
| Present compound 5 + Sedaxane | 500 + 0.5 |
| Present compound 5 + Tebuconazole | 200 + 200 |
| Present compound 5 + Tebuconazole | 500 + 0.5 |
| Present compound 5 + Triadimenol | 200 + 200 |
| Present compound 5 + Triadimenol | 500 + 0.5 |
| Present compound 5 + Trifloxystrobin | 200 + 200 |
| Present compound 5 + Trifloxystrobin | 500 + 0.5 |
| Present compound 5 + Triticonazole | 200 + 200 |
| Present compound 5 + Triticonazole | 500 + 0.5 |

TABLE 51

| Composition | Concentration (ppm) |
| --- | --- |
| Present compound 6 + Clothianidin | 200 + 2000 |
| Present compound 6 + Clothianidin | 500 + 50 |
| Present compound 6 + Imidacloprid | 200 + 2000 |
| Present compound 6 + Imidacloprid | 500 + 50 |
| Present compound 6 + Thiamethoxam | 200 + 2000 |
| Present compound 6 + Thiamethoxam | 500 + 50 |
| Present compound 6 + Azoxystrobin | 200 + 200 |
| Present compound 6 + Azoxystrobin | 500 + 0.5 |
| Present compound 6 + Difenoconazole | 200 + 200 |
| Present compound 6 + Difenoconazole | 500 + 0.5 |
| Present compound 6 + Ethaboxam | 200 + 200 |
| Present compound 6 + Ethaboxam | 500 + 0.5 |
| Present compound 6 + Fludioxonil | 200 + 200 |
| Present compound 6 + Fludioxonil | 500 + 0.5 |
| Present compound 6 + Fluopyram | 200 + 2000 |
| Present compound 6 + Fluopyram | 500 + 0.5 |
| Present compound 6 + Fluoxastrobin | 200 + 200 |
| Present compound 6 + Fluoxastrobin | 500 + 0.5 |
| Present compound 6 + Flutolanil | 200 + 200 |
| Present compound 6 + Flutolanil | 500 + 0.5 |
| Present compound 6 + Flutriafol | 200 + 200 |
| Present compound 6 + Flutriafol | 500 + 0.5 |
| Present compound 6 + Fluxapyroxad | 200 + 200 |
| Present compound 6 + Fluxapyroxad | 500 + 0.5 |
| Present compound 6 + Ipconazole | 200 + 200 |
| Present compound 6 + Ipconazole | 500 + 0.5 |
| Present compound 6 + Mandestrobin | 200 + 200 |
| Present compound 6 + Mandestrobin | 500 + 0.5 |
| Present compound 6 + Metalaxyl M | 200 + 200 |
| Present compound 6 + Metalaxyl M | 500 + 0.5 |
| Present compound 6 + Metalaxyl | 200 + 200 |
| Present compound 6 + Metalaxyl | 500 + 0.5 |
| Present compound 6 + Metconazole | 200 + 200 |
| Present compound 6 + Metconazole | 500 + 0.5 |
| Present compound 6 + Oxathiapiprolin | 200 + 200 |
| Present compound 6 + Oxathiapiprolin | 500 + 0.5 |
| Present compound 6 + Penfurufen | 200 + 200 |
| Present compound 6 + Penfurufen | 500 + 0.5 |
| Present compound 6 + Penthiopyrad | 200 + 200 |
| Present compound 6 + Penthiopyrad | 500 + 0.5 |
| Present compound 6 + Picoxystrobin | 200 + 200 |

TABLE 51-continued

| Composition | Concentration (ppm) |
|---|---|
| Present compound 6 + Picoxystrobin | 500 + 0.5 |
| Present compound 6 + Prothioconazole | 200 + 200 |
| Present compound 6 + Prothioconazole | 500 + 0.5 |
| Present compound 6 + Pyraclostrobin | 200 + 200 |
| Present compound 6 + Pyraclostrobin | 500 + 0.5 |
| Present compound 6 + Fungicide compound β2 | 200 + 200 |
| Present compound 6 + Fungicide compound β2 | 500 + 0.5 |
| Present compound 6 + Sedaxane | 200 + 200 |
| Present compound 6 + Sedaxane | 500 + 0.5 |
| Present compound 6 + Tebuconazole | 200 + 200 |
| Present compound 6 + Tebuconazole | 500 + 0.5 |
| Present compound 6 + Triadimenol | 200 + 200 |
| Present compound 6 + Triadimenol | 500 + 0.5 |
| Present compound 6 + Trifloxystrobin | 200 + 200 |
| Present compound 6 + Trifloxystrobin | 500 + 0.5 |
| Present compound 6 + Triticonazole | 200 + 200 |
| Present compound 6 + Triticonazole | 500 + 0.5 |

TABLE 52

| Composition | Concentration (ppm) |
|---|---|
| Present compound 7 + Clothianidin | 200 + 2000 |
| Present compound 7 + Clothianidin | 500 + 50 |
| Present compound 7 + Imidacloprid | 200 + 2000 |
| Present compound 7 + Imidacloprid | 500 + 50 |
| Present compound 7 + Thiamethoxam | 200 + 2000 |
| Present compound 7 + Thiamethoxam | 500 + 50 |
| Present compound 7 + Azoxystrobin | 200 + 200 |
| Present compound 7 + Azoxystrobin | 500 + 0.5 |
| Present compound 7 + Difenoconazole | 200 + 200 |
| Present compound 7 + Difenoconazole | 500 + 0.5 |
| Present compound 7 + Ethaboxam | 200 + 200 |
| Present compound 7 + Ethaboxam | 500 + 0.5 |
| Present compound 7 + Fludioxonil | 200 + 200 |
| Present compound 7 + Fludioxonil | 500 + 0.5 |
| Present compound 7 + Fluopyram | 200 + 2000 |
| Present compound 7 + Fluopyram | 500 + 0.5 |
| Present compound 7 + Fluoxastrobin | 200 + 200 |
| Present compound 7 + Fluoxastrobin | 500 + 0.5 |
| Present compound 7 + Flutolanil | 200 + 200 |
| Present compound 7 + Flutolanil | 500 + 0.5 |
| Present compound 7 + Flutriafol | 200 + 200 |
| Present compound 7 + Flutriafol | 500 + 0.5 |
| Present compound 7 + Fluxapyroxad | 200 + 200 |
| Present compound 7 + Fluxapyroxad | 500 + 0.5 |
| Present compound 7 + Ipconazole | 200 + 200 |
| Present compound 7 + Ipconazole | 500 + 0.5 |
| Present compound 7 + Mandestrobin | 200 + 200 |
| Present compound 7 + Mandestrobin | 500 + 0.5 |
| Present compound 7 + Metalaxyl M | 200 + 200 |
| Present compound 7 + Metalaxyl M | 500 + 0.5 |
| Present compound 7 + Metalaxyl | 200 + 200 |
| Present compound 7 + Metalaxyl | 500 + 0.5 |
| Present compound 7 + Metconazole | 200 + 200 |
| Present compound 7 + Metconazole | 500 + 0.5 |
| Present compound 7 + Oxathiapiprolin | 200 + 200 |
| Present compound 7 + Oxathiapiprolin | 500 + 0.5 |
| Present compound 7 + Penfurufen | 200 + 200 |
| Present compound 7 + Penfurufen | 500 + 0.5 |
| Present compound 7 + Penthiopyrad | 200 + 200 |
| Present compound 7 + Penthiopyrad | 500 + 0.5 |
| Present compound 7 + Picoxystrobin | 200 + 200 |
| Present compound 7 + Picoxystrobin | 500 + 0.5 |
| Present compound 7 + Prothioconazole | 200 + 200 |
| Present compound 7 + Prothioconazole | 500 + 0.5 |
| Present compound 7 + Pyraclostrobin | 200 + 200 |
| Present compound 7 + Pyraclostrobin | 500 + 0.5 |
| Present compound 7 + Fungicide compound β2 | 200 + 200 |
| Present compound 7 + Fungicide compound β2 | 500 + 0.5 |
| Present compound 7 + Sedaxane | 200 + 200 |
| Present compound 7 + Sedaxane | 500 + 0.5 |
| Present compound 7 + Tebuconazole | 200 + 200 |

TABLE 52-continued

| Composition | Concentration (ppm) |
|---|---|
| Present compound 7 + Tebuconazole | 500 + 0.5 |
| Present compound 7 + Triadimenol | 200 + 200 |
| Present compound 7 + Triadimenol | 500 + 0.5 |
| Present compound 7 + Trifloxystrobin | 200 + 200 |
| Present compound 7 + Trifloxystrobin | 500 + 0.5 |
| Present compound 7 + Triticonazole | 200 + 200 |
| Present compound 7 + Triticonazole | 500 + 0.5 |

TABLE 53

| Composition | Concentration (ppm) |
|---|---|
| Present compound 8 + Clothianidin | 200 + 2000 |
| Present compound 8 + Clothianidin | 500 + 50 |
| Present compound 8 + Imidacloprid | 200 + 2000 |
| Present compound 8 + Imidacloprid | 500 + 50 |
| Present compound 8 + Thiamethoxam | 200 + 2000 |
| Present compound 8 + Thiamethoxam | 500 + 50 |
| Present compound 8 + Azoxystrobin | 200 + 200 |
| Present compound 8 + Azoxystrobin | 500 + 0.5 |
| Present compound 8 + Difenoconazole | 200 + 200 |
| Present compound 8 + Difenoconazole | 500 + 0.5 |
| Present compound 8 + Ethaboxam | 200 + 200 |
| Present compound 8 + Ethaboxam | 500 + 0.5 |
| Present compound 8 + Fludioxonil | 200 + 200 |
| Present compound 8 + Fludioxonil | 500 + 0.5 |
| Present compound 8 + Fluopyram | 200 + 2000 |
| Present compound 8 + Fluopyram | 500 + 0.5 |
| Present compound 8 + Fluoxastrobin | 200 + 200 |
| Present compound 8 + Fluoxastrobin | 500 + 0.5 |
| Present compound 8 + Flutolanil | 200 + 200 |
| Present compound 8 + Flutolanil | 500 + 0.5 |
| Present compound 8 + Flutriafol | 200 + 200 |
| Present compound 8 + Flutriafol | 500 + 0.5 |
| Present compound 8 + Fluxapyroxad | 200 + 200 |
| Present compound 8 + Fluxapyroxad | 500 + 0.5 |
| Present compound 8 + Ipconazole | 200 + 200 |
| Present compound 8 + Ipconazole | 500 + 0.5 |
| Present compound 8 + Mandestrobin | 200 + 200 |
| Present compound 8 + Mandestrobin | 500 + 0.5 |
| Present compound 8 + Metalaxyl M | 200 + 200 |
| Present compound 8 + Metalaxyl M | 500 + 0.5 |
| Present compound 8 + Metalaxyl | 200 + 200 |
| Present compound 8 + Metalaxyl | 500 + 0.5 |
| Present compound 8 + Metconazole | 200 + 200 |
| Present compound 8 + Metconazole | 500 + 0.5 |
| Present compound 8 + Oxathiapiprolin | 200 + 200 |
| Present compound 8 + Oxathiapiprolin | 500 + 0.5 |
| Present compound 8 + Penfurufen | 200 + 200 |
| Present compound 8 + Penfurufen | 500 + 0.5 |
| Present compound 8 + Penthiopyrad | 200 + 200 |
| Present compound 8 + Penthiopyrad | 500 + 0.5 |
| Present compound 8 + Picoxystrobin | 200 + 200 |
| Present compound 8 + Picoxystrobin | 500 + 0.5 |
| Present compound 8 + Prothioconazole | 200 + 200 |
| Present compound 8 + Prothioconazole | 500 + 0.5 |
| Present compound 8 + Pyraclostrobin | 200 + 200 |
| Present compound 8 + Pyraclostrobin | 500 + 0.5 |
| Present compound 8 + Fungicide compound β2 | 200 + 200 |
| Present compound 8 + Fungicide compound β2 | 500 + 0.5 |
| Present compound 8 + Sedaxane | 200 + 200 |
| Present compound 8 + Sedaxane | 500 + 0.5 |
| Present compound 8 + Tebuconazole | 200 + 200 |
| Present compound 8 + Tebuconazole | 500 + 0.5 |
| Present compound 8 + Triadimenol | 200 + 200 |
| Present compound 8 + Triadimenol | 500 + 0.5 |
| Present compound 8 + Trifloxystrobin | 200 + 200 |
| Present compound 8 + Trifloxystrobin | 500 + 0.5 |
| Present compound 8 + Triticonazole | 200 + 200 |
| Present compound 8 + Triticonazole | 500 + 0.5 |

TABLE 54

| Composition | Concentration (ppm) |
| --- | --- |
| Present compound 9 + Clothianidin | 200 + 2000 |
| Present compound 9 + Clothianidin | 500 + 50 |
| Present compound 9 + Imidacloprid | 200 + 2000 |
| Present compound 9 + Imidacloprid | 500 + 50 |
| Present compound 9 + Thiamethoxam | 200 + 2000 |
| Present compound 9 + Thiamethoxam | 500 + 50 |
| Present compound 9 + Azoxystrobin | 200 + 200 |
| Present compound 9 + Azoxystrobin | 500 + 0.5 |
| Present compound 9 + Difenoconazole | 200 + 200 |
| Present compound 9 + Difenoconazole | 500 + 0.5 |
| Present compound 9 + Ethaboxam | 200 + 200 |
| Present compound 9 + Ethaboxam | 500 + 0.5 |
| Present compound 9 + Fludioxonil | 200 + 200 |
| Present compound 9 + Fludioxonil | 500 + 0.5 |
| Present compound 9 + Fluopyram | 200 + 2000 |
| Present compound 9 + Fluopyram | 500 + 0.5 |
| Present compound 9 + Fluoxastrobin | 200 + 200 |
| Present compound 9 + Fluoxastrobin | 500 + 0.5 |
| Present compound 9 + Flutolanil | 200 + 200 |
| Present compound 9 + Flutolanil | 500 + 0.5 |
| Present compound 9 + Flutriafol | 200 + 200 |
| Present compound 9 + Flutriafol | 500 + 0.5 |
| Present compound 9 + Fluxapyroxad | 200 + 200 |
| Present compound 9 + Fluxapyroxad | 500 + 0.5 |
| Present compound 9 + Ipconazole | 200 + 200 |
| Present compound 9 + Ipconazole | 500 + 0.5 |
| Present compound 9 + Mandestrobin | 200 + 200 |
| Present compound 9 + Mandestrobin | 500 + 0.5 |
| Present compound 9 + Metalaxyl M | 200 + 200 |
| Present compound 9 + Metalaxyl M | 500 + 0.5 |
| Present compound 9 + Metalaxyl | 200 + 200 |
| Present compound 9 + Metalaxyl | 500 + 0.5 |
| Present compound 9 + Metconazole | 200 + 200 |
| Present compound 9 + Metconazole | 500 + 0.5 |
| Present compound 9 + Oxathiapiprolin | 200 + 200 |
| Present compound 9 + Oxathiapiprolin | 500 + 0.5 |
| Present compound 9 + Penfurufen | 200 + 200 |
| Present compound 9 + Penfurufen | 500 + 0.5 |
| Present compound 9 + Penthiopyrad | 200 + 200 |
| Present compound 9 + Penthiopyrad | 500 + 0.5 |
| Present compound 9 + Picoxystrobin | 200 + 200 |
| Present compound 9 + Picoxystrobin | 500 + 0.5 |
| Present compound 9 + Prothioconazole | 200 + 200 |
| Present compound 9 + Prothioconazole | 500 + 0.5 |
| Present compound 9 + Pyraclostrobin | 200 + 200 |
| Present compound 9 + Pyraclostrobin | 500 + 0.5 |
| Present compound 9 + Fungicide compound β2 | 200 + 200 |
| Present compound 9 + Fungicide compound β2 | 500 + 0.5 |
| Present compound 9 + Sedaxane | 200 + 200 |
| Present compound 9 + Sedaxane | 500 + 0.5 |
| Present compound 9 + Tebuconazole | 200 + 200 |
| Present compound 9 + Tebuconazole | 500 + 0.5 |
| Present compound 9 + Triadimenol | 200 + 200 |
| Present compound 9 + Triadimenol | 500 + 0.5 |
| Present compound 9 + Trifloxystrobin | 200 + 200 |
| Present compound 9 + Trifloxystrobin | 500 + 0.5 |
| Present compound 9 + Triticonazole | 200 + 200 |
| Present compound 9 + Triticonazole | 500 + 0.5 |

TABLE 55

| Composition | Concentration (ppm) |
| --- | --- |
| Present compound 10 + Clothianidin | 200 + 2000 |
| Present compound 10 + Clothianidin | 500 + 50 |
| Present compound 10 + Imidacloprid | 200 + 2000 |
| Present compound 10 + Imidacloprid | 500 + 50 |
| Present compound 10 + Thiamethoxam | 200 + 2000 |
| Present compound 10 + Thiamethoxam | 500 + 50 |
| Present compound 10 + Azoxystrobin | 200 + 200 |
| Present compound 10 + Azoxystrobin | 500 + 0.5 |
| Present compound 10 + Difenoconazole | 200 + 200 |
| Present compound 10 + Difenoconazole | 500 + 0.5 |
| Present compound 10 + Ethaboxam | 200 + 200 |
| Present compound 10 + Ethaboxam | 500 + 0.5 |
| Present compound 10 + Fludioxonil | 200 + 200 |
| Present compound 10 + Fludioxonil | 500 + 0.5 |
| Present compound 10 + Fluopyram | 200 + 2000 |
| Present compound 10 + Fluopyram | 500 + 0.5 |
| Present compound 10 + Fluoxastrobin | 200 + 200 |
| Present compound 10 + Fluoxastrobin | 500 + 0.5 |
| Present compound 10 + Flutolanil | 200 + 200 |
| Present compound 10 + Flutolanil | 500 + 0.5 |
| Present compound 10 + Flutriafol | 200 + 200 |
| Present compound 10 + Flutriafol | 500 + 0.5 |
| Present compound 10 + Fluxapyroxad | 200 + 200 |
| Present compound 10 + Fluxapyroxad | 500 + 0.5 |
| Present compound 10 + Ipconazole | 200 + 200 |
| Present compound 10 + Ipconazole | 500 + 0.5 |
| Present compound 10 + Mandestrobin | 200 + 200 |
| Present compound 10 + Mandestrobin | 500 + 0.5 |
| Present compound 10 + Metalaxyl M | 200 + 200 |
| Present compound 10 + Metalaxyl M | 500 + 0.5 |
| Present compound 10 + Metalaxyl | 200 + 200 |
| Present compound 10 + Metalaxyl | 500 + 0.5 |
| Present compound 10 + Metconazole | 200 + 200 |
| Present compound 10 + Metconazole | 500 + 0.5 |
| Present compound 10 + Oxathiapiprolin | 200 + 200 |
| Present compound 10 + Oxathiapiprolin | 500 + 0.5 |
| Present compound 10 + Penfurufen | 200 + 200 |
| Present compound 10 + Penfurufen | 500 + 0.5 |
| Present compound 10 + Penthiopyrad | 200 + 200 |
| Present compound 10 + Penthiopyrad | 500 + 0.5 |
| Present compound 10 + Picoxystrobin | 200 + 200 |
| Present compound 10 + Picoxystrobin | 500 + 0.5 |
| Present compound 10 + Prothioconazole | 200 + 200 |
| Present compound 10 + Prothioconazole | 500 + 0.5 |
| Present compound 10 + Pyraclostrobin | 200 + 200 |
| Present compound 10 + Pyraclostrobin | 500 + 0.5 |
| Present compound 10 + Fungicide | 200 + 200 |
| Present compound 10 + Fungicide | 500 + 0.5 |
| Present compound 10 + Sedaxane | 200 + 200 |
| Present compound 10 + Sedaxane | 500 + 0.5 |
| Present compound 10 + Tebuconazole | 200 + 200 |
| Present compound 10 + Tebuconazole | 500 + 0.5 |
| Present compound 10 + Triadimenol | 200 + 200 |
| Present compound 10 + Triadimenol | 500 + 0.5 |
| Present compound 10 + Trifloxystrobin | 200 + 200 |
| Present compound 10 + Trifloxystrobin | 500 + 0.5 |
| Present compound 10 + Triticonazole | 200 + 200 |
| Present compound 10 + Triticonazole | 500 + 0.5 |

TABLE 56

| Composition | Concentration (ppm) |
| --- | --- |
| Present compound 11 + Clothianidin | 200 + 2000 |
| Present compound 11 + Clothianidin | 500 + 50 |
| Present compound 11 + Imidacloprid | 200 + 2000 |
| Present compound 11 + Imidacloprid | 500 + 50 |
| Present compound 11 + Thiamethoxam | 200 + 2000 |
| Present compound 11 + Thiamethoxam | 500 + 50 |
| Present compound 11 + Azoxystrobin | 200 + 200 |
| Present compound 11 + Azoxystrobin | 500 + 0.5 |
| Present compound 11 + Difenoconazole | 200 + 200 |
| Present compound 11 + Difenoconazole | 500 + 0.5 |
| Present compound 11 + Ethaboxam | 200 + 200 |
| Present compound 11 + Ethaboxam | 500 + 0.5 |
| Present compound 11 + Fludioxonil | 200 + 200 |
| Present compound 11 + Fludioxonil | 500 + 0.5 |
| Present compound 11 + Fluopyram | 200 + 2000 |
| Present compound 11 + Fluopyram | 500 + 0.5 |
| Present compound 11 + Fluoxastrobin | 200 + 200 |
| Present compound 11 + Fluoxastrobin | 500 + 0.5 |
| Present compound 11 + Flutolanil | 200 + 200 |
| Present compound 11 + Flutolanil | 500 + 0.5 |

TABLE 56-continued

| Composition | Concentration (ppm) |
|---|---|
| Present compound 11 + Flutriafol | 200 + 200 |
| Present compound 11 + Flutriafol | 500 + 0.5 |
| Present compound 11 + Fluxapyroxad | 200 + 200 |
| Present compound 11 + Fluxapyroxad | 500 + 0.5 |
| Present compound 11 + Ipconazole | 200 + 200 |
| Present compound 11 + Ipconazole | 500 + 0.5 |
| Present compound 11 + Mandestrobin | 200 + 200 |
| Present compound 11 + Mandestrobin | 500 + 0.5 |
| Present compound 11 + Metalaxyl M | 200 + 200 |
| Present compound 11 + Metalaxyl M | 500 + 0.5 |
| Present compound 11 + Metalaxyl | 200 + 200 |
| Present compound 11 + Metalaxyl | 500 + 0.5 |
| Present compound 11 + Metconazole | 200 + 200 |
| Present compound 11 + Metconazole | 500 + 0.5 |
| Present compound 11 + Oxathiapiprolin | 200 + 200 |
| Present compound 11 + Oxathiapiprolin | 500 + 0.5 |
| Present compound 11 + Penfurufen | 200 + 200 |
| Present compound 11 + Penfurufen | 500 + 0.5 |
| Present compound 11 + Penthiopyrad | 200 + 200 |
| Present compound 11 + Penthiopyrad | 500 + 0.5 |
| Present compound 11 + Picoxystrobin | 200 + 200 |
| Present compound 11 + Picoxystrobin | 500 + 0.5 |
| Present compound 11 + Prothioconazole | 200 + 200 |
| Present compound 11 + Prothioconazole | 500 + 0.5 |
| Present compound 11 + Pyraclostrobin | 200 + 200 |
| Present compound 11 + Pyraclostrobin | 500 + 0.5 |
| Present compound 11 + Fungicide | 200 + 200 |
| Present compound 11 + Fungicide | 500 + 0.5 |
| Present compound 11 + Sedaxane | 200 + 200 |
| Present compound 11 + Sedaxane | 500 + 0.5 |
| Present compound 11 + Tebuconazole | 200 + 200 |
| Present compound 11 + Tebuconazole | 500 + 0.5 |
| Present compound 11 + Triadimenol | 200 + 200 |
| Present compound 11 + Triadimenol | 500 + 0.5 |
| Present compound 11 + Trifloxystrobin | 200 + 200 |
| Present compound 11 + Trifloxystrobin | 500 + 0.5 |
| Present compound 11 + Triticonazole | 200 + 200 |
| Present compound 11 + Triticonazole | 500 + 0.5 |

TABLE 57

| Composition | Concentration (ppm) |
|---|---|
| Present compound 12 + Clothianidin | 200 + 2000 |
| Present compound 12 + Clothianidin | 500 + 50 |
| Present compound 12 + Imidacloprid | 200 + 2000 |
| Present compound 12 + Imidacloprid | 500 + 50 |
| Present compound 12 + Thiamethoxam | 200 + 2000 |
| Present compound 12 + Thiamethoxam | 500 + 50 |
| Present compound 12 + Azoxystrobin | 200 + 200 |
| Present compound 12 + Azoxystrobin | 500 + 0.5 |
| Present compound 12 + Difenoconazole | 200 + 200 |
| Present compound 12 + Difenoconazole | 500 + 0.5 |
| Present compound 12 + Ethaboxam | 200 + 200 |
| Present compound 12 + Ethaboxam | 500 + 0.5 |
| Present compound 12 + Fludioxonil | 200 + 200 |
| Present compound 12 + Fludioxonil | 500 + 0.5 |
| Present compound 12 + Fluopyram | 200 + 2000 |
| Present compound 12 + Fluopyram | 500 + 0.5 |
| Present compound 12 + Fluoxastrobin | 200 + 200 |
| Present compound 12 + Fluoxastrobin | 500 + 0.5 |
| Present compound 12 + Flutolanil | 200 + 200 |
| Present compound 12 + Flutolanil | 500 + 0.5 |
| Present compound 12 + Flutriafol | 200 + 200 |
| Present compound 12 + Flutriafol | 500 + 0.5 |
| Present compound 12 + Fluxapyroxad | 200 + 200 |
| Present compound 12 + Fluxapyroxad | 500 + 0.5 |
| Present compound 12 + Ipconazole | 200 + 200 |
| Present compound 12 + Ipconazole | 500 + 0.5 |
| Present compound 12 + Mandestrobin | 200 + 200 |
| Present compound 12 + Mandestrobin | 500 + 0.5 |
| Present compound 12 + Metalaxyl M | 200 + 200 |
| Present compound 12 + Metalaxyl M | 500 + 0.5 |

TABLE 57-continued

| Composition | Concentration (ppm) |
|---|---|
| Present compound 12 + Metalaxyl | 200 + 200 |
| Present compound 12 + Metalaxyl | 500 + 0.5 |
| Present compound 12 + Metconazole | 200 + 200 |
| Present compound 12 + Metconazole | 500 + 0.5 |
| Present compound 12 + Oxathiapiprolin | 200 + 200 |
| Present compound 12 + Oxathiapiprolin | 500 + 0.5 |
| Present compound 12 + Penfurufen | 200 + 200 |
| Present compound 12 + Penfurufen | 500 + 0.5 |
| Present compound 12 + Penthiopyrad | 200 + 200 |
| Present compound 12 + Penthiopyrad | 500 + 0.5 |
| Present compound 12 + Picoxystrobin | 200 + 200 |
| Present compound 12 + Picoxystrobin | 500 + 0.5 |
| Present compound 12 + Prothioconazole | 200 + 200 |
| Present compound 12 + Prothioconazole | 500 + 0.5 |
| Present compound 12 + Pyraclostrobin | 200 + 200 |
| Present compound 12 + Pyraclostrobin | 500 + 0.5 |
| Present compound 12 + Fungicide compound β2 | 200 + 200 |
| Present compound 12 + Fungicide compound β2 | 500 + 0.5 |
| Present compound 12 + Sedaxane | 200 + 200 |
| Present compound 12 + Sedaxane | 500 + 0.5 |
| Present compound 12 + Tebuconazole | 200 + 200 |
| Present compound 12 + Tebuconazole | 500 + 0.5 |
| Present compound 12 + Triadimenol | 200 + 200 |
| Present compound 12 + Triadimenol | 500 + 0.5 |
| Present compound 12 + Trifloxystrobin | 200 + 200 |
| Present compound 12 + Trifloxystrobin | 500 + 0.5 |
| Present compound 12 + Triticonazole | 200 + 200 |
| Present compound 12 + Triticonazole | 500 + 0.5 |

TABLE 58

| Composition | Concentration (ppm) |
|---|---|
| Present compound 13 + Clothianidin | 200 + 2000 |
| Present compound 13 + Clothianidin | 500 + 50 |
| Present compound 13 + Imidacloprid | 200 + 2000 |
| Present compound 13 + Imidacloprid | 500 + 50 |
| Present compound 13 + Thiamethoxam | 200 + 2000 |
| Present compound 13 + Thiamethoxam | 500 + 50 |
| Present compound 13 + Azoxystrobin | 200 + 200 |
| Present compound 13 + Azoxystrobin | 500 + 0.5 |
| Present compound 13 + Difenoconazole | 200 + 200 |
| Present compound 13 + Difenoconazole | 500 + 0.5 |
| Present compound 13 + Ethaboxam | 200 + 200 |
| Present compound 13 + Ethaboxam | 500 + 0.5 |
| Present compound 13 + Fludioxonil | 200 + 200 |
| Present compound 13 + Fludioxonil | 500 + 0.5 |
| Present compound 13 + Fluopyram | 200 + 2000 |
| Present compound 13 + Fluopyram | 500 + 0.5 |
| Present compound 13 + Fluoxastrobin | 200 + 200 |
| Present compound 13 + Fluoxastrobin | 500 + 0.5 |
| Present compound 13 + Flutolanil | 200 + 200 |
| Present compound 13 + Flutolanil | 500 + 0.5 |
| Present compound 13 + Flutriafol | 200 + 200 |
| Present compound 13 + Flutriafol | 500 + 0.5 |
| Present compound 13 + Fluxapyroxad | 200 + 200 |
| Present compound 13 + Fluxapyroxad | 500 + 0.5 |
| Present compound 13 + Ipconazole | 200 + 200 |
| Present compound 13 + Ipconazole | 500 + 0.5 |
| Present compound 13 + Mandestrobin | 200 + 200 |
| Present compound 13 + Mandestrobin | 500 + 0.5 |
| Present compound 13 + Metalaxyl M | 200 + 200 |
| Present compound 13 + Metalaxyl M | 500 + 0.5 |
| Present compound 13 + Metalaxyl | 200 + 200 |
| Present compound 13 + Metalaxyl | 500 + 0.5 |
| Present compound 13 + Metconazole | 200 + 200 |
| Present compound 13 + Metconazole | 500 + 0.5 |
| Present compound 13 + Oxathiapiprolin | 200 + 200 |
| Present compound 13 + Oxathiapiprolin | 500 + 0.5 |
| Present compound 13 + Penfurufen | 200 + 200 |
| Present compound 13 + Penfurufen | 500 + 0.5 |
| Present compound 13 + Penthiopyrad | 200 + 200 |
| Present compound 13 + Penthiopyrad | 500 + 0.5 |

TABLE 58-continued

| Composition | Concentration (ppm) |
| --- | --- |
| Present compound 13 + Picoxystrobin | 200 + 200 |
| Present compound 13 + Picoxystrobin | 500 + 0.5 |
| Present compound 13 + Prothioconazole | 200 + 200 |
| Present compound 13 + Prothioconazole | 500 + 0.5 |
| Present compound 13 + Pyraclostrobin | 200 + 200 |
| Present compound 13 + Pyraclostrobin | 500 + 0.5 |
| Present compound 13 + Fungicide compound β2 | 200 + 200 |
| Present compound 13 + Fungicide compound β2 | 500 + 0.5 |
| Present compound 13 + Sedaxane | 200 + 200 |
| Present compound 13 + Sedaxane | 500 + 0.5 |
| Present compound 13 + Tebuconazole | 200 + 200 |
| Present compound 13 + Tebuconazole | 500 + 0.5 |
| Present compound 13 + Triadimenol | 200 + 200 |
| Present compound 13 + Triadimenol | 500 + 0.5 |
| Present compound 13 + Trifloxystrobin | 200 + 200 |
| Present compound 13 + Trifloxystrobin | 500 + 0.5 |
| Present compound 13 + Triticonazole | 200 + 200 |
| Present compound 13 + Triticonazole | 500 + 0.5 |

TABLE 59

| Composition | Concentration (ppm) |
| --- | --- |
| Present compound 16 + Clothianidin | 200 + 2000 |
| Present compound 16 + Clothianidin | 500 + 50 |
| Present compound 16 + Imidacloprid | 200 + 2000 |
| Present compound 16 + Imidacloprid | 500 + 50 |
| Present compound 16 + Thiamethoxam | 200 + 2000 |
| Present compound 16 + Thiamethoxam | 500 + 50 |
| Present compound 16 + Azoxystrobin | 200 + 200 |
| Present compound 16 + Azoxystrobin | 500 + 0.5 |
| Present compound 16 + Difenoconazole | 200 + 200 |
| Present compound 16 + Difenoconazole | 500 + 0.5 |
| Present compound 16 + Ethaboxam | 200 + 200 |
| Present compound 16 + Ethaboxam | 500 + 0.5 |
| Present compound 16 + Fludioxonil | 200 + 200 |
| Present compound 16 + Fludioxonil | 500 + 0.5 |
| Present compound 16 + Fluopyram | 200 + 2000 |
| Present compound 16 + Fluopyram | 500 + 0.5 |
| Present compound 16 + Fluoxastrobin | 200 + 200 |
| Present compound 16 + Fluoxastrobin | 500 + 0.5 |
| Present compound 16 + Flutolanil | 200 + 200 |
| Present compound 16 + Flutolanil | 500 + 0.5 |
| Present compound 16 + Flutriafol | 200 + 200 |
| Present compound 16 + Flutriafol | 500 + 0.5 |
| Present compound 16 + Fluxapyroxad | 200 + 200 |
| Present compound 16 + Fluxapyroxad | 500 + 0.5 |
| Present compound 16 + Ipconazole | 200 + 200 |
| Present compound 16 + Ipconazole | 500 + 0.5 |
| Present compound 16 + Mandestrobin | 200 + 200 |
| Present compound 16 + Mandestrobin | 500 + 0.5 |
| Present compound 16 + Metalaxyl M | 200 + 200 |
| Present compound 16 + Metalaxyl M | 500 + 0.5 |
| Present compound 16 + Metalaxyl | 200 + 200 |
| Present compound 16 + Metalaxyl | 500 + 0.5 |
| Present compound 16 + Metconazole | 200 + 200 |
| Present compound 16 + Metconazole | 500 + 0.5 |
| Present compound 16 + Oxathiapiprolin | 200 + 200 |
| Present compound 16 + Oxathiapiprolin | 500 + 0.5 |
| Present compound 16 + Penfurufen | 200 + 200 |
| Present compound 16 + Penfurufen | 500 + 0.5 |
| Present compound 16 + Penthiopyrad | 200 + 200 |
| Present compound 16 + Penthiopyrad | 500 + 0.5 |
| Present compound 16 + Picoxystrobin | 200 + 200 |
| Present compound 16 + Picoxystrobin | 500 + 0.5 |
| Present compound 16 + Prothioconazole | 200 + 200 |
| Present compound 16 + Prothioconazole | 500 + 0.5 |
| Present compound 16 + Pyraclostrobin | 200 + 200 |
| Present compound 16 + Pyraclostrobin | 500 + 0.5 |
| Present compound 16 + Fungicide compound β2 | 200 + 200 |
| Present compound 16 + Fungicide compound β2 | 500 + 0.5 |
| Present compound 16 + Sedaxane | 200 + 200 |
| Present compound 16 + Sedaxane | 500 + 0.5 |

TABLE 59-continued

| Composition | Concentration (ppm) |
| --- | --- |
| Present compound 16 + Tebuconazole | 200 + 200 |
| Present compound 16 + Tebuconazole | 500 + 0.5 |
| Present compound 16 + Triadimenol | 200 + 200 |
| Present compound 16 + Triadimenol | 500 + 0.5 |
| Present compound 16 + Trifloxystrobin | 200 + 200 |
| Present compound 16 + Trifloxystrobin | 500 + 0.5 |
| Present compound 16 + Triticonazole | 200 + 200 |
| Present compound 16 + Triticonazole | 500 + 0.5 |

TABLE 60

| Composition | Concentration (ppm) |
| --- | --- |
| Present compound 18 + Clothianidin | 200 + 2000 |
| Present compound 18 + Clothianidin | 500 + 50 |
| Present compound 18 + Imidacloprid | 200 + 2000 |
| Present compound 18 + Imidacloprid | 500 + 50 |
| Present compound 18 + Thiamethoxam | 200 + 2000 |
| Present compound 18 + Thiamethoxam | 500 + 50 |
| Present compound 18 + Azoxystrobin | 200 + 200 |
| Present compound 18 + Azoxystrobin | 500 + 0.5 |
| Present compound 18 + Difenoconazole | 200 + 200 |
| Present compound 18 + Difenoconazole | 500 + 0.5 |
| Present compound 18 + Ethaboxam | 200 + 200 |
| Present compound 18 + Ethaboxam | 500 + 0.5 |
| Present compound 18 + Fludioxonil | 200 + 200 |
| Present compound 18 + Fludioxonil | 500 + 0.5 |
| Present compound 18 + Fluopyram | 200 + 2000 |
| Present compound 18 + Fluopyram | 500 + 0.5 |
| Present compound 18 + Fluoxastrobin | 200 + 200 |
| Present compound 18 + Fluoxastrobin | 500 + 0.5 |
| Present compound 18 + Flutolanil | 200 + 200 |
| Present compound 18 + Flutolanil | 500 + 0.5 |
| Present compound 18 + Flutriafol | 200 + 200 |
| Present compound 18 + Flutriafol | 500 + 0.5 |
| Present compound 18 + Fluxapyroxad | 200 + 200 |
| Present compound 18 + Fluxapyroxad | 500 + 0.5 |
| Present compound 18 + Ipconazole | 200 + 200 |
| Present compound 18 + Ipconazole | 500 + 0.5 |
| Present compound 18 + Mandestrobin | 200 + 200 |
| Present compound 18 + Mandestrobin | 500 + 0.5 |
| Present compound 18 + Metalaxyl M | 200 + 200 |
| Present compound 18 + Metalaxyl M | 500 + 0.5 |
| Present compound 18 + Metalaxyl | 200 + 200 |
| Present compound 18 + Metalaxyl | 500 + 0.5 |
| Present compound 18 + Metconazole | 200 + 200 |
| Present compound 18 + Metconazole | 500 + 0.5 |
| Present compound 18 + Oxathiapiprolin | 200 + 200 |
| Present compound 18 + Oxathiapiprolin | 500 + 0.5 |
| Present compound 18 + Penfurufen | 200 + 200 |
| Present compound 18 + Penfurufen | 500 + 0.5 |
| Present compound 18 + Penthiopyrad | 200 + 200 |
| Present compound 18 + Penthiopyrad | 500 + 0.5 |
| Present compound 18 + Picoxystrobin | 200 + 200 |
| Present compound 18 + Picoxystrobin | 500 + 0.5 |
| Present compound 18 + Prothioconazole | 200 + 200 |
| Present compound 18 + Prothioconazole | 500 + 0.5 |
| Present compound 18 + Pyraclostrobin | 200 + 200 |
| Present compound 18 + Pyraclostrobin | 500 + 0.5 |
| Present compound 18 + Fungicide compound β2 | 200 + 200 |
| Present compound 18 + Fungicide compound β2 | 500 + 0.5 |
| Present compound 18 + Sedaxane | 200 + 200 |
| Present compound 18 + Sedaxane | 500 + 0.5 |
| Present compound 18 + Tebuconazole | 200 + 200 |
| Present compound 18 + Tebuconazole | 500 + 0.5 |
| Present compound 18 + Triadimenol | 200 + 200 |
| Present compound 18 + Triadimenol | 500 + 0.5 |
| Present compound 18 + Trifloxystrobin | 200 + 200 |
| Present compound 18 + Trifloxystrobin | 500 + 0.5 |
| Present compound 18 + Triticonazole | 200 + 200 |
| Present compound 18 + Triticonazole | 500 + 0.5 |

TABLE 61

| Composition | Concentration (ppm) |
|---|---|
| Present compound 24 + Clothianidin | 200 + 2000 |
| Present compound 24 + Clothianidin | 500 + 50 |
| Present compound 24 + Imidacloprid | 200 + 2000 |
| Present compound 24 + Imidacloprid | 500 + 50 |
| Present compound 24 + Thiamethoxam | 200 + 2000 |
| Present compound 24 + Thiamethoxam | 500 + 50 |
| Present compound 24 + Azoxystrobin | 200 + 200 |
| Present compound 24 + Azoxystrobin | 500 + 0.5 |
| Present compound 24 + Difenoconazole | 200 + 200 |
| Present compound 24 + Difenoconazole | 500 + 0.5 |
| Present compound 24 + Ethaboxam | 200 + 200 |
| Present compound 24 + Ethaboxam | 500 + 0.5 |
| Present compound 24 + Fludioxonil | 200 + 200 |
| Present compound 24 + Fludioxonil | 500 + 0.5 |
| Present compound 24 + Fluopyram | 200 + 2000 |
| Present compound 24 + Fluopyram | 500 + 0.5 |
| Present compound 24 + Fluoxastrobin | 200 + 200 |
| Present compound 24 + Fluoxastrobin | 500 + 0.5 |
| Present compound 24 + Flutolanil | 200 + 200 |
| Present compound 24 + Flutolanil | 500 + 0.5 |
| Present compound 24 + Flutriafol | 200 + 200 |
| Present compound 24 + Flutriafol | 500 + 0.5 |
| Present compound 24 + Fluxapyroxad | 200 + 200 |
| Present compound 24 + Fluxapyroxad | 500 + 0.5 |
| Present compound 24 + Ipconazole | 200 + 200 |
| Present compound 24 + Ipconazole | 500 + 0.5 |
| Present compound 24 + Mandestrobin | 200 + 200 |
| Present compound 24 + Mandestrobin | 500 + 0.5 |
| Present compound 24 + Metalaxyl M | 200 + 200 |
| Present compound 24 + Metalaxyl M | 500 + 0.5 |
| Present compound 24 + Metalaxyl | 200 + 200 |
| Present compound 24 + Metalaxyl | 500 + 0.5 |
| Present compound 24 + Metconazole | 200 + 200 |
| Present compound 24 + Metconazole | 500 + 0.5 |
| Present compound 24 + Oxathiapiprolin | 200 + 200 |
| Present compound 24 + Oxathiapiprolin | 500 + 0.5 |
| Present compound 24 + Penfurufen | 200 + 200 |
| Present compound 24 + Penfurufen | 500 + 0.5 |
| Present compound 24 + Penthiopyrad | 200 + 200 |
| Present compound 24 + Penthiopyrad | 500 + 0.5 |
| Present compound 24 + Picoxystrobin | 200 + 200 |
| Present compound 24 + Picoxystrobin | 500 + 0.5 |
| Present compound 24 + Prothioconazole | 200 + 200 |
| Present compound 24 + Prothioconazole | 500 + 0.5 |
| Present compound 24 + Pyraclostrobin | 200 + 200 |
| Present compound 24 + Pyraclostrobin | 500 + 0.5 |
| Present compound 24 + Fungicide compound β2 | 200 + 200 |
| Present compound 24 + Fungicide compound β2 | 500 + 0.5 |
| Present compound 24 + Sedaxane | 200 + 200 |
| Present compound 24 + Sedaxane | 500 + 0.5 |
| Present compound 24 + Tebuconazole | 200 + 200 |
| Present compound 24 + Tebuconazole | 500 + 0.5 |
| Present compound 24 + Triadimenol | 200 + 200 |
| Present compound 24 + Triadimenol | 500 + 0.5 |
| Present compound 24 + Trifloxystrobin | 200 + 200 |
| Present compound 24 + Trifloxystrobin | 500 + 0.5 |
| Present compound 24 + Triticonazole | 200 + 200 |
| Present compound 24 + Triticonazole | 500 + 0.5 |

INDUSTRIAL APPLICABILITY

The Present compound shows an excellent control effect against a harmful arthropod. Also, the composition comprising the Present compound and one or more kinds of ingredients selected from the group consisting of Group (a), Group (b), Group (c) and Group (d) shows an excellent control effect against a harmful arthropod.

The invention claimed is:

1. A compound represented by formula (M-4):

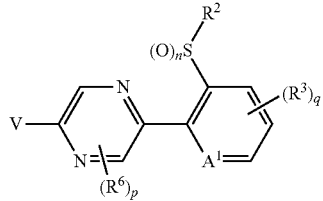

(M-4)

wherein
V represents a halogen atom;
$A^1$ represents a nitrogen atom or a $CR^4$;
$R^4$ represents a hydrogen atom, a $OR^{27}$, a $NR^{27}R^{28}$, a cyano group, a nitro group, or a halogen atom;
$R^{27}$ and $R^{28}$ represent independently of each other, a hydrogen atom, or a C1-C6 alkyl group optionally having one or more halogen atoms;
$R^2$ represents a C1-C6 alkyl group optionally having one or more halogen atoms, a cyclopropylmethyl group, or a cyclopropyl group;
q represents 0, 1, 2, or 3;
$R^3$ represents independently of each other a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{29}NR^{11}R^{12}$, a $NR^{29}OR^{11}$, A $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $S(O)_yR^{15}$, a $C(O)OR^{17}$, a $C(O)NR^{11}R^{12}$, a cyano group, a nitro group, or a halogen atom, and when q is 2 or 3, a plurality of $R^3$ may be identical or different;
x represents 0 or 1;
y represents 0, 1, or 2;
$R^{11}$, $R^{17}$, $R^{18}$, $R^{19}$, $R^{24}$ and $R^{29}$ represent independently of each other a hydrogen atom, or a C1-C6 chain hydrocarbon group optionally having one or more halogen atoms;
$R^{12}$ represents a hydrogen atom, a C1-C6 chain hydrocarbon group optionally having one or more halogen atoms, a C1-C6 alkyl group having one substituent selected from Group F, or a $S(O)_2R^{23}$;
$R^{23}$ represents a C1-C6 chain hydrocarbon group optionally having one or more halogen atoms, or a phenyl group optionally having one or more substituents selected from Group D;
$R^{11a}$ and $R^{12a}$ combine together with a nitrogen atom to which they are attached to form a 3 to 7 membered nonaromatic heterocyclic group optionally having one or more substituents selected from Group E {the 3 to 7 membered nonaromatic heterocyclic group represents aziridine, azetidine, pyrrolidine, imidazoline, imidazolidine, piperidine, tetrahydropyrimidine, hexahydropyrimidine, piperazine, azepane, oxazolidine, isooxazolidine, 1,3-oxazinane, morpholine, 1,4-oxazepane, thiazolidine, isothiazolidine, 1,3-thiazinane, thiomorpholine, or 1,4-thiazepane};
$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a 5 or 6 membered aromatic heterocyclic group optionally having one or more substituents selected from Group D;

$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenylC1-C3 alkyl group {the phenyl moiety in the phenylC1-C3 alkyl group may optionally have one or more substituents selected from Group D};

$R^{15}$ and $R^{16}$ represent independently of each other, a C1-C6 alkyl group optionally having one or more halogen atoms;

n represents 0, 1, or 2;

p represents 0, 1, or 2; and $R^6$ represents independently of each other a C1-C6 alkyl group optionally having one or more halogen atoms, a $OR^{18}$, a $NR^{18}R^{19}$, a cyano group, a nitro group, or a halogen atom, and when p is 2, a plurality of $R^6$ may be identical or different;

Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom {$R^{21}$ and $R^{22}$ represent independently of each other a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, an amino group, a $NHR^{21}$, a $NR^{21}R^{22}$, a cyano group, a phenyl group optionally having one or more substituents selected from Group D, a 5 or 6 membered aromatic heterocyclic group optionally having one or more substituents selected from Group D, a C3-C7 cycloalkyl group optionally having one or more halogen atoms, and a 3 to 7 membered nonaromatic heterocyclic group optionally having one or more substituents selected from Group C.

* * * * *